(12) United States Patent
Kamberov et al.

(10) Patent No.: US 8,206,913 B1
(45) Date of Patent: *Jun. 26, 2012

(54) AMPLIFICATION AND ANALYSIS OF WHOLE GENOME AND WHOLE TRANSCRIPTOME LIBRARIES GENERATED BY A DNA POLYMERIZATION PROCESS

(75) Inventors: Emmanuel Kamberov, Ann Arbor, MI (US); Tong Sun, Houston, TX (US); Eric Bruening, Chelsea, MI (US); Jonathon H. Pinter, Ypsilanti, MI (US); Irina Sleptsova, Ann Arbor, MI (US); Takao Kurihara, Ann Arbor, MI (US); Vladimir L. Makarov, Ann Arbor, MI (US)

(73) Assignee: Rubicon Genomics, Inc., Ann Arbor, MI (US)

( * ) Notice: Subject to any disclaimer, the term of this patent is extended or adjusted under 35 U.S.C. 154(b) by 114 days.

This patent is subject to a terminal disclaimer.

(21) Appl. No.: 12/716,681

(22) Filed: Mar. 3, 2010

Related U.S. Application Data

(63) Continuation-in-part of application No. 10/795,667, filed on Mar. 8, 2004, now Pat. No. 7,718,403.

(60) Provisional application No. 60/453,060, filed on Mar. 7, 2003, provisional application No. 61/157,165, filed on Mar. 3, 2009.

(51) Int. Cl.
   *C12Q 1/68* (2006.01)
   *C12P 19/34* (2006.01)
(52) U.S. Cl. .................. 435/6.1; 435/6.11; 435/6.12
(58) Field of Classification Search .................. None
   See application file for complete search history.

(56) References Cited

U.S. PATENT DOCUMENTS

| | | |
|---|---|---|
| 5,043,272 A | 8/1991 | Hartley |
| 5,104,792 A | 4/1992 | Silver et al. |
| 5,106,727 A | 4/1992 | Hartley et al. |
| 5,514,545 A | 5/1996 | Eberwine |
| 5,523,204 A | 6/1996 | Singer et al. |
| 5,554,516 A | 9/1996 | Kacian et al. |
| 5,731,171 A | 3/1998 | Bohlander |
| 5,750,341 A | 5/1998 | Macevicz |
| 5,756,702 A | 5/1998 | Lohman et al. |
| 5,814,444 A | 9/1998 | Rabinovitch |

(Continued)

FOREIGN PATENT DOCUMENTS

EP  0 466 520  1/1992

(Continued)

OTHER PUBLICATIONS

Prevost et al., "Comparison of DNA polymerase for real-time PCR with SYBR® Green I," Spartan Bioscience Inc., 2008, pp. 1-3.*

(Continued)

*Primary Examiner* — Young J Kim
(74) *Attorney, Agent, or Firm* — Fulbright & Jaworski L.L.P.

(57) ABSTRACT

The present invention regards a variety of methods and compositions for whole genome amplification and whole transcriptome amplification. In a particular aspect of the present invention, there is a method of amplifying a genome comprising a library generation step followed by a library amplification step. In specific embodiments, the library generating step utilizes specific primer mixtures and a DNA polymerase, wherein the specific primer mixtures are designed to eliminate ability to self-hybridize and/or hybridize to other primers within a mixture but efficiently and frequently prime nucleic acid templates.

18 Claims, 59 Drawing Sheets

U.S. PATENT DOCUMENTS

| | | | |
|---|---|---|---|
| 5,871,920 | A | 2/1999 | Page et al. |
| 5,932,451 | A | 8/1999 | Wang et al. |
| 5,948,649 | A | 9/1999 | Stewart et al. |
| 5,994,058 | A | 11/1999 | Senapathy |
| 6,030,814 | A | 2/2000 | Jendrisak |
| 6,040,138 | A | 3/2000 | Lockhart et al. |
| 6,045,994 | A | 4/2000 | Zabeau et al. |
| 6,107,023 | A | 8/2000 | Reyes et al. |
| 6,114,149 | A | 9/2000 | Fry et al. |
| 6,124,120 | A | 9/2000 | Lizardi |
| 6,280,949 | B1 | 8/2001 | Lizardi |
| 6,365,375 | B1 | 4/2002 | Dietmaier et al. |
| 6,379,932 | B1 | 4/2002 | Arnold et al. |
| 6,506,594 | B1 | 1/2003 | Barany et al. ............ 435/287.2 |
| 6,509,160 | B1 | 1/2003 | Sapolsky et al. |
| 6,521,428 | B1 | 2/2003 | Senapathy |
| 6,638,722 | B2 | 10/2003 | Ji et al. |
| 6,692,932 | B1 | 2/2004 | Ankenbauer et al. |
| 6,794,141 | B2 | 9/2004 | Erlander et al. |
| 6,808,888 | B2 | 10/2004 | Zhang et al. |
| 6,846,626 | B1 | 1/2005 | Senapathy |
| 7,718,403 | B2 * | 5/2010 | Kamberov et al. ......... 435/91.2 |
| 2001/0021518 | A1 | 9/2001 | Goudsmit et al. |
| 2002/0045169 | A1 | 4/2002 | Shoemaker et al. |
| 2003/0017591 | A1 | 1/2003 | Kurn |
| 2003/0108870 | A1 | 6/2003 | Ji et al. |
| 2003/0165885 | A1 | 9/2003 | Arnold et al. |
| 2003/0186237 | A1 | 10/2003 | Ginsberg et al. |
| 2003/0211528 | A1 | 11/2003 | Iscove |
| 2004/0014076 | A1 | 1/2004 | Gabriel et al. |
| 2004/0043416 | A1 | 3/2004 | Ji et al. |
| 2004/0063144 | A1 | 4/2004 | Lizardi |
| 2004/0209298 | A1* | 10/2004 | Kamberov et al. ............ 435/6 |
| 2005/0202490 | A1 | 9/2005 | Makarov et al. |
| 2006/0194246 | A1 | 8/2006 | Schuster et al. |

FOREIGN PATENT DOCUMENTS

| | | |
|---|---|---|
| EP | 1 275 738 | 1/2003 |
| JP | 08173164 | 7/1996 |
| WO | WO 96/15264 | 5/1996 |
| WO | WO 97/30062 | 8/1997 |
| WO | WO 98/02575 | 1/1998 |
| WO | WO 00/17390 | 3/2000 |
| WO | WO 01/09384 | 2/2001 |
| WO | WO 01/51661 | 7/2001 |
| WO | WO 02/06533 | 1/2002 |
| WO | WO 02/20571 | 3/2002 |
| WO | WO 02/072772 | 9/2002 |
| WO | WO 02/001022 | 12/2002 |
| WO | WO 02/103054 | 12/2002 |
| WO | WO 03/012118 | 2/2003 |
| WO | WO 03/016546 | 2/2003 |
| WO | WO 03/050242 | 6/2003 |

OTHER PUBLICATIONS

Agarwal et al., "PCR amplification of highly GC-rich DNA template after denaturation by NaOH," *Nucleic Acids Research*, 21:5283-5284, 1993.

Alburquerque-Silva, et al., "Tailing cDNAs with terminal deoxynucleotidyl transferase in RT-PCR assays to identify ribozyme cleavage products," *Nucleic Acids Res.*, 26:3314-6, 1998.

Bachmann et al, "Successful amplification of extremely GC-rich promoter regions using a novel 'slowdown PCR' technique," *Pharmacogenetics*, 13(12): 759-766, 2003.

Baldini, et al., "Chromosomal assignment of human YAC clones by fluorescence in situ hybridization: use of single-yeast-colony PCR and multiple labeling," *Genomics*, 14:181-4, 1992.

Bellizi et al., "A procedure for cloning genomic DNA fragments with increasing thermoresistance," *International Journal of Genes and Genomes*, 219: 63-71, 1998.

Bohlander, et al., "A method for the rapid sequence-independent amplification of microdissected chromosomal material," *Genomics*, 13:1322-4, 1992.

Breen, et al., "YAC mapping by FISH using Alu-PCR-generated probes," *Genomics*, 13:726-30, 1992.

Buchanan, et al., "Long DOP-PCR of rare archival anthropological samples," *Hum. Biol.*, 72:911-25, 2000.

Cano, "Analysing ancient DNA," *Endeavour*, 20:162-7, 1996.

Chakrabarti, et al., "Novel sulfoxides facilitate GC-rich template amplification," *Biotechniques*, 32:866-74, 2002.

Champoux, "DNA topoisomerases: structure, function, and mechanism," *Annu. Rev. Biochem.*, 70:369-413, 2001.

Cheng, et al., "Degenerate oligonucleotide primed-polymerase chain reaction and capillary electrophoretic analysis of human DNA on microchip-based devices," *Anal. Biochem.*, 257:101-6, 1998.

Cheung, et al., "Whole genome amplification using a degenerate oligonucleotide primer allows hundreds of genotypes to be performed on less than one nanogram of genomic DNA," *Proc. Natl. Acad. Sci. USA*, 93:14676-9, 1996.

Cusi et al., "PCR amplification of GC-rich templates containing palindromic sequences using initial alkali denaturation," *Biotechniques*, 12:502-504, 1992.

DeRisi Laboratory, Dept. of Biochemistry and Biophysics, Univ. of California at San Francisco, Random DNA Amplification, Directions for amplifying products for prints on arrays, 2001.

Grothues, et al., "PCR amplification of megabase DNA with tagged random primers (T-PCR)," *Nucleic Acids Res.*, 21:1321-2, 1993.

Guan, et al., "Generation of band-specific painting probes from a single microdissected chromosome," *Hum. Mol Genet.*, 2:1117-21, 1993.

Kinzler, et al., "Whole genome PCR: application to the identification of sequences bound by gene regulatory proteins," *Nucleic Acids Res.*, 17:3645-53, 1989.

Kittler, et al., "A whole genome amplification method to generate long fragments from low quantities of genomic DNA," *Anal. Biochem.*, 300:237-44, 2002.

Klein, et al., "Comparative genomic hybridization, loss of heterozygosity, and DNA sequence analysis of single cells," *Proc. Natl Acad. Sci. USA*, 96:4494-9, 1999.

Krieger, et al., "Prokaryotic DNA sequences in patients with chronic idiopathic prostatitis," *J. Clin. Microbiol*, 34:3120-8, 1996.

Kusov, et al., "A new G-tailing method for the determination of the poly(A) tail length applied to hepatitis A virus RNA," *Nucleic Acids Res.*, 29:E57, 2001.

Lengauer, et al., "Fluorescence in situ hybridization of YAC clones after Alu-PCR amplification," *Genomics*, 13:826-8, 1992.

Lucito, et al., "Genetic analysis using genomic representations," *Proc. Natl. Acad. Sci. USA*, 95:4487-92, 1998.

Ludecke, et al., "Cloning defined regions of the human genome by microdissection of banded chromosomes and enzymatic amplification," *Nature*, 338:348-50, 1989.

Makrigiorgos, et al., "A PCR-based amplification method retaining the quantitative difference between two complex genomes," *Nat. Biotechnol*, 20:936-9, 2002.

Martel, et al., "A simple method for elimination of false positive results in RT-PCR," *J. Biochem. Mol. Biol.*, 35:248-50, 2002.

McGrath, et al., "Sequence analysis of DNA randomly amplified from the *Saccharomyces cerevisiae* genome," *Mol. Cell. Probes*, 12:397-405, 1998.

Mullis, et al., "Specific enzymatic amplification of DNA in vitro: the polymerase chain reaction," Cold Spring Harbor Symp., pp. 263-273, 1986.

Nelson, et al., "Alu-primed polymerase chain reaction for regional assignment of 110 yeast artificial chromosome clones from the human X chromosome: identification of clones associated with a disease locus," *Proc. Natl. Acad. Sci. USA*, 88:6157-61, 1991.

Office Action, issued in European Application No. 04 718 499.9, mail date Dec. 28, 2005.

Office Action, issued in European Application No. 04 718 499.9, mail date Nov. 22, 2006.

Office Action, issued in European Application No. 04 718 499.9, mail date Oct. 18, 2007.

Office Action, issued in European Application No. 04 718 499.9 , mail date Sep. 10, 2008.

Office Action, issued in Japanese Application No. 2006-509236, mail date Dec. 2, 2009.

Office Action, issued in Japanese Application No. 2006-509236, mail date Nov. 18, 2010.

Office Action, issued in U.S. Appl. No. 10/795,667, mail date Jan. 31, 2007.
Office Action, issued in U.S. Appl. No. 10/795,667, mail date Jul. 26, 2007.
Office Action, issued in U.S. Appl. No. 10/795,667, mail date Feb. 13, 2008.
Office Action, issued in U.S. Appl. No. 10/795,667, mail date Apr. 27, 2009.
Office Action, issued in related U.S. Appl. No. 11/071,864, mail date Jul. 23, 2007.
Office Action, issued in related U.S. Appl. No. 11/071,864, mail date Nov. 15, 2007.
Office Action, issued in related U.S. Appl. No. 11/071,864, mail date Oct. 30, 2008.
Office Action, issued in related U.S. Appl. No. 11/071,864, mail date Jun. 16, 2008.
Office Action, issued in related U.S. Appl. No. 11/071,864, mail date Dec. 31, 2009.
PCT International Preliminary Examination Report, PCT NL01 00020, dated Mar. 25, 2003.
PCT International Search, PCT-NL01 00020, dated Jul. 18, 2002.
Phillips, et al., "Antisense RNA Amplification: A Linear Amplification Method for Analyzing the mRNA Population from Single Living Cells," *Methods*, 10:283-8, 1996.
Rose, et al., "Consensus-degenerate hybrid oligonucleotide primers for amplification of distantly related sequences," *Nucleic Acids Res.*, 26:1628-35, 1998.
Sanchez-Cespedes, et al., "Degenerate oligonucleotide-primed PCR (DOP-PCR): evaluation of its reliability for screening of genetic alterations in neoplasia," *Biotechniques*, 25:1036-8, 1998.
Schmidt, et al., "CapSelect: a highly sensitive method for 5' CAP-dependent enrichment of full-length cDNA in PCR-mediated analysis of mRNAs," *Nucleic Acids Res.*, 27:e31, 1999.
Schmidt, et al., "Controlled ribonucleotide tailing of cDNA ends (CRTC) by termination deoxynucleotidyl transferase: a new approach n PCR-mediated analysis of mRNA sequences," *Nucleic Acids Res.*, 24:1789-91, 1996.
Sharrocks, et al., "The design of primers for PCR," PCR Technology Current Innovations, Chapter 2, pp. 5-11, 1994.
Shiraishi et al., "Preferential isolation of DNA fragments associated with CpG islands," *Proc. Natl. Acad. Sci.*, 92:4229-4233, 1995.
Smith, et al., "Automated differential display using a fluorescently labeled universal primer," *Biotechniques*, 23:274-9, 1997.
Smith, et al., "Single primer amplification (SPA) of cDNA for microarray expression analysis," *Nucleic Acids Res.*, 31:e9, 2003.
Stellrecht and Gandhi, "Concurrent isolation of ribosomal, messenger, and low molecular weight RNA," *Biotechniques*, 33:1122-4, 2002.
Studier, "Relationships among different strains of T7 and among T7-related bacteriophages," *Virology*, 95:70-84, 1979.
Sutcliffe, et al., "PCR amplification and analysis of yeast artificial chromosomes," *Genomics*, 13:1303-6, 1992.
Tanabe, et al., "Evaluation of a whole-genome amplification method based on adaptor-ligation PCR of randomly sheared genomic DNA," *Genes, Chromosomes and Cancer*, 38:168-76, 2003.
Telenius, et al., "Degenerate oligonucleotide-primed PCR: general amplification of target DNA by a single degenerate primer," *Genomics*, 13:718-25, 1992.
Ussery, "DNA denaturation," Center for Biological Sequence Analysis, Institute of Biotechnology, Academic Press, pp. 1-3, 2001.
Wells, et al., "Detailed chromosomal and molecular genetic analysis of single cells by whole genome amplification and comparative genomic hybridization," *Nucleic Acids Res.*, 27:1214-8, 1999.
Wesley, et al., "Cloning regions of the Drosophila genome by microdissection of polytene chromosome DNA and PCR with non-specific primer," *Nucleic Acids Res.*, 18:599-603, 1990.
Wold, "Replication protein A: a heterotrimeric, single-stranded DNA-binding protein required for eukaryotic DNA metabolism," *Annu. Rev. Biochem.*, 66:61-92, 1997.
Wong, et al., "Use of tagged random hexamer amplification (TRHA) to clone and sequence minute quantities of DNA—application to a 180 kb plasmid isolated from Sphingomonas F199," *Nucleic Acids Res.*, 24:3778-83, 1996.
Zhang, et al., "Whole genome amplification from a single cell: implications for genetic analysis," *Proc. Natl. Acad. Sci. USA*, 89:5847-51, 1992.
Zheleznaya, et al., "PCR fragmentation of DNA," *Biochemistry*, 64:373-78, 1999.
Kiss et al., "Optimisation of the degenerate oligonucleotide primed PCR (DOP-PCR) for capillary thermocycler," *Biomolecular Engineering*, 19(1): 31-34, 2002.
European Search Report issued in Applicant No. 10 01 1482, dated Aug. 5, 2011.

\* cited by examiner

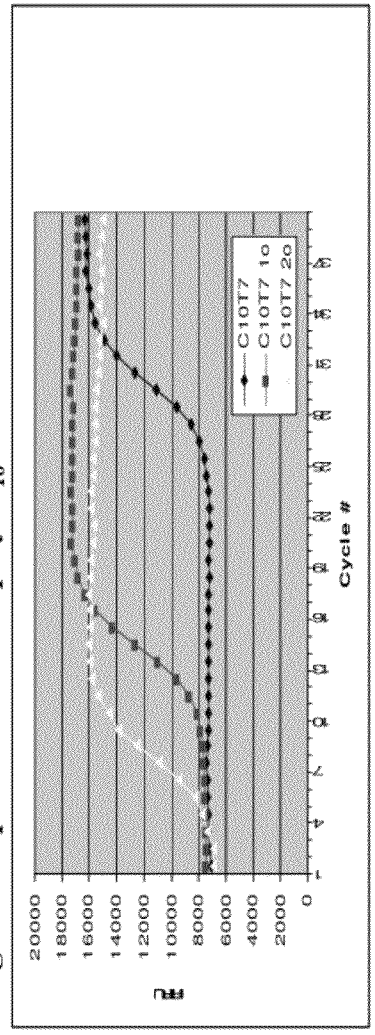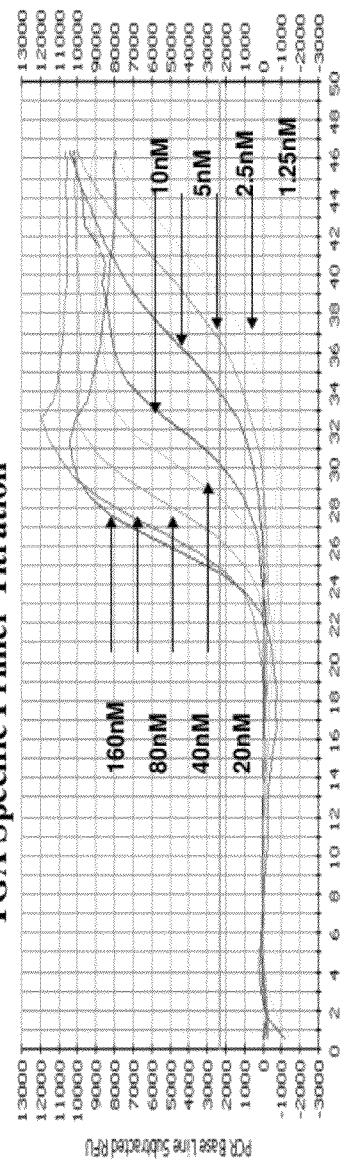
FIG. 47

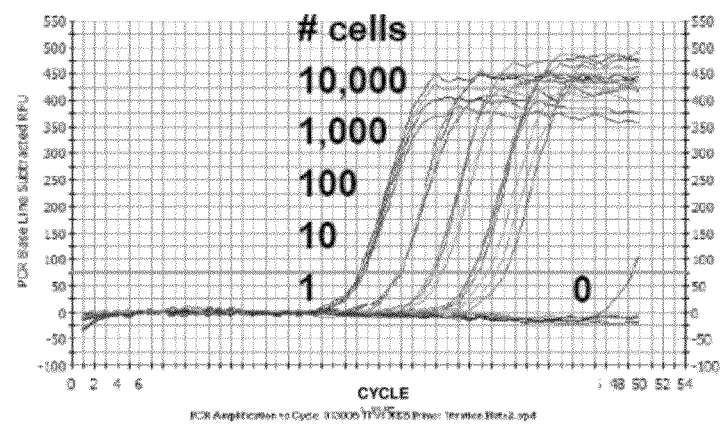
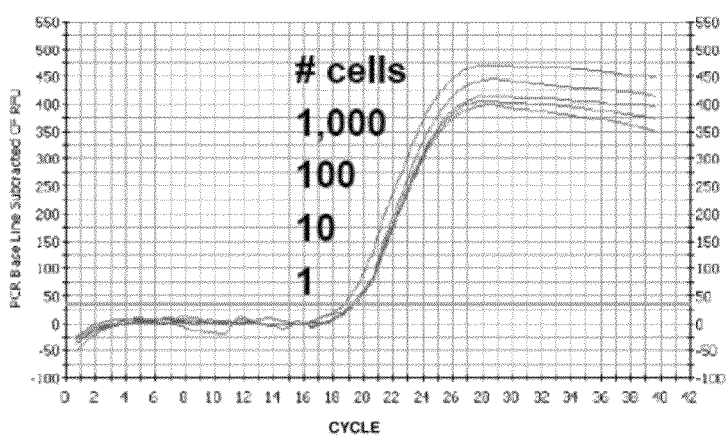
FIG. 54

AMPLIFICATION AND ANALYSIS OF WHOLE GENOME AND WHOLE TRANSCRIPTOME LIBRARIES GENERATED BY A DNA POLYMERIZATION PROCESS

This application is a continuation-in-part (CIP) application that claims priority to U.S. patent application Ser. No. 10/795,667, filed Mar. 8, 2004, which claims priority to U.S. Provisional Patent Application Ser. No. 60/453,060, filed Mar. 7, 2003, and this CIP application also claims priority to U.S. Provisional Patent Application Ser. No. 61/157,165, filed Mar. 3, 2009, all of which applications are incorporated by reference herein in their entirety.

FIELD OF THE INVENTION

The present invention is directed to the fields of genomics, molecular biology, genotyping, and expression profiling. In some embodiments, the present invention relates to methods for the amplification of DNA or cDNA yielding a product that is a non-biased representation of the original genomic or transcribed sequences, wherein the methods utilize primers substantially incapable of forming primer dimers.

BACKGROUND OF THE INVENTION

For genomic studies, the quality and quantity of DNA samples is crucial. High-throughput genetic analysis requires large amounts of template for testing. However, the amount of DNA extracted from individual patient samples, for example, is limited. DNA sample size also limits forensic and paleobiology work. Thus, there has been a concerted effort in developing methods to amplify the entire genome. The goal of whole genome amplification (WGA) is to supply a sufficient amount of genomic sequence for a variety of procedures, as well as long-term storage for future work and archiving of patient samples. There is a clear need to amplify entire genomes in an automatable, robust, representative fashion. Whole genome amplification has historically been accomplished using one of three techniques: polymerase chain reaction (PCR), strand displacement, or cell immortalization.

PCR™

PCR™ is a powerful technique to amplify DNA (Saiki, 1985). This in vitro technique amplifies DNA by repeated thermal denaturation, primer annealing and polymerase extension, thereby amplifying a single target DNA molecule to detectable quantities. PCR™ is not amenable to the amplification of long DNA molecules such as entire chromosomes, which in humans are approximately $10^8$ bases in length. The commonly used polymerase in PCR reactions is Taq polymerase, which cannot amplify regions of DNA larger than about 5000 bases. Moreover, knowledge of the exact nucleotide sequences flanking the amplification target is necessary in order to design primers used in the PCR reaction.

Whole Genome PCR™

Whole genome PCR™ results in the amplification either of complete pools of DNA or of unknown intervening sequences between specific primer binding sites. The amplification of complete pools of DNA, termed known amplification (Lüdecke et al., 1989) or general amplification (Telenius et al., 1992), can be achieved by different means. Common to all approaches is the capability of the PCR™ system to unanimously amplify DNA fragments in the reaction mixture without preference for specific DNA sequences. The structure of primers used for whole genome PCR™ is described as totally degenerate (i.e., all nucleotides are termed N,N=A, T, G, C), partially degenerate (i.e., several nucleotides are termed N) or non-degenerate (i.e., all positions exhibit defined nucleotides).

Whole genome PCR™ involves converting total genomic DNA to a form which can be amplified by PCR (Kinzler and Vogelstein, 1989). In this technique, total genomic DNA is fragmented via shearing or enzymatic digestion with, for instance, a restriction enzyme such as MboI, to an average size of 200-300 base pairs. The ends of the DNA are made blunt by incubation with the Klenow fragment of DNA polymerase. The DNA fragments are ligated to catch linkers consisting of a 20 base pair DNA fragment synthesized in vitro. The catch linkers consist of two phosphorylated oligomers: 5'-GAGTAGAATTCTAATATCTA-3' (SEQ ID NO:1) and 5'-GAGATATTAGAATTCTACTC-3' (SEQ ID NO:2). To select against the "catch" linkers that were self-ligated, the ligation product is cleaved with XhoI. Each catch linker has one half of an XhoI site at its termini; therefore, XhoI cleaves catch linkers ligated to themselves but will not cleave catch linkers ligated to most genomic DNA fragments. The linked DNA is in a form that can be amplified by PCR™ using the catch oligomers as primers. The DNA of interest can then be selected via binding to a specific protein or nucleic acid and recovered. The small amount of DNA fragments specifically bound can be amplified using PCR™. The steps of selection and amplification may be repeated as often as necessary to achieve the desired purity. Although 0.5 ng of starting DNA was amplified 5000-fold, Kinzler and Vogelstein (1989) did report a bias toward the amplification of smaller fragments.

Whole Genome PCR™ with Non-Degenerate Primers

Lone Linker PCR™

Because of the inefficiency of the conventional catch linkers due to self-hybridization of two complementary primers, asymmetrical linkers for the primers were designed (Ko et al., 1990). The sequences of the catch linker oligonucleotides (Kinzler and Vogelstein, 1989) were used with the exception of a deleted 3 base pair sequence from the 3'-end of one strand. This "lone-linker" has both a non-palindromic protruding end and a blunt end, thus preventing multimerization of linkers. Moreover, as the orientation of the linker was defined, a single primer was sufficient for amplification. After digestion with a four-base cutting enzyme, the lone linkers were ligated. Lone-linker PCR™ (LL-PCR™) produces fragments ranging from 100 bases to ~2 kb that were reported to be amplified with similar efficiency.

Interspersed Repetitive Sequence PCR

As used for the general amplification of DNA, interspersed repetitive sequence PCR™ (IRS-PCR™) uses non-degenerate primers that are based on repetitive sequences within the genome. This allows for amplification of segments between suitable positioned repeats and has been used to create human chromosome- and region-specific libraries (Nelson et al., 1989). IRS-PCR™ is also termed Alu element mediated-PCR™ (ALU-PCR™), which uses primers based on the most conserved regions of the Alu repeat family and allows the amplification of fragments flanked by these sequences (Nelson et al., 1989). A major disadvantage of IRS-PCR™ is that abundant repetitive sequences like the Alu family are not uniformly distributed throughout the human genome, but preferentially found in certain areas (e.g., the light bands of human chromosomes) (Korenberg and Rykowski, 1988). Thus, IRS-PCR™ results in a bias toward these regions and a lack of amplification of other, less represented areas. Moreover, this technique is dependent on the knowledge of the presence of abundant repeat families in the genome of interest.

Linker Adapter PCR™

The limitations of IRS-PCR™ are abated to some extent using the linker adapter technique (LA-PCR™) (Lüdecke et al., 1989; Saunders et al., 1989; Kao and Yu, 1991). This technique amplifies unknown restricted DNA fragments with the assistance of ligated duplex oligonucleotides (linker adapters). DNA is commonly digested with a frequently cutting restriction enzyme such as RsaI, yielding fragments that are on average 500 bp in length. After ligation, PCR™ can be performed using primers complementary to the sequence of the adapters. Temperature conditions are selected to enhance annealing specifically to the complementary DNA sequences, which leads to the amplification of unknown sequences situated between the adapters. Post-amplification, the fragments are cloned. There should be little sequence selection bias with LA-PCR™ except on the basis of distance between restriction sites. Methods of LA-PCR™ overcome the hurdles of regional bias and species dependence common to IRS-PCR™. However, LA-PCR™ is technically more challenging than other whole genome amplification (WGA) methods.

A large number of band-specific microdissection libraries of human, mouse, and plant chromosomes have been established using LA-PCR™ (Chang et al., 1992; Wesley et al., 1990; Saunders et al., 1989; Vooijs et al., 1993; Hadano et al., 1991; Miyashita et al., 1994). PCR™ amplification of a microdissected region of a chromosome is conducted by digestion with a restriction enzyme (e.g., Sau3A, MboI) to generate a number of short fragments, which are ligated to linker-adapter oligonucleotides that provide priming sites for PCR™ amplification (Saunders et al., 1989). Two oligonucleotides, a 20-mer and a 24-mer creating a 5' overhang that was phosphorylated with T4 polynucleotide kinase and complementary to the end generated by the restriction enzyme, were mixed in equimolar amounts and allowed to anneal. Following this amplification, as much as 1 µg of DNA can be amplified from as little as one band dissected from a polytene chromosome (Saunders et al., 1989; Johnson, 1990). Ligation of a linker-adapter to each end of the chromosomal restriction fragment provides the primer-binding site necessary for in vitro semiconservative DNA replication. Other applications of this technology include amplification of one flow-sorted mouse chromosome 11 and use of resulting DNA library as a probe in chromosome painting (Miyashita et al., 1994), and amplification of DNA of a single flow-sorted chromosome (VanDeanter et al., 1994).

A different adapter used in PCR™ is the Vectorette (Riley et al., 1990). This technique is largely used for the isolation of terminal sequences from yeast artificial chromosomes (YAC) (Kleyn et al., 1993; Naylor et al., 1993; Valdes et al., 1994). Vectorette is a synthetic oligonucleotide duplex containing an overhang complementary to the overhang generated by a restriction enzyme. The duplex contains a region of non-complementarity as a primer-binding site. After ligation of digested YACs and a Vectorette unit, amplification is performed between primers identical to Vectorette and primers derived from the yeast vector. Products will only be generated if, in the first PCR™ cycle, synthesis has taken place from the yeast vector primer, thus synthesizing products from the termini of YAC inserts.

Priming Authorizing Random Mismatches PCR™

Another whole genome PCR™ method using non-degenerate primers is Priming Authorizing Random Mismatches-PCR™ (PARM-PCR™), which uses specific primers and unspecific annealing conditions resulting in a random hybridization of primers leading to universal amplification (Milan et al., 1993). Annealing temperatures are reduced to 30° C. for the first two cycles and raised to 60° C. in subsequent cycles to specifically amplify the generated DNA fragments. This method has been used to universally amplify flow sorted porcine chromosomes for identification via fluorescent in situ hybridization (FISH) (Milan et al., 1993). A similar technique was also used to generate chromosome DNA clones from microdissected DNA (Hadano et al., 1991). In this method, a 22-mer primer unique in sequence, which randomly primes and amplifies any target DNA, was utilized. The primer contained recognition sites for three restriction enzymes. Thermocycling was done in three stages: stage one had an annealing temperature of 22° C. for 120 minutes, and stages two and three were conducted under stringent annealing conditions.

Single Cell Comparative Genomic Hybridization

A method allowing the comprehensive analysis of the entire genome on a single cell level has been developed termed single cell comparative genomic hybridization (SCOMP) (Klein et al., 1999; WO 00/17390). Genomic DNA from a single cell is fragmented with a four base cutter, such as MseI, giving an expected average length of 256 bp ($4^4$) based on the premise that the four bases are evenly distributed. Ligation mediated PCR™ was utilized to amplify the digested restriction fragments. Briefly, two primers ((5'-AGTGGGATTCCGCATGCTAGT-3'; SEQ ID NO:3); and (5'-TAACTAGCATGC-3'; SEQ ID NO:4)); were annealed to each other to create an adapter with two 5' overhangs. The 5' overhang resulting from the shorter oligo is complementary to the ends of the DNA fragments produced by MseI cleavage. The adapter was ligated to the digested fragments using T4 DNA ligase. Only the longer primer was ligated to the DNA fragments as the shorter primer did not have the 5' phosphate necessary for ligation. Following ligation, the second primer was removed via denaturation, and the first primer remained ligated to the digested DNA fragments. The resulting 5' overhangs were filled in by the addition of DNA polymerase. The resulting mixture was then amplified by PCR™ using the longer primer.

As this method is reliant on restriction digests to fragment the genomic DNA, it is dependent on the distribution of restriction sites in the DNA. Very small and very long restriction fragments will not be effectively amplified, resulting in a biased amplification. The average fragment length of 256 generated by MseI cleavage will result in a large number of fragments that are too short to amplify.

Whole Genome PCR™ with Degenerate Primers

In order to overcome difficulties associated with many techniques using non-degenerate primers for universal amplification, techniques using partially or totally degenerate primers were developed for universal amplification of minute amounts of DNA.

Degenerate Oligonucleotide Primed PCR

Degenerate oligonucleotide-primed PCR™ (DOP-PCR™) was developed using partially degenerate primers, thus providing a more general amplification technique than IRS-PCR (Wesley et al., 1990; Telenius, 1992). A system was described using non-specific primers (5'-TTGCGGCCG-CATTNNNNTTC-3' (SEQ ID NO:5); showing complete degeneration at positions 4, 5, 6, and 7 from the 3' end (Wesley et al., 1990). The three specific bases at the 3' end are statistically expected to hybridize every 64 ($4^3$) bases, thus the last seven bases will match due to the partial degeneration of the primer. The first cycles of amplification are conducted at a low annealing temperature (30° C.), allowing sufficient priming to initiate DNA synthesis at frequent intervals along the template. The defined sequence at the 3' end of the primer tends to separate initiation sites, thus increasing product size. As the PCR product molecules all contain a common specific 5' sequence, the annealing temperature is raised to 56° C. after the first eight cycles. The system was developed to unspecifically amplify microdissected chromosomal DNA from *Drosophila*, replacing the microcloning system of Lüdecke et al. (1989) described above.

The term DOP-PCR™ was introduced by Telenius et al. (1992) who developed the method for genome mapping research using flow sorted chromosomes. A single primer is used in DOP-PCR™ as used by Wesley et al. (1990). The primer (5'-CCGACTCGACNNNNNNATGTGG-3' (SEQ ID NO:6); shows six specific bases on the 3'-end, a degenerate part with 6 bases in the middle and a specific region with a rare restriction site at the 5'-end. Amplification occurs in two stages. Stage one encompasses the low temperature cycles. In the first cycle, the 3'-end of the primers hybridize to multiple sites of the target DNA initiated by the low annealing temperature. In the second cycle, a complementary sequence is generated according to the sequence of the primer. In stage two, primer annealing is performed at a temperature restricting all non-specific hybridization. Up to 10 low temperature cycles are performed to generate sufficient primer binding sites. Up to 40 high temperature cycles are added to specifically amplify the prevailing target fragments.

DOP-PCR™ is based on the principle of priming from short sequences specified by the 3'-end of partially degenerate oligonucleotides used during initial low annealing temperature cycles of the PCR™ protocol. As these short sequences occur frequently, amplification of target DNA proceeds at multiple loci simultaneously. DOP-PCR™ is applicable to the generation of libraries containing high levels of single copy sequences, provided uncontaminated DNA in a substantial amount is obtainable (e.g., flow-sorted chromosomes). This method has been applied to less than one nanogram of starting genomic DNA (Cheung and Nelson, 1996).

Advantages of DOP-PCR™ in comparison to systems of totally degenerate primers are the higher efficiency of amplification, reduced chances for unspecific primer-primer binding and the availability of a restriction site at the 5' end for further molecular manipulations. However, DOP-PCR™ does not claim to replicate the target DNA in its entirety (Cheung and Nelson, 1996). Moreover, as relatively short products are generated, specific amplification of fragments up to approximately 500 bp in length are produced (Telenius et al., 1992; Cheung and Nelson, 1996; Wells et al., 1999; Sanchez-Cespedes et al., 1998; Cheung et al., 1998).

In light of these limitations, a method has been described that produces long DOP-PCR™ products ranging from 0.5 to 7 kb in size, allowing the amplification of long sequence targets in subsequent PCR (long DOP-PCR™) (Buchanan et al., 2000). However, long DOP-PCR utilizes 200 ng of genomic DNA, which is more DNA than most applications will have available. Subsequently, a method was described that generates long amplification products from picogram quantities of genomic DNA, termed long products from low DNA quantities DOP-PCR™ (LL-DOP-PCR™) (Kittler et al., 2002). This method achieves this by the 3'-5' exonuclease proofreading activity of DNA polymerase Pwo and an increased annealing and extension time during DOP-PCR™, which are necessary steps to generate longer products. Although an improvement in success rate was demonstrated in comparison with other DOP-PCR™ methods, this method did have a 15.3% failure rate due to complete locus dropout for the majority of the failures and sporadic locus dropout and allele dropout for the remaining genotype failures. There was a significant deviation from random expectations for the occurrence of failures across loci, thus indicating a locus-dependent effect on whole genome coverage.

Sequence Independent PCR™

Another approach using degenerate primers is described by Bohlander et al., (1992), called sequence-independent DNA amplification (SIA). In contrast to DOP-PCR™, SIA incorporates a nested DOP-primer system. The first primer (5'-TGGTAGCTCTTGATCANNNNN-3' (SEQ ID NO:7); consisted of a five base random 3'-segment and a specific 16 base segment at the 5' end containing a restriction enzyme site. Stage one of PCR™ starts with 97° C. for denaturation, followed by cooling down to 4° C., causing primers to anneal to multiple random sites, and then heating to 37° C. A T7 DNA polymerase is used. In the second low-temperature cycle, primers anneal to products of the first round. In the second stage of PCR™, a primer (5'-AGAGTTGG-TAGCTCTTGATC-3' (SEQ ID NO:8); is used that contains, at the 3' end, 15 5'-end bases of primer A. Five cycles are performed with this primer at an intermediate annealing temperature of 42° C. An additional 33 cycles are performed at a specific annealing temperature of 56° C. Products of SIA range from 200 bp to 800 bp.

Primer-Extension Preamplification

Primer-extension preamplification (PEP) is a method that uses totally degenerate primers to achieve universal amplification of the genome (Zhang et al., 1992). PEP uses a random mixture of 15-base fully degenerated oligonucleotides as primers, thus any one of the four possible bases could be present at each position. Theoretically, the primer is composed of a mixture of $4\times10^9$ different oligonucleotide sequences. This leads to amplification of DNA sequences from randomly distributed sites. In each of the 50 cycles, the template is first denatured at 92° C. Subsequently, primers are allowed to anneal at a low temperature (37° C.), which is then continuously increased to 55° C. and held for another four minutes for polymerase extension.

A method of improved PEP (I-PEP) was developed to enhance the efficiency of PEP, primarily for the investigation of tumors from tissue sections used in routine pathology to reliably perform multiple microsatellite and sequencing studies with a single or few cells (Dietmaier et al., 1999). I-PEP differs from PEP (Zhang et al., 1992) in cell lysis approaches, improved thermal cycle conditions, and the addition of a higher fidelity polymerase. Specifically, cell lysis is performed in EL buffer, Taq polymerase is mixed with proofreading Pwo polymerase, and an additional elongation step at 68° C. for 30 seconds before the denaturation step at 94° C. was added. This method was more efficient than PEP and DOP-PCR™ in amplification of DNA from one cell and five cells.

Both DOP-PCR™ and PEP have been used successfully as precursors to a variety of genetic tests and assays. These techniques are integral to the fields of forensics and genetic disease diagnosis where DNA quantities are limited. However, neither technique claims to replicate DNA in its entirety (Cheung and Nelson, 1996) or provide complete coverage of particular loci (Paunio et al., 1996). These techniques produce an amplified source for genotyping or marker identification. The products produced by these methods are consistently short (<3 kb) and as such cannot be used in many applications (Telenius et al., 1992). Moreover, numerous tests are required to investigate a few markers or loci.

Tagged PCR™

Tagged PCR™ (T-PCR™) was developed to increase the amplification efficiency of PEP in order to amplify efficiently from small quantities of DNA samples with sizes ranging from 400 bp to 1.6 kb (Grothues et al., 1993). T-PCR™ is a two-step strategy, which uses, for the first few low-stringent cycles, a primer with a constant 17 base pair at the 5' end and a tagged random primer containing 9 to 15 random bases at the 3' end. In the first PCR™ step, the tagged random primer is used to generate products with tagged primer sequences at both ends, which is achieved by using a low annealing temperature. The unincorporated primers are then removed and amplification is carried out with a second primer containing only the constant 5' sequence of the first primer under high-stringency conditions to allow exponential amplification. This method is more labor intensive than other methods due to the requirement for removal of unincorporated degenerate primers, which also can cause the loss of sample material. This is critical when working with subnanogram quantities of DNA template. The unavoidable loss of template during the purification steps could affect the coverage of T-PCR™. Moreover, tagged primers with 12 or more random bases could generate non-specific products resulting from primer-primer extensions or less efficient elimination of these longer primers during the filtration step.

Tagged Random Hexamer Amplification

Based on problems related to T-PCR™, tagged random hexamer amplification (TRHA) was developed on the premise that it would be advantageous to use a tagged random primer with shorter random bases (Wong et al., 1996). In TRHA, the first step is to produce a size distributed population of DNA molecules from a pNL1 plasmid. This was done via a random synthesis reaction using Klenow fragment and random hexamer tagged with T7 primer at the 5'-end (T7-$dN_6$, 5'-GTAATACGACTCACTATAGGGCNNNNNN-3' (SEQ ID NO:9). Klenow-synthesized molecules (size range 28 bp-<23 kb) were then amplified with T7 primer (5'-GTAATACGACTCACTATAGGGC-3' (SEQ ID NO:10). Examination of bias indicated that only 76% of the original DNA template was preferentially amplified and represented in the TRHA products.

Strand Displacement

The isothermal technique of rolling circle amplification (RCA) has been developed for amplifying large circular DNA templates such as plasmid and bacteriophage DNA (Dean et al., 2001). Using φ29 DNA polymerase, which synthesizes DNA strands 70 kb in length using random exonuclease-resistant hexamer primers, DNA was amplified in a 30° C. isothermal reaction. Secondary priming events occur on the displaced product DNA strands, resulting in amplification via strand displacement.

In this technique, two sets of primers are used. The right set of primers each have a portion complementary to nucleotide sequences flanking one side of a target nucleotide sequence, and primers in the left set of primers each have a portion complementary to nucleotide sequences flanking the other side of the target nucleotide sequence. The primers in the right set are complementary to one strand of the nucleic acid molecule containing the target nucleotide sequence, and the primers in the left set are complementary to the opposite strand. The 5' end of primers in both sets is distal to the nucleic acid sequence of interest when the primers are hybridized to the flanking sequences in the nucleic acid molecule. Ideally, each member of each set has a portion complementary to a separate and non-overlapping nucleotide sequence flanking the target nucleotide sequence. Amplification proceeds by replication initiated at each primer and continuing through the target nucleic acid sequence. A key feature of this method is the displacement of intervening primers during replication. Once the nucleic acid strands elongated from the right set of primers reaches the region of the nucleic acid molecule to which the left set of primers hybridizes, and vice versa, another round of priming and replication commences. This allows multiples copies of a nested set of the target nucleic acid sequence to be synthesized.

Multiple Displacement Amplification

The principles of RCA have been extended to WGA in a technique called multiple displacement amplification (MDA) (Dean et al., 2002; U.S. Pat. No. 6,280,949 B1). In this technique, a random set of primers is used to prime a sample of genomic DNA. By selecting a sufficiently large set of primers of random or partially random sequence, the primers in the set will be collectively, and randomly, complementary to nucleic acid sequences distributed throughout nucleic acids in the sample. Amplification proceeds by replication with a highly possessive polymerase, φ29 DNA polymerase, initiating at each primer and continuing until spontaneous termination. Displacement of intervening primers during replication by the polymerase allows multiple overlapping copies of the entire genome to be synthesized.

The use of random primers to universally amplify genomic DNA is based on the assumption that random primers equally prime over the entire genome, thus allowing representative amplification. Although the primers themselves are random, the location of primer hybridization in the genome is not random, as different primers have unique sequences and thus different characteristics (such as different melting temperatures). As random primers do not equally prime everywhere over the entire genome, amplification is not completely representative of the starting material. Such protocols are useful in studying specific loci, but the result of random-primed amplification products is not representative of the starting material (e.g., the entire genome).

Cell Immortalization

Normal human somatic cells have a limited life span and enter senescence after a limited number of cell divisions (Hayflick and Moorhead, 1961; Hayflick 1965; Martin et al., 1970). At senescence, cells are viable but no longer divide. This limit on cell proliferation represents an obstacle to the study of normal human cells, especially since many rounds of cell division are used, as cells are shared between laboratories or to produce large quantities of cells required for biochemical analysis, for genetic manipulations, or for genetic screens. This limitation is of particular concern for the study of rare hereditary human diseases, since the volume of the biological samples collected (biopsies or blood) is usually small and contains a limited number of cells.

The establishment of permanent cell lines is one way to circumvent this lack of critical material. Some tumor cells yield cultures with unlimited growth potential, and in vitro transformation with oncogenes or carcinogens have proven a successful means to establish permanent fibroblast and lymphoblast cell lines. Such cell lines have been valuable in the analysis of mammalian biochemistry and the identification of disease-related genes. However, such transformed cells typically exhibit significant alterations in physiological and biological properties. Most notably, these cells are associated with aneuploidy, spontaneous hypermutability, loss of contact inhibition and alterations in biochemical functions related to cell cycle checkpoints. These cellular properties that differ from their normal counterparts pose significant limitations to the analysis of many cellular functions, in particular those related to genomic integrity and the study of the human chromosome instability syndromes.

Recent advances have shown the onset of replicative senescence to be controlled by the shortening of the telomeres that occurs each time normal human cells divide (Allsopp et al., 1992; Allsopp et al., 1995; Bodnar et al., 1998; Vaziri and Benchimol, 1998). This loss of telomeric DNA is a consequence of the inability of DNA polymerase alpha to fully replicate the ends of linear DNA molecules (Watson, 1972; Olovnikov, 1973). It has been proposed that senescence is induced when the shortest one or two telomeres can no longer be protected by telomere-binding proteins, and thus is recognized as a double-stranded (ds) DNA break. In cells with functional checkpoints, the introduction of dsDNA breaks leads to the activation of p53 and of the p16/pRB checkpoint and to a growth arrest state that mimics senescence (Vaziri and Benchimol, 1996; Di Leonardo et al., 1994; Robles and Adami, 1998). Cell cycle progression in senescent cells is also blocked by the same two mechanisms (Bond et al., 1996; Hara et al., 1996; Shay et al., 1991). This block can be overcome by viral oncogenes, such as SV40 large T antigen, that can inactivate both p53 and pRB. Cells that express SV40 large T antigen escape senescence but continue to lose telomeric repeats during their extended life span. These cells are not yet immortal, and terminal telomere shortening eventually causes the cells to reach a second non-proliferative stage termed 'crisis' (Counter et al., 1992; Wright and Shay; 1992). Escape from crisis is a very rare event (1 in $10^7$) usually accompanied by the reactivation of telomerase (Shay et al., 1993).

Telomerase is a specialized cellular reverse transcriptase that can compensate for the erosion of telomeres by synthesizing new telomeric DNA. The activity of telomerase is present in certain germline cells but is repressed during development in most somatic tissues, with the exception of proliferative descendants of stem cells such as those in the skin, intestine and blood (Ulaner and Giudice, 1997; Wright et al., 1996; Yui et al., 1998; Ramirez et al., 1997; Hiyama et al., 1996). The enzyme telomerase is a ribonuclear protein composed of at least two subunits; an integral RNA, that serves as a template for the synthesis of telomeric repeats (hTR), and a protein (hTERT), that has reverse transcriptase activity. The RNA component (hTR) is ubiquitous in human cells, but the presence of the mRNA encoding hTERT is restricted to the cells with telomerase activity. The forced expression of exogenous hTERT in normal human cells is sufficient to produce telomerase activity in these cells and prevent the erosion of telomeres and circumvent the induction of both senescence and crisis (Bodnar et al., 1998; Vaziri and Benchimol, 1998). Recent studies have shown that telomerase can immortalize a variety of cell types. Cells immortalized with hTERT have normal cell cycle controls, functional p53 and pRB checkpoints, are contact inhibited, are anchorage dependent, require growth factors for proliferation, and possess a normal karyotype (Morales et al., 1999; Jiang et al., 1999).

Thus, the related art provides a variety of techniques for whole genome amplification, although there remains a need in the art for methods and compositions amenable to non-biased highthroughput library generation and/or preparation of DNA molecules. For example, Japan Patent No. JP8173164A2 describes a method of preparing DNA by sorting-out PCR™ amplification in the absence of cloning, fragmenting a double-stranded DNA, ligating a known-sequence oligomer to the cut end, and amplifying the resultant DNA fragment with a primer having the sorting-out sequence complementary to the oligomer. The sorting-out sequences consist of a fluorescent label and one to four bases at the 5' and 3' termini to amplify the number of copies of the DNA fragment.

U.S. Pat. No. 6,107,023 describes a method of isolating duplex DNA fragments which are unique to one of two fragment mixtures, i.e., fragments which are present in a mixture of duplex DNA fragments derived from a positive source, but absent from a fragment mixture derived from a negative source. In practicing the method, double-strand linkers are attached to each of the fragment mixtures, and the number of fragments in each mixture is amplified by successively repeating the steps of (i) denaturing the fragments to produce single fragment strands; (ii) hybridizing the single strands with a primer whose sequence is complementary to the linker region at one end of each strand, to form strand/primer complexes; and (iii) converting the strand/primer complexes to double-stranded fragments in the presence of polymerase and deoxynucleotides. After the desired fragment amplification is achieved, the two fragment mixtures are denatured, then hybridized under conditions in which the linker regions associated with the two mixtures do not hybridize. DNA species unique to the positive-source mixture, i.e., which are not hybridized with DNA fragment strands from the negative-source mixture, are then selectively isolated.

Patent WO/016545 A1 details a method for amplifying DNA or RNA using a single primer for use as a fingerprinting method. This protocol was designed for the analysis of microbial, bacterial and other complex genomes that are present within samples obtained from organisms containing even more complex genomes, such as animals and plants. The advantage of this procedure for amplifying targeted regions is the structure and sequence of the primer. Specifically, the primer is designed to have very high cytosine and very low guanine content, resulting in a high melting temperature. Furthermore, the primer is designed in such a way as to have a negligible ability to form secondary structure. This results in limited production of primer-dimer artifacts and improves amplification of regions of interest, without a priori knowledge of these regions. In contrast to the current invention, this method is only able to prime a subset of regions within a genome, due to the utilization of a single priming sequence. Furthermore, the structure of the primer contains only a constant priming region, as opposed to a constant amplification region and a variable priming region in the present invention. Thus, a single primer consisting of non-degenerate sequence results in priming of a limited number of areas within the genome, preventing amplification of the whole-genome.

U.S. Pat. No. 6,114,149 regards a method of amplifying a mixture of different-sequence DNA fragments that may be formed from RNA transcription, or derived from genomic single- or double-stranded DNA fragments. The fragments are treated with terminal deoxynucleotide transferase and a selected deoxynucleotide to form a homopolymer tail at the 3' end of the anti-sense strands, and the sense strands are provided with a common 3'-end sequence. The fragments are mixed with a homopolymer primer that is homologous to the homopolymer tail of the anti-sense strands, and a defined-sequence primer which is homologous to the sense-strand common 3'-end sequence, with repeated cycles of fragment denaturation, annealing, and polymerization, to amplify the fragments. In one embodiment, the defined-sequence and homopolymer primers are the same, i.e., only one primer is used. The primers may contain selected restriction-site sequences to provide directional restriction sites at the ends of the amplified fragments.

U.S. Pat. Nos. 6,124,120 and 6,280,949 describe compositions and a method for amplification of nucleic acid sequences based on multiple strand displacement amplification (MSDA). Amplification takes place not in cycles, but in a continuous, isothermal replication. Two sets of primers are used, a right set and a left set complementary to nucleotide sequences flanking the target nucleotide sequence. Amplification proceeds by replication initiated at each primer and continuation through the target nucleic acid sequence through displacement of intervening primers during replication. This allows multiple copies of a nested set of the target nucleic acid sequence to be synthesized in a short period of time. In another form of the method, referred to as whole genome strand displacement amplification (WGSDA), a random set of primers is used to randomly prime a sample of genomic nucleic acid. In an alternative embodiment, referred to as multiple strand displacement amplification of concatenated DNA (MSDA-CD), fragments of DNA are first concatenated together with linkers. The concatenated DNA is then amplified by strand displacement synthesis with appropriate primers. A random set of primers can be used to randomly prime synthesis of the DNA concatemers in a manner similar to whole genome amplification. Primers complementary to linker sequences can be used to amplify the concatemers. Synthesis proceeds from the linkers through a section of the concatenated DNA to the next linker, and continues beyond. As the linker regions are replicated, new priming sites for DNA synthesis are created. In this way, multiple overlapping copies of the entire concatenated DNA sample can be synthesized in a short time.

U.S. Pat. No. 6,365,375 describes a method for primer extension pre-amplification of DNA with completely random primers in a pre-amplification reaction, and locus-specific primers in a second amplification reaction using two thermostable DNA polymerases, one of which possesses 3'-5' exonuclease activity. Pre-amplification is performed by 20 to 60 thermal cycles. The method uses a slow transition between the annealing phase and the elongation phase. Two elongation steps are performed: one at a lower temperature and a second at a higher temperature. Using this approach, populations of especially long amplicons are claimed. The specific primers used in the second amplification reaction are identical to a sequence of the target nucleic acid or its complementary sequence. Specific primers used to carry out a nested PCR in a potential third amplification reaction are selected according to the same criteria as the primers used in the second amplification reaction. A claimed advantage of the method is its improved sensitivity to the level of a few cells and increased fidelity of the amplification due to the presence of proofreading 3'-5' exonuclease activity, as compared to methods using only one thermostable DNA polymerase, i.e. Taq polymerase.

Bohlander et al. (1992) have developed a method by which microdissected material can be amplified in two initial rounds of DNA synthesis with T7 DNA polymerase using a primer that contains a random five base sequence at its 3' end and a defined sequence at its 5' end. The pre-amplified material is then further amplified by PCR using a second primer equivalent to the constant 5' sequence of the first primer.

Using modification of Bohlander's procedure and DOP-PCR, Guan et al. (1993) were able to increase sensitivity of amplification of microdissected chromosomes using DOP-PCR primers in a cycling pre-amplification reaction with Sequenase version 2 (replenished after each denaturing step by fresh enzyme) followed by PCR amplification with Taq polymerase.

Another modification of the original Bohlander's method has been published in a collection of protocols for DNA preparation in microarray analysis on the World Wide Web by the Department of Biochemistry and Biophysics at the University of California at San Francisco. This protocol has been used to amplify genomic representations of less than 1 ng of DNA. The protocol consists of three sets of enzymatic reactions. In Round A, Sequenase is used to extend primers containing a completely random sequence at its 3' end and a defined sequence at its 5' end to generate templates for subsequent PCR. During Round B, the specific primer B is used to amplify the templates previously generated. Finally, Round C consists of additional PCR cycles to incorporate either amino allyl dUTP or cyanine modified nucleotides.

Zheleznaya et al. (1999) developed a method to prepare random DNA fragments in which two cycles are performed with Klenow fragment of DNA polymerase I and primers with random 3'-sequences and a 5'-constant part containing a restriction site. After the first cycle, the DNA is denatured and new Klenow fragment is added. Routine PCR amplification is then performed utilizing the constant primer.

In contrast to other methods in the art, the present invention provides a variety of new ways of preparing DNA templates, particularly for whole genome amplification, and preferentially in a manner representative of a native genome.

RNA Expression Analysis

The expression of genes and regulatory transcripts encoded within DNA is the primary mechanism regulating cellular metabolism. Transcription and the post-transcriptional processing of RNA sets the framework for all phases of cellular function. For proteins that control essential cellular functions, such as replication and differentiation, the levels of RNA expression and protein synthesis are tightly correlated. Changes within the environment of a cell or tissue often result in necessary alterations in cellular functions. For example, a cell may alter the pattern of gene expression in response to environmental factors, such as ligand and metabolite stimulated signaling. Furthermore, cellular expression of RNA and proteins may be altered intentionally as with the use of some therapeutic drugs. These changes in gene expression may be due to both the beneficial and the toxic effects of these drugs. Alterations in gene expression in both the normal or diseased state can be utilized for determining the efficacy and mechanisms of action of potential treatments. In the case of oncogenic transformation, cells may exhibit subtle changes in expression during cancer progression. Changes in gene expression of key proteins involved in cellular transformation have the potential to be used as predictive markers of oncogenesis. The sequencing and mapping of the human genome has resulted in a database of potentially expressed genes. Several tools, including high-density micro-arrays have been developed to measure the expression of each of these genes, including potential splice variants.

Transcribed genes at any given moment in the life of a cell or tissue represent the regulatory and protein-coding responses involved in cellular function. In some embodiments, the present invention relates to the unbiased amplification of sequences representative of the RNA profile. High fidelity amplification of expressed genes from localized tissues, small groups of cells, or a single cell, will allow the analysis of subtle alterations in gene expression. The need to profile a wide range of potentially expressed RNA molecules from limited sample material requires an amplification method that maintains the representation of the starting material. The invention described herein provides a method to produce a large amount of cDNA from amounts of RNA typically recovered in clinical and diagnostic applications that are not sufficient for direct processing. Whole transcriptome amplification has a relatively brief history with methods based primarily on quasi-linear amplification and exponential amplification.

Both transcription based and PCR based methods for amplification of RNA sequences rely on the activity of RNA dependent DNA polymerases such as the various reverse transcriptases of viral origin. It can be argued that regardless of the priming and amplification strategy, sequence specific bias for reverse transcription is unavoidable. This source of bias is addressed in gene profiling experiments by drawing comparisons between similarly amplified control and test samples.

Linear transcription based and single primer amplification (SPA) based methods require an initial reverse transcription step using either random or poly-T priming. To facilitate amplification of the resulting cDNA, primers utilized for reverse transcription may contain a non-complementary tail introducing a specific universal sequence. In the case of in vitro transcription (IVT) based amplification methods, specific binding and initiation sites are introduced as 5' oligo extensions corresponding to one of the phage RNA polymerase priming and recognition sites (Phillips and Eberwine, 1996; US005514545A). RNA/DNA duplexes resulting from reverse transcription or first strand cDNA synthesis serve as the template for second strand cDNA synthesis after degradation of the RNA strand by RNase H. Second strand cDNA products may be primed randomly or terminally to incorporate the RNA polymerase recognition sites in the tailed primers, thereby generating substrate for linear amplification. Various modifications to the protocol include second strand priming utilizing terminal transferase to extend first strand cDNA products to introduce short stretches of guanine (Wang and Chung; US005932451A), and utilizing the native terminal transferase activity of Moloney murine leukemia virus reverse transcriptase, which has the propensity to add three to five cytosine ribonucleotides to the 3' terminus of extension products. This activity has been used for second strand priming by Ginsberg and Che (US20030186237A1), and in the "SMART" adaptation (Clontech), wherein a strand-switching adapter is employed, having a series of guanine residues at its 3' end which can prime the extended poly-C tail (Schmidt et al., 1999).

An alternative to linear amplification by RNA polymerase is "Single Primer Amplification" (SPA), whereby the initial reverse transcriptase incorporated primer sequence designates the binding site for primer annealing in sequential rounds of primer extension with Taq polymerase (Smith et al., 2003). In a specialized version of SPA the reaction is carried out under isothermal conditions whereby the primer consists partially of DNA and partially of RNA. In the presence of stand displacing polymerase activity and RNase H activity, each primer extension product generates substrate for RNase H within the 5' RNA component of the primer. Cleavage of the extension products generates successive priming sites, and the reaction cycles in a linear strand displacement isothermal mode. (NuGEN Technologies Inc.; WO 02/72772; US2003/0017591 A1; US2003/0017591 A1). Sequential rounds of transcription and reverse transcription are capable of producing as much as a million fold amplification.

PCR based amplification of RNA involves the same initial steps of reverse transcription and second strand synthesis. While those familiar with the art will appreciate the potential to introduce bias upon exponential amplification, several methods have demonstrated the amplified products to have minimal distortion and be highly representative of the original RNA transcripts. The standard method employs double stranded cDNA generated by classical first and second strand synthesis. Briefly, reverse transcriptase initiates from oligo dT and random primers to promote first strand synthesis followed by a cocktail of DNA polymerase I, RNase H and DNA ligase for second strand synthesis and repair. Universal adaptors, containing a known sequence, can then be ligated to the double strand cDNA molecules for subsequent amplification. This process can be substantially improved by avoiding the requirement for ligation mediated adapter ligation through the use of a reverse transcriptase non-template directed addition of cytosine residues. A universal sequence is subsequently introduced as a primer for strand switching mediated second strand cDNA synthesis (Schmidt et al., 1999).

Further improvements aimed at neutralizing bias introduced between samples have been demonstrated using modified primers that contain both universal and unique priming sites. Makrigiorgos et al. (2002) demonstrated the utility of "balanced PCR" using a bipartite primer construction to co-amplify multiple samples that share a common distal primer sequence. The mixture of samples can be co-amplified, minimizing effects of any impurities or other factors affecting the amplification. The pooled samples are subsequently separated based on the individual sequence tags, from their respective proximal primer sequence, in either a secondary low cycle amplification or a primer extension labeling reaction.

Although exponential amplification has the reputation of degrading the relative abundance relationships between transcripts, much of the bias can be attributed to the various steps required in generating the amplimers. The specific sequence of any given transcript may affect the efficiency of reverse transcription, and these effects may be exaggerated as the length of the transcript increases. Methods employing combinations of IVT-based and PCR-based amplification provide both a sensitive and a specific approach, although they retain an intermediate stepwise synthesis of first and second strand cDNA (Rosetta Inpharmatics, Inc. US006271002B1; Roche Diagnostics Co. US20030113754A1).

The present invention minimizes the introduction of bias by capturing transcripts, in a single step, in the form of amplimers with a uniform size distribution. WTA products are synthesized independent of the integrity of the RNA molecule, the ability to complete reverse transcription of the entire RNA molecule, the requirement for template switching during second strand synthesis, and the ligation of adapters. Subsequent amplification of the products using a universal non-self-complementary primer results in unbiased representation suitable for all applications, such as downstream expression studies.

SUMMARY OF THE INVENTION

The present invention regards the amplification of a whole genome, or whole transcriptome, including various methods and compositions to achieve that goal. In specific embodiments, a whole genome is amplified from a single cell, whereas in another embodiment the whole genome is amplified from a plurality of cells. In specific embodiments the whole transcriptome is amplified from poly A+ RNA, or in another embodiment the whole transcriptome is amplified from total RNA.

In a particular aspect of the present invention, the invention is directed to methods for the amplification of substantially the entire genome or entire transcriptome without loss of representation of specific sites (herein defined as "whole genome amplification" and "whole transcriptome amplification", respectively). In a specific embodiment, whole genome amplification comprises simultaneous amplification of substantially all fragments of a genomic library. In a further specific embodiment, "substantially entire" or "substantially all" refers to about 80%, about 85%, about 90%, about 95%, about 97%, or about 99% of all sequence in a genome. A skilled artisan recognizes that amplification of the whole genome will, in some embodiments, comprise non-equivalent amplification of particular sequences over others, although the relative difference in such amplification is not considerable.

In specific embodiments, the present invention regards immortalization of DNA following generation of a library comprising a representative amplifiable copy of the template DNA. The library generation step utilizes special self-inert degenerate primers designed to eliminate their ability to form primer-dimers and a polymerase comprising strand-displacement activity.

In one particular aspect of the present invention, there is a method for uniform amplification of DNA or RNA using self-inert degenerate primers comprised essentially of non-self-complementary nucleotides. In specific embodiments, the degenerate oligonucleotides do not participate in Watson-Crick base-pairing with one another. This lack of primer complementarity overcomes major problems known in the art associated with DNA amplification by random primers, such as excessive primer-dimer formation, complete or sporadic locus dropout, generation of very short amplification products, and in some cases the inability to amplify single stranded, short, or fragmented DNA and RNA molecules.

In specific embodiments, the invention provides a two-step procedure that can be performed in a single tube or in a micro-titer plate, for example, in a high throughput format. The first step (termed the "library synthesis step") involves incorporation of known sequence at both ends of amplicons using highly degenerate primers and at least one enzyme possessing strand-displacement activity. The resulting branching process creates molecules having self-complementary ends. The resulting library of molecules are then amplified in a second step by PCR™ using, for example, Taq polymerase and a primer corresponding to the known sequence, resulting in several thousand-fold amplification of the entire genome or transcriptome without significant bias. The products of this amplification can be re-amplified additional times, resulting in amplification that exceeds, for example, several million fold.

Thus, in one particular aspect of the present invention, there is a method of preparing a nucleic acid molecule, comprising obtaining at least one single stranded nucleic acid molecule; subjecting said single stranded nucleic acid molecule to a plurality of primers to form a single stranded nucleic acid molecule/primer mixture, wherein the primers comprise nucleic acid sequence that is substantially non-self-complementary and substantially non-complementary to other primers in the plurality, wherein said sequence comprises in a 5' to 3' orientation a constant region and a variable region; and subjecting said single stranded nucleic acid molecule/primer mixture to a strand-displacing polymerase, under conditions wherein said subjecting steps generate a plurality of molecules including all or part of the known nucleic acid sequence at each end. In a specific aspect, the method is further defined as comprising: (1) a first series of polymerase chain reaction steps comprising subjecting the nucleic acid molecule/primer mixture to a thermostable polymerase in the presence of the primers; and (2) a second series of polymerase chain reaction steps using primers that comprise the constant region and under temperatures no less than about 60° C. (wherein about 60° C. may include 57° C., 58° C., or 59° C.

The method may further comprise the step of designing the primers such that they purposefully are substantially non-self-complementary and substantially noncomplementary to other primers in the plurality. The method may also further comprise the step of amplifying a plurality of the molecules comprising the known nucleic acid sequence to produce amplified molecules. Such amplification may comprise polymerase chain reaction, such as that utilizes a primer complementary to the known nucleic acid sequence.

The primers may comprise a constant region and a variable region, both of which include nucleic acid sequence that is substantially non-self-complementary and substantially non-complementary to other primers in the plurality. In specific embodiments, the constant region and variable region for a particular primer are comprised of the same two nucleotides, although the sequence of the two regions are usually different. The constant region is preferably known and may be a targeted sequence for a primer in amplification methods. The variable region may or may not be known, but in preferred embodiments is known. The variable region may be randomly selected or may be purposefully selected commensurate with the frequency of its representation in a source DNA, such as genomic DNA. In specific embodiments, the nucleotides of the variable region will prime at target sites in a source DNA, such as a genomic DNA, containing the corresponding Watson-Crick base partners. In a particular embodiment, the variable region is considered degenerate.

The single stranded nucleic acid molecule may be DNA, in some embodiments, and in alternative embodiments the single stranded nucleic acid molecule is RNA or a DNA-RNA chimera.

In other aspects of the invention, a tag is incorporated on the ends of the amplified molecules, preferably wherein the known sequence is penultimate to the tags on each end of the amplified molecules. The tag may be a homopolymeric sequence, in specific embodiments, such as a purine. The homopolymeric sequence may be single stranded, such as a single stranded poly G or poly C. Also, the homopolymeric sequence may refer to a region of double stranded DNA wherein one strand of homopolymeric sequence comprises all of the same nucleotide, such as poly C, and the opposite strand of the double stranded region complementary thereto comprises the appropriate poly G.

The incorporation of the homopolymeric sequence may occur in a variety of ways known in the art. For example, the incorporation may comprise terminal deoxynucleotidyl transferase activity, wherein a homopolymeric tail is added via the terminal deoxynucleotidyl transferase enzyme. Other enzymes having analogous activities may be utilized, also. The incorporation of the homopolymeric sequence may comprise ligation of an adaptor comprising the homopolymeric sequence to the ends of the amplified molecules. An additional example of incorporation of the homopolymeric sequence employs replicating the amplified molecules with DNA polymerase by utilizing a primer comprising in a 5' to 3' orientation, the homopolymeric sequence, and the known sequence.

In additional embodiments of the present invention, the amplified molecules comprising the homopolymeric sequence are further amplified using a primer complementary to a known sequence and a primer complementary to the homopolymeric sequence. The present inventors have demonstrated that when the molecules comprise a guanine homopolymeric sequence, for example, surprisingly, the amplification of molecules with just the homo-cytosine primer is suppressed in favor of amplification of molecules with the primer complementary to a specific sequence (such as the known sequence) and the homo-cytosine primer. These embodiments may be utilized, for example, in the scenario wherein a small amount of DNA is available for processing, and it is converted into a library, amplified using universal primer, and then re-amplified or replicated with a new universal primer that has the same universal sequence at the 3' end plus a homopolymeric (such as poly C) stretch at the 5' end. This may then be used as an unlimited resource for targeted amplification/sequencing, for example, in specific embodiments.

In specific embodiments of the present invention, the obtaining step may be further defined as comprising the steps of obtaining at least one double stranded DNA molecule and subjecting the double stranded DNA molecule to heat to produce at least one single stranded DNA molecule.

Nucleic acids processed by methods described herein may be DNA, RNA, or DNA-RNA chimeras, and they may be obtained from any useful source, such as, for example, a human sample. In specific embodiments, a double stranded DNA molecule is further defined as comprising a genome, such as, for example, one obtained from a sample from a human. The sample may be any sample from a human, such as blood, serum, plasma, cerebrospinal fluid, cheek scrapings, nipple aspirate, biopsy, semen (which may be referred to as ejaculate), urine, feces, hair follicle, saliva, sweat, immunoprecipitated or physically isolated chromatin, and so forth. In specific embodiments, the sample comprises a single cell.

In particular embodiments of the present invention, the prepared nucleic acid molecule from the sample provides diagnostic or prognostic information. For example, the prepared nucleic acid molecule from the sample may provide genomic copy number and/or sequence information, allelic variation information, cancer diagnosis, prenatal diagnosis, paternity information, disease diagnosis, detection, monitoring, and/or treatment information, sequence information, and so forth.

In particular aspects of the present invention, the primers are further defined as having a constant first and variable second regions each comprised of two non-complementary nucleotides. The first and second regions may be each comprised of guanines, adenines, or both; of cytosines, thymidines, or both; of adenines, cytosines, or both; or of guanines, thymidines, or both. The first region may comprise about 6 to about 100 nucleotides. The second region may comprise about 4 nucleotides to about 20 nucleotides. The polynucleotide (primer) may be further comprised of 0 to about 3 random bases at its distal 3' end. In particular embodiments, the nucleotides are base or backbone analogs.

In particular embodiments, the first region and the second region are each comprised of guanines and thymidines and the polynucleotide (primer) comprises about 1, 2, or 3 random bases at its 3' end, although it may comprise 0 random bases at its 3' end.

The known nucleic acid sequence may be used for subsequent amplification, such as with polymerase chain reaction.

In some embodiments, methods of the present invention utilize a strand-displacing polymerase, such as Φ29 Polymerase, Bst Polymerase, Vent Polymerase, 9° Nm Polymerase, Klenow fragment of DNA Polymerase I, MMLV Reverse Transcriptase, AMV reverse transcriptase, HIV reverse transcriptase, a mutant form of T7 phage DNA polymerase that lacks 3'-5' exonuclease activity, or a mixture thereof. In a specific embodiment, the strand-displacing polymerase is Klenow or is the mutant form of T7 phage DNA polymerase that lacks 3'-->5' exonuclease activity.

Methods utilized herein may further comprise subjecting single stranded nucleic acid molecule/primer mixtures to a polymerase-processivity enhancing compound, such as, for example, single-stranded DNA binding protein or helicase.

In some embodiments of the present invention, there is a method of amplifying at least one RNA molecule, comprising obtaining an RNA molecule; subjecting the RNA molecule to a plurality of primers to form a RNA molecule/primer mixture, wherein the primers comprise nucleic acid sequence that is substantially non-self-complementary and substantially non-complementary to other primers in the plurality, wherein the sequence comprises in a 5' to 3' orientation a constant region and a variable region; subjecting the RNA molecule/primer mixture to a polymerase, under conditions wherein the subjecting steps generate a plurality of DNA molecules comprising the constant region at each end; and amplifying a plurality of the DNA molecules through polymerase chain reaction, said reaction utilizing a primer complementary to the constant region.

The RNA molecule may be obtained from a sample, such as a sample comprising total cellular RNA, a transcriptome, or both; the sample may be obtained from one or more viruses; from one or more bacteria; or from a mixture of animal cells, bacteria, and/or viruses, for example. The sample may comprise mRNA, such as mRNA that is obtained by affinity capture In another aspect of the present invention, there is a method of amplifying a genome, transcriptome, or both comprising obtaining genomic DNA, RNA (such as mRNA) or both; modifying the genomic DNA, RNA, or both to generate at least one single stranded nucleic acid molecule; subjecting said single stranded nucleic acid molecule to a plurality of primers to form a nucleic acid/primer mixture, wherein the primers comprise nucleic acid sequence that is substantially non-self-complementary and substantially non-complementary to other primers in the plurality, wherein said sequence comprises in a 5' to 3' orientation a constant region and a variable region; subjecting said nucleic acid/primer mixture to a strand-displacing polymerase, under conditions wherein said subjecting steps generate a plurality of DNA molecules comprising the constant region at each end; and amplifying a plurality of the DNA molecules through polymerase chain reaction, said reaction utilizing a primer complementary to the constant nucleic acid sequence.

The method may further comprise the steps of modifying double stranded DNA molecules to produce single stranded molecules, said single stranded molecules comprising the known nucleic acid sequence at both the 5' and 3' ends; hybridizing a region of at least one of the single stranded DNA molecules to a complementary region in the 3' end of an oligonucleotide immobilized to a support to produce a single stranded DNA/oligonucleotide hybrid; and extending the 3' end of the oligonucleotide to produce an extended polynucleotide. In specific embodiments, the method further comprises the step of removing the single stranded DNA molecule from the single stranded DNA/oligonucleotide hybrid.

In one aspect of the invention, there is a method of obtaining a total nucleic acid from a sample comprising a mixture of DNA and RNA, comprising providing the mixture of DNA and RNA; optionally heating the mixture to a temperature that denatures double stranded nucleic acids; and subjecting the mixture to a polymerase that replicates both single stranded DNA and RNA. In some embodiments, the method consists essentially of said providing, optionally heating, and subjecting steps. The subjecting step may be further defined as subjecting the mixture to a plurality of primers to form a nucleic acid/primer mixture, wherein the primers comprise nucleic acid sequence that is substantially non-self-complementary and substantially non-complementary to other primers in the plurality, wherein said sequence comprises in a 5' to 3' orientation a constant region and a variable region; subjecting said nucleic acid/primer mixture to the polymerase that efficiently replicates both DNA and RNA, under conditions wherein said subjecting steps generate a plurality of DNA molecules comprising the constant nucleic acid sequence at each end; and amplifying a plurality of the DNA molecules comprising the constant region at each end through polymerase chain reaction, said reaction utilizing a primer complementary to the constant region.

In another aspect of the present invention, there is a method of amplifying a total transcriptome, comprising obtaining total RNA; subjecting said RNA molecule to a plurality of primers to form an RNA/primer mixture, wherein the primers comprise nucleic acid sequence that is substantially non-self-complementary and substantially non-complementary to other primers in the plurality, wherein said sequence comprises in a 5' to 3' orientation a constant region and a variable region; subjecting said RNA/primer mixture to a reverse transcriptase, under conditions wherein said subjecting steps generate a plurality of DNA molecules comprising the constant region at each end; and amplifying a plurality of the DNA molecules through polymerase chain reaction, said reaction utilizing a primer complementary to the known nucleic acid sequence.

In another aspect of the present invention, there is a method of amplifying a protein-coding transcriptome, comprising obtaining mRNA; subjecting the mRNA molecule to a plurality of primers to form an mRNA/primer mixture, wherein the primers comprise nucleic acid sequence that is substantially non-self-complementary and substantially non-complementary to other primers in the plurality, wherein said sequence comprises in a 5' to 3' orientation a constant region and a variable region; subjecting said mRNA/primer mixture to a reverse transcriptase, under conditions wherein said subjecting steps generate a plurality of DNA molecules comprising the constant region at each end; and amplifying a plurality of the DNA molecules through polymerase chain reaction, said reaction utilizing a primer complementary to the constant region.

In other aspects of the present invention, there is a method of amplifying a DNA molecule generated from at least one mRNA molecule, comprising obtaining a cDNA molecule from the mRNA molecule; modifying the cDNA molecule to generate at least one ssDNA molecule; subjecting the ssDNA molecule to a plurality of primers to form a ssDNA molecule/primer mixture, wherein the primers comprise nucleic acid sequence that is substantially non-self-complementary and substantially non-complementary to other primers in the plurality, wherein the sequence comprises, in a 5' to 3' orientation, a constant region and a variable region; subjecting the ssDNA molecule/primer mixture to a strand-displacing polymerase, under conditions wherein the subjecting steps generate a plurality of DNA molecules comprising the constant region at each end; and amplifying a plurality of the DNA molecules comprising the constant region at each end through polymerase chain reaction, said reaction utilizing a primer complementary to the constant region.

The obtaining step may be further defined as comprising generation of the cDNA molecule by reverse transcribing the mRNA molecule with a reverse transcriptase, such as, for example Tth DNA polymerase, HIV Reverse Transcriptase, AMV Reverse Transcriptase, MMLV Reverse Transcriptase, or a mixture thereof.

In another aspect of the present invention, there is a kit comprising a plurality of polynucleotides, wherein the polynucleotides comprise nucleic acid sequence that is substantially non-self-complementary and substantially non-complementary to other polynucleotides in the plurality, said plurality dispersed in a suitable container. The kit may further comprise a polymerase, such as a strand displacing polymerase, including, for example, Φ29 Polymerase, Bst Polymerase, Vent Polymerase, 9° Nm Polymerase, Klenow fragment of DNA Polymerase I, MMLV Reverse Transcriptase, a mutant form of T7 phage DNA polymerase that lacks 3'-5' exonuclease activity, or a mixture thereof.

In an additional aspect of the invention, there is a method of amplifying a population of DNA molecules comprised in a plurality of populations of DNA molecules, said method comprising the steps of obtaining a plurality of populations of DNA molecules, wherein at least one population in said plurality comprises DNA molecules having in a 5' to 3' orientation a known identification sequence specific for the population and a known primer amplification sequence; and amplifying the population of DNA molecules by polymerase chain reaction, the reaction utilizing a primer for the identification sequence.

The obtaining step may be further defined as obtaining a population of DNA molecules comprising a known primer amplification sequence; amplifying said DNA molecules with a primer having in a 5' to 3' orientation the known identification sequence and the known primer amplification sequence, and mixing the population with at least one other population of DNA molecules. In specific embodiments, the population of DNA molecules comprises genomic DNA, is a genome, or is a transcriptome.

In another aspect of the present invention, there is a method of amplifying a population of DNA molecules comprised in a plurality of populations of DNA molecules by obtaining a plurality of populations of DNA molecules, wherein at least one population in the plurality comprises DNA molecules, wherein the 5' ends of the DNA molecules comprise in a 5' to 3' orientation a single-stranded region comprising a known identification sequence specific for the population and a known primer amplification sequence; isolating the population through binding of at least part of the single stranded known identification sequence of a plurality of the DNA molecules to a surface; and amplifying the isolated DNA molecules by polymerase chain reaction that utilizes a primer complementary to the primer amplification sequence.

The obtaining step may be further defined as obtaining a population of DNA molecules comprising a known primer amplification sequence; amplifying the DNA molecules with a primer comprising in a 5' to 3' orientation: the known identification sequence; a non-replicable linker; and the known primer amplification sequence; and mixing the population with at least one other population of DNA molecules. Furthermore, the isolating step may be further defined as binding at least part of the single stranded known identification sequence to an immobilized oligonucleotide comprising a region complementary to the known identification sequence.

In other aspects of the invention, there is a plurality of polynucleotides, wherein the polynucleotides in the plurality comprise nucleic acid sequence that is substantially non-self-complementary and substantially non-complementary to other polynucleotides in the plurality. The nucleic acid sequence may be further defined as rendering the polynucleotides substantially incapable of at least one of the following: self-hybridization; self-priming; hybridization to another polynucleotide in the plurality; and initiation of a polymerization reaction in the plurality. The polynucleotides in the plurality may be further defined as having a 5' to 3' orientation and comprising a constant first region 5' to a variable second region. In specific embodiments, the constant region is for subsequent amplification and/or the variable region is for random annealing, random priming, or both.

The first and second regions of the polynucleotides may each be comprised of two non-complementary nucleotides, such as guanines, adenines, or both; cytosines, thymidines, or both; adenines, cytosines, or both; or guanines, thymidines, or both. The first region may comprise about 6 to about 100 nucleotides and/or the second region may comprise about 4 nucleotides to about 20 nucleotides. Furthermore, the polynucleotide may further comprise 0 to about 3 random bases at its distal 3' end. The nucleic acid sequence may be comprised of base or backbone analogs, or both, in some embodiments.

In a particular embodiment, the first region and the second region are each comprised of guanines and thymidines and the polynucleotide comprises 0, 1, 2, or 3 random bases at its 3' end.

In some embodiments, there is a method of differentially obtaining RNA from a sample comprising dsDNA and RNA, comprising providing the mixture of dsDNA and RNA; optionally heating said mixture to a temperature not exceeding about 75° C. to prevent denaturation of dsDNA; and subjecting the mixture to a polymerase that replicates only single stranded RNA templates. In specific embodiments, the method consists essentially of the providing and subjecting steps, or of the providing, optionally heating, and subjecting steps. The subjecting step is further defined as subjecting the mixture to a plurality of primers to form a ssRNA/dsDNA/primer mixture, wherein the primers comprise nucleic acid sequence that is substantially non-self-complementary and substantially non-complementary to other primers in the plurality, wherein said sequence comprises in a 5' to 3' orientation a constant region and a variable region; subjecting said ssRNA/dsDNA/primer mixture to a polymerase that prime and replicate only single-stranded RNA, under conditions wherein said subjecting steps generate a plurality of DNA molecules comprising the constant nucleic acid sequence at each end; and amplifying a plurality of the DNA molecules comprising the constant region at each end through polymerase chain reaction, said reaction utilizing a primer complementary to the constant region.

In another aspect of the present invention, there is a method of immobilizing an amplified genome, transcriptome, or both, by obtaining an amplified genome, transcriptome, or both, wherein a plurality of molecules from the genome, transcriptome, or both comprise a known primer amplification sequence at both the 5' and 3' ends of the molecules; and attaching a plurality of the molecules to a support. The attaching step may be further defined as comprising covalently attaching the plurality of molecules to the support through said known primer amplification sequence.

In specific embodiments, the covalently attaching step is further defined as hybridizing a region of at least one single stranded molecule to a complementary region in the 3' end of a oligonucleotide immobilized to said support; and extending the 3' end of the oligonucleotide to produce a single stranded molecule/extended polynucleotide hybrid. The method may also further comprise the step of removing the single stranded molecule from the single stranded molecule/extended polynucleotide hybrid to produce an extended polynucleotide. The method may also further comprise the step of replicating the extended polynucleotide. The replicating step may be further defined as providing to said extended polynucleotide a polymerase and a primer complementary to the known primer amplification sequence; extending the 3' end of said primer to form an extended primer molecule; and releasing said extended primer molecule.

In another particular aspect of the invention, there is a method of immobilizing an amplified genome, comprising the steps of obtaining an amplified genome, wherein a plurality of DNA molecules from the genome and comprise a tag; and a known primer amplification sequence at both the 5' and 3' ends of the molecules; and attaching a plurality of the DNA molecules to a support. In a specific embodiment, the attaching step is further defined as comprising attaching the plurality of DNA molecules to the support through said tag. The tag may be biotin and the support may comprise streptavidin. In specific embodiments, the tag comprises an amino group or a carboxy group, for example, although other tags useful in the art are contemplated.

However, in a particular aspect of the invention, the tag comprises a single stranded region and the support comprises an oligonucleotide comprising a sequence complementary to a region of the tag. The tag may comprise a single stranded region further defined as an identification sequence. Furthermore, the DNA molecules may be further defined as comprising a non-replicable linker that is 3' to the identification sequence and that is 5' to the known primer amplification sequence. In a specific embodiment, the method further comprises the steps of removing contaminants from the immobilized genome.

Methods having amplified molecules may further comprise the steps of modifying the amplified molecules, the molecules further defined as double stranded molecules, to incorporate modified nucleotide bases, thereby producing labeled molecules; generating single stranded molecules from the labeled molecules, the single stranded molecules capable of hybridizing to complementary sequences arrayed in known locations on a substrate; and analyzing at least one hybridization signal. The modifying step may comprise chemical, enzymatic, or physical incorporation of modified nucleotide bases, which, for example, are radioactive or fluorescent. In specific embodiments, the generating step comprises denaturation of the double stranded molecules. The substrate may comprise a microarray substrate. Furthermore, the analyzing step may comprise measuring the background subtracted intensity of the at least one hybridization signal and/or measuring copy number, representation, or both of the amplified molecules.

In an additional embodiment of the present invention, there is a method of differentially obtaining DNA or RNA, respectively, from a sample comprising a mixture of DNA and RNA, comprising providing the mixture of DNA and RNA; heating the mixture to a temperature that selectively affects the DNA or RNA; subjecting the mixture to a polymerase that selectively replicates the respective DNA or RNA. The subjecting step may be further defined as subjecting the mixture to a plurality of primers to form a ssDNA/RNA/primer mixture, wherein the primers comprise nucleic acid sequence that is substantially non-self-complementary and substantially non-complementary to other primers in the plurality, wherein said sequence comprises in a 5' to 3' orientation a constant region and a variable region; subjecting said ssDNA/RNA/primer mixture to the polymerase that selectively replicates the respective DNA or RNA, under conditions wherein said subjecting steps generate a plurality of DNA molecules comprising the constant region at each end; and amplifying a plurality of the DNA molecules comprising the constant region at each end through polymerase chain reaction that utilizes a primer complementary to the constant region.

In certain aspects, there is a method of differentially obtaining DNA from a sample comprising DNA and RNA, comprising providing the mixture of DNA and RNA; heating said mixture to a temperature of at least about 94° C. to about 100° C. to generate single stranded nucleic acids; and subjecting the mixture to a polymerase that replicates only DNA templates. The method may further comprise subjecting the mixture to a plurality of primers to form a ssDNA/RNA/primer mixture, wherein the primers comprise nucleic acid sequence that is substantially non-self-complementary and substantially non-complementary to other primers in the plurality, wherein said sequence comprises in a 5' to 3' orientation a constant region and a variable region; and subjecting said ssDNA/RNA/primer mixture to a polymerase that selectively replicates DNA, under conditions wherein the subjecting steps generate a plurality of DNA molecules comprising the known nucleic acid sequence at each end. The method may further comprise the step of amplifying a plurality of the DNA molecules through polymerase chain reaction, said reaction utilizing a primer complementary to the constant region. The polymerase may be a DNA-dependent DNA polymerase, in specific embodiments, such as φ29 Polymerase, Bst Polymerase, Vent Polymerase, 9° Nm Polymerase, Klenow Exo⁻ fragment of DNA Polymerase I, a mutant form of T7 phage DNA polymerase that lacks 3'-5' exonuclease activity, or a mixture thereof. The DNA-dependent DNA polymerase is preferably Klenow Exo⁻ fragment of DNA Polymerase I.

In another aspect to the invention, there is a method of differentially obtaining RNA from a sample comprising DNA and RNA, comprising providing the mixture of DNA and RNA; heating said mixture to a temperature not exceeding about 75° C., to prevent denaturing of dsDNA; and subjecting the mixture to a polymerase that replicates only single stranded RNA templates. The method may further comprise subjecting the mixture to a plurality of primers to form a snRNA/dsDNA/primer mixture, wherein the primers comprise nucleic acid sequence that is substantially non-self-complementary and substantially non-complementary to other primers in the plurality and wherein the primers comprise a known nucleic acid sequence; and subjecting said ssRNA/dsDNA/primer mixture to a polymerase that primes and replicates only single stranded RNA, such as M-MuLV reverse transcriptase, under conditions wherein the subjecting steps generate a plurality of DNA molecules comprising the known nucleic acid sequence at each end.

In specific embodiments, the method further comprises the step of amplifying a plurality of the DNA molecules through polymerase chain reaction, said reaction utilizing a primer complementary to the known nucleic acid sequence.

In some embodiments of the present invention, there is a plurality of ds DNA molecules comprising genomic DNA, wherein when the molecules are denatured to produce first and second strand molecules, each of which comprises a first and second end region at the respective ends of the first and second strand molecules, each of the first and second end regions of the first molecule comprise nucleic acid sequence that is substantially non-self-complementary to sequence in the first and second end regions in said first molecule, and each of the first and second end regions of the second molecule comprise nucleic acid sequence that is substantially non-self-complementary to sequence in the first and second end regions in said second molecule. In some embodiments, each of the first and second end regions of the first strand molecule are substantially non-complementary to the first and second end regions of the first strand of other molecules in the plurality, and wherein each of the first and second end regions of the second strand molecule are substantially non-complementary to the first and second end regions of the second strand of other molecules in the plurality. The DNA molecules may further comprise a homopolymeric tag at the first and second end regions, wherein said end regions are penultimate on the molecules to the homopolymeric tag. In specific embodiments, the amplified molecules are further defined as a genomic library.

In additional embodiments of the present invention, there is a method of sequencing a genome from a limited source of material, comprising the steps of: obtaining at least one double stranded or single stranded DNA molecule from a limited source of material; subjecting said double stranded DNA molecule to heat to produce at least one single stranded DNA molecule; subjecting said single stranded DNA molecule to a plurality of primers to form a DNA molecule/primer mixture, wherein the primers comprise nucleic acid sequence that is substantially non-self-complementary and substantially non-complementary to other primers in the plurality, wherein said sequence comprises in a 5' to 3' orientation a constant region and a variable region; subjecting said DNA molecule/primer mixture to a polymerase, under conditions wherein said subjecting steps generate a plurality of DNA molecules comprising the constant region at each end; and amplifying a plurality of the DNA molecules through polymerase chain reaction, said reaction utilizing a primer complementary to the constant region; providing from the plurality of the amplified molecules a first and second sample of amplified DNA molecules; sequencing at least some of the amplified DNA molecules from the first sample to obtain at least one specific DNA sequence; incorporating homopolymeric poly C/poly G sequence to the ends of the amplified DNA molecules from the second sample to produce homopolymeric amplified molecules; amplifying at least some of the homopolymeric amplified molecules from the second sample with a poly C primer and a primer complementary to the specific DNA sequence; and repeating the sequencing and amplifying steps related to additional specific sequences, thereby producing a substantially complete contig of the genome.

In some embodiments, the incorporating of the homopolymeric sequence comprises one of the following steps: extending the 3' end of the amplified DNA fragments by terminal deoxynucleotidyl transferase in the presence of dGTP; ligating an adaptor comprising the homopolymeric poly C/poly G sequence to the ends of the amplified DNA fragments; or replicating the amplified DNA fragments with a primer comprising the homopolymeric poly C sequence at its 5' end and constant region at the 3' end. The sequencing step may be further defined as cloning the amplified DNA fragments from the first sample into a vector; and sequencing at least some of the cloned fragments.

The specific sequence of the amplified molecule may be obtained by the sequencing step of the first sample and wherein one or more of the additional specific sequences is obtained by the sequencing step of amplified molecules from the second sample. The limited source of material may be a microorganism substantially resistant to culturing, or an extinct species, for example. In specific embodiments, sequencing a genome is achieved with minimal redundancy.

In particular embodiments, the present invention is directed to amplification of DNA including whole-genome DNA from lower amounts of sample than are generally sufficient to produce results from other methods. The present disclosure provides methods and compositions to successfully amplify DNA, including whole genomic DNA, from single cells. Reproducible and accurate whole genome amplifications of DNA from single cells are disclosed. Degenerate self-inert oligonucleotide primers having a universal region and appropriate polymerase enzymes are used to amplify a substantial portion of genomic DNA from samples containing very low number of cells including single cells. Due to the reduced background amplification, clinical diagnosis from single cell DNA is improved.

The present disclosure relates to methods and compositions for the amplification of a whole genome, or whole transcriptome. In specific embodiments, a whole genome is amplified from a single cell. In a specific embodiment the whole transcriptome is amplified from poly A+RNA, or in another embodiment, the whole transcriptome is amplified from total RNA.

In a particular aspect of the present invention, the invention is directed to methods for the amplification of substantially the entire genome or entire transcriptome without loss of representation of specific sites (herein defined as "whole genome amplification" and "whole transcriptome amplification", respectively). In a specific embodiment, whole genome amplification includes simultaneous amplification of substantially all fragments of a genomic library. In a further specific embodiment, "substantially entire" or "substantially all" refers to about 80%, about 85%, about 90%, about 95%, about 97%, or about 99% of all sequences in a genome.

A skilled artisan recognizes that amplification of the whole genome will, in some embodiments, include non-equivalent amplification of particular sequences over others, although the relative difference in such amplification is not considerable. In an embodiment, the methods and composition disclosed herein reproducibly amplify total DNA from single cells about 1 million-fold to produce about 4-5 micrograms of amplified DNA in about 2 hours. In some embodiments, the methods and composition disclosed herein are capable of producing greater than 90% amplification success rate with flow-sorted cells, faithful representation of GC-rich genomic regions, and about 94% correlation coefficient for quantitative PCR (qPCR) data from replicate single-cell reactions.

The methods and compositions disclosed herein enhance single-copy sensitivity and high specificity and also produce amplified DNA fragments that are suitable for copy number variation (CNV), SNP genotyping, mutation detection, and sequencing. The methods and compositions disclosed herein are capable of improved analytical and clinical performance for clinical testing of embryo biopsies and polar body and other small samples such as characterize forensic and paleobiology analyses. The methods and compositions disclosed herein are capable of amplifying about 70-80% or 80-90% or 90-95% of the genome, e.g, human genome. The amplified products display high sequence fidelity and substantially lower background noise, e.g., less than 1% or 2% or 5% of the total amplified products. The methods and compositions disclosed herein provide enhanced performance with single cells that is equivalent to those obtained with more than 1,000 cells. In some embodiments, about 70% of the probe sequences are highly represented among the amplicons. Reproducibility analysis by qPCR demonstrated that 60% of the loci tested have a standard deviation less than 1 PCR cycle.

In certain embodiments of the invention, there is a method of amplifying a substantial portion of genomic DNA from a single cell or a small number of cells, the method comprising: (a) providing a sample comprising a single cell or a small number of cells or DNA from the cells thereof; (b) providing degenerate self-inert oligonucleotide primers selected from the group consisting of oligonucleotides listed in Table III and Table VII provided herein, wherein the primers comprise a universal portion; (c) providing a suitable thermostable DNA polymerase enzyme; and (d) providing conditions for amplifying the genomic DNA. In specific embodiments, the polymerase is a KAPA polymerase (KAPA Biosystems). In certain aspects, the oligonucleotide primers comprise a detectable moiety. In specific cases, a small number of cells includes about 1-5 cells. Exemplary thermostable polymerases include but are not limited to KAPA 2G Robust (KAPA Biosystems); Taq Polymerase (BD/Clontech, Life Technologies); Phire (Finnzymes/New England Biolabs (NEB)); Pfu (Agilent Technologies/Stratagene); AccuPrime Pfx (Life Technologies); Phusion (Finnzymes/NEB); Vent (NEB); Deep Vent (NEB); and DyNAzyme (Finnzymes/NEB).

In specific embodiments of the invention, the nucleic acid molecule/primer mixture is subjected to polymerase chain reaction having polymerization steps comprising two or more DNA denaturation steps.

In certain aspects of the invention, the method comprises (1) a first series of polymerase chain reaction steps comprising subjecting the nucleic acid molecule/primer mixture to a thermostable polymerase in the presence of the primers under conditions having two or more cycling DNA denaturation steps; and (2) a second series of polymerase chain reaction steps using primers that comprise the constant region sequence.

Other objects, features and advantages of the present invention will become apparent from the following detailed description. It should be understood, however, that the detailed description and the specific examples, while indicating the preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In FIG. 3A, YN primers containing 0, 1, 2 or 3 random N bases were used with or without dNTPs. In FIG. 3B, YN primers containing 0, 1, 2 or 3 random N bases and a model template oligonucleotide (Table III, primer 9) were used. In FIG. 3C, self-priming of YN-primers were tested. Note: Pyrimidine bases do not stain efficiently with Sybr Gold. The presence of purine bases within the completely random portion (N) of YN-primers greatly increases the efficiency of staining these oligonucleotides.

In FIG. 6A, pyrimidine primers with 0 to 3 random 3' bases were used for the library synthesis step and in FIG. 6B, pyrimidine primers with 4 to 6 random 3' bases were used. The number of completely random bases (N) is shown at the end of each primer's abbreviation.

FIG. 18A illustrates replicable known primer with the known primer sequence U at the 3'-end and individual ID sequence tag T at the 5' end. FIG. 18B shows non-replicable known primer with the known primer sequence U at the 3' end, individual ID sequence tag T at the 5' end, and non-replicable organic linker L between them. FIG. 18C shows 5' overhanging structure of the ends of DNA fragments in the WGA library after amplification with non-replicable known primer.

FIG. 21A—library tagging by incorporation of a (dG)n tail using TdT enzyme; FIG. 21B—library tagging by ligation of an adaptor with the $C_{10}$ sequence at the 5' end of the long oligonucleotide; FIG. 21C—library tagging by secondary replication of the WGA library using known primer with the $C_{10}$ sequence at the 5' end.

FIG. 22A illustrates an embodiment utilizing covalent attachment of the libraries to a solid support. FIG.

22B illustrates an embodiment utilizing non-covalent attachment of the libraries to a solid support.

Figure 24:
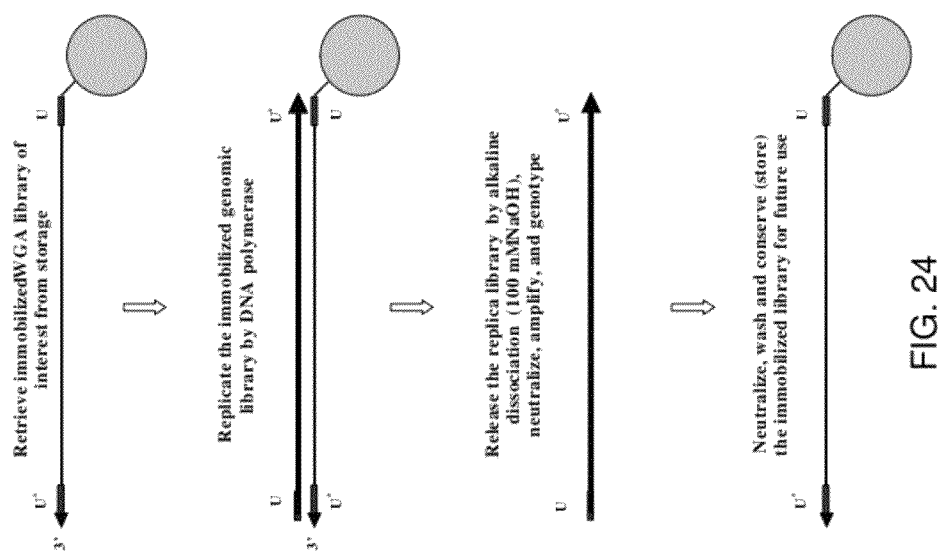

FIG. 24 shows an embodiment wherein the immobilized WGA library may be used repeatedly.

Figure 25:
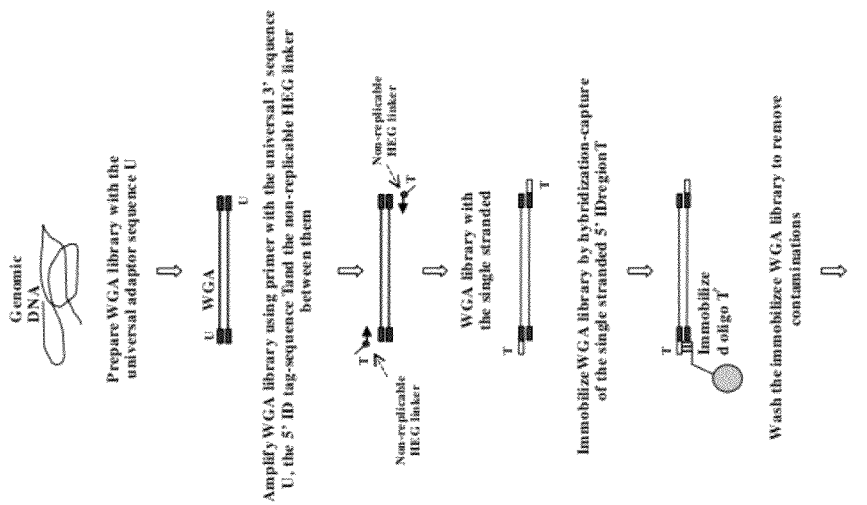

FIG. 25 describes the method of WGA product purification utilizing a non-replicable known primer and magnetic bead affinity capture.

Figure 26:
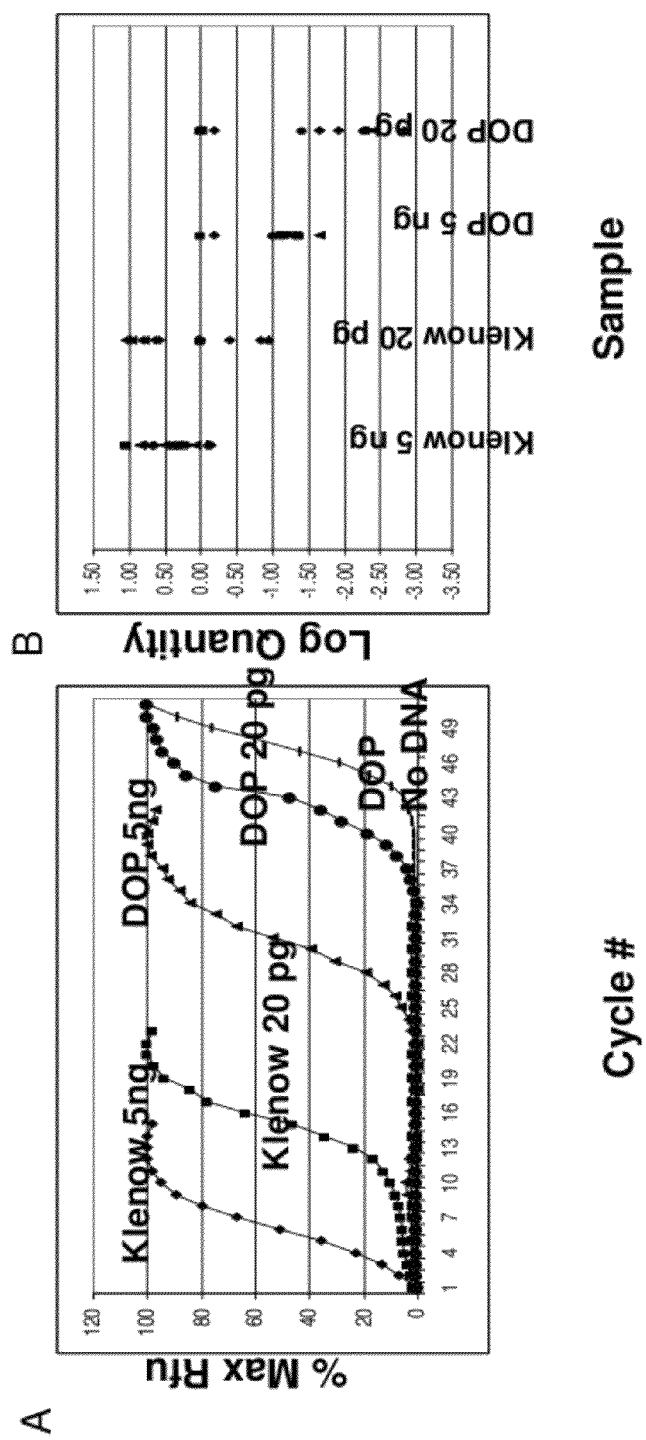

FIGS. 26A and 26B shows comparison between the whole genome amplification described in the present invention and a commercially available kit for DOP-PCR amplification. Aliquots of 5 ng and 20 pg of genomic DNA were amplified with Klenow Exo– fragment of DNA polymerase I and 1 µM of self-inert degenerate primer $K(N)_2$ or with DOP PCR Master™ Kit (Roche Molecular Biochemicals). (A) Real-time PCR amplification curves for libraries form 5 ng gDNA, 20 pg gDNA, or blank control. (B) Logarithmic distribution plots of 16 genomic STS markers amplified from the whole genome libraries amplified in FIG. 25A. Amplification with Klenow Exo– fragment of DNA polymerase I and self-inert degenerate primer $K(N)_2$ was superior both in sensitivity and in representation of genomic markers as compared to that with DOP PCR FIG. 27 displays the amplification curves of libraries generated from DNA isolated from serum collected in a serum separator tube. The amplification was performed for 17 cycles.

Figure 28:
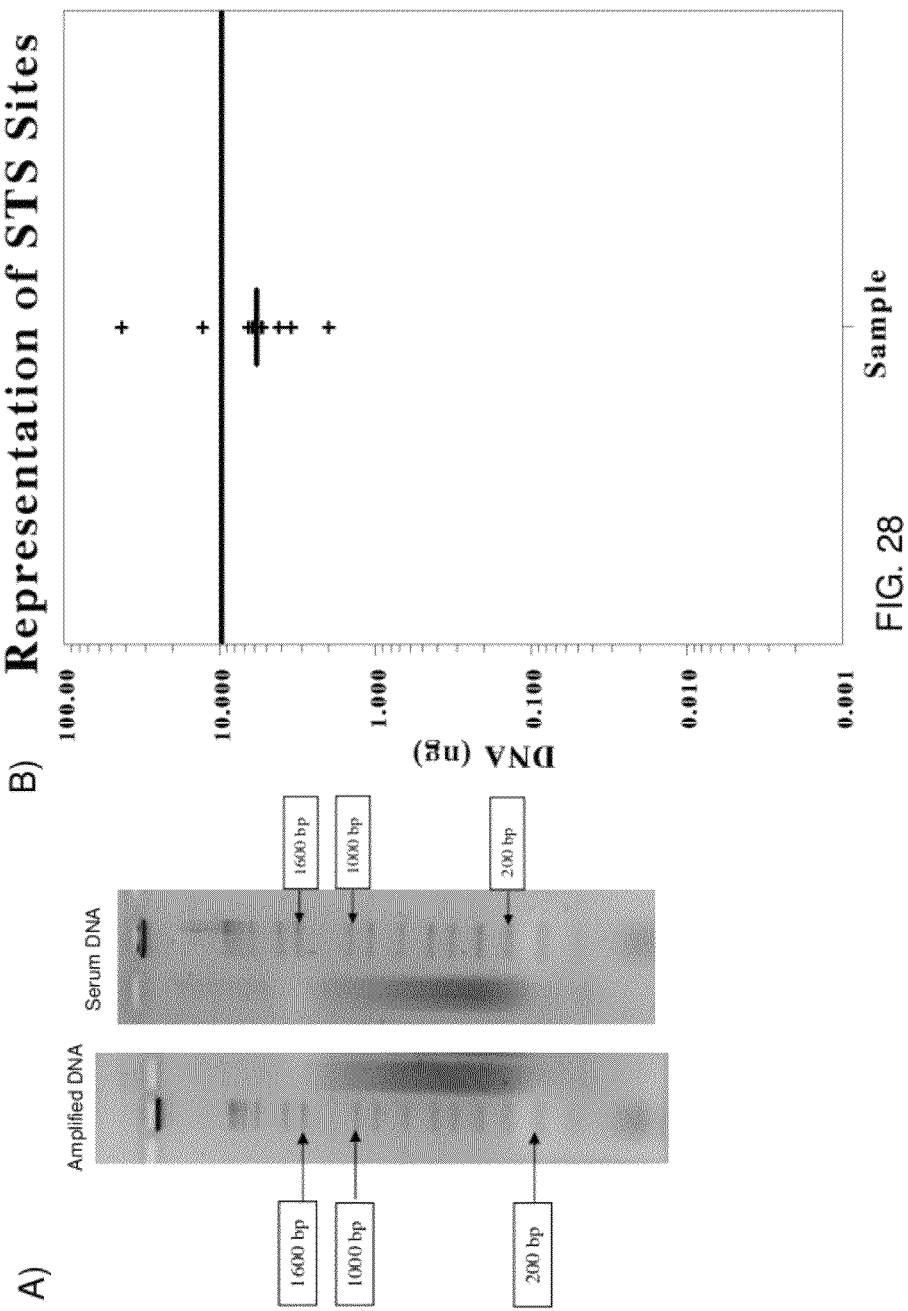
Figure 29:
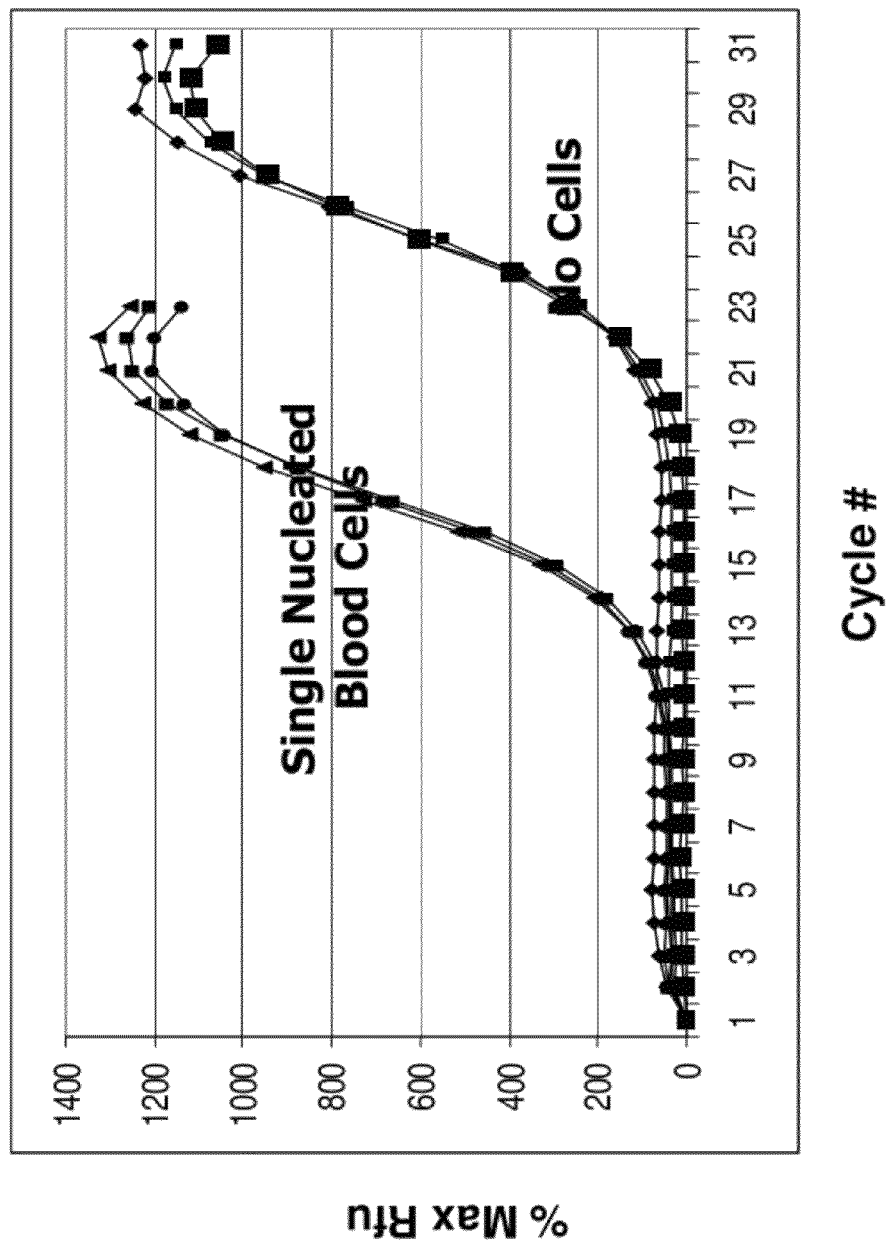

FIGS. 28A and 28B represent the analysis of the amplified products from serum DNA. In FIG. 28A, there is gel analysis of both serum DNA (Right) and amplified products (Left). Both the starting serum DNA and amplified material demonstrate a size range of 200 bp to 1.6 kb, indicating that the amplified material maintains the same size distribution as the DNA isolated from the serum. In FIG. 28B, there is real-time STS analysis of 8 STS sites in amplified products from serum DNA. The solid line crossing the entire graph represents both the amount of DNA added to the STS assay based on optical density, and the average value of the 8 STS sites. The short line represents the median value of the 8 STS sites obtained by real-time PCR analysis. All 8 sites were represented within a factor of 5 of the mean amplification FIG. 29 illustrates amplification of single blood nucleated cells by a method of the present invention.

Figure 30:
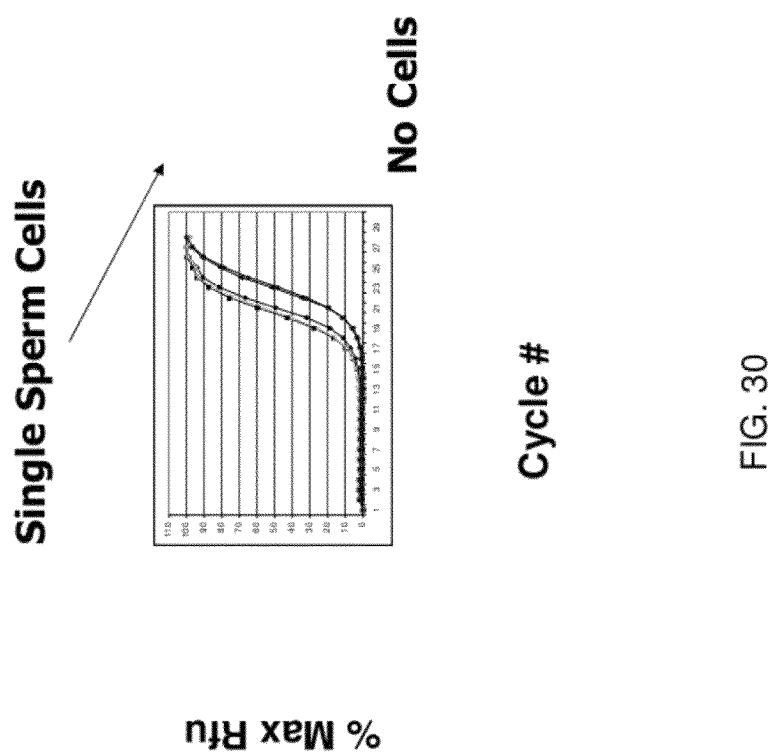

FIG. 30 shows amplification of single sperm cells by a method of the present invention.

Figure 31:
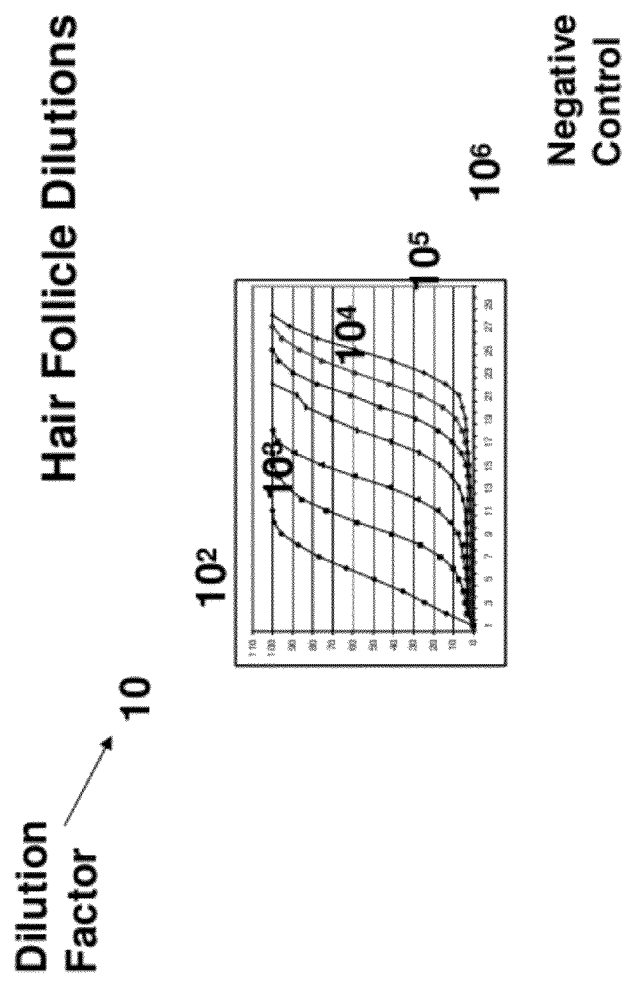

FIG. 31 shows dilution of hair follicle samples for an exemplary forensic application of a method described herein.

Figure 32:
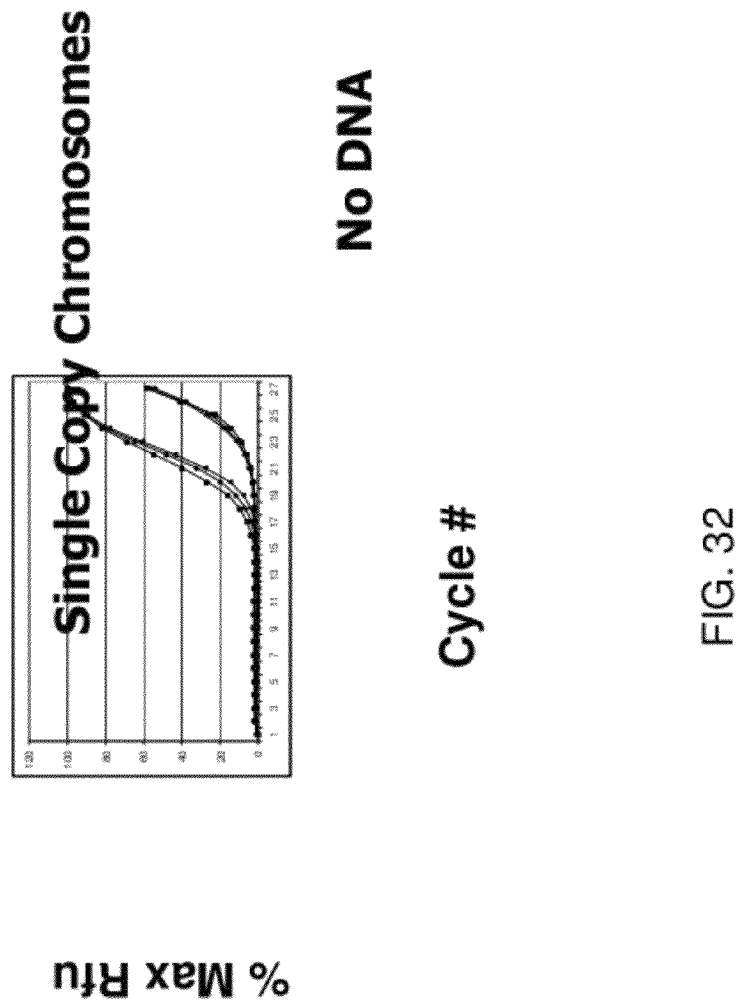

FIG. 32 illustrates amplification of a single copy chromosome.

Figure 33:
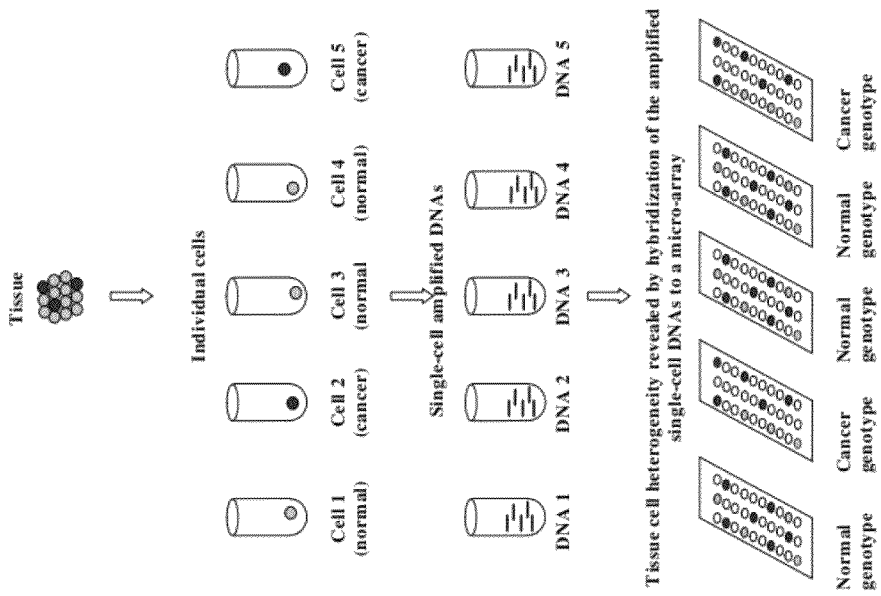

FIG. 33 shows micro-array hybridization analysis of the amplified DNA from a single-cell DNA produced by whole genome amplification.

Figure 34:
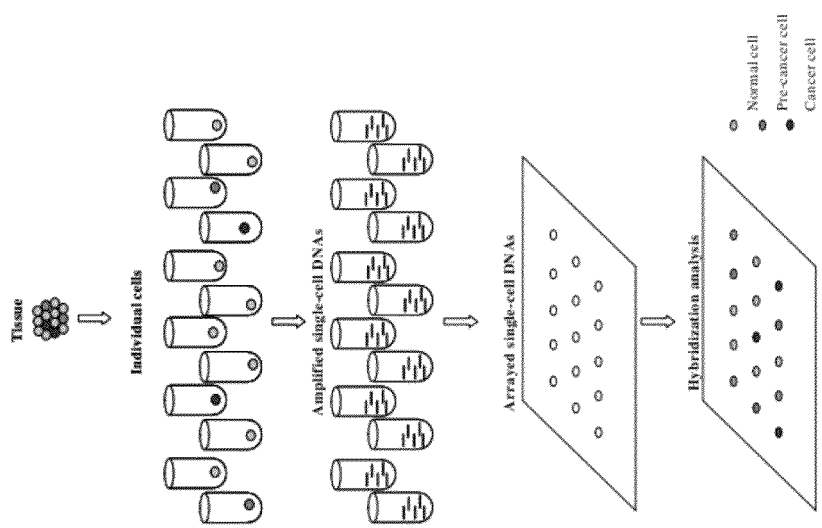

FIG. 34 illustrates single-cell DNA arrays for detection and analysis of cells, such as cancer cells.

Figure 35:
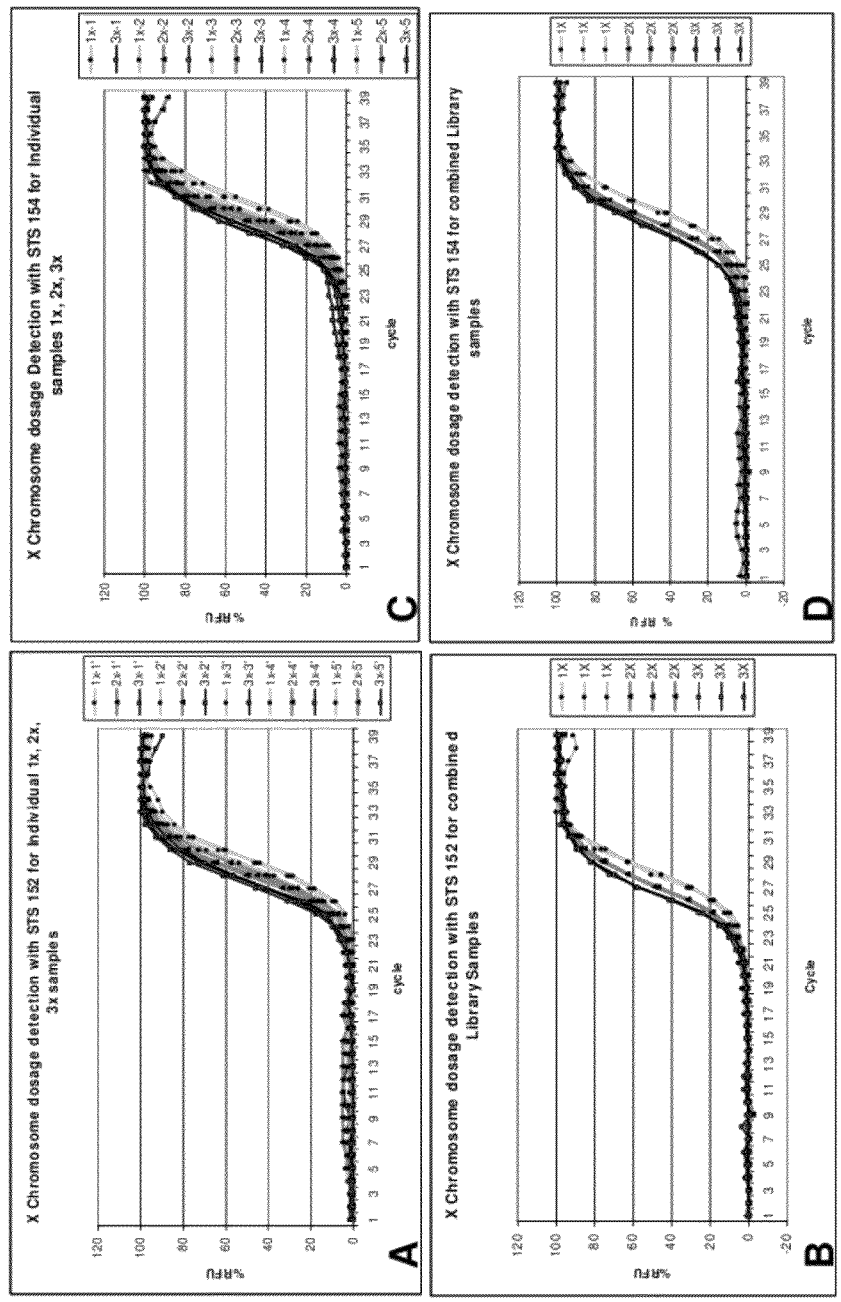

FIG. 35 shows real-time PCR amplification using two X-chromosome specific primer pairs to evaluate loci copy number values in WGA libraries synthesized from patient DNA of known aneuploidies of XO, XX, and XXX. Panels A and C show curves from each of 5 individual amplifications. Panels B and D show mixtures of the five libraries tested in triplicate demonstrating the maintenance of copy number information in WGA libraries.

Figure 36:
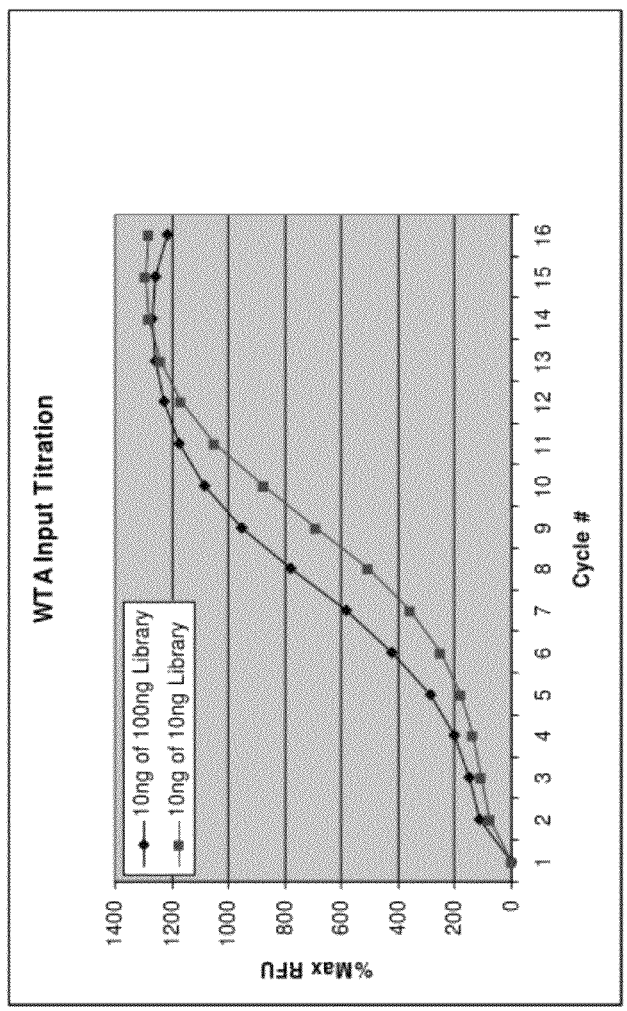

FIG. 36 shows real-time PCR amplification of WTA libraries prepared from 10 ng and 100 ng from human B-lymphocyte RNA using self-inert degenerate primer $K(N)_2$ and MMLV reverse transcriptase. Amplification profiles show about a one-cycle difference between 100 ng of input and 10 ng of input template.

Figure 37:
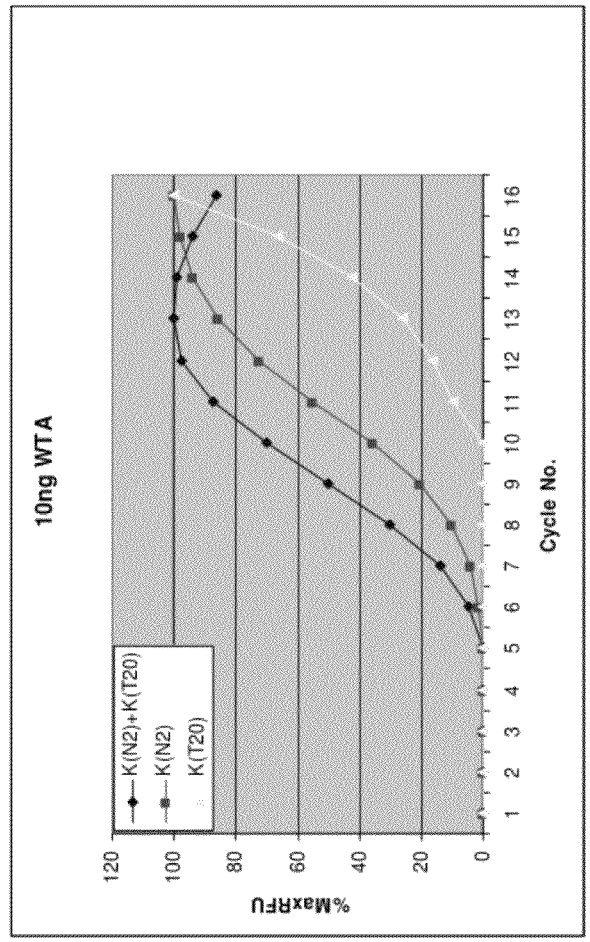

FIG. 37 shows real-time PCR amplification of WTA libraries prepared with two different self-inert primers $K(N)_2$ and K(T20) and their combination. Significant improvement was observed when a combination of $K(N)_2$ and K(T20) is used.

Figure 38:
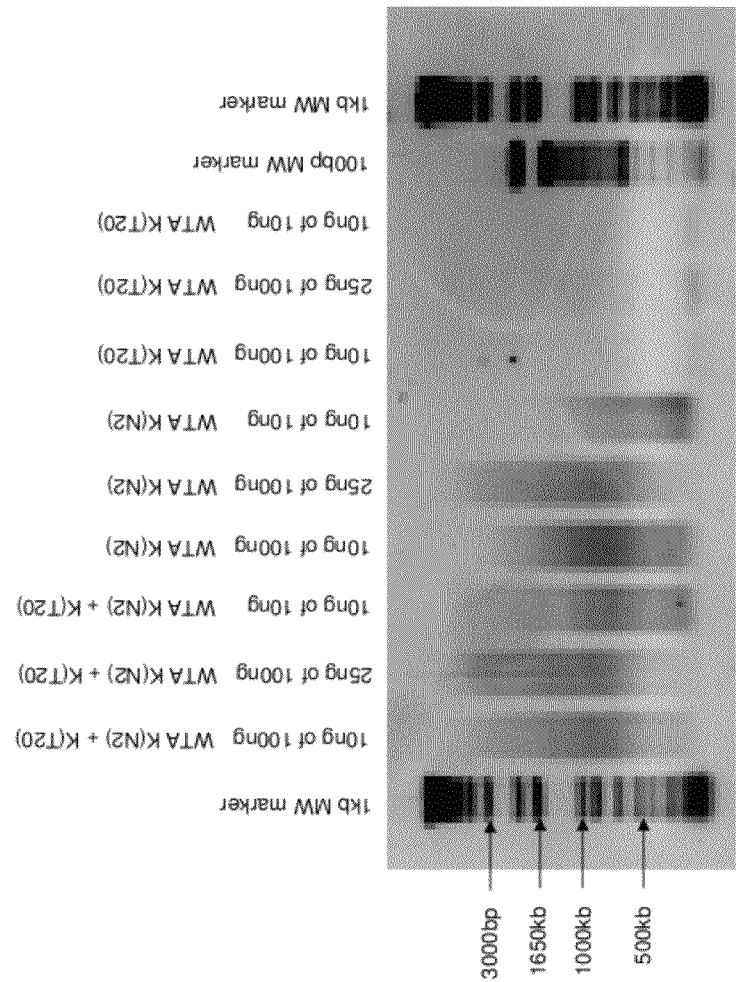

FIG. 38 shows gel electrophoretic analysis of amplified WTA libraries. The observed pattern of ethidium bromide staining visualized by fluorescence transillumination (Fluor-S, Bio-Rad) shows the range of fragment sizes and intensity resulting from varying the amounts of input RNA in library synthesis and from varying the primer combinations utilized. 100 ng of input RNA yields larger products without significant effect of the primer K(T20). Libraries from 10 ng of input RNA yield generally smaller amplification products and show significant improvement with the addition of K(T20) primer.

Figure 39:
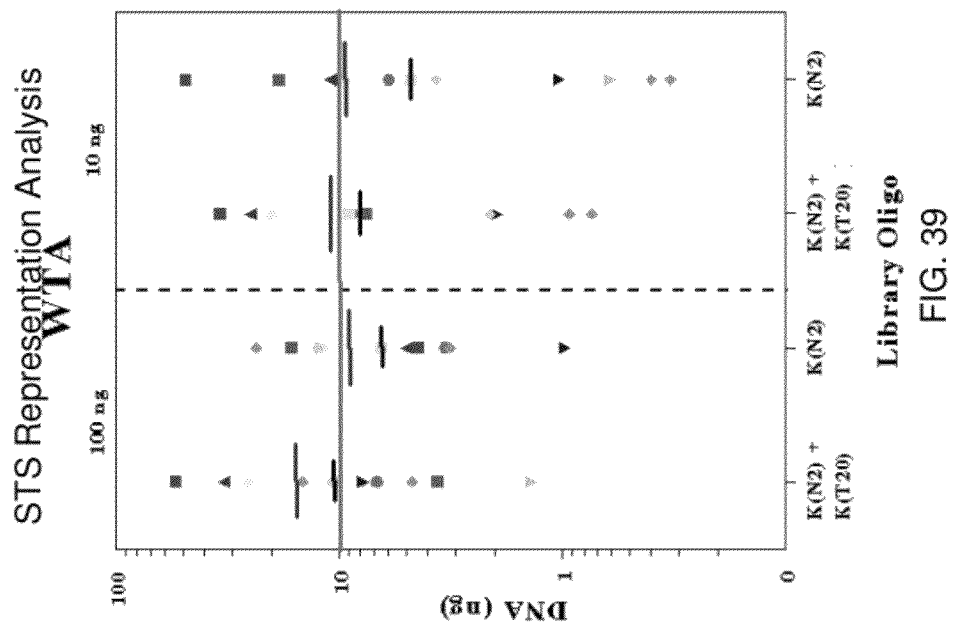

FIG. 39 provides quantitative real-time PCR analysis of amplified WTA libraries. The plots show analysis of 11 sites corresponding to human STS markers. The long bar in each column represents the average value while the short bar represents the median value. The line at 10 ng represents the amount of amplified DNA, by spectrophotometric analysis, added to each assay. All 11 sites were detected in each sample, indicating that all sites were efficiently amplified in all samples. The representation of these 11 markers is similar between the K(N2) and K(N2)+K(T20) 100 ng libraries. The distribution is wider for the 10 ng libraries than the 100 ng libraries and the distribution of the 10 ng K(N2) library is slightly broader than the 10 ng K(N2)+K(T20) library.

Figure 40:
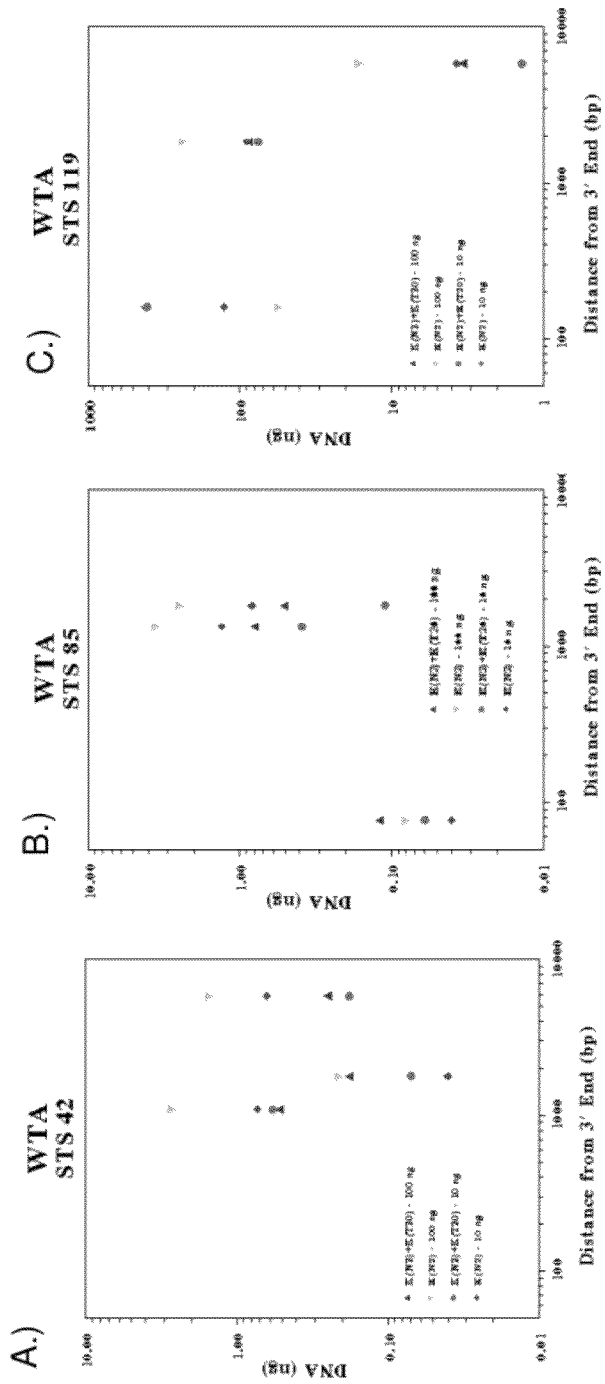

FIG. 40 illustrates results of real-time PCR analysis of three exemplary expressed mRNA loci at three different distances from the 3' end using human STS markers. The lengths of the mRNA for each STS are 6,642 bp for STS 42, 3,100 bp for STS 85, and 9,301 bp for STS 119. The distances from the 3' end for the STS 42 locus are 1,087 bp, 1,795 bp, and 5,835 bp. The distances from the 3' end for the STS 85 locus are 77 bp, 1,331 bp, and 1,827 bp. The distances from the 3' end for the STS 119 locus are 1,834 bp, 3,746 bp, and 5,805 bp. Results are shown for 100 ng and 10 ng input libraries with either $K(N)_2$ or $K(N)_2$+K(T20) library synthesis primers. Representation of marker sequences for WTA libraries at different lengths along a specific transcript show consistent results between libraries made from different quantities of RNA and display only minor improvements in 3' representation with the addition of K(T20).

Figure 41:
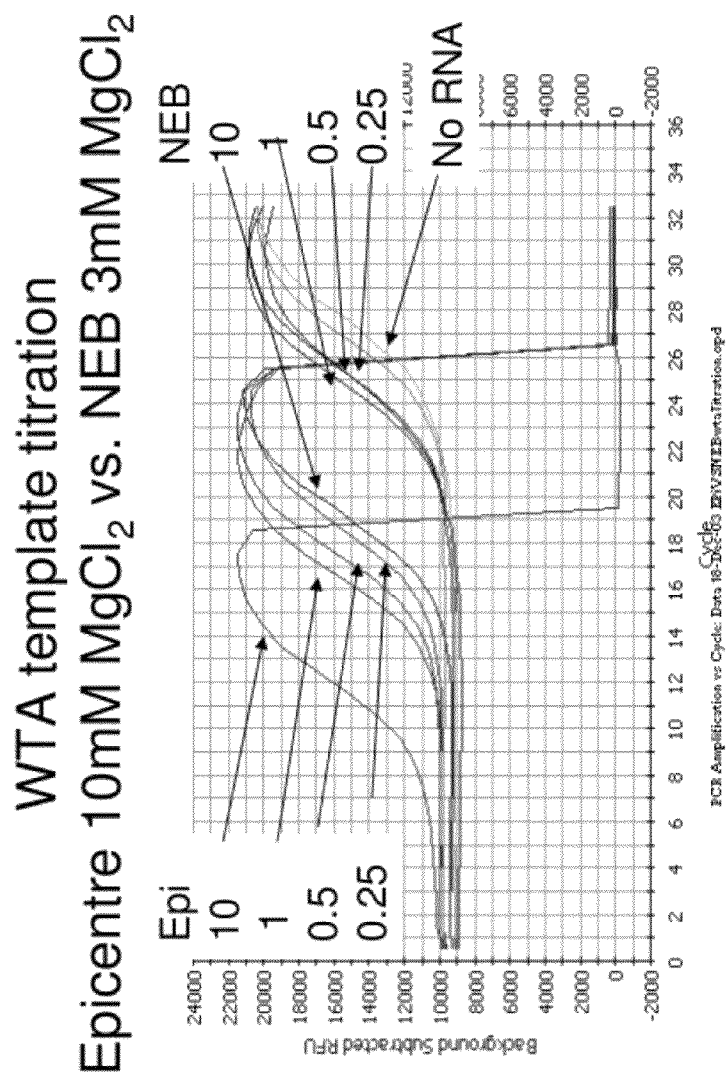

FIG. 41 illustrates results of real-time PCR analysis of input template and two principal $MgCl_2$ concentrations typically used with the RNA dependent DNA polymerase, reverse transcriptase.

Figure 42:
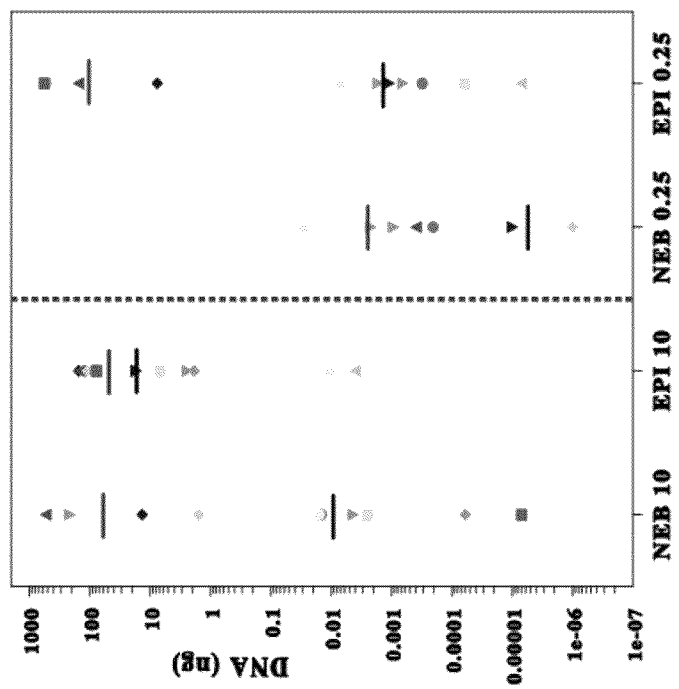

FIG. 42 shows the resulting representation of specific sites analyzed by real-time PCR for their relative abundance within a subset of the samples described in FIG. 41 41 (10 ng and 0.25 ng input template; 3 mM and 10 mM $MgCl_2$ concentration). As is typical of such experiments, samples that amplify more robustly also show better representation of specific sites.

Figure 43:
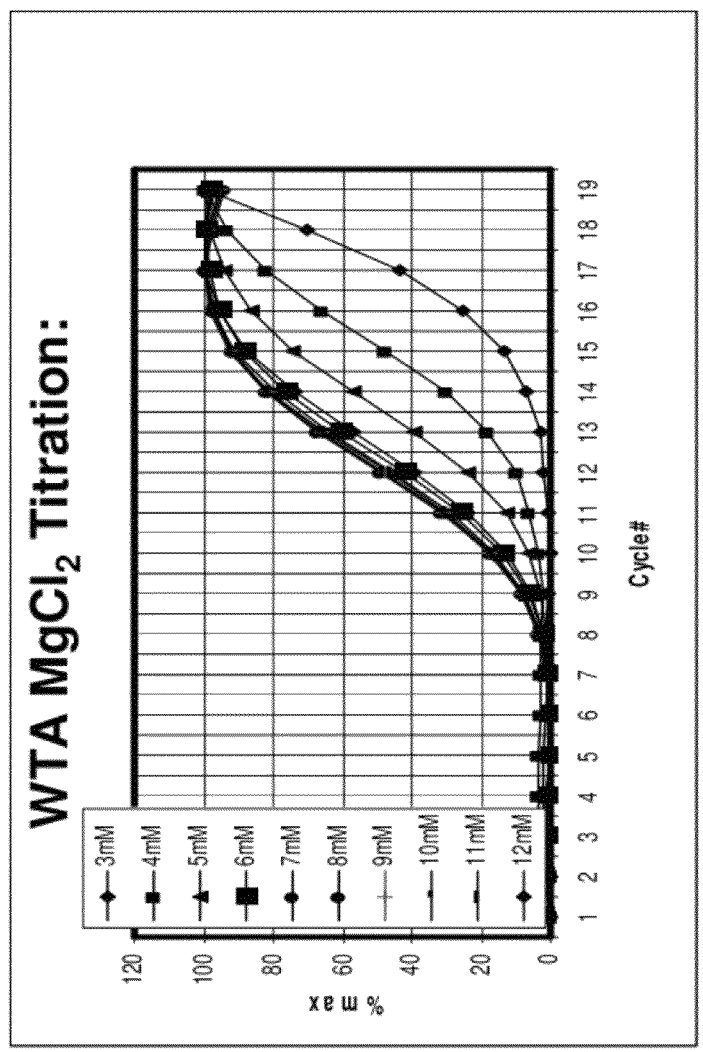

FIG. 43 illustrates the effect of $MgCl_2$ concentration on WTA amplification of total RNA. Using a constant 10 ng template RNA the $MgCl_2$ concentration was varied over a range of between 3 mM and 12 mM. A clear dependence is observed in WTA performance under these reaction conditions, with optimal amplification performance occurring between 6 mM and 10 mM.

Figure 44:
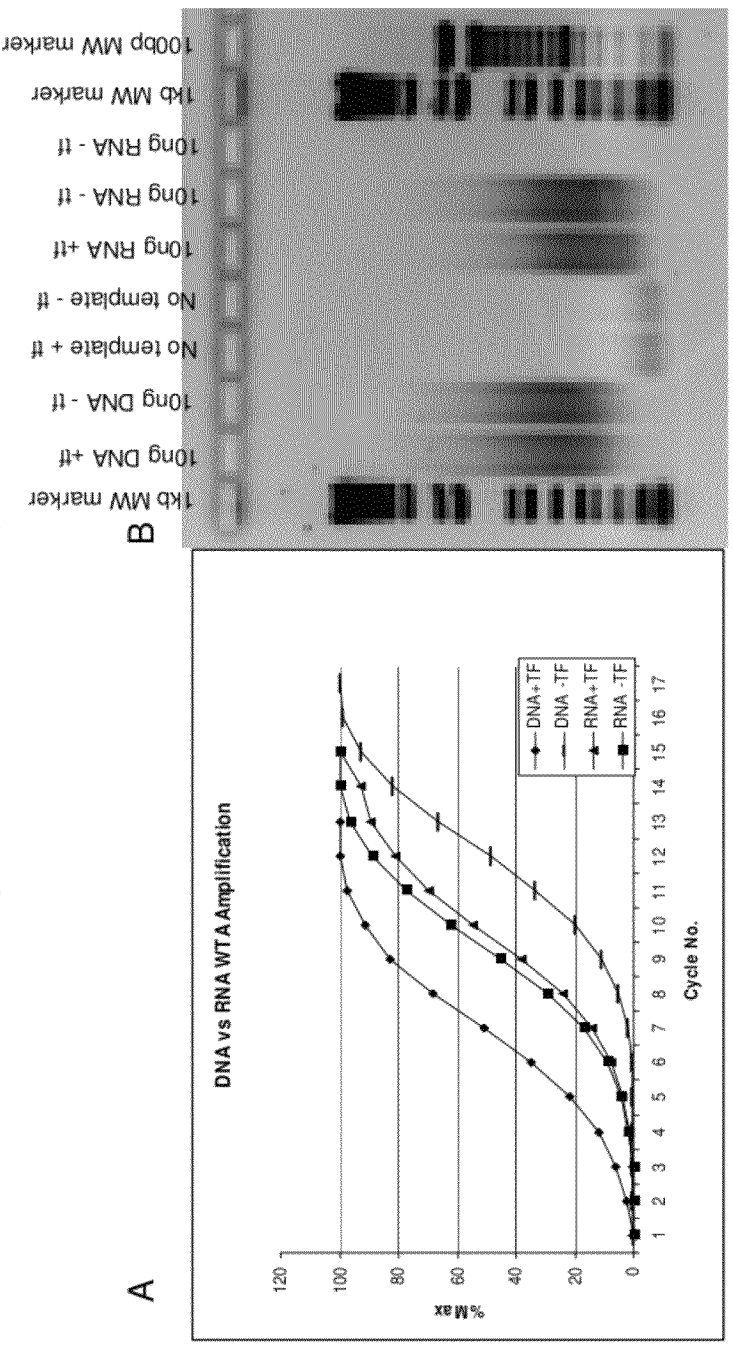

FIG. 44 demonstrates the selective amplification of single stranded templates in WTA library synthesis using either DNA or RNA with or without denaturation. Panel A shows real-time PCR curves of the amplification of these libraries. Panel B shows the resulting products run on a 0.8% agarose gel stained with ethidium bromide. Only about 1% of DNA sample can be converted into library amplimers without denaturation, while denaturation had little effect on RNA templates.

Figure 45:
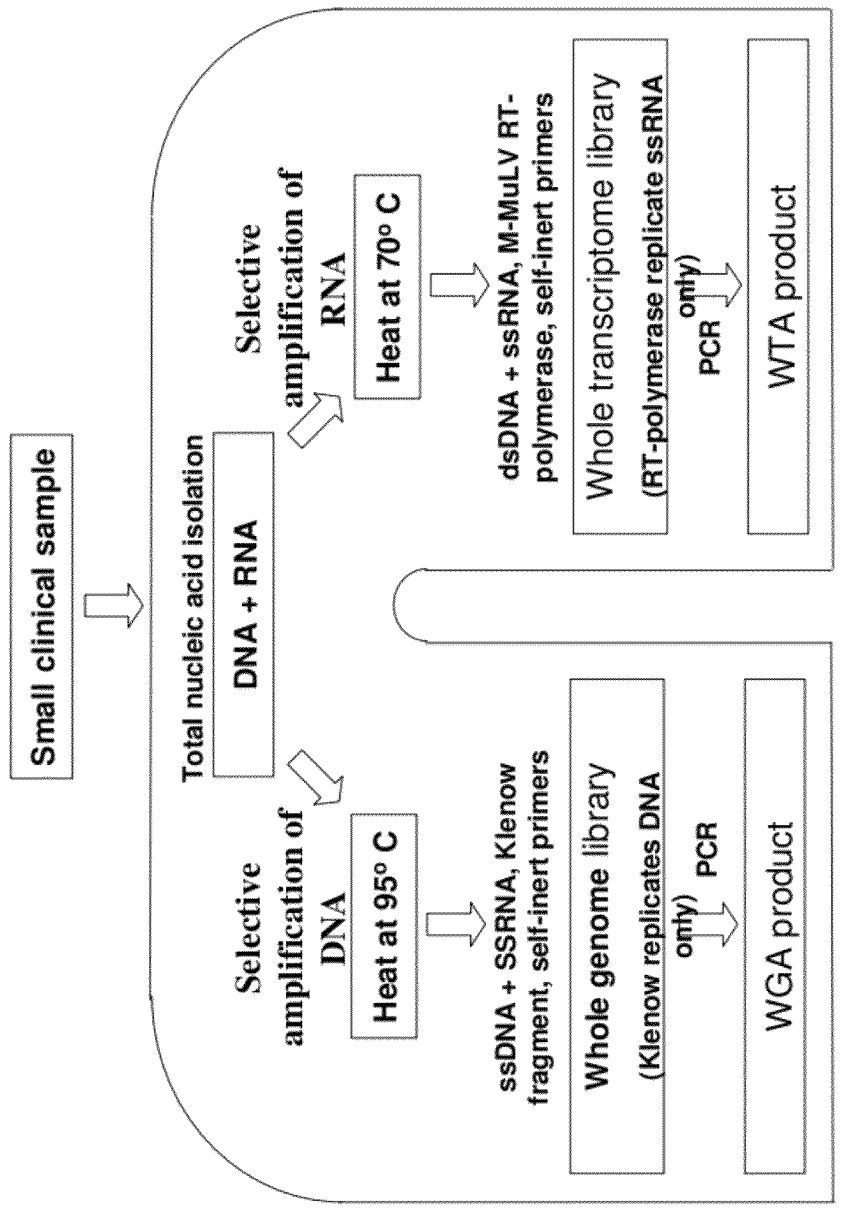

FIG. 45 illustrates principle of selective amplification of DNA and RNA from a total nucleic acid isolate using self-inert degenerate primers in combination with Klenow Exo– fragment of DNA polymerase I and heat-denatured nucleic acid (WGA) or MMLV reverse transcriptase and non-denatured nucleic acid (WTA), and a hypothetical device for isolation of DNA and RNA by selective amplification from total nucleic acid preparation.

Figure 46:
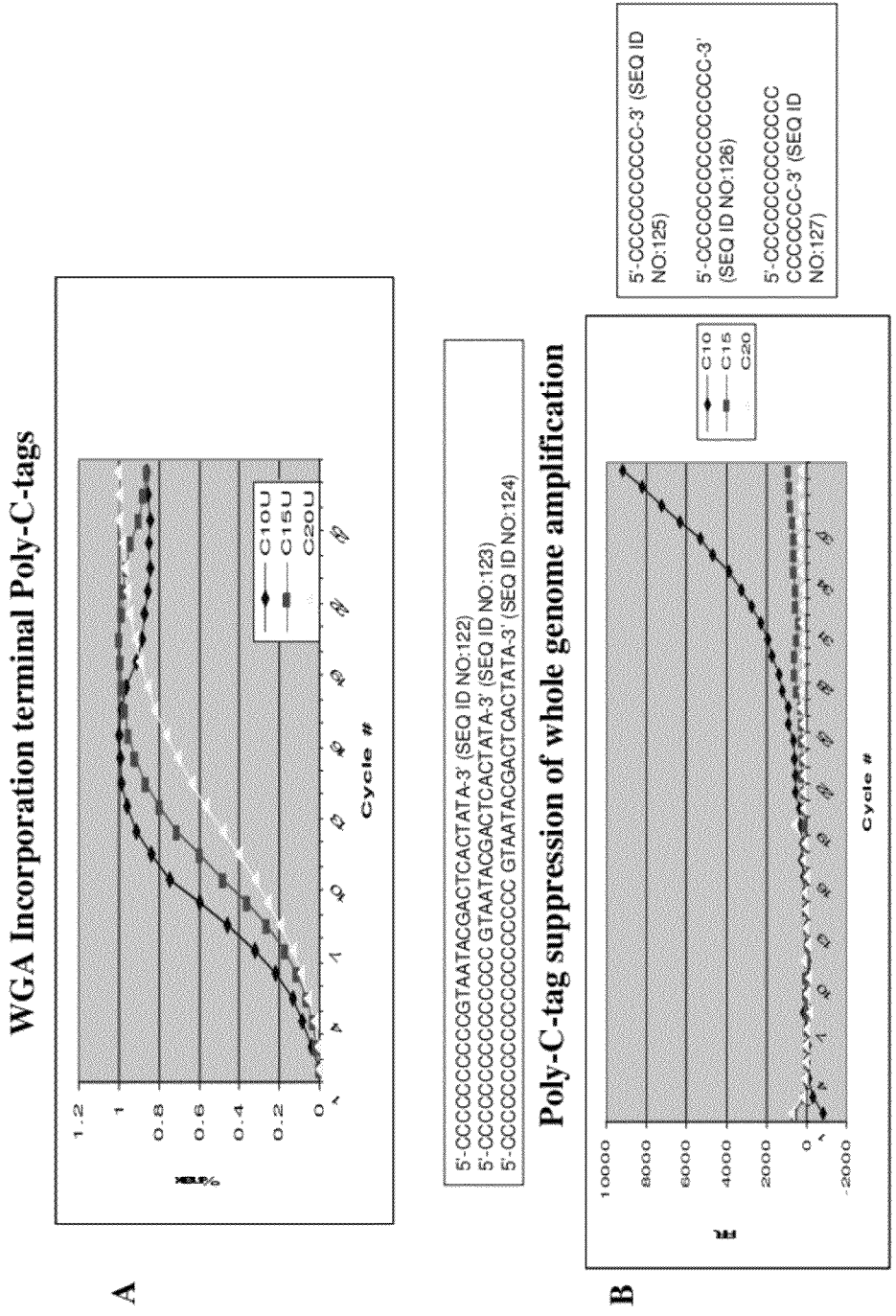

FIGS. 46A and 46B show the inhibitory effect of poly-C tags on amplification of synthesized WGA libraries. FIG. 46A shows real-time PCR amplification chromatograms of different length poly-C tags incorporated by polymerization. FIG. 46B shows delayed kinetics or suppression of amplification of C-tagged libraries amplified with corresponding poly-C primers.

FIGS. 47A and 47B display real-time PCR results of targeted amplification using a specific primer and the universal $C_{10}$ tag primer. Panel A shows the sequential shift with primary and secondary specific primers with a combined enrichment above input template concentrations. FIG. 47B shows the effect of specific primer concentration on selective amplification. Real-time PCR curves show a gradient of specific enrichment with respect to primer concentration.

Figure 48:
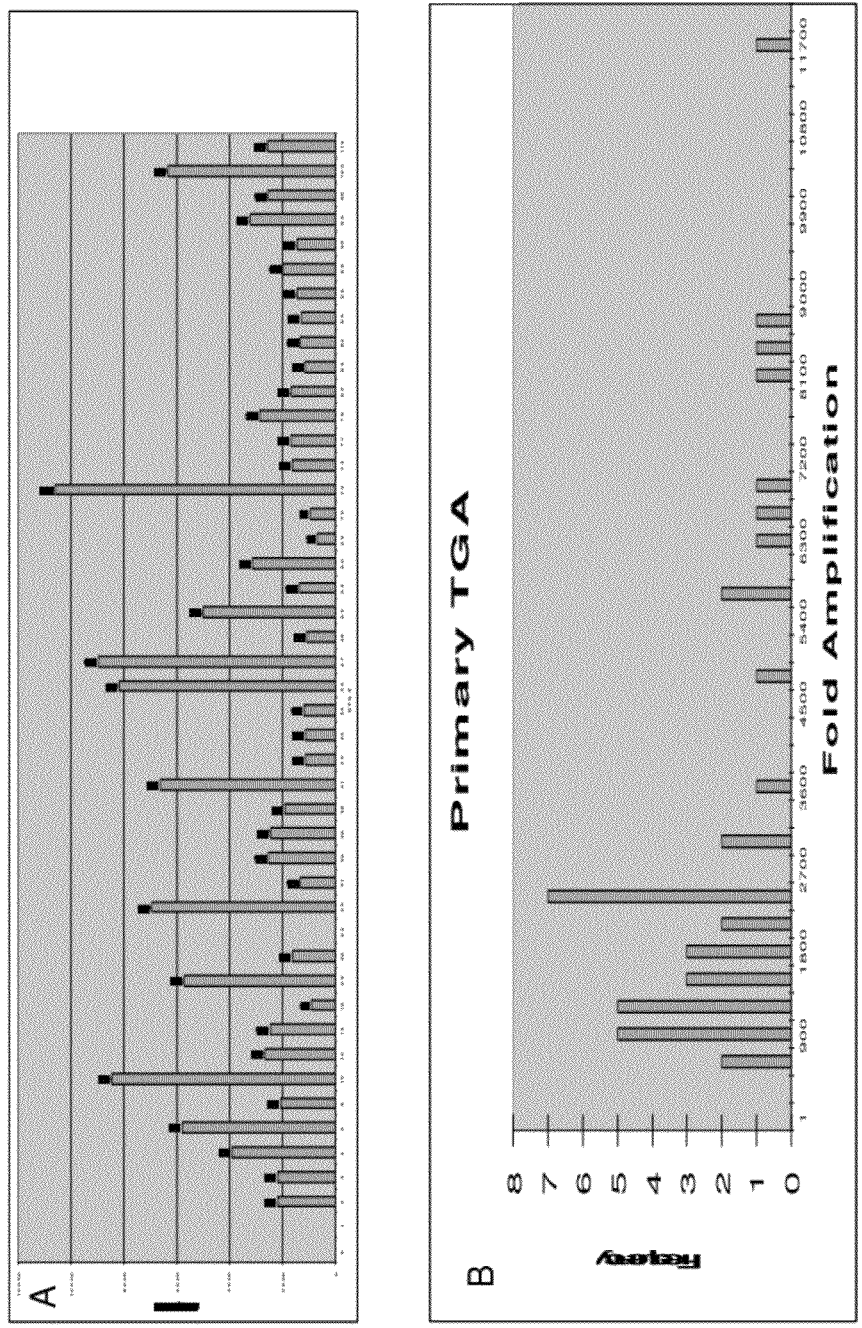

FIGS. 48A and 48B detail the individual specific site enrichment for each unique primary oligonucleotide in the multiplexed targeted amplification. FIG. 48A shows values of enrichment for each site relative to an equal amount of starting template, while FIG. 48B displays the same data as a histogram of frequency of amplification.

Figure 49:
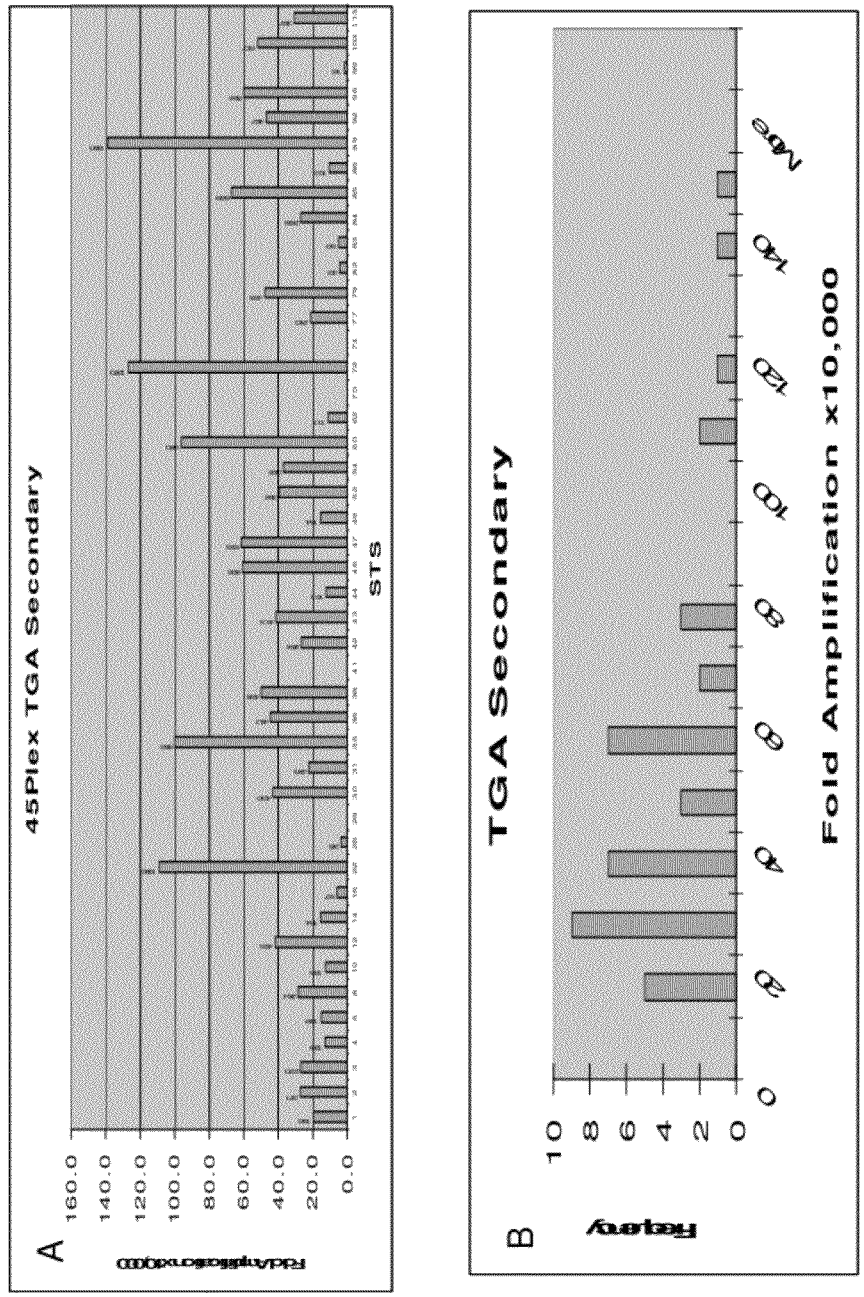

FIG. 49A shows the analysis of secondary "nested" real-time PCR results for 45 multiplexed specific primers. Enrichment is expressed as fold amplification above starting template ranging from 100,000 fold to over 1,000,000 fold. FIG. 49B shows the distribution frequency for all 45 multiplexed sites.

Figure 50:
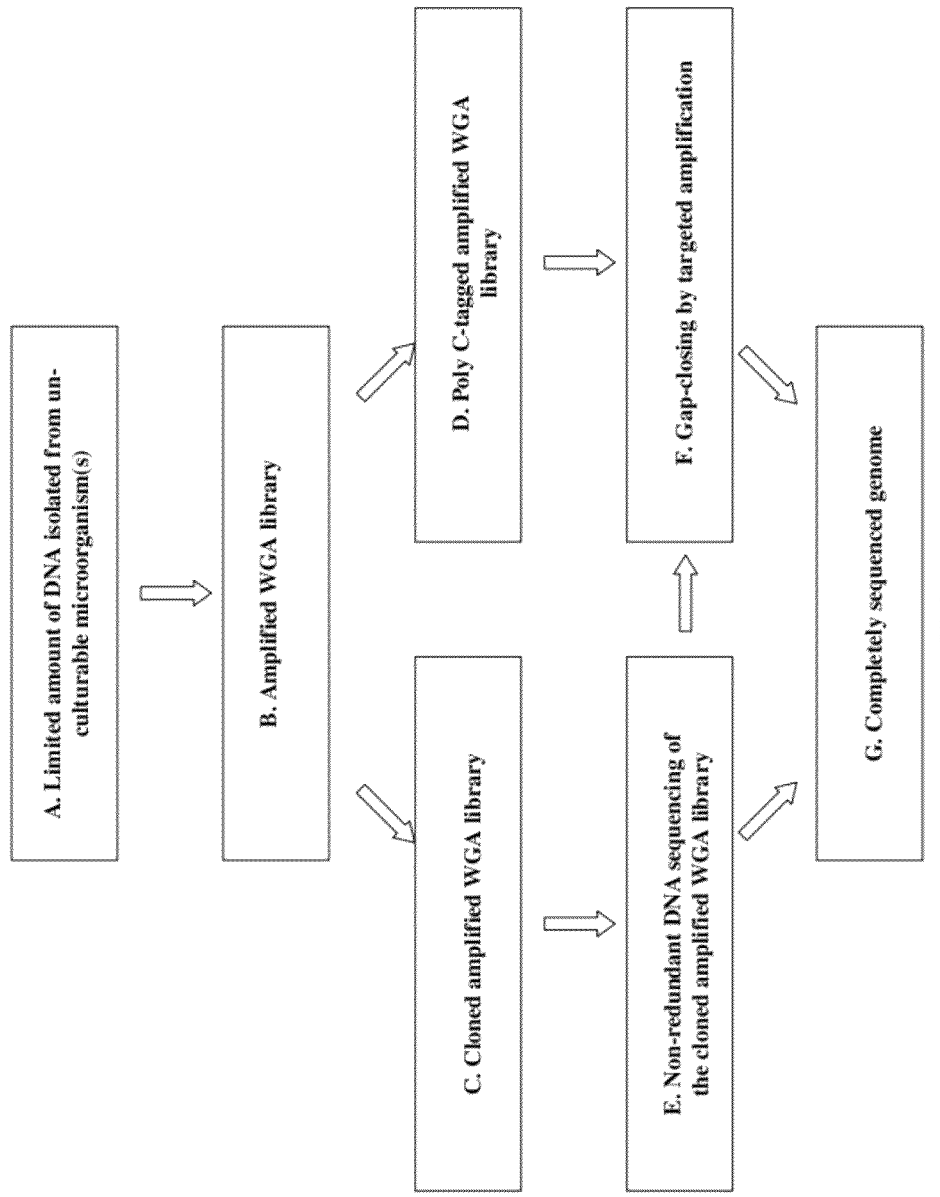

FIG. 50 shows a schematic representation of a whole genome sequencing project using tagged libraries synthesized from limited starting material. Libraries provide a means to recover precious or rare samples in an amplifiable form that can function both as substrate for cloning approaches and through conversion to C-tagged format a directed sequencing template for gap filling and primer walking.

Figure 51:
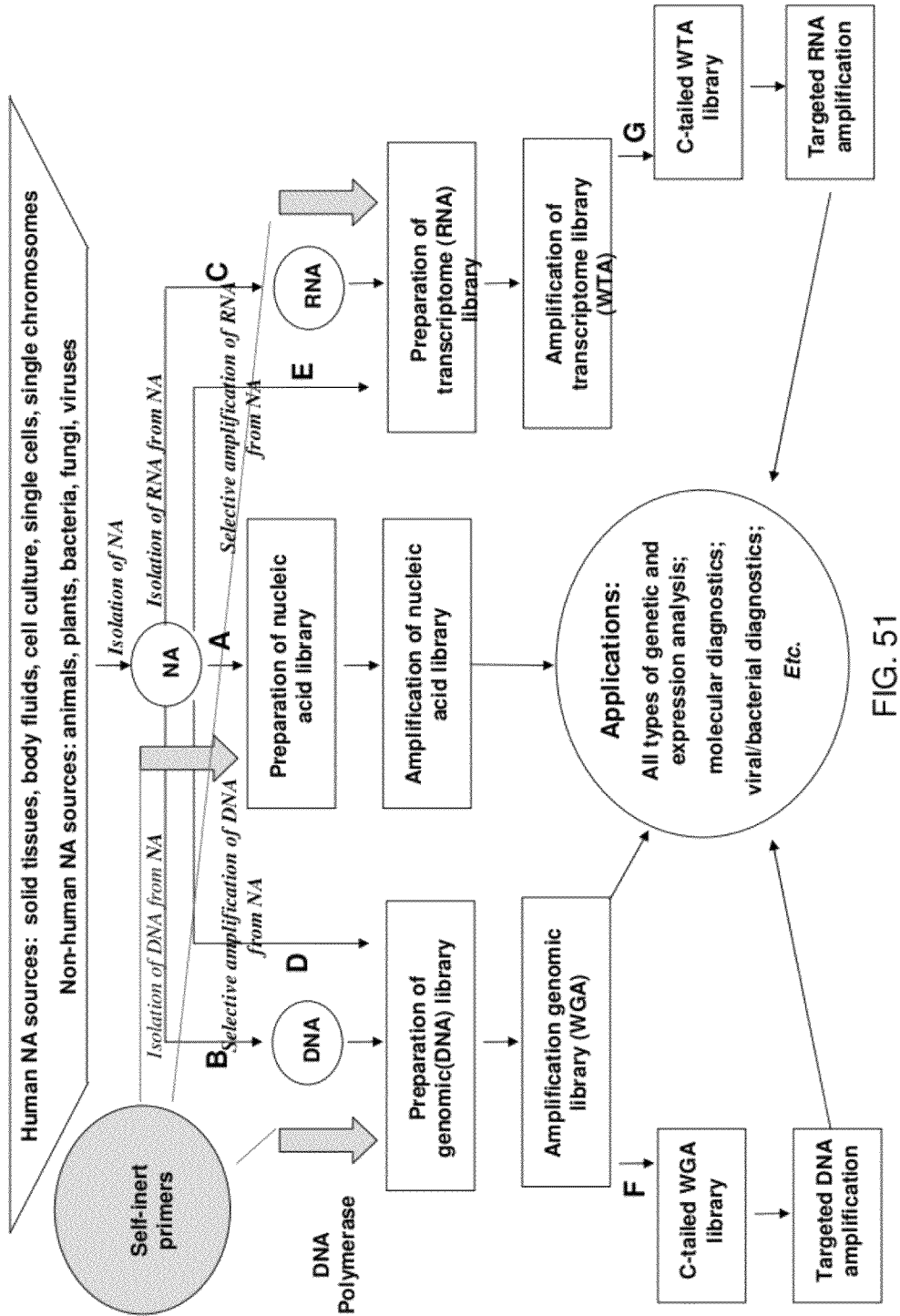

FIG. 51 shows a diagram illustrating universality of the nucleic acid amplification methods of the present invention and their compatibility with different sources of DNA or RNA, and the diversity of possible applications for the amplified material.

Figure 52:
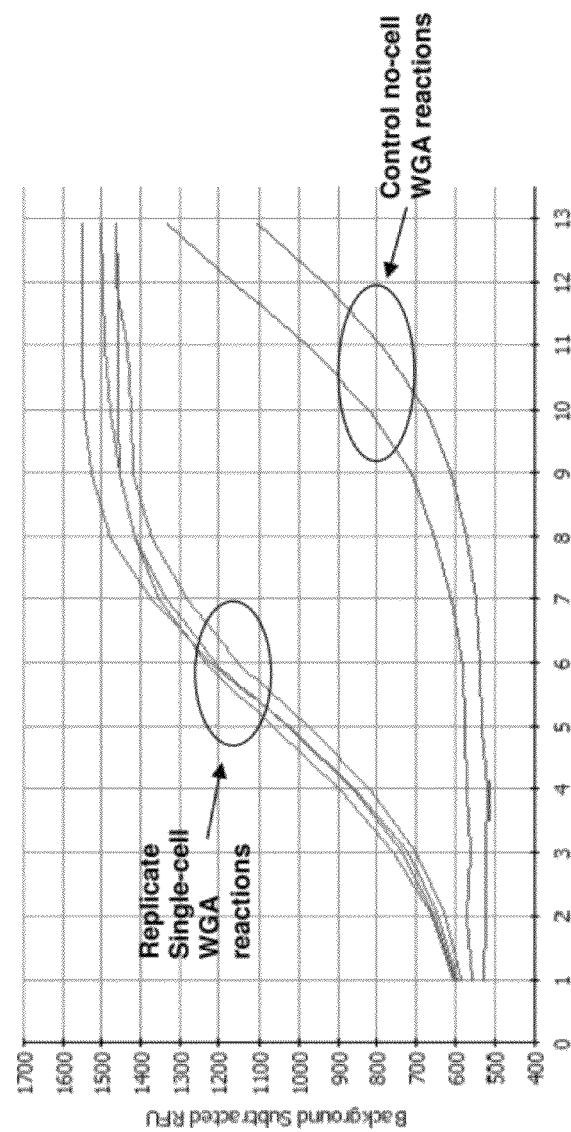

FIG. 52 demonstrates an example of Background Subtracted RFU amplification curves for replicate single-cell and control no-cell whole genome amplification (WGA) reactions monitored on a Bio-Rad I-Cycler iQ.

Figure 53:
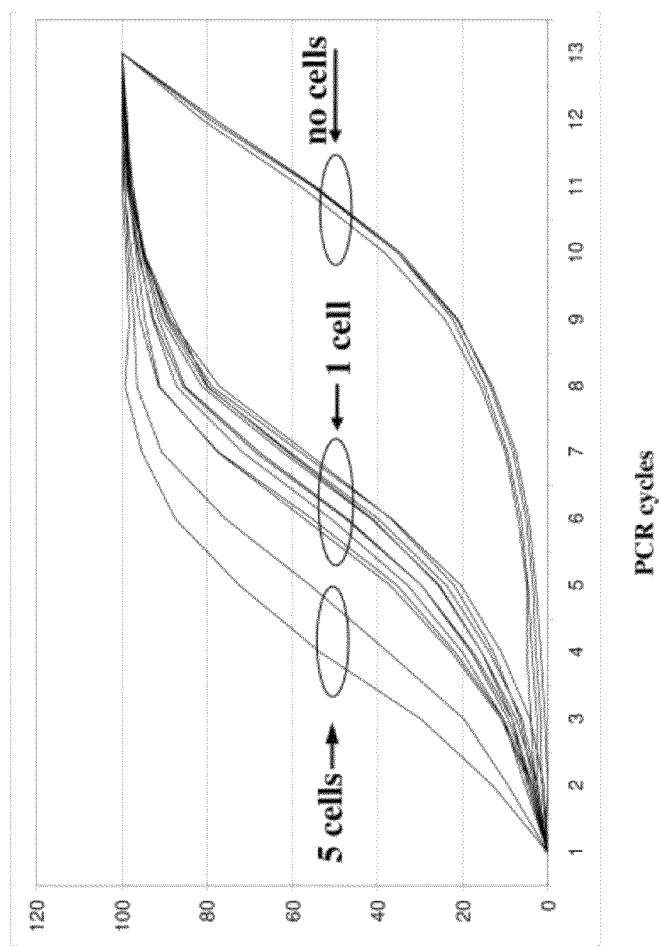

FIG. 53 shows PCR cycles for 5 cells, 1 cell and control (0 cells) as starting materials.

FIG. 54 shows locus-specific PCR QC-testing of single-cell whole genomic amplification of DNA; (A) Locus-specific PCR of genomic DNA with increasing number cell-equivalents; (B) Locus-specific PCR of whole genome-amplified DNA from 1, 10, 100, and 1000 cell-equivalents (DNA amplified from a single cell gives the same test result as from 1,000 cells).

Figure 55:
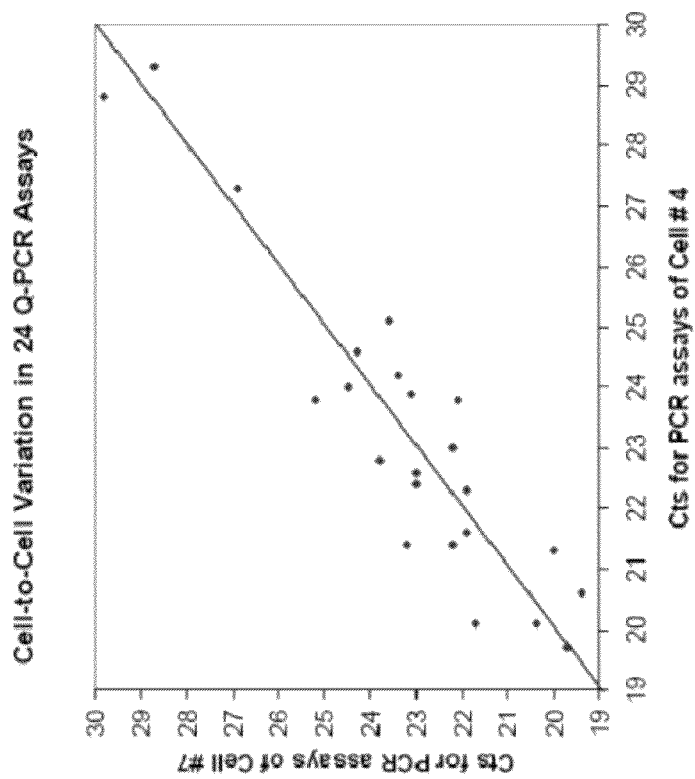

FIG. 55 compares cell to cell variation for 2 cells in 24 Q PCR assays; single-cell whole genome amplification produces highly reproducible representation of multiple loci tested in different single cells.

Figure 56:
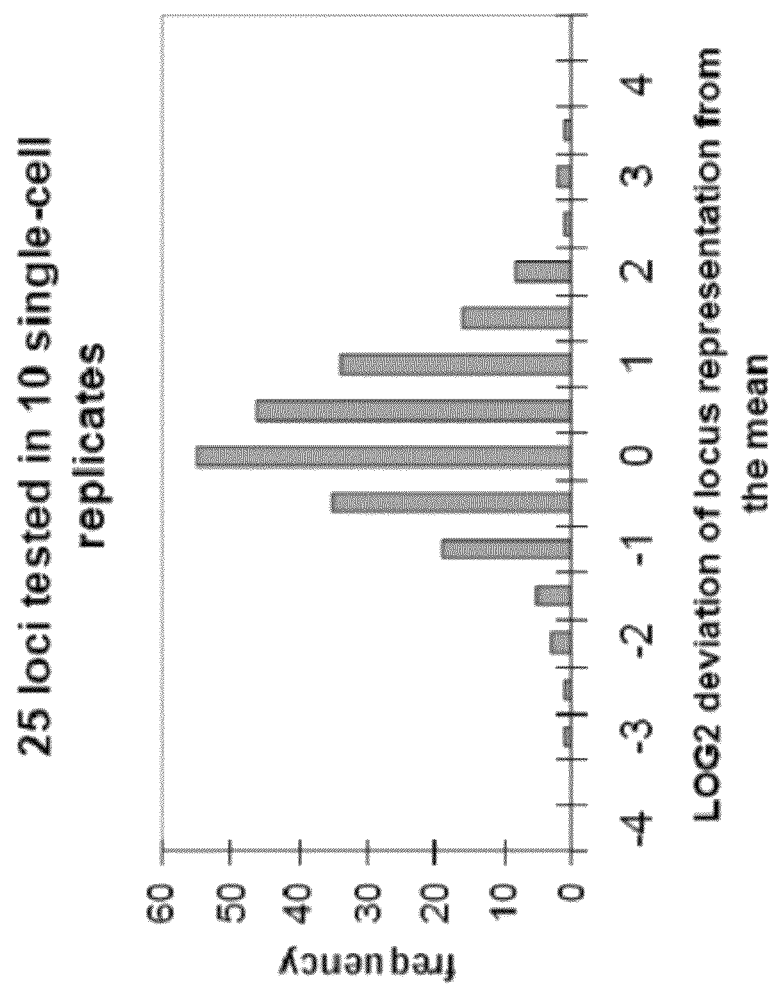

FIG. 56 illustrates reproducibility of representation, assayed by individual QPCR reactions across 10 replicate single cells.

Figure 57A:
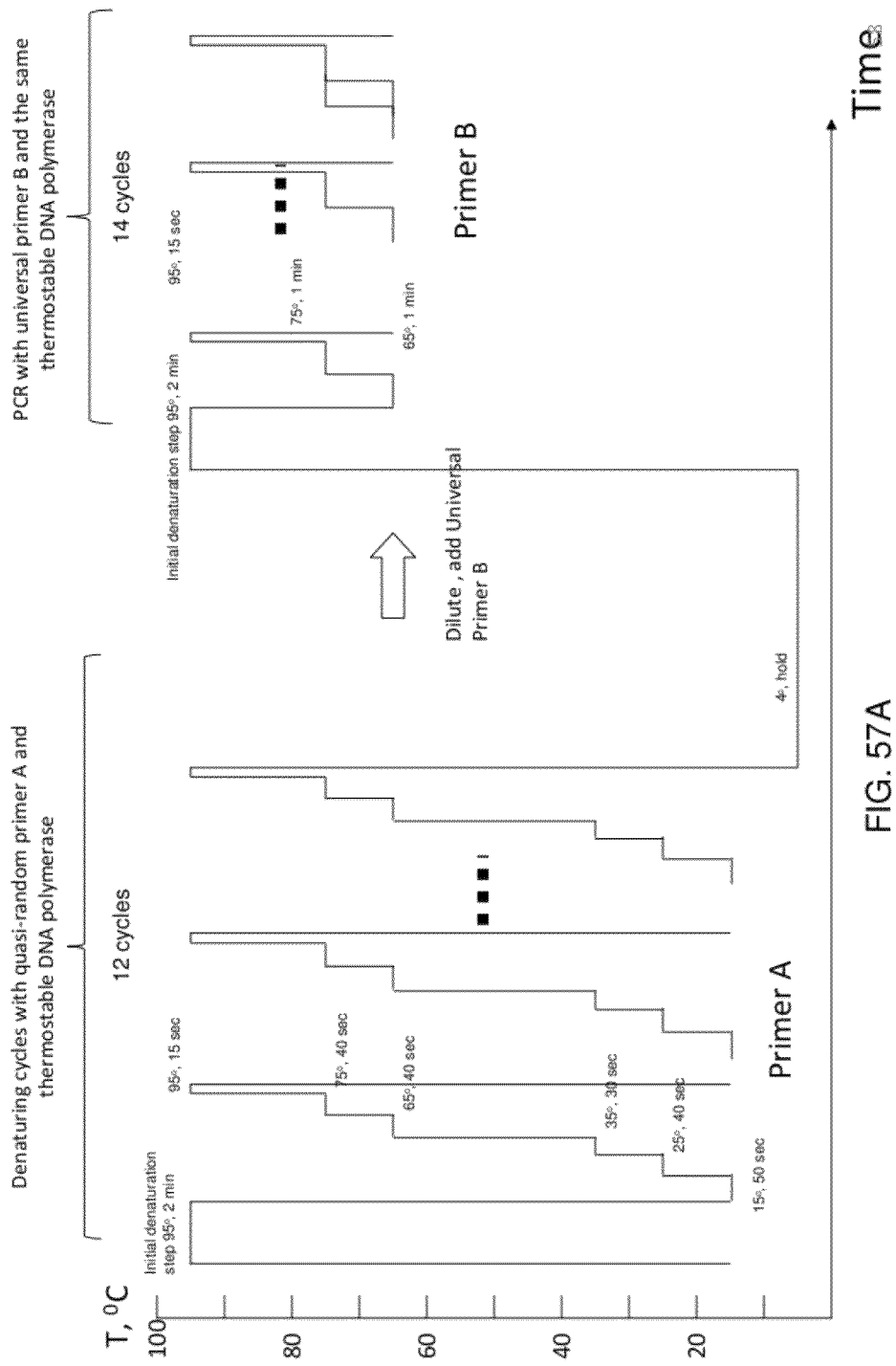
Figure 57B:
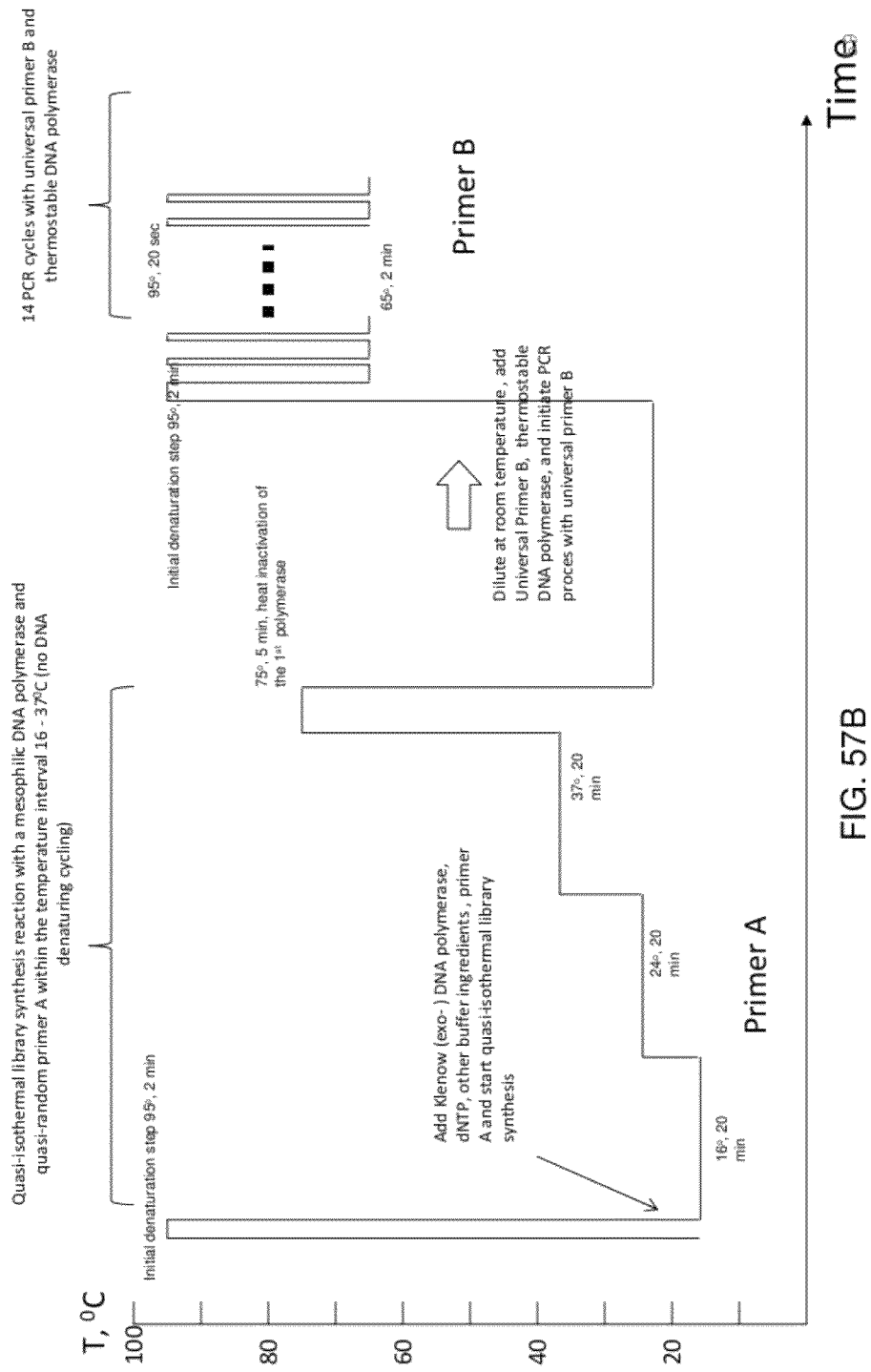

FIGS. 57A and 57B illustrate a comparison between a particular exemplary method of the claimed invention (FIG. 57A) with a method known in the art (FIG. 57B).

DETAILED DESCRIPTION OF THE INVENTION

In keeping with long-standing patent law convention, the words "a" and "an" when used in the present specification in concert with the word comprising, including the claims, denote "one or more."

The practice of the present invention will employ, unless otherwise indicated, conventional techniques of molecular biology, microbiology, recombinant DNA, and so forth which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

U.S. Provisional Patent Application No. 60/453,071, filed Mar. 7, 2003 is hereby incorporated by reference herein in its entirety. U.S. Nonprovisional patent application Ser. No. 10/797,333 is also hereby incorporated by reference herein in its entirety. U.S. Patent Application 20030143599 is also incorporated by reference herein in its entirety.

I. DEFINITIONS

The term "base analog" as used herein refers to a compound similar to one of the four DNA bases (adenine, cytosine, guanine, and thymine) but having a different composition and, as a result, different pairing properties. For example, 5-bromouracil is an analog of thymine but sometimes pairs with guanine, and 2-aminopurine is an analog of adenine but sometimes pairs with cytosine.

The term "backbone analog" as used herein refers to a compound wherein the deoxyribose phosphate backbone of DNA has been modified. The modifications can be made in a number of ways to change nuclease stability or cell membrane permeability of the modified DNA. For example, peptide nucleic acid (PNA) is a new DNA derivative with an amide backbone instead of a deoxyribose phosphate backbone. Other examples in the art include methylphosphonates.

The term "blocked 3' end" as used herein is defined as a 3' end of DNA lacking a hydroxyl group.

The term "blunt end" as used herein refers to the end of a double stranded DNA molecule having 5' and 3' ends, wherein the 5' and 3' ends terminate at the same position. Thus, the blunt end comprises no 5' or 3' overhang.

The term "complementarity" as used herein refers to the ability to form a Watson-Crick base pair through specific hydrogen bonds.

The term "contig" as used herein refers to a contiguous (continuous) sequence of DNA constructed from overlapping sequences.

The term "degenerate" as used herein refers to a nucleotide or series of nucleotides wherein the identity can be selected from a variety of choices of nucleotides, as opposed to a defined sequence. In specific embodiments, there can be a choice from two or more different nucleotides. In further specific embodiments, the selection of a nucleotide at one particular position comprises selection from only purines, only pyrimidines, or from non-pairing purines and pyrimidines.

The term "self-inert" as used herein refers to the inability of a primer or a mixture of primers to self-prime and initiate DNA synthesis in the presence of DNA polymerase and dNTPs but in the absence of other DNA templates. It may also refer to a collective set of mRNAs in a cell.

The term "DNA immortalization" as used herein refers to the conversion of a mixture of DNA molecules into a form that allows repetitive, unlimited amplification without loss of representation and/or without size reduction. In a specific embodiment, the mixture of DNA molecules comprises more than one copy of a particular DNA sequence. In another specific embodiment, the mixture of DNA molecules comprises a genome.

The term "genome" as used herein is defined as the collective gene set carried by an individual, cell, or organelle.

The term "genomic DNA" as used herein is defined as DNA material comprising the partial or full collective gene set carried by an individual, cell, or organelle.

The term "transcriptome" as used herein is defined as the collective RNA set expressed within a cell.

The term "hybridization" as used herein refers to a process of formation of double stranded DNA regions between one, two or many complementary single stranded DNA molecules. In some embodiments, however, triple stranded DNA regions are generated through hybridization.

The term "minimal redundancy" as used herein refers to a minimal number of sequenced DNA fragments that produces a contig. A skilled artisan recognizes this is as opposed to "shotgun" sequencing where high redundancy is necessary to complete all gaps. Typically, the redundancy of "shotgun" sequencing is about 10-15 (where redundancy=total amount of sequenced DNA divided by the size of the genome), whereas with minimal redundancy the redundancy may be between 1 and about 2.

The term "non-canonical or non-Watson-Crick base pair" as used herein refers to all possible interactions between bases that do not include standard (Watson-Crick) A-T and G-C pairing. In a specific embodiment, the non-canonical base pair comprises an adenine nucleobase and a guanine nucleobase, an adenine nucleobase and a cytosine nucleobase, a cytosine nucleobase and a thymidine nucleobase, a guanine nucleobase and a thymidine nucleobase, an adenine nucleobase and an adenine nucleobase, a guanine nucleobase and a guanine nucleobase, a cytosine nucleobase and a cytosine nucleobase, or a thymidine nucleobase and a thymidine nucleobase.

The term "non-complementary" refers to nucleic acid sequence that lacks the ability to form intermolecularly at least one Watson-Crick base pair through specific hydrogen bonds.

The term "non-self-complementary" refers to nucleic acid sequence that lacks the ability to form intramolecularly at least one Watson-Crick base pair through specific hydrogen bonds.

The term "non strand-displacing polymerase" as used herein is defined as a polymerase that extends until it is stopped by the presence of, for example, a downstream primer. In a specific embodiment, the polymerase lacks 5'-3' exonuclease activity.

The term "randomly fragmenting" as used herein refers to fragmenting a DNA molecule in a non-ordered fashion, such as irrespective of the sequence identity or position of the nucleotide comprising and/or surrounding the break. In a specific embodiment, the random fragmentation is mechanical, chemical, or enzymatic, by well-known methods in the art.

The term "RNA immortalization" as used herein refers to the conversion of a mixture of RNA molecules, such as a transcriptome, into a form that allows repetitive, unlimited amplification without loss of representation and/or without size reduction. In a specific embodiment, a transcriptome is defined as a collection of transcribed mRNA molecules from a cell, an individual, or an organelle.

The term "single stranded nucleic acid molecule/primer mixture" as used herein refers to a mixture comprising at least one single stranded nucleic acid molecule wherein at least one primer, as described herein, is hybridized to a region in said single stranded nucleic acid molecule. In specific embodiments, multiple degenerate primers comprise complementary sequence to at least some part of the single stranded nucleic acid molecule. In further specific embodiments, the mixture comprises a plurality of single stranded nucleic acid molecules having multiple degenerate primers hybridized thereto. In additional specific embodiments, the single stranded nucleic acid molecule is DNA or RNA.

The term "strand-displacing polymerase" as used herein is defined as a polymerase that will displace downstream fragments as it extends. In a specific embodiment, the polymerase comprises 5'-3' exonuclease activity.

The term "substantially incapable" as used herein refers to a majority of polynucleotides being incapable of an activity upon subjection to standard conditions known in the art. In a specific embodiment, the activities include self-hybridization; self-priming; hybridization to another polynucleotide in the plurality; initiation of a polymerization reaction in the plurality, or a combination thereof. In a specific embodiment, the term refers to at least about 70% of a primer molecule being comprised of two noncomplementary and non-self-complementary nucleotides, more preferably at least about 75%, more preferably at least about 80%, more preferably at least about 85%, more preferably at least about 90%, more preferably at least about 95%, more preferably at least about 97%, more preferably at least about 99%, and most preferably 100% of a primer molecule being comprised of two non-complementary and non-self-complementary nucleotides.

The term "substantially non-self-complementary and substantially non-complementary" as used herein refers to a plurality of primers that lack the ability to form intramolecularly and intermolecularly a Watson-Crick base pair through specific hydrogen bonds. In a specific embodiment, at least about 70% of a primer molecule in the plurality is comprised of two noncomplementary and non-self-complementary nucleotides, more preferably at least about 75%, more preferably at least about 80%, more preferably at least about 85%, more preferably at least about 90%, more preferably at least about 95%, more preferably at least about 97%, more preferably at least about 99%, and most preferably 100% of a primer molecule in the plurality is comprised of two noncomplementary and non-self-complementary nucleotides.

The term "thermophilic DNA polymerase, as used herein refers to a heat-stable DNA polymerase.

A skilled artisan recognizes that there is a conventional single letter code in the art to represent a selection of nucleotides for a particular nucleotide site. For example, R refers to A or G; Y refers to C or T; M refers to A or C; K refers to G or T; S refers to C or G; W refers to A or T; H refers to A or C or T; B refers to C or G or T; V refers to A or C or G; D refers to A or G or T; and N refers to A or C or G or T. Thus, a YN primer comprises at least one, and preferably more, series of dinucleotide sets each comprising a C or a T at the first position and an A, C, G, or T at the second position. These dinucleotide sets may be repeated in the primer (and/or adaptor).

II. PREPARATION OF DNA LIBRARIES FOR WHOLE GENOME AND WHOLE TRANSCRIPTOME AMPLIFICATION BY INCORPORATING A KNOWN UNIVERSAL SEQUENCE USING SELF-INERT DEGENERATE PRIMERS

In embodiments of the present invention, there is whole genome or whole transcriptome amplification comprising incorporation of known universal sequence followed by a subsequent PCR amplification step using a known universal primer complementary to at least part of the known universal sequence. In a specific embodiment, the primers for incorporating the known universal sequence comprise a degenerate region, and in further specific embodiments, the known universal sequence and the degenerate region comprise non-self-complementary nucleic acid sequence. Thus, there is significant reduction in self-hybridization and intermolecular primer hybridization compared to primers lacking non-self-complementary sequence.

Formation of primer dimers is a common problem in existing methods for DNA or RNA amplification using random primers. In order to achieve efficient priming for each individual sequence, random primers must be applied at very high concentrations. The efficiency of annealing to a specific target DNA or RNA template or the entire population of template molecules is greatly reduced by the formation of primer-dimers resulting from the high primer concentrations required for efficient priming.

Other problems known in the art when using random primers to amplify DNA include an inability to amplify the genome in its entirety due to locus dropout (loss), generation of short amplification products, and in some cases, the inability to amplify degraded or artificially fragmented DNA.

The described invention utilizes a novel type of oligonucleotide primer comprising at least as the majority of its sequence only two types of nucleotide bases that do not participate in stable Watson-Crick pairing with each other, and thus do not self-prime. The primers comprise a constant known sequence at their 5' end and a variable degenerate nucleotide sequence located 3' to the constant known sequence. There are four possible two-base combinations known not to participate in Watson-Crick base pairing: C-T, G-A, A-C and G-T. They suggest four different types of degenerate primers that should not form a single Watson-Crick base pair that could lead to the generation of primer-dimers in the presence of DNA polymerase and dNTPs. These primers are illustrated in FIG. 2A and are referred to as primers Y, R, M and K, respectively, in accordance with common nomenclature for degenerate nucleotides: Y=C or T, R=G or A, M=A or C and K=G or T.

For example, Y-primers have a 5' known sequence $Y_U$ comprised of C and T bases and a degenerate region $(Y)_{10}$ at the 3' end comprising ten, for example, randomly selected pyrimidine bases of C and T. R-primers have a 5' known sequence $R_U$ comprised of G and A bases and a degenerate region $(R)_{10}$ at the 3' end comprising ten, for example, randomly selected purine bases of G and A. M-primers have a 5' known sequence $M_U$ comprised of A and C bases and a degenerate region $(M)_{10}$ at the 3' end comprising ten for example, randomly selected bases of A and C. Finally, K-primers have a 5' known sequence $K_U$ comprised of G and T bases and a degenerate region $(K)_{10}$ at the 3' end comprising ten, for example, randomly selected bases of G and T. Primers of the described design will not self-prime and thus will not form primer dimers. For this reason, the term "self-inert primers" is used herein. However, they will prime at target sites containing the corresponding Watson-Crick base partners, albeit with reduced overall frequency compared to completely random primers. In specific embodiments, these primers under specific conditions are capable of forming primer dimers, but at a greatly reduced level compared to primers lacking such structure.

In some embodiments, these primers are supplemented with a completely random (i.e. containing any of the four bases) short nucleotide sequence at their 3' end. Such primers are shown on FIG. 2 and labeled as YN, RN, MN and KN. If a limited number of completely random bases are present at the 3' end of the Y, R, M or K primers, that will increase their priming frequency, yet maintain limited ability for self-priming. By using a different number of completely random bases at the 3' end of the degenerate Y, R, M or K primers and by carefully optimizing the reaction conditions, one can precisely control the outcome of the polymerization reaction in favor of the desired DNA product with minimum primer-dimer formation.

Figure 1:
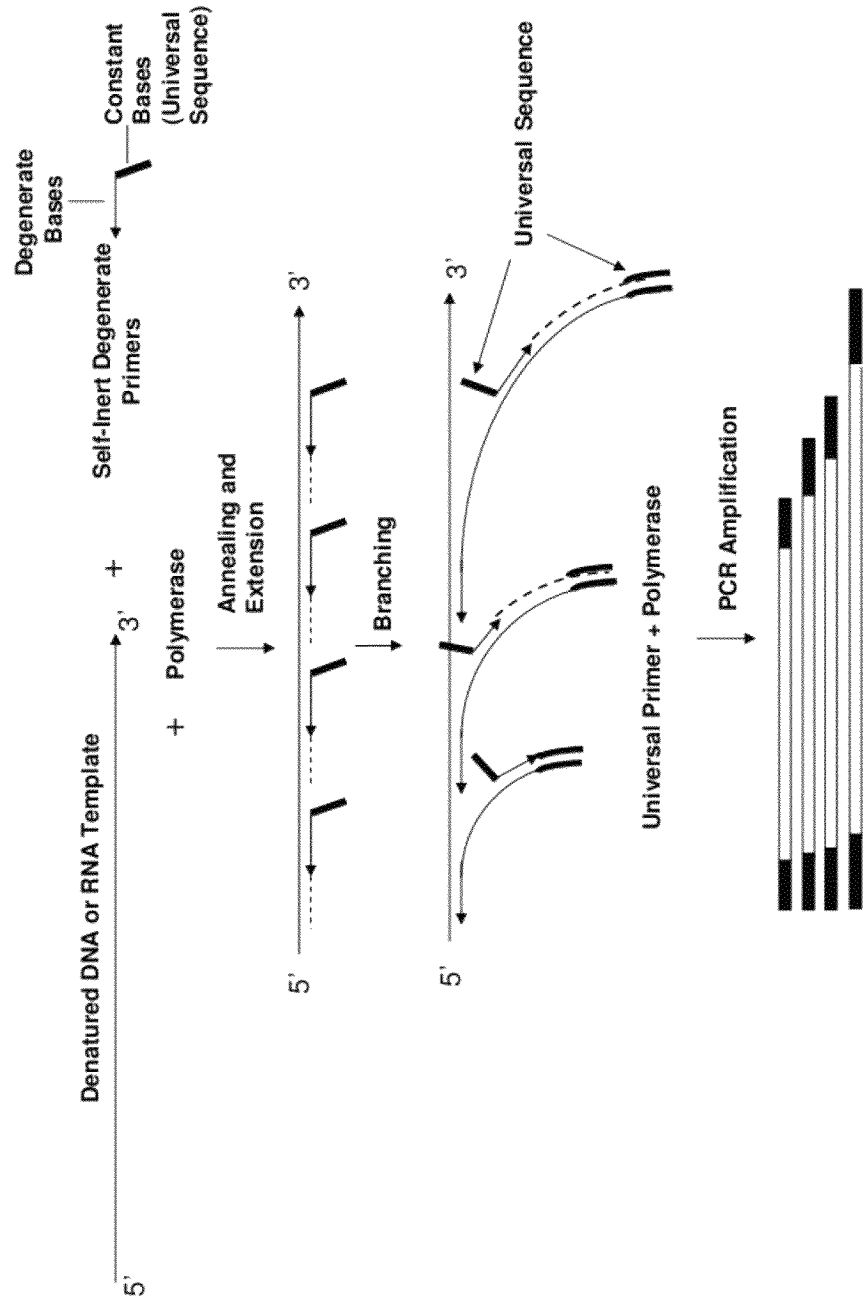
FIG. 1 illustrates a schematic presentation of whole genome and whole transcriptome amplification by incorporating known sequence with self-inert degenerate primers followed by PCR amplification. Dashed lines represent newly synthesized strands. Thicker lines represent the known sequence.

Thus, in the first step of library synthesis primers of the described design are randomly incorporated in an extension/polymerization reaction with a DNA polymerase possessing at least a limited strand-displacement activity. The resulting branching process creates DNA molecules having known (universal) self-complementary sequences at their ends. In a second step referred to as the "amplification" step, these molecules are amplified exponentially by polymerase chain reaction using Taq polymerase (or other thermostable DNA polymerase) and a single primer corresponding to at least part of the known 5'-tail of the random primers. FIG. 1 presents a schematic outline of the invention. The invention overcomes major problems known in the art for DNA and RNA amplification by previously described random primers.

1. Source of Nucleic Acid

Single-stranded or double-stranded nucleic acid of any source or complexity, or fragments thereof, can be used as a source material and amplified by the method described in the invention. That is, in some embodiments single stranded DNA is obtained and processed according to the methods described herein, and in other embodiments double stranded DNA is obtained and manipulated to generate ssDNA, wherein the ssDNA is subjected to the methods described herein. In a specific embodiment, dsDNA is denatured with heat, chemical treatment (such as alkaline pH), mechanical manipulation, radiation, or a combination thereof. In another specific embodiment, substantially single stranded RNA is obtained and processed according to the methods described herein. In a specific embodiment, total nucleic acid is obtained as a mixture of double stranded DNA and single stranded RNA molecules and then processed to selectively amplify the DNA fraction or RNA fraction only, or both separately, or both in a mixture.

2. Design of Degenerate Primers

Figure 2:
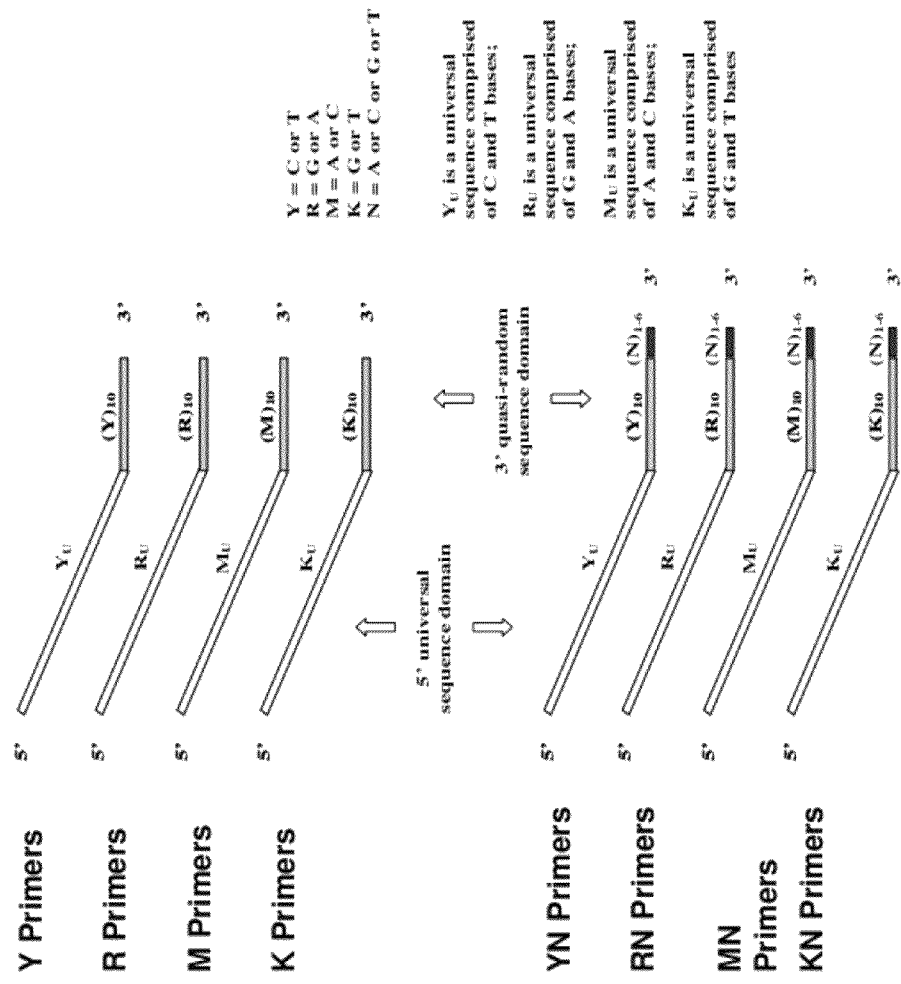
FIG. 2 is a schematic presentation of design of exemplary self-inert degenerate primers designed to eliminate their ability to form primer-dimers.

FIG. 2 illustrates the design of degenerate primers utilized in this aspect of the invention. In principle, the invention employs application of oligonucleotide primers comprising a constant known sequence at their 5' end (which may be referred to as universal sequence) and a variable degenerate nucleotide sequence at their 3' end, each comprised of any of at least four possible base combinations known not to participate in Watson-Crick base pairing. The possible primer compositions include pyrimidines only (C and T), purines only (A and G), or non-pairing purines and pyrimidines (A and C or G and T). The last combination (G and T) is known in the art to permit non-canonical Watson-Crick base-pairing. In a preferred embodiment, the G and T pair is utilized in the invention. In a specific embodiment, the primers comprise a constant part of about 18 base sequence comprised of C and T, G and A, A and C, or G and T bases at the 5' end, followed by about 10 random Y, R, M or K bases, respectively, and between 0 and about 6 completely random bases, N, at the 3' end (FIG. 2, Table III, primers 1-7). Examples 1 and 2 show that Y and YN primers form only a limited amount of primer-dimers, and this is proportional to the number of completely random bases N at their 3' termini. In contrast, a primer of similar design but comprised of bases that can participate in Watson-Crick base-pairing generates an excessive amount of primer-dimers, which greatly reduces the efficiency of DNA or RNA amplification (see Example 2).

The choice of primers will depend on the base composition, complexity, and the presence and abundance of repetitive elements in the target DNA or RNA. By combining the products of individual amplification reactions with degenerate primers comprising different non-Watson-Crick pairs, but having the same known sequence at the ends, one can achieve the highest possible level of representative and uniform DNA amplification. A skilled artisan recognizes how to select the optimal primers and reaction conditions to achieve the desired result.

Example 2 describes a comparison of different pyrimidine-only primers in their ability to form primer-dimers, efficiency of amplification, and uniformity (representation of randomly selected genomic markers) in a human whole genome amplification reaction with Klenow fragment of DNA Polymerase I. Of all pyrimidine-only primers tested, primers with two random 3' bases $(Y(N)_2)$ result in the most uniform whole genome amplification and at the same time form undetectable amounts of primer dimers. Thus, in a preferred embodiment degenerate primers comprising between about 1 and about 3 completely random bases at their 3' end are utilized.

3. Choice of DNA Polymerases

In a preferred embodiment, a DNA polymerase is utilized that possesses strand-displacement activity. Preferred strand-displacement DNA polymerases are: Klenow fragment of *E. coli* DNA polymerase I, exo– DNA polymerases of the T7 family, i.e. polymerases that require host thioredoxin subunit as co-factor, such as: T7, T3, fI, fII, W31, H, Y, gh-1, SP6, or All22, Studier (1979), exo– Bst large fragment, Bca DNA polymerase, 9oNm polymerase, MMLV Reverse Transcriptase, AMV Reverse Transcriptase, HIV Reverse Transcriptase, phage f29 polymerase, phage M2 polymerase, phage fPRD1 polymerase, exo– VENT polymerase, and phage T5 exo– DNA polymerase.

Klenow exo– fragment of DNA Polymerase I, phage T7 DNA polymerase with reduced or eliminated 3'-5' exonuclease activities, and MMLV Reverse Transcriptase are most preferred in the present invention. Thus, in a preferred embodiment the Klenow exo– fragment of DNA Polymerase I, or Sequenase version 2 is used as the polymerase for whole genome amplification (Example 2), and MMLV reverse transcriptase is used as the polymerase for whole transcriptome amplification (Example 14).

4. Reaction Conditions

In general, factors increasing priming efficiency, such as reduced temperature or elevated salt and/or $Mg^{2+}$ ion concentration, inhibit the strand-displacement activity and the rate of DNA polymerases, and elevated temperatures and low $Mg^{2+}$ ion or salt concentrations increase the efficiency of polymerization/strand-displacement but reduce the priming efficiency. On the other hand, factors promoting efficient priming also increase the chances of primer-dimer formation. Strand-displacement activity can be facilitated by several protein factors. Any polymerase that can perform strand-displacement replication, in the presence or in the absence of such strand-displacement or processivity enhancing factors, is suitable for use in the disclosed invention, even if the polymerase does not perform strand-displacement replication in the absence of such factor. Factors useful in strand-displacement replication are (i) any of a number of single-stranded DNA binding proteins (SSB proteins) of bacterial, viral, or eukaryotic origin, such as SSB protein of *E. coli*, phage T4 gene 32 product, phage T7 gene 2.5 protein, phage Pf3 SSB, replication protein A RPA32 and RPA14 subunits (Wold, 1997); (ii) other DNA binding proteins, such as adenovirus DNA-binding protein, herpes simplex protein ICP8, BMRF1 polymerase accessory subunit, herpes virus UL29 SSB-like protein; (iii) any of a number of replication complex proteins known to participate in DNA replication such as phage T7 helicase/primase, phage T4 gene 41 helicase, *E. coli* Rep helicase, *E. coli* recBCD helicase, *E. coli* and eukaryotic topoisomerases (Champoux, 2001).

The exact parameters of the polymerization reaction will depend on the choice of polymerase and degenerate primers and a skilled artisan recognizes based on the teachings provided herein how to modify such parameters. By varying the number of random bases at the 3' end of the degenerate primers and by carefully optimizing the reaction conditions, formation of primer-dimers can be kept to a minimum and at the same time the amplification efficiency and representation can be maximized.

Random fragmentation of DNA, and if necessary, RNA can be performed by mechanical, chemical, or enzymatic treatment as described. In a preferred embodiment, DNA is fragmented by heating at about 95° C. in low salt buffers such as TE (10 mM Tris-HCl, 1 mM EDTA, having pH between 7.5 and 8.5) or TE-L (10 mM Tris-HCl, 0.1 mM EDTA, having pH between 7.5 and 8.5) for between about 1 min and about 10 min (for example, see U.S. patent application Ser. No. 10/293,048, filed Nov. 13, 2002, incorporated by reference herein in its entirety).

An exemplary library synthesis reaction of the present invention is performed in a mixture having volume ranging between about 10 and about 25 μl. The reaction mixture preferably comprises about 0.5 to about 100 ng of thermally or mechanically fragmented DNA, or in particular embodiments less than about 0.5 ng DNA, about 0.5- about 30 μM of self-inert degenerate primer, about 0- about 200 nM of known sequence primer (i.e., primer corresponding to the known 5' end of the respective degenerate primer), between about 2 and about 10 units of Klenow Exo⁻ (New England Biolabs) or Sequenase version 2 (USB Corporation), between 0- about 360 ng SSB protein, and between about 5- about 10 mM $MgCl_2$, and between 0 and about 100 mM NaCl. The reaction buffer preferably has a buffering capacity that is operative at physiological pH between about 6.5 and about 9. Preferably, the incubation time of the reaction is between about 10- about 180 min, and the incubation temperature between about 12° C. and about 37° C. Incubation is performed by cycling between about 12° C. and about 37° C. for a total of 3 to 5 min per cycle, or preferably by a single isothermal step between about 12° C. and about 30° C. or sequential isothermal steps between about 12° C. and about 37° C. The reaction is terminated by addition of a sufficient amount of EDTA to chelate $Mg^{2+}$ or preferably by heat-inactivation of the polymerase, or both.

In a preferred embodiment of the present invention, the library synthesis reaction is performed in a volume of about 15 μl. The reaction mixture comprises about 5 ng or less of thermally or mechanically fragmented DNA, for example, about 2 μM of self-inert degenerate primer $K(N)_2$ comprising G and T bases at the known and degenerate regions and 2 completely random 3' bases, (Table III, primer #14), between about 2 units and about 4 units of Sequenase version 2 DNA polymerase (USB Corporation), between about 5 mM and about 10 mM $MgCl_2$, about 100 mM NaCl, about 10 mM Tris-HCl buffer having pH of about 7.5, and about 7.5 mM dithiothreitol. Preferably, the incubation time of the reaction is between about 60 min and about 120 min and the incubation temperature is about 24° C. in an isothermal mode or in another preferred embodiment by sequential isothermal steps at between about 16° C. and about 37° C.

In another preferred embodiment of the present invention, the library synthesis reaction is performed in a volume of about 20 μl. The reaction mixture comprises about 25 ng or less of thermally or fragmented or unfragmented RNA, for example, about 1 μM of self-inert degenerate primer $K(N)_2$ comprising G and T bases at the known and degenerate regions and 2 completely random 3' bases, (Table III, primer #14), about 200 nM of a primer $K(T)_{20}$ comprising G and T bases at the 5' known and poly T bases at the 3' end (Table III, primer #19) between about 50 units and about 200 units of MMLV Reverse transcriptase (Epicentre Corporation), between about 3 mM and about 10 mM $MgCl_2$, about 75 mM KCl, about 50 mM Tris-HCl buffer having pH of about 8.3, and about 10 mM dithiothreitol. Preferably, the incubation time of the reaction is between about 30 min and about 120 min and the incubation temperature is about 42° C. in an isothermal mode or in another preferred embodiment by sequential isothermal steps at between about 24° C. and about 42° C.

A typical amplification step with known sequence primer comprises between about 1 and about 10 ng of library synthesis products and between about 0.3 and about 2 μM of known sequence primer in a standard PCR reaction well known in the art, under conditions optimal for thermostable DNA polymerases, such as Taq DNA polymerase, Pfu polymerase, or derivatives and mixtures thereof. For sequences known to be difficult to amplify, such as those high in G/C content that are known otherwise to benefit from PCR optimization efforts such as temperature and time of denaturation and polymerization steps, reaction additives such as DMSO and/or 7-Deaza dGTP may also improve representation in libraries constructed by the method of the invention.

III. NUCLEIC ACIDS

The term "nucleic acid" or "polynucleotide" will generally refer to at least one molecule or strand of DNA, RNA, DNA-RNA chimera or a derivative or analog thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "nucleic acid" encompasses the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially, or fully complementary to at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double stranded nucleic acid by the prefix "ds", and a triple stranded nucleic acid by the prefix "ts."

Nucleic acid(s) that are "complementary" or "complement(s)" are those that are capable of base-pairing according to the standard Watson-Crick, Hoogsteen or reverse Hoogsteen binding complementarity rules. However, in a specific embodiment, a primer of the present invention comprises a majority of nucleotides that are incapable of forming standard Watson-Crick base pairs, particularly with other nucleotides within the same primer.

As used herein, the term "complementary" or "complement(s)" may refer to nucleic acid(s) that are substantially complementary, as may be assessed by the same nucleotide comparison set forth above. The term "substantially complementary" may refer to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double stranded nucleic acid molecule during hybridization. In certain embodiments, the term "substantially complementary" refers to at least one nucleic acid that may hybridize to at least one nucleic acid strand or duplex in stringent conditions. In certain embodiments, a "partially complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating at least one nucleic acid, such as a gene or nucleic acid segment thereof, or detecting at least one specific mRNA transcript or nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence of formamide, tetramethylammonium chloride or other solvent(s) in the hybridization mixture. It is generally appreciated that conditions may be rendered more stringent, such as, for example, the addition of increasing amounts of formamide.

It is also understood that these ranges, compositions and conditions for hybridization are mentioned by way of non-limiting example only, and that the desired stringency for a particular hybridization reaction is often determined empirically by comparison to one or more positive or negative controls. Depending on the application envisioned, it is preferred to employ varying conditions of hybridization to achieve varying degrees of selectivity of the nucleic acid(s) towards target sequence(s). In a non-limiting example, identification or isolation of related target nucleic acid(s) that do not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

As used herein a "nucleobase" refers to a naturally occurring heterocyclic base, such as A, T, G, C or U ("naturally occurring nucleobase(s)"), found in at least one naturally occurring nucleic acid (i.e. DNA and RNA), and their naturally or non-naturally occurring chimeras, derivatives, and analogs. Non-limiting examples of nucleobases include purines and pyrimidines, as well as derivatives and analogs thereof, which generally can form one or more hydrogen bonds ("anneal" or "hybridize") with at least one naturally occurring nucleobase in a manner that may substitute for naturally occurring nucleobase pairing (e.g. the hydrogen bonding between A and T, G and C, and A and U).

As used herein, a "nucleotide" refers to a nucleoside further comprising a "backbone moiety" generally used for the covalent attachment of one or more nucleotides to another molecule or to each other to form one or more nucleic acids. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety, and non-limiting examples are described herein.

IV. AMPLIFICATION OF NUCLEIC ACIDS

Nucleic acids useful as templates for amplification are generated by methods described herein. In a specific embodiment, the DNA molecule from which the methods generate the nucleic acids for amplification may be isolated from cells, tissues or other samples according to standard methodologies (Sambrook et al., 1989).

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety. Briefly, two synthetic oligonucleotide primers, which are complementary to two regions of the template DNA (one for each strand) to be amplified, are added to the template DNA (that need not be pure), in the presence of excess deoxynucleotides (dNTP's) and a thermostable polymerase, such as, for example, Taq (*Thermus aquaticus*) DNA polymerase. In a series (typically 30-35) of temperature cycles, the target DNA is repeatedly denatured (around 95° C.), annealed to the primers (typically at 50-60° C.) and a daughter strand extended from the primers (72° C.). As the daughter strands are created they act as templates in subsequent cycles. Thus, the template region between the two primers is amplified exponentially, rather than linearly.

A reverse transcriptase PCR™ amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR™ are described in U.S. Pat. No. 5,882,864.

A. LCR

Another method for amplification is the ligase chain reaction ("LCR"), disclosed in European Patent Application No. 320,308, incorporated herein by reference. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

B. Qbeta Replicase

Qbeta Replicase, described in PCT Patent Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which can then be detected and quantified

C. Isothermal Amplification

An isothermal amplification method, in which restriction endonucleases and ligases are used to achieve the amplification of target molecules that contain nucleotide thiophosphates in one strand of a restriction site also may be useful in the amplification of nucleic acids in the present invention. Such an amplification method is described by Walker et al. 1992, incorporated herein by reference.

D. Strand Displacement Amplification

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA.

E. Cyclic Probe Reaction

Target specific sequences can also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

F. Transcription-Based Amplification

Other nucleic acid amplification procedures include transcription-based amplification systems (TAS), including nucleic acid sequence based amplification (NASBA) and 3SR, Kwoh et al., 1989; PCT Patent Application WO 88/10315, each incorporated herein by reference).

In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of a second target specific primer, followed by polymerization. The double-stranded DNA molecules are then multiply transcribed by an RNA polymerase, such as T7 or SP6. In an isothermal cyclic reaction, the RNAs are reverse transcribed into double stranded DNA, and transcribed once again with an RNA polymerase, such as T7 or SP6. The resulting products, whether truncated or complete, indicate target specific sequences.

G. Rolling Circle Amplification

Rolling circle amplification (U.S. Pat. No. 5,648,245) is a method to increase the effectiveness of the strand displacement reaction by using a circular template. The polymerase, which does not have a 5' exonuclease activity, makes multiple copies of the information on the circular template as it makes multiple continuous cycles around the template. The length of the product is very large—typically too large to be directly sequenced. Additional amplification is achieved if a second strand displacement primer is added to the reaction using the first strand displacement product as a template.

H. Other Amplification Methods

Other amplification methods, as described in British Patent Application No. GB 2,202,328, and in PCT Patent Application No. PCT/US89/01025, each incorporated herein by reference, may be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Miller et al., PCT Patent Application WO 89/06700 (incorporated herein by reference) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts.

Other suitable amplification methods include "RACE" and "one-sided PCR™" (Frohman, 1990; Ohara et al., 1989, each herein incorporated by reference). Methods based on ligation of two (or more) oligonucleotides in the presence of nucleic acid having the sequence of the resulting "di-oligonucleotide", thereby amplifying the di-oligonucleotide, also may be used in the amplification step of the present invention, Wu et al., 1989, incorporated herein by reference).

V. ENZYMES

Enzymes that may be used in conjunction with the invention include nucleic acid modifying enzymes listed in the following tables.

TABLE I

| POLYMERASES AND REVERSE TRANSCRIPTASES |
|---|
| Thermostable DNA Polymerases: |
| OmniBase ™ Sequencing Enzyme |
| Pfu DNA Polymerase |

TABLE I-continued

POLYMERASES AND REVERSE TRANSCRIPTASES

Taq DNA Polymerase
Taq DNA Polymerase, Sequencing Grade
TaqBead ™ Hot Start Polymerase
AmpliTaq Gold
Tfl DNA Polymerase
Tli DNA Polymerase
Tth DNA Polymerase
DNA Polymerases:

DNA Polymerase I, Klenow Fragment, Exonuclease Minus
DNA Polymerase I
DNA Polymerase I Large (Klenow) Fragment
Terminal Deoxynucleotidyl Transferase
T4 DNA Polymerase
Reverse Transcriptases:

AMV Reverse Transcriptase
MMLV Reverse Transcriptase
HIV Reverse Transcriptase

TABLE II

DNA/RNA MODIFYING ENZYMES

Ligases:

T4 DNA Ligase
Kinases

T4 Polynucleotide Kinase

VI. DNA POLYMERASES

In a preferred embodiment, a DNA polymerase is used in methods of the present invention. In some embodiments, it is envisioned that the methods of the invention could be carried out with one or more enzymes where multiple enzymes combine to carry out the function of a single DNA polymerase molecule retaining 5'-3' exonuclease activities. Effective polymerases that retain 5'-3' exonuclease activity include, for example, E. coli DNA polymerase I, Taq DNA polymerase, S. pneumoniae DNA polymerase I, Tfl DNA polymerase, D. radiodurans DNA polymerase I, Tth DNA polymerase, Tth XL DNA polymerase, M. tuberculosis DNA polymerase I, M. thermoautotrophicum DNA polymerase I, Herpes simplex-1 DNA polymerase, E. coli DNA polymerase I Klenow fragment, Vent DNA polymerase, thermosequenase and wild-type or modified T7 DNA polymerases. In preferred embodiments, the effective polymerase is E. coli DNA polymerase I, Klenow, or Taq DNA polymerase, or MMLV reverse transcriptase.

Where a break in the substantially double stranded nucleic acid template is a gap of at least a base or nucleotide in length that comprises, or is reacted to comprise, a 3' hydroxyl group, the range of effective polymerases that may be used is even broader. In such aspects, the effective polymerase may be, for example, E. coli DNA polymerase I, Taq DNA polymerase, S. pneumoniae DNA polymerase I, Tfl DNA polymerase, D. radiodurans DNA polymerase I, Tth DNA polymerase, Tth XL DNA polymerase, M. tuberculosis DNA polymerase I, M. thermoautotrophicum DNA polymerase I, Herpes simplex-1 DNA polymerase, E. coli DNA polymerase I Klenow fragment, T4 DNA polymerase, Vent DNA polymerase, thermosequenase or a wild-type or modified T7 DNA polymerase. In preferred aspects, the effective polymerase is E. coli DNA polymerase I, M. tuberculosis DNA polymerase I, Taq DNA polymerase, or T4 DNA polymerase.

VII. HYBRIDIZATION

Depending on the application envisioned, one would desire to employ varying conditions of hybridization to achieve varying degrees of selectivity of the probe or primers for the target sequence, such as in the adaptor. For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 35 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Design of Degenerate Pyrimidine Primers and Analysis of Self-Priming and Extension Pyrimidine primers comprising a constant 18 base sequence, followed by 10 random pyrimidines and between 0 and 6 completely random bases at the 3' end (Table III, primers 1-7), are compared for their ability to self prime and to extend a model template oligonucleotide.

TABLE III

OLIGONUCLEOTIDE SEQUENCES

| No | Code | Sequence 5'-3'* | |
|---|---|---|---|
| 1. | Y | CCTTTCTCTCCCTTCTCTYYYYYYYYYY | (SEQ ID NO: 11) |
| 2. | YN | CCTTTCTCTCCCTTCTCTYYYYYYYYYYN | (SEQ ID NO: 12) |
| 3. | Y(N)$_2$ | CCTTTCTCTCCCTTCTCTYYYYYYYYYYNN | (SEQ ID NO: 13) |
| 4. | Y(N)$_3$ | CCTTTCTCTCCCTTCTCTYYYYYYYYYYNNN | (SEQ ID NO: 14) |
| 5. | Y(N)$_4$ | CCTTTCTCTCCCTTCTCTYYYYYYYYYYNNNN | (SEQ ID NO: 15) |
| 6. | Y(N)$_5$ | CCTTTCTCTCCCTTCTCTYYYYYYYYYYNNNNN | (SEQ ID NO: 16) |
| 7. | Y(N)$_6$ | CCTTTCTCTCCCTTCTCTYYYYYYYYYYNNNNNN | (SEQ ID NO: 17) |
| 8. | Y$_U$ | CCTTTCTCTCCCTTCTCT | (SEQ ID NO: 18) |
| 9. | Template | GTAATACGACTCACTATAGGRRRRRRRRRR | (SEQ ID NO: 19) |
| 10. | R(N)$_2$ | AGAGAAGGGAGAGAAAGGRRRRRRRRRRNN | (SEQ ID NO: 20) |
| 11. | R$_U$ | AGAGAAGGGAGAGAAAGG | (SEQ ID NO: 21) |
| 12. | M(N)$_2$ | CCAAACACACCCAACACAMMMMMMMMMMNN | (SEQ ID NO: 22) |
| 13. | M$_U$ | CCAAACACACCCAACACA | (SEQ ID NO: 23) |
| 14. | K(N)$_2$ | TGTGTTGGGTGTGTTTGGKKKKKKKKKKNN | (SEQ ID NO: 24) |
| 15. | K | TGTGTTGGGTGTGTTTGGKKKKKKKKKK | (SEQ ID NO: 25) |
| 16. | K$_U$ | TGTGTTGGGTGTGTTTGG | (SEQ ID NO: 26) |
| 17. | T7(N)$_6$ | GTAATACGACTCACTATAGGNNNNNN | (SEQ ID NO: 27) |
| 18. | T7 | GTAATACGACTCACTATAGG | (SEQ ID NO: 28) |
| 19. | K(T20) | TGTGTTGGGTGTGTTTGGTTTTTTTTTTTTTTTTTTTT | (SEQ ID NO: 29) |

\* Random bases definitions:
Y = C or T; R = A or G; M = A or C; K = G or T

Figure 3:
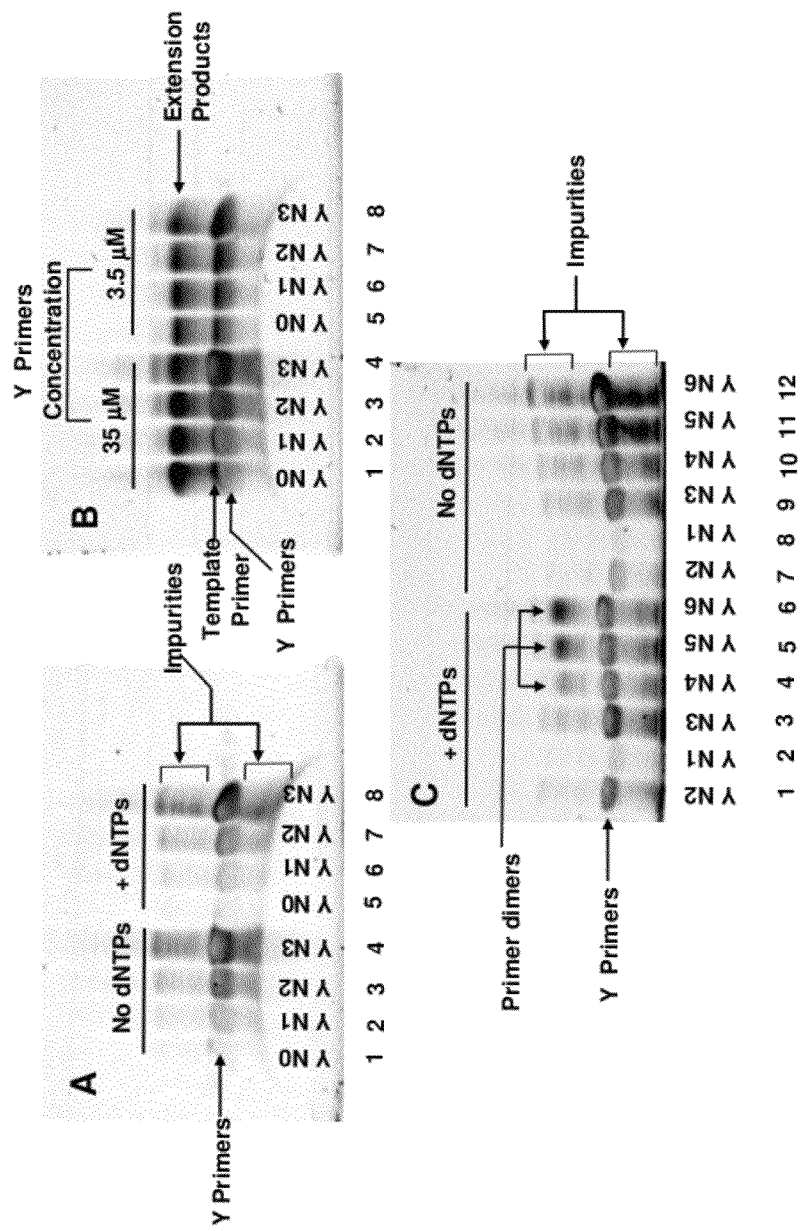
FIGS. 3A through 3C provide an analysis of self-priming and extension of degenerate YN-primers (primers containing from 0 to about 6 completely random bases (N) at the 3' end, 10 degenerate pyrimidine bases Y, and the known pyrimidine sequence YU at the 5' end (FIG. 2)).

The model template oligonucleotide (Table III, Oligonucleotide 9) was comprised of T7 promoter sequence followed by 10 random purine bases at its 3'-terminus. The reaction mixture contained 1× ThermoPol reaction buffer (NEB), 4 units of Bst DNA Polymerase Large Fragment (NEB), 200 uM dNTPS, 350 nM template oligo 9, and 3.5 or 35 µM of degenerate pyrimidine primers Y and YN (Table III, primers 1 to 7) in a final volume of 25 µl Controls comprising no dNTPs are also included for each Y or YN primer. Samples were incubated for 5 min or 15 min at 45° C. and stopped by adding 2 µl of 0.5 M EDTA. Aliquots of the reactions were analyzed on 10% TB-urea denaturing polyacrylamide gels (Invitrogen) after staining with SybrGold dye (Molecular Probes). FIG. 3 shows the result of the comparison experiment. No evidence of self-priming was found with primers having up to 3 random bases at their 3'-end when applied at 35 µM concentration after 5 min incubation with Bst polymerase and dNTPs at 45° C. (FIG. 3A). In contrast, in the samples containing template oligonucleotide, a new band corresponding to extension products was observed at both 35 µM and 3.5 µM primers concentration (FIG. 3B). In a separate experiment degenerate pyrimidine primers having up to six random bases at the 3'-end were analyzed for their ability to self-prime (FIG. 3C). After 15 min of incubation with Bst polymerase, no extension products were observed with primers having 3 random bases or less (FIG. 3C, lanes 1-3), whereas the primers with higher complexity (N3 and above) showed progressively increasing amount of extension products (FIG. 3C, lanes 4-6). Control samples incubated with Bst polymerase but no dNTPs, showed no extension products (FIG. 3C, lanes 7-12).

Example 2

Figure 4:
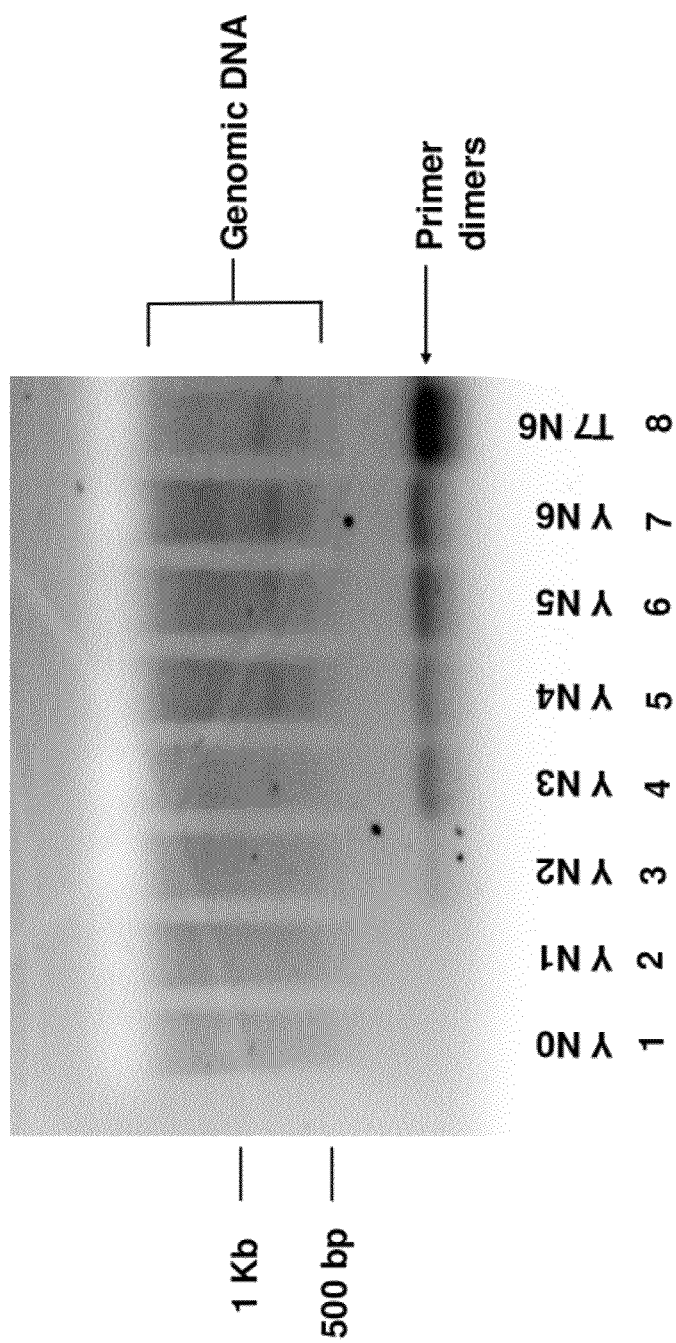
FIG. 4 shows an assay for primer-dimer formation by degenerate YN primers having from 0 to 6 completely random bases at the 3' end or by a primer comprised of T7 promoter sequence at the 5' region and 6 completely random bases at the 3' end (Table III, primer 17) in human whole genome amplification with the Klenow Exo– fragment of DNA Polymerase I. The number of completely random bases (N) is shown at the end of each primer's abbreviation.

Comparison of Different Degenerate Pyrimidine Primers Used in the Library Synthesis with Klenow Exo– Fragment of DNA Polymerase-I and Subsequent Whole Genome Amplification Human lymphocyte genomic DNA isolated by standard procedures was randomly fragmented in TE buffer to an average size of 1.5 Kb using the Hydro Shear™ device (Gene Machines; Palo Alto, Calif.). The reaction mixture contained 50 ng of fragmented DNA in 1× EcoPol buffer (NEB), 200 µM of each dNTP, 360 ng of Single Stranded DNA Binding Protein (USB), 500 nM of known Y$_U$ primer (Table III, primer 8), and 1 µM of degenerate pyrimidine primers with 0 to 6 random 3' bases (Table III, primers 1-7) or 1 µM of T7 primer with six random N bases at the 3' end (Table III, T7(N)$_6$ primer 16,) in a final volume of 25 µl. After a denaturing step of 2 min at 95° C., the samples were cooled to 16° C., and the reaction was initiated by adding 5 units of Klenow enzyme that lacks 3'-5' exonuclease activity (NEB). WGA library synthesis was carried out in a three-step protocol for 10 min at 16° C., 10 min at 24° C., and 15 min at 37° C. Reactions were stopped with 1 µl of 250 mM EDTA (pH 8.0), and samples were heated for 3 min at 95° C. Aliquots were analyzed on a 1% agarose gel after staining with EtBr (FIG. 4). FIG. 4 shows that under the conditions used in the assay, primer dimers were formed only when using YN primers with 3 or more completely random 3' bases. The amount of dimers increased progressively with an increase in the number of random bases (FIG. 4, lanes 4-7). In contrast, no primer dimers were formed when using primers with up to 2 completely random 3' bases (FIG. 4, lanes 1-3). When a primer containing a constant T7 promoter sequence (which contains both purines and pyrimidines) and completely random hexamers at its 3' end was used (Table III, primer 16), excessive amount of dimers was generated (FIG. 4, lane 8).

Figure 5:
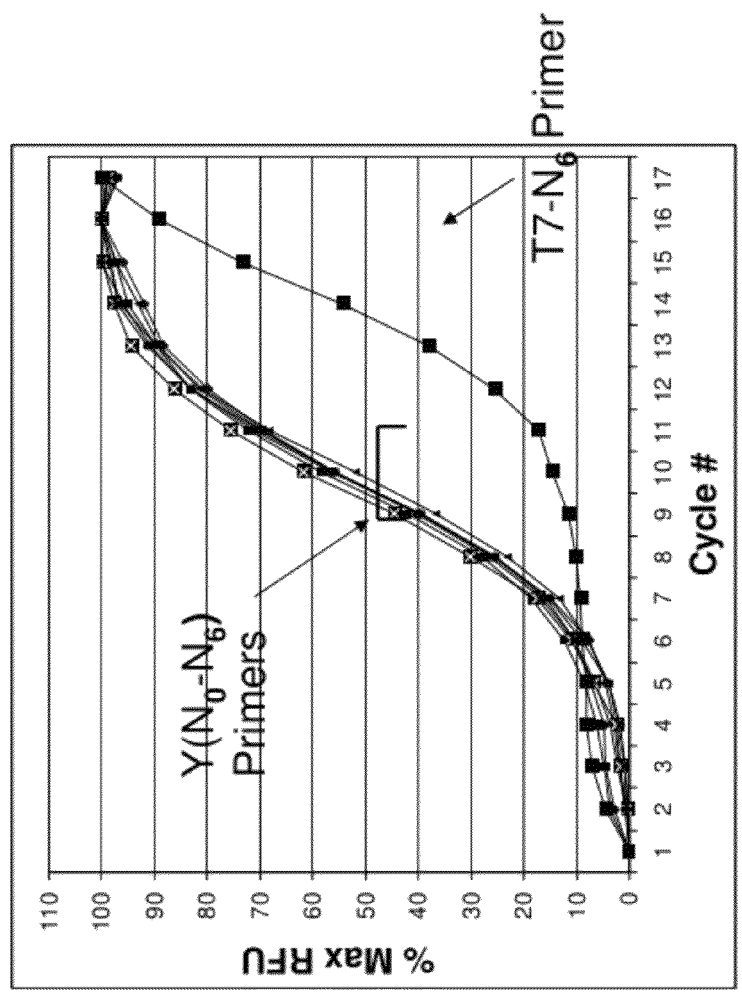
FIG. 5 demonstrates real-time PCR amplification of 5 ng aliquots of whole genome libraries synthesized with Klenow exo– fragment of DNA Polymerase I and self-inert degenerate primers described in FIG. 4.

Aliquots of the library reactions corresponding to 5 ng of input DNA were further amplified by real-time PCR. The PCR reaction mixture contained: 1× Titanium Taq reaction buffer (Clontech), 200 µM each dNTP, 100,000× dilutions of fluorescein and SybrGold I (Molecular Probes), 1 µM known $Y_U$ primer (or in the case of degenerate $T7(N)_6$ primers, known primer T7 (Table III, primer 17), 5 units of Titanium Taq polymerase (Clontech), and 3 µl aliquots (approximately 5 ng input genomic DNA) of the Klenow library synthesis reactions in a final volume of 50 µl. Reactions were carried out for 18 cycles at 94° C. for 15 sec and 65° C. for 2 min on I-Cycler™ real-time PCR instruments (Bio-Rad). FIG. 5 shows the chromatograms of the real-time PCR. All degenerate pyrimidine primers showed similar efficiency of amplification with a signal corresponding to 50% of the maximum centered around cycle 9, whereas the T7 sequence with random hexamers at the 3' end (Table III, primer 16) is more than an order of magnitude less efficient (4 cycles right shifted) due to formation of excessive primer dimers (see FIG. 5, lane 8).

Representation analysis of the samples prepared with pyrimidine primers with 0 to 6 random 3' bases was conducted using a panel of 30 human genomic STS markers (Table IV, STS markers 1-6, 8-10, 12, 14, 16, 19, 20, 23, 26, 29-31, 35, 36, 38, 40, 41, 43, 44, 46, 47, and 49)

TABLE IV

EXEMPLARY HUMAN STS MARKERS USED FOR REPRESENTATION ANALYSIS BY QUANTITATIVE REAL-TIME PCR

| No.* | UniSTS Database Name** |
|---|---|
| 1 | RH18158 |
| 2 | SHGC-100484 |
| 3 | SHGC-82883 |
| 4 | SHGC-149956 |
| 5 | SHGC-146783 |
| 6 | SHGC-102934 |
| 8 | csnpmnat1-per1-1 |
| 9 | stSG62224 |
| 10 | SHGC-142305 |
| 12 | SHGC-80958 |
| 13 | SHGC-74059 |
| 14 | SHGC-83724 |
| 16 | SHGC-145896 |
| 19 | SHGC-155401 |
| 20 | csnpharp-per2-3 |
| 22 | stb39J12.sp6 |
| 23 | SHGC-149127 |
| 26 | 949_F_8Left |
| 29 | SHGC-148759 |
| 30 | SHGC-154046 |
| 31 | WI-19180 |
| 35 | SHGC-146602 |
| 36 | SHGC-130262 |
| 38 | SHGC-130314 |
| 40 | SHGC-147491 |

TABLE IV-continued

EXEMPLARY HUMAN STS MARKERS USED FOR REPRESENTATION ANALYSIS BY QUANTITATIVE REAL-TIME PCR

| No.* | UniSTS Database Name** |
|---|---|
| 41 | stSG53466 |
| 42 | SHGC-105883 |
| 42a | GDB:533006 |
| 42b | D19S1101 |
| 43 | SHGC-79237 |
| 44 | SHGC-153761 |
| 46 | stSG50529 |
| 47 | SHGC-132199 |
| 49 | stSG49452 |
| 51 | SGC32543 |
| 52 | SHGC-2457 |
| 53 | stSG53950 |
| 54 | stSG43297 |
| 55 | SHGC-81536 |
| 58 | stSG48086 |
| 60 | stSG62388 |
| 62 | stSG50542 |
| 63 | stSG44393 |
| 66 | SHGC-9458 |
| 67 | SHGC-5506 |
| 68 | SHGC-153324 |
| 69 | stSG53179 |
| 70 | sts-X16316 |
| 71 | stSG51782 |
| 72 | stSG48421 |
| 74 | stGDB:442878 |
| 76 | WI-6290 |
| 77 | T94852 |
| 79 | SHGC-11640 |
| 80 | H58497 |
| 81 | stSG34953 |
| 82 | KIAA0108 |
| 83 | Y00805 |
| 84 | sts-W93373 |
| 85 | stSG45551 |
| 85a | Cda0ge01 |
| 85b | RH18026 |
| 86 | U34806 |
| 88 | SHGC-12728 |
| 89 | SHGC-10570 |
| 91 | stSG52141 |
| 92 | SHGC-58853 |
| 94 | SHGC-36464 |
| 96 | stSG8946 |
| 97 | SHGC-10187 |
| 99 | WI-13668 |
| 103 | stSG49584 |
| 104 | M55047 |
| 105 | SHGC-102231 |
| 106 | stSG60168 |
| 107 | stSG50880 |
| 108 | stSG39197 |
| 110 | sts-AA035504 |
| 111 | SGC35140 |
| 113 | stSG53011 |
| 114 | sts-R44709 |
| 116 | SHGC-149512 |
| 117 | stSG55021 |
| 118 | SHGC-79529 |
| 119 | KIAA0181 |
| 119a | GDB:314031 |
| 119b | RH28558 |
| 120 | SHGC-105119 |
| 121 | SHGC-79242 |
| 122 | SHGC-170363 |
| 123 | stSG50637 |
| 126 | RH69540 |
| 130 | GDB:181552 |
| 133 | 1770 |
| 134 | 1314 |
| 135 | SHGC-104164 |
| 136 | SHGC-101034 |
| 137 | stSG62239 |
| 138 | stSG60144 |

TABLE IV-continued

EXEMPLARY HUMAN STS MARKERS USED FOR REPRESENTATION ANALYSIS BY QUANTITATIVE REAL-TIME PCR

| No.* | UniSTS Database Name** |
|---|---|
| 139 | stSG58407 |
| 140 | stSG58405 |
| 141 | sts-T50718 |
| 144 | SHGC-17057 |
| 145 | sts-N90764 |
| 152 | SHGC-132991 |
| 154 | SHGC-57595 |
| Alu | Yb8 |

*Omitted sequential numbers indicate dropped STS sequences that did not amplify well in quantitative RT-PCR
**Unique names of STS marker sequences are from the National Center for Biotechnology Information UniSTS database. Sequences of the STS regions as well as the forward and backward primers used in quantitative real-time PCR can be found in the UniSTS database at the National Center for Biotechnology Information's website.

Figure 6:
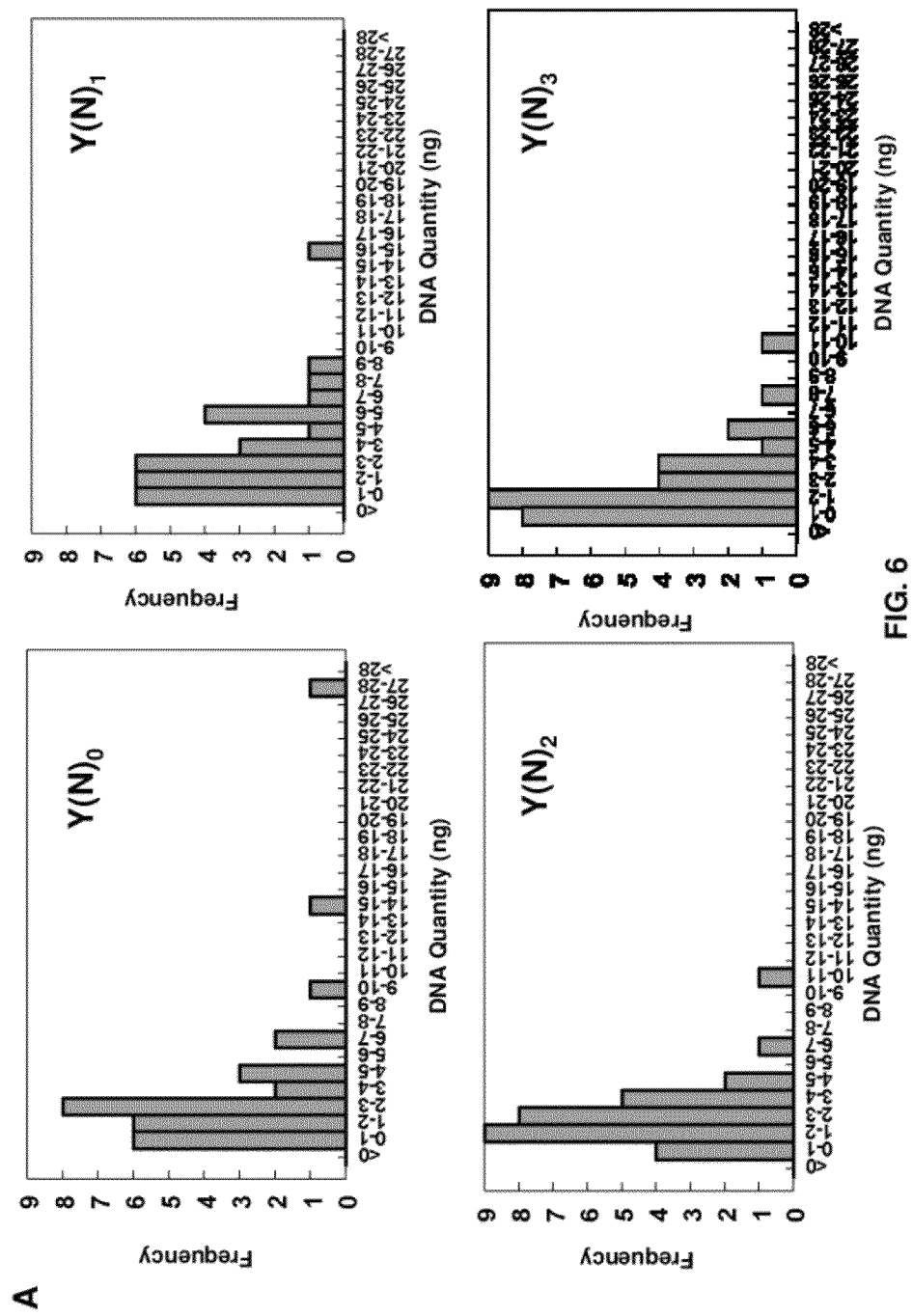
FIGS. 6A and 6B show representation analysis of 30 exemplary human STS markers following whole genome amplification with exemplary degenerate pyrimidine YN primers specified in the description of FIG. 4 and the Klenow Exo– fragment of DNA Polymerase I. Aliquots corresponding to 10 ng of amplified DNA were used for PCR analysis of STS markers.
Figure 6:
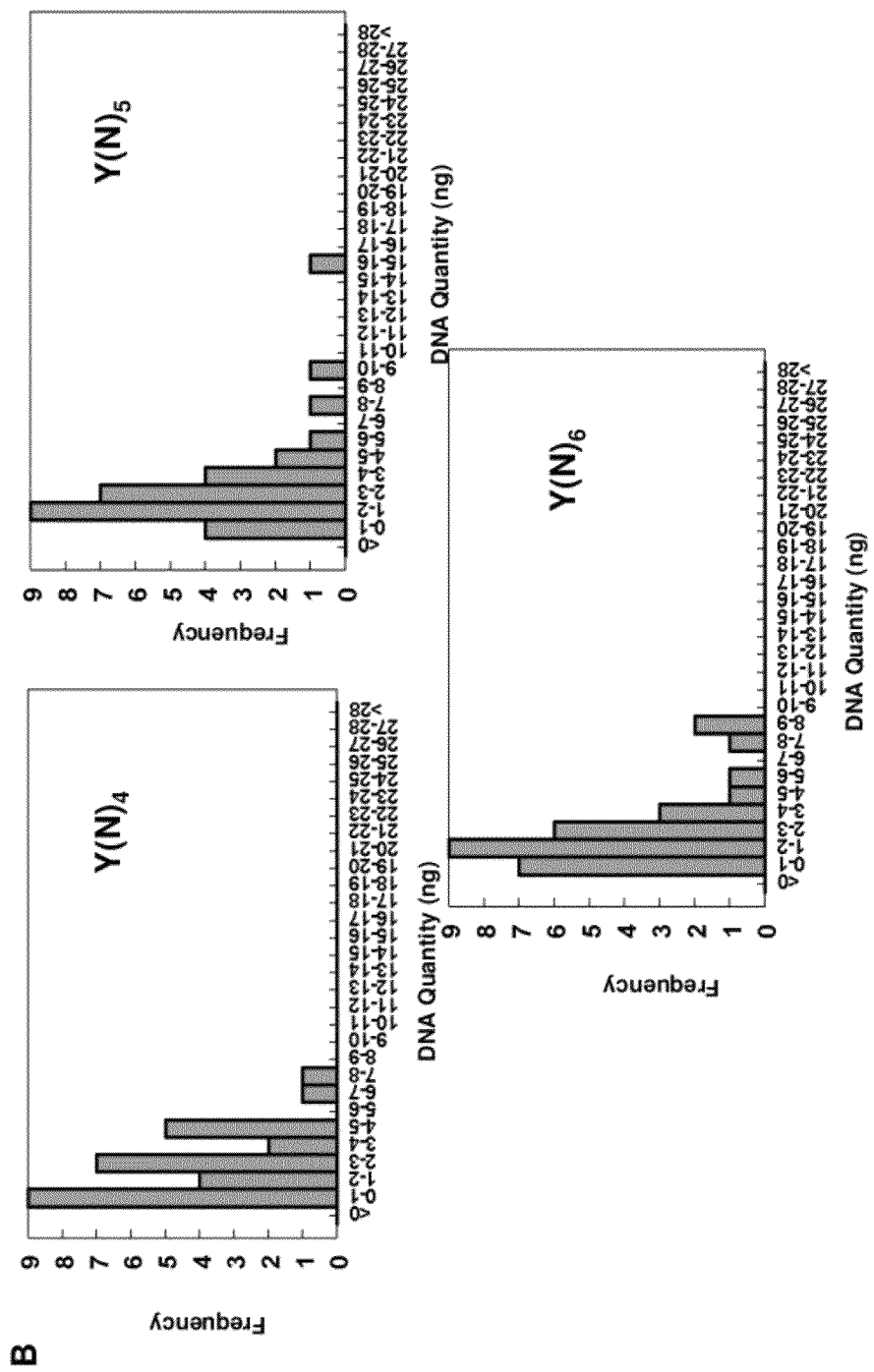

The material amplified by PCR with the known $Y_U$ primer was purified with Qiaquick filters (Qiagen), and 10 ng aliquots were analyzed in real-time PCR. Reactions were carried out for 45 cycles at 94° C. for 15 sec and 68° C. for 1 min on an I-Cycler (Bio-Rad), as described above, in a 25 µl volume. Standards corresponding to 10, 1, and 0.2 ng of fragmented DNA were used for each STS, quantities were calculated by standard curve fit for each STS (I-Cycler software, Bio-Rad) and were plotted as frequency histograms (FIG. 6). Of all pyrimidine primers tested, $Y(N)_2$ supported the most uniform whole genome amplification (FIG. 6A) with Klenow fragment of DNA polymerase I, yet produced limited amount of primer dimers (FIG. 3 and FIG. 4). Eighty three percent of the STS markers analyzed after whole genome amplification with $Y(N)_2$ primer were within a factor of 2 times the mean and 90% within a factor of 3 times the mean, whereas on average these numbers were in the range of 63 to 70% and 73 to 80% respectively for all other YN-primers analyzed.

Example 3

Figure 7:
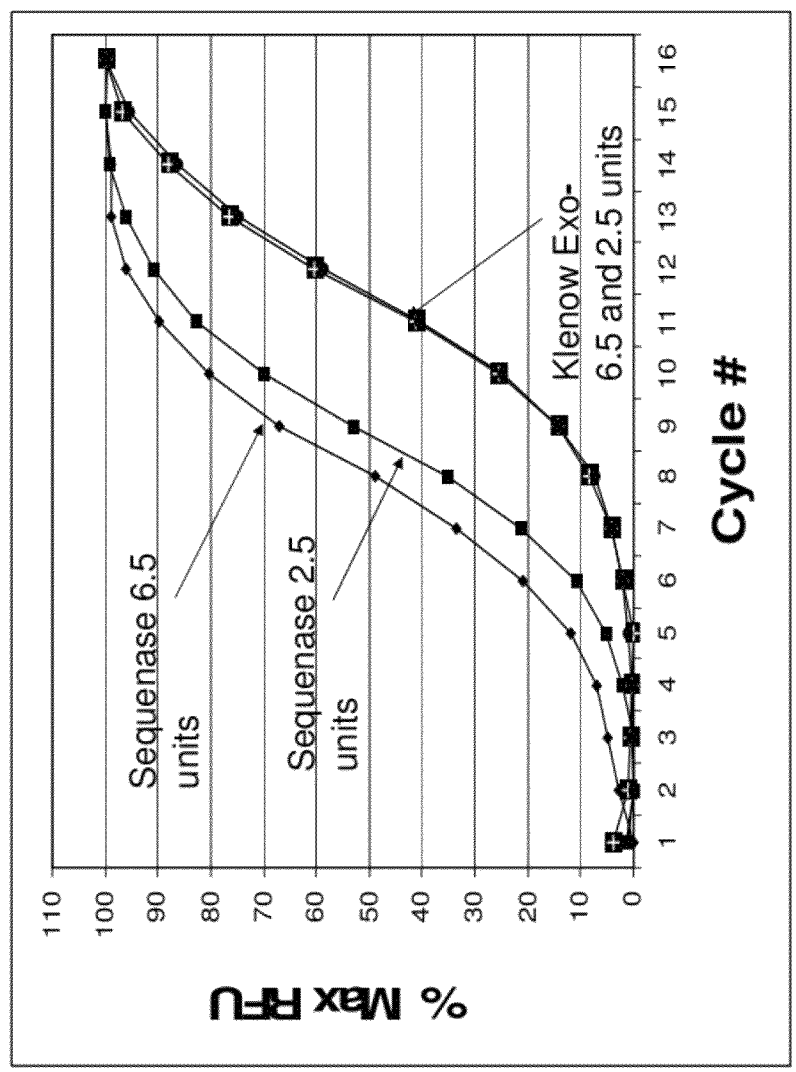
FIG. 7 shows real-time PCR amplification of 5 ng aliquots of whole genome pre-amplified samples of thermally fragmented human genomic DNA with Klenow Exo– fragment of DNA Polymerase I or Sequenase version 2 using self-inert degenerate pyrimidine primer $Y(N)_2$ with 2 random bases at the 3' end.
Figure 8:
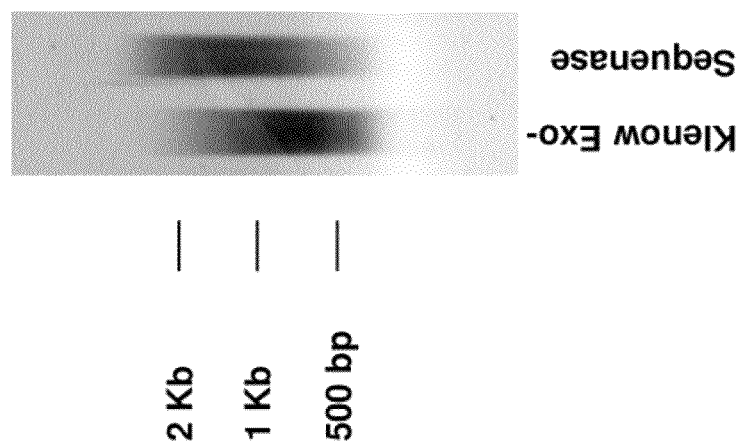
FIG. 8 demonstrates gel analysis of amplification products of thermally fragmented human genomic DNA with Klenow Exo– fragment of DNA Polymerase I or Sequenase version 2 using self-inert degenerate pyrimidine primer $Y(N)_2$ as specified in the description to FIG. 7.

Whole Genome Amplification of Thermally Fragmented Genomic DNA Converted into an Amplifiable DNA Library Using Klenow Exo– Fragment of DNA Polymerase-I or Sequenase Version-2 and Degenerate Primers $Y(N)_2$ Human lymphocyte genomic DNA isolated by standard procedures was randomly fragmented in TE-L buffer (10 mM Tris, 0.1 mM EDTA, pH 7.5) by heating at 95° C. for 5 min. The reaction mixture contained 100 ng of thermally fragmented DNA in 1× EcoPol buffer (NEB) or 1× Sequenase buffer (USB), 200 µM of each dNTP, 360 ng of Single Stranded DNA Binding Protein (USB), 200 nM of known $Y_U$ primer (Table III, primer 8), and 500 nM of degenerate $Y(N)_2$ primer (Table III, primer 3) in a final volume of 25 µl. After a denaturing step of 2 min at 95° C., the samples were cooled to 16° C., and the reaction initiated by adding 2.5 units or 6.5 units of Klenow Exo⁻ polymerase (NEB) or Sequenase version 2 (USB), respectively. WGA library synthesis was carried out in a three-step protocol for 10 min at 16° C., 10 min at 24° C., and 12 min at 37° C. Reactions were stopped with 1 µl of 500 mM EDTA (pH 8.0), and samples were heated for 3 min at 75° C. Aliquots of the library synthesis reactions corresponding to 5 ng of input DNA were further amplified by real-time PCR. The PCR reaction mixture contained: 1× Titanium Taq reaction buffer (Clontech), 200 uM each dNTP, 100,000× dilutions of fluorescein and SybrGreen I (Molecular Probes) 1 uM known $Y_U$ primer (or in the case of random T7(N)₆ primers, known T7 (primer 18), 5 units of Titanium Taq polymerase (Clontech), and a volume of the library synthesis reaction corresponding to 5 ng of the input genomic DNA in a final volume of 50 µl Reactions were carried out for 17 cycles at 94° C. for 15 sec and 65° C. for 2 min on an I-Cycler real-time PCR instrument (Bio-Rad). FIG. 7 shows the chromatograms of the real-time PCR. Sequenase version 2 showed an order of magnitude higher efficiency as compared to Klenow Exo⁻ polymerase at both concentrations tested. Aliquots of the PCR amplification reactions were analyzed on a 1% agarose gel after staining with EtBr. Sequenase synthesis yielded amplicons of larger average size compared to Klenow Exo⁻ polymerase (FIG. 8). Representation analysis of the PCR amplified libraries generated with Sequenase or Klenow Exo– polymerases was done using a panel of 33 human genomic STS markers (Table IV, STS markers 1, 5, 6, 14, 19, 22, 26, 38, 43, 46, 47, 52, 53, 54, 58, 60, 62, 63, 69, 72, 74, 80, 81, 82, 85, 89, 91, 94, 96, 99, 104, 107, 108)

Figure 9:
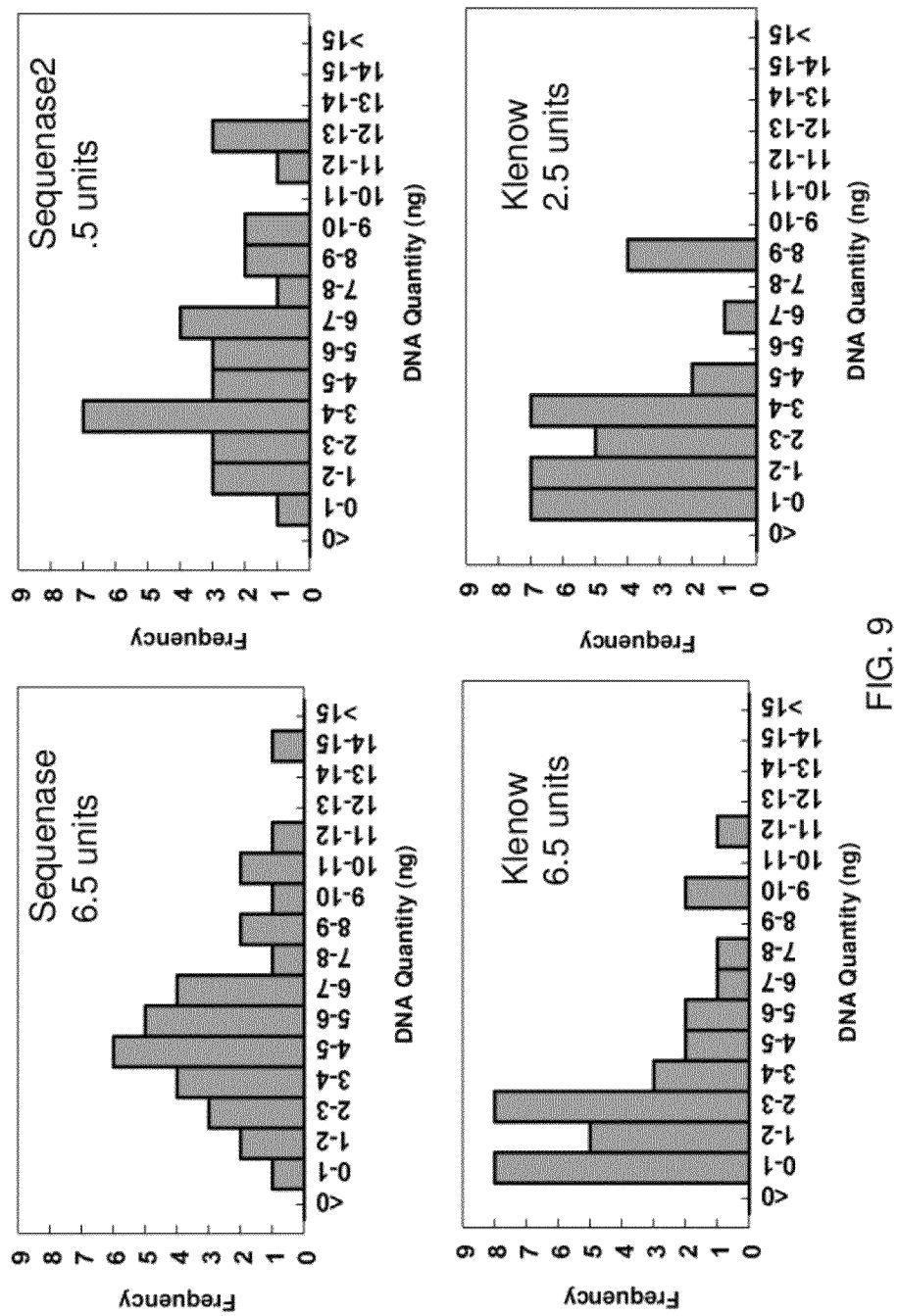
FIG. 9 shows representation analysis of 33 exemplary human STS markers following whole genome amplification with exemplary self-inert degenerate pyrimidine primer $Y(N)_2$ and Klenow Exo– fragment of DNA Polymerase I or Sequenase version 2. Aliquots corresponding to 10 ng of amplified DNA were used for PCR analysis of STS markers.

The material amplified by PCR with the known $Y_U$ primer was purified with Qiaquick filters (Qiagen), and 10 ng aliquots were analyzed in real-time PCR. Reactions were carried out for 45 cycles at 94° C. for 15 sec and 68° C. for 1 min on I-Cycler (Bio-Rad), as described above in a 25 µl volume. Standards corresponding to 10, 1, and 0.2 ng of fragmented genomic DNA were used for each STS. Quantities were calculated by standard curve fit for each STS (I-Cycler software, Bio-Rad), and plotted as frequency histograms (FIG. 9). Sequenase library preparations resulted in a more representative amplification compared to Klenow Exo⁻ with fewer outliers. Between 80 and 85% of the STS markers analyzed after amplification of libraries prepared with Sequenase were within a factor of 2 times the mean value, whereas those analyzed after amplification of libraries prepared with Klenow fragment of DNA polymerase I averaged 67%.

Example 4

Figure 10:
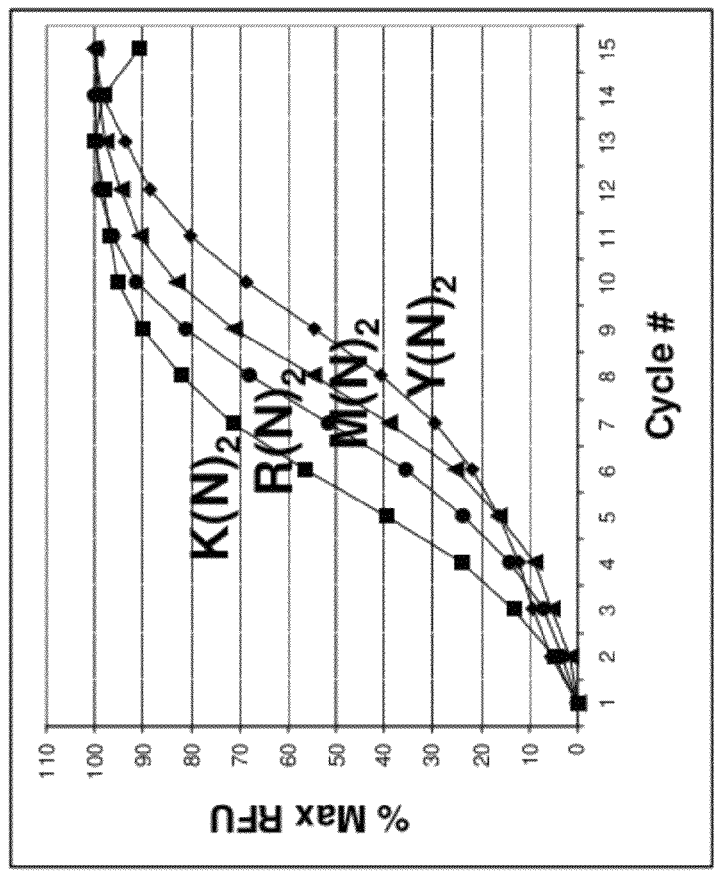
FIG. 10 illustrates comparison between four self-inert degenerate primers comprising four possible base pair combinations known not to participate in Watson-Crick base pairing and containing two completely random bases at their 3' ends in library synthesis reactions with Sequenase version 2 DNA polymerase. Shown is quantitative real-time PCR amplification of aliquots corresponding to 5 ng of input DNA of the library synthesis reactions. Abbreviations show the base composition of the self-inert degenerate primers.
Figure 11:
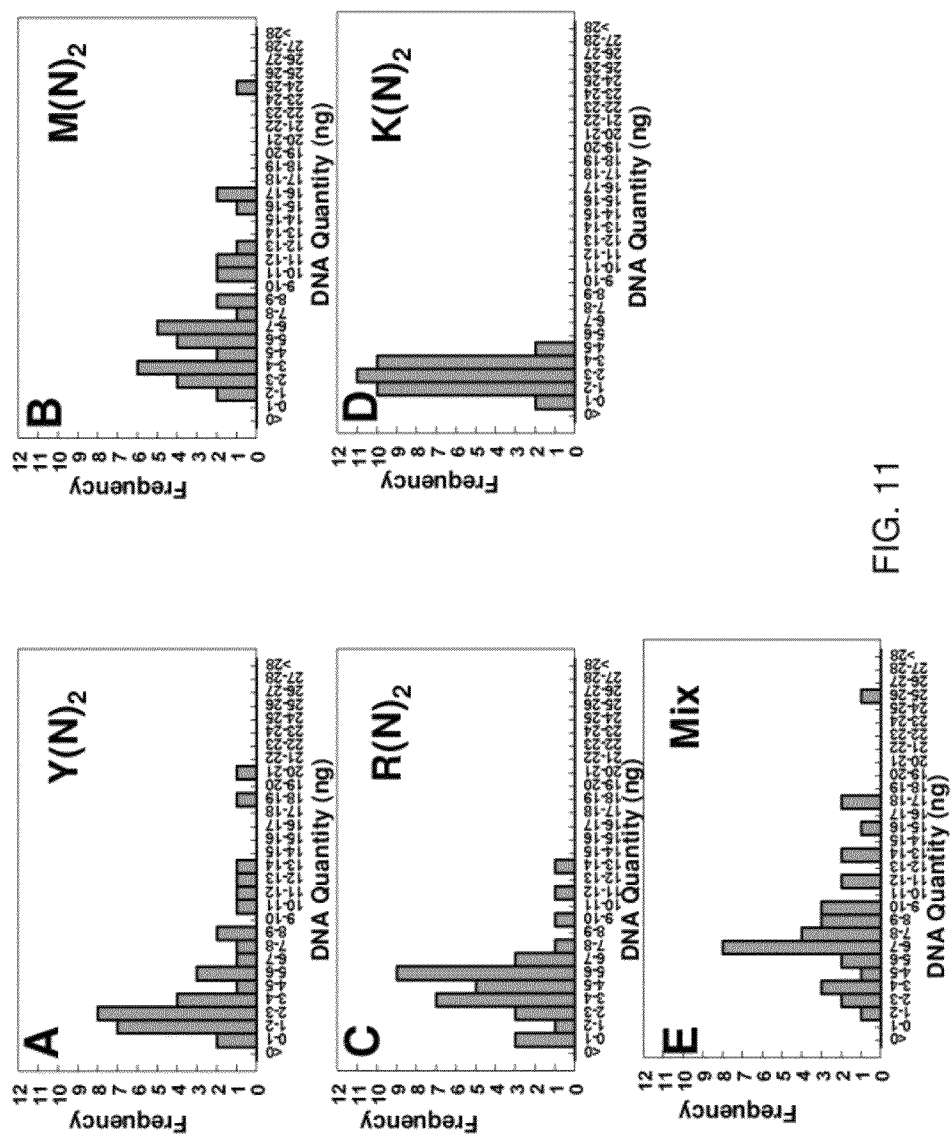
FIGS. 11A through 11E show representation analysis of 35 exemplary human STS markers following whole genome amplification with self-inert degenerate primers specified in the description to FIG. 10 and Sequenase version 2 DNA polymerase or a combined sample in which equal amounts of four individual reactions each with a separate degenerate primer were combined prior to PCR amplification of the STS markers. Aliquots corresponding to 10 ng of amplified DNA were used for PCR analysis of STS markers. Abbreviations show the base composition of the self-inert degenerate primers.

Comparison of Degenerate Primers $Y(N)_2$, $R(N)_2$, $M(N)_2$ and $K(N)_2$ Comprised of Only Two Non-Complementary Bases and Containing Two Truly Random Bases at their 3' Terminus in their Efficiency of Human Whole Genome Library Preparation and Amplification Human lymphocyte genomic DNA isolated by standard procedures was randomly fragmented in TE-L buffer by heating at 95° C. for 4 min. The reaction mixtures (one for each degenerate primer) contained 100 ng of thermally fragmented DNA in 1× EcoPol buffer (NEB), 200 µM of each dNTP, and 1 µM of degenerate $Y(N)_2$, $R(N)_2$, $M(N)_2$, or $K(N)_2$ primers (Table III, primers 3, 10, 12, and 14) in a final volume of 24 µl. After denaturing at 95° C. for 2 min the samples were cooled to 16° C. and the library synthesis reaction was initiated by adding 1 µl (3 units) of Sequenase version 2 (USB Corporation). The reaction was carried out in a three-step protocol for 15 min at 16° C., 15 min at 24° C., and 15 min at 37° C. Reactions were stopped by adding 1 ul of 250 mM EDTA (pH 8.0) and samples were heated for 5 min at 75° C. Aliquots of the library reactions corresponding to 5 ng of input DNA were further amplified by quantitative real-time PCR. The PCR reaction mixture contained: 1× Titanium Taq reaction buffer (Clontech), 200 µM each dNTP, 100,000× dilutions of fluorescein and SybrGreen I (Molecular Probes) 1 uM known $Y_U$, $R_U$, $M_U$, or $K_U$ primer whose sequence is identical to the known 5' portion of the respective degenerate primer (Table III, primers 8, 11, 13, and 16), 5 units of Titanium Taq polymerase (Clontech), and 5 ng input genomic DNA equivalent of the library synthesis reactions in a final volume of 50 ul. Amplifications were carried out for 16 cycles at 94° C. for 15 sec and 65° C. for 2 min on the I-Cycler real-time PCR instrument (Bio-Rad). FIG. 10 demonstrates that degenerate primer containing guanine and thymidine ($K(N)_2$ primer) is priming most efficiently of all primers tested. Also, both guanine containing degenerate primers ($R(N)_2$ and $K(N)_2$) are more effective as compared to cytosine containing primers ($M(N)_2$ and $Y(N)_2$). These findings can be explained by the fact that guanine and thymidine can participate in non-canonical base pairing more readily compared to the other two bases. Overall $K(N)_2$ primer was about an order of magnitude more effective as compared to $Y(N)_2$ primer (FIG. 10). Representation analysis of the PCR amplified libraries generated with Sequenase was done using a panel of 35 human genomic STS markers (Table IV, STS markers 40-44, 46, 47, 49, 52, 54, 55, 58, 60, 62, 63, 66-70, 72, 74, 76, 77, 79, 80, 81-86, 88, and 89). The material amplified by PCR with known primers was purified with Qiaquick filters (Qiagen) and 10 ng aliquots were analyzed in real-time PCR. In addition, a combined sample containing 2.5 ng of each individual amplification reaction was run in parallel. Reactions were carried out for 45 cycles at 94° C. for 15 sec and 68° C. for 1 min on I-Cycler (Bio-Rad) in a 25 µl volume. Standards corresponding to 10. 1, and 0.2 ng of fragmented genomic DNA were used for each STS. Quantities were derived by standard curve fit for each STS (I-Cycler software, Bio-Rad) and plotted as frequency histograms. As shown on FIG. 11, the use of $K(N)_2$ primer resulted in the most uniform and representative DNA amplification. In this study, 91% of the STS markers analyzed after amplification with $K(N)_2$ primer were within 2 fold of the mean value, whereas for $Y(N)_2$, $M(N)_2$, and $R(N)_2$ primers they were 63%, 74%, and 83%, respectively.

Example 5

Figure 12:
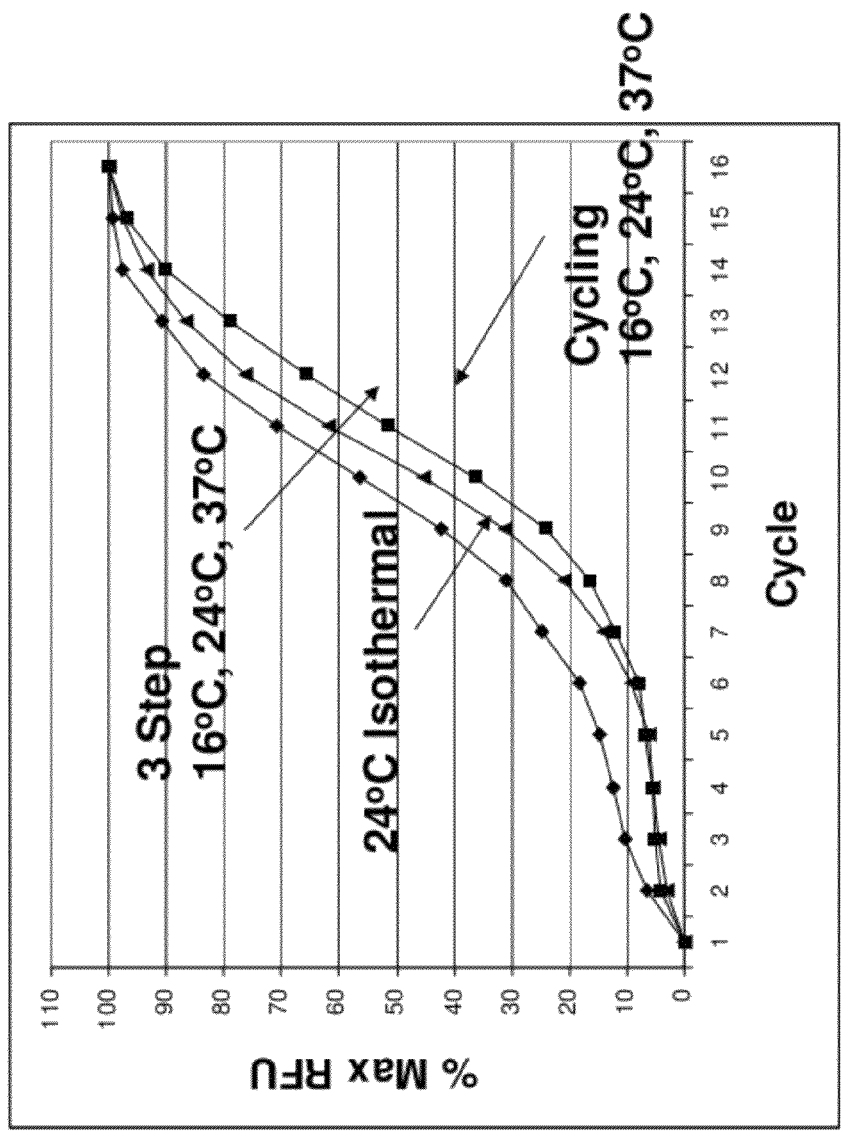
FIG. 12 demonstrates comparison between isothermal incubation at 24° C. for 60 min, a three-step incubation at 16° C., 24° C., and 37° C. for 20 min each, and a cycling incubation for 19 cycles at 16° C., 24° C., and 37° C. for 1 min each in whole genome amplification of human DNA with Sequenase version 2 DNA polymerase and self-inert degenerate primer $Y(N)_2$. Aliquots corresponding to 5 ng of input DNA of the WGA library synthesis reactions were amplified by quantitative real-time PCR.
Figure 13:
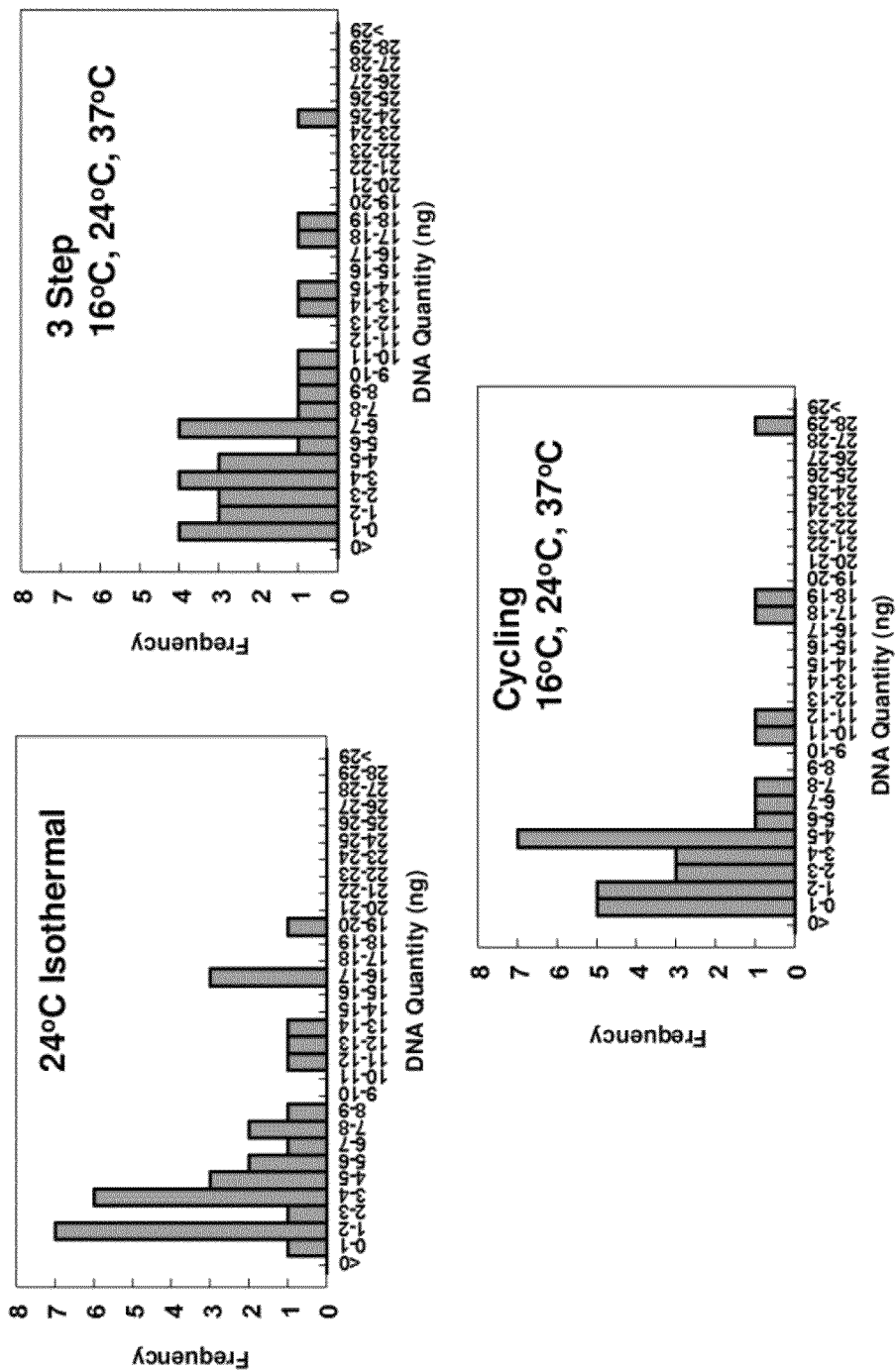
FIG. 13 shows representation analysis of 17 Human STS markers following whole genome amplification with self-inert degenerate primer $Y(N)_2$ and Sequenase version 2 DNA polymerase as detailed in the description to FIG. 12 Aliquots corresponding to 10 ng of amplified DNA were used for PCR analysis of STS markers.

Comparison Between Different Modes of Incubation During Preparation of Whole Genome Libraries with Sequenase Version-2 and $Y(N)_2$ Degenerate Primers and Subsequent Representative Amplification of Human DNA Human lymphocyte genomic DNA isolated by standard procedures was randomly fragmented in TE-L buffer by heating at 95° C. for 4 min. The reaction mixture contained 100 ng of thermally fragmented DNA in 1× EcoPol buffer (NEB), 200 µM of each dNTP, and 1 µM of degenerate $Y(N)_2$ primer (Table III, primer 3) in a final volume of 25 µl. After a denaturing step of 2 min at 95° C., the samples were cooled to 16° C., or 24° C. and the WGA library synthesis reactions were initiated by adding 3 units or of Sequenase version 2 (USB). The reactions were carried out in three different protocols as follows: (i) isothermal 24° C. for 1 hour (ii) cycling between 16° C., 24° C., and 37° C. for 1 min each for total of 19 cycles (total duration 1 hour), and (iii) three step incubation protocol for 20 min at 16° C., 20 min at 24° C., and 20 min at 37° C. Reactions were stopped with 1 µl of 250 mM EDTA (pH 8.0), and samples were heated for 5 min at 75° C. Aliquots of the library synthesis reactions corresponding to 5 ng of input DNA were further amplified by real-time PCR. The PCR reaction mixture contained: 1× Titanium Taq reaction buffer (Clontech), 200 µM each dNTP, 100,000× dilutions of fluorescein and SybrGreen I (Molecular Probes) 1 µM known $Y_U$ primer (or Table III, primer 8), 5 units of Titanium Taq polymerase (Clontech), and 5 ng input genomic DNA of the library synthesis reactions in a final volume of 50 µl. Reactions were carried out for 17 cycles at 94° C. for 15 sec and 65° C. for 2 mm on I-Cycler real-time PCR instrument (Bio-Rad). FIG. 12 shows the chromatogram of the real-time PCR. Isothermal incubation at 24° C. for 1 hour resulted in the highest efficiency of amplification, followed by the 3-step incubation protocol. The cycling incubation resulted in 2 cycles delayed kinetics as compared to isothermal incubation (FIG. 12). Representation analysis of the samples amplified by PCR following library preparation with Sequenase was done using a panel of 31 human genomic STS markers (Table IV, STS markers 40, 42-44, 46, 47, 49, 52, 54, 58, 60, 62, 66, 67, 68, 71, 72, 74, 77, 79, 80-86, 88, and 89). The material amplified by PCR with the known $Y_U$ primer was purified with Qiaquick filters (Qiagen), and 10 ng aliquots were analyzed in real-time PCR. Reactions were carried out for 45 cycles at 94° C. for 15 sec and 68° C. for 1 min on I-Cycler (Bio-Rad), as described above in a 25 µl volume. Standards corresponding to 10, 1, and 0.2 ng of fragmented genomic DNA were used for each STS. Quantities were derived by a standard curve fit for each STS (I-Cycler software, Bio-Rad) and plotted as frequency histograms (FIG. 13). As shown, the isothermal amplification resulted in a slightly better representation as compared to the other two incubation protocols.

Example 6

Figure 14:
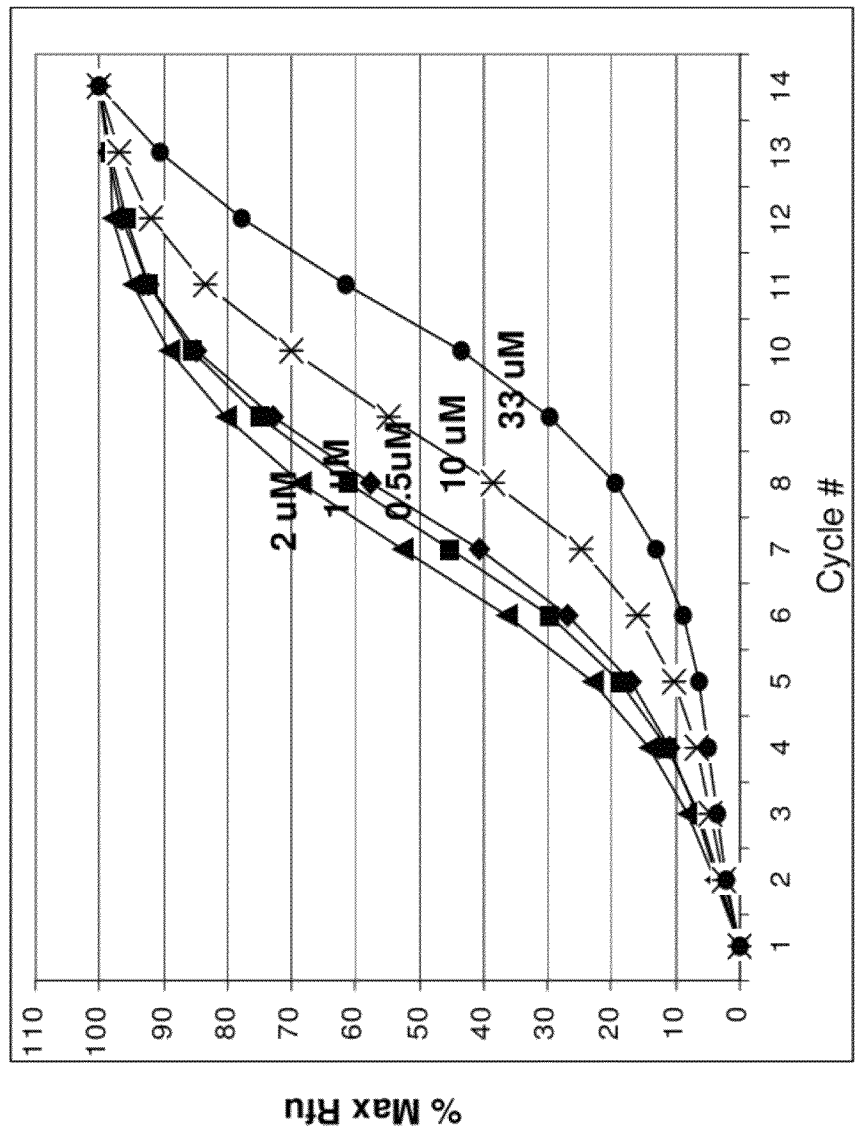
FIG. 14 shows titration from 0.5 μM to 33 μM of self-inert degenerate primer $K(N)_2$ in human WGA with Sequenase version 2 DNA polymerase. Aliquots corresponding to 5 ng of input DNA of the WGA library synthesis reactions were amplified by quantitative real-time PCR.
Figure 15:
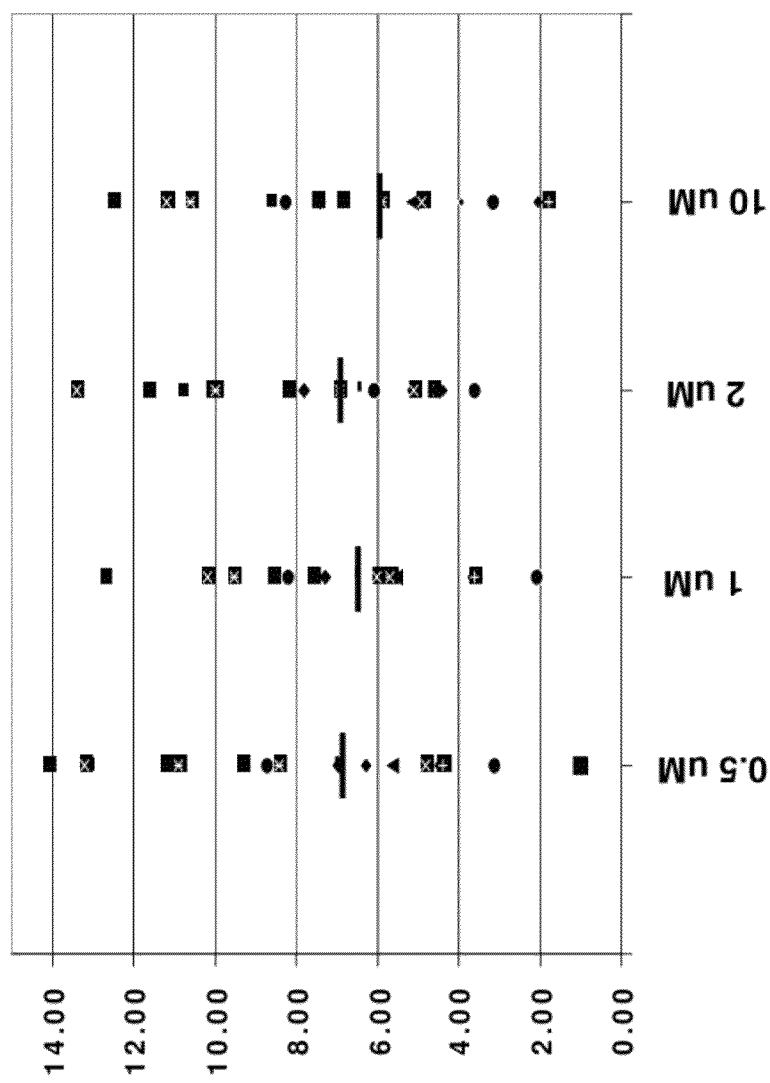
FIG. 15 shows representation analysis of 17 exemplary human STS markers following whole genome amplification with exemplary self-inert degenerate primer $K(N)_2$ applied at concentrations of 0.5 to 10 μM and Sequenase version 2 DNA polymerase as specified in the description to FIG. 14. Aliquots corresponding to 10 ng of amplified DNA were used for PCR analysis of STS markers. Shown is a distribution plot of DNA amounts derived from quantitative real-time PCR. Horizontal bars represent median values.

Titration of Self-Inert Degenerate Primer $K(N)_2$ Concentration in Human Whole Genome Amplification Protocol with Sequenase Human lymphocyte genomic DNA isolated by standard procedures was randomly fragmented in TE-L buffer by heating at 95° C. for 4 min. The reaction mixture (25 ul) contained 100 ng of thermally fragmented DNA in 1× EcoPol buffer (NEB), 200 µM of each dNTP, and 500 nM, 1 µM, 2 µM, 10 µM, or 33 µM of the self-inert degenerate primer $K(N)_2$ containing G and T bases and 2 completely random bases at the 3' end (Table III, primer 14). After a denaturing step of 2 min at 95° C., the samples were cooled to 24° C., and the library synthesis reaction was initiated by the addition of 3 units of Sequenase version 2 DNA polymerase (USB). WGA library synthesis was carried out isothermally at 24° C. for 45 min. Reactions were stopped with 1 µl of 250 mM EDTA (pH 8.0), and samples were heated for 5 min at 75° C. Aliquots of the library synthesis reactions corresponding to 5 ng of the input DNA were further amplified by real-time PCR. The PCR reaction mixture contained: 1× Titanium Taq reaction buffer (Clontech), 200 µM each dNTP, 100,000× dilutions of fluorescein and SybrGreen I (Molecular Probes) 1 uM known $K_U$ primer (Table III, primer 16), 5 units of Titanium Taq polymerase (Clontech), and a volume of the library synthesis reaction corresponding to 5 ng of input genomic DNA in a final volume of 50 µl. Reactions were carried out for 15 cycles at 94° C. for 15 sec and 65° C. for 2 min on I-Cycler real-time PCR instrument (Bio-Rad). FIG. 14 shows the chromatograms of the real-time PCR. The efficiency of amplification was similar at concentrations of the self-inert degenerate primer $K(N)_2$ between 0.5 and 2 µM. At 10 µM and at 33 µM, the amplification was inhibited (FIG. 14). Representation analysis of the samples amplified by PCR was done using a panel of 17 human STS markers (Table IV, STS markers: 40-44, 46, 47, 49, 52, 54, 55, 58, 60, 62, 63, 66, and 67). The material amplified by PCR with the known $K_U$ primer was purified with Qiaquick filters (Qiagen), and 10 ng aliquots were analyzed in real-time PCR. Reactions were carried out for 45 cycles at 94° C. for 15 sec and 68° C. for 1 min on I-Cycler (Bio-Rad), in a 25 μl volume. Standards corresponding to 10, 1, and 0.2 ng of fragmented genomic DNA were used for each STS. Quantities were calculated by standard curve fit for each STS (I-Cycler software, Bio-Rad), and plotted as distribution plot (FIG. 15). As shown, the representation of STS markers improved significantly by increasing the primer K(N)$_2$ concentration from 0.5 μM to 2 μM. When 10 μM or 33 μM of the primer K(N)$_2$ was applied this resulted in a compromised representation of genomic markers (FIG. 15; data not shown for 33 μM). With primer concentrations between 0.5 and 2 μM, on average 91% of the STS markers were within a factor of 2 fold the mean, whereas at 10 μM primer the percentage was 82.

Example 7

Figure 16:
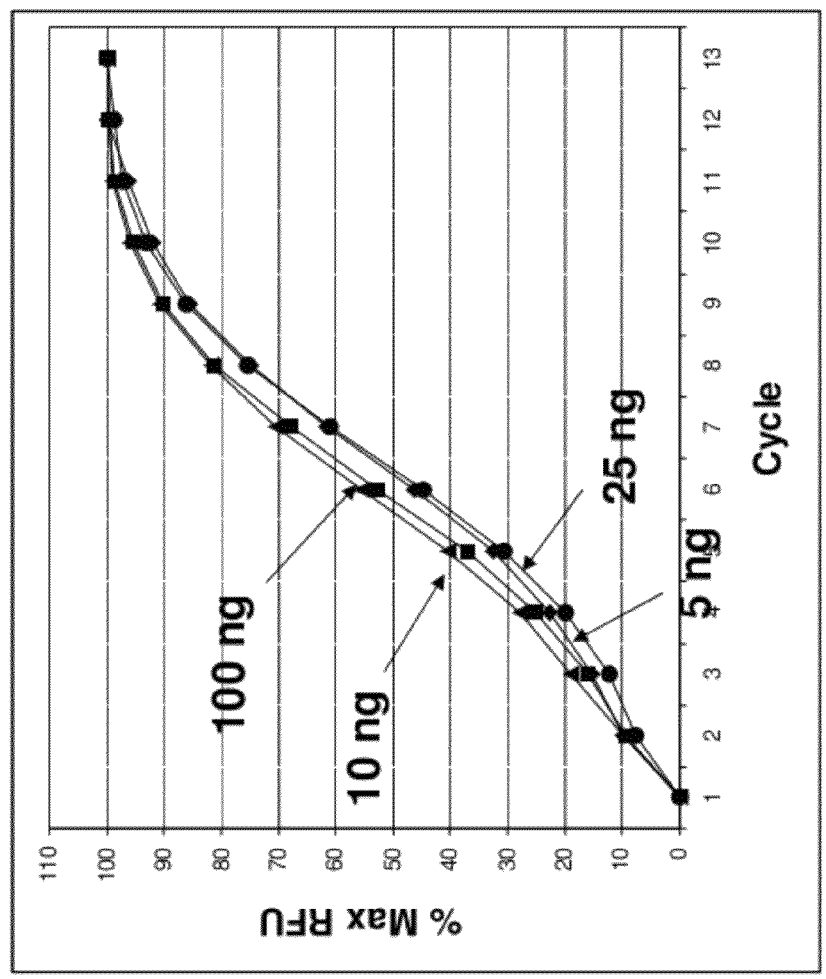
FIG. 16 shows titration from 5 ng to 100 ng of thermally fragmented genomic DNA in WGA reaction with self-inert degenerate primer $K(N)_2$ and Sequenase version 2 DNA polymerase. Aliquots corresponding to 5 ng of input DNA of the WGA library synthesis reactions were amplified by quantitative real-time PCR.
Figure 17:
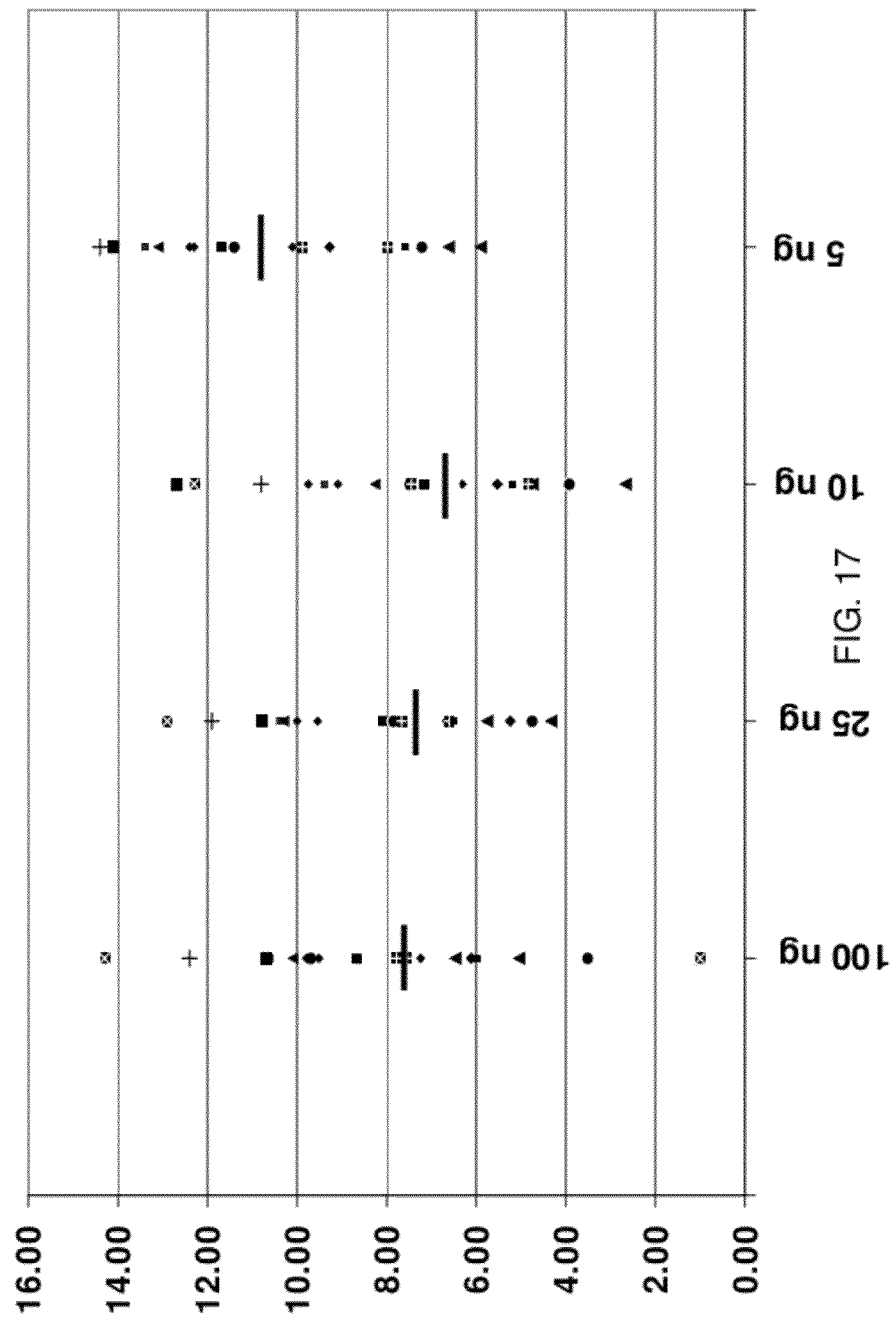
FIG. 17 shows representation analysis of 20 exemplary human STS markers following whole genome amplification of between 5 ng and 100 ng of thermally fragmented DNA with self-inert degenerate primer $K(N)_2$ and Sequenase version 2 DNA polymerase as specified in the description to FIG. 16. Aliquots corresponding to 10 ng of amplified DNA were used for PCR analysis of STS markers. Shown is a distribution plot of DNA amounts derived from quantitative real-time PCR. Horizontal bars represent median values.

Titration of the Input Amount of DNA in Human Whole Genome Amplification with Degenerate Primer K(N)$_2$ and Sequenase Human lymphocyte genomic DNA isolated by standard procedures was randomly fragmented in TE-L buffer by heating at 95° C. for 4 min. The reaction mixtures contained 100 ng, 25 ng, 10 ng, or 5 ng of thermally fragmented DNA (or just TE-L buffer as negative control) in 1× EcoPol buffer (NEB), 200 μM of each dNTP, and 1 uM degenerate primer K(N)$_2$ (Table III, primer 14) in a total volume of 15 μl. After a denaturing step of 2 min at 95° C., the samples were cooled to 16° C., and the reaction initiated by adding 1.85 units of Sequenase version 2 DNA polymerase (USB). Library synthesis was done at 16° C. for 20 min 24° C. for 20 min, and 37° C. for 20 min. Reactions were stopped with 1 μl of 83 mM EDTA (pH 8.0), and samples were heated for 5 min at 75° C. Aliquots of the synthesis reactions corresponding to 5 ng of input DNA (or in the case of 5 ng DNA the entire reaction mixture) were further amplified by real-time PCR. The PCR reaction mixture contained: 1× Titanium Taq reaction buffer (Clontech), 200 μM each dNTP, 100,000× dilutions of fluorescein and SybrGreen I (Molecular Probes) 1 μM known K$_U$ primer (Table III, primer 16), 5 units of Titanium Taq polymerase (Clontech), and 5 ng input genomic DNA of the library synthesis reactions in a final volume of 75 μl Reactions were carried out for 14 cycles at 94° C. for 15 sec and 65° C. for 2 min on I-Cycler real-time PCR instrument (Bio-Rad). FIG. 16 shows the chromatograms of the real-time PCR. Representation analysis of the samples amplified by PCR was done using a panel of 20 human STS markers (Table IV, STS markers: 40, 42-44, 46, 47, 49, 52, 54, 55, 58, 60, 62, 63, 66-69, and 74). The material amplified by PCR with known K$_U$ primer was purified with Qiaquick filters (Qiagen), and 10 ng aliquots were analyzed in real-time PCR. Reactions were carried out for 45 cycles at 94° C. for 15 sec and 68° C. for 1 min on I-Cycler (Bio-Rad), in a 25 μl volume. Standards corresponding to 10, 1, and 0.2 ng of fragmented genomic DNA were used for each STS. Quantitation was done by standard curve fit for each STS (I-Cycler software, Bio-Rad), and quantities were plotted as a distribution plot (FIG. 17). As shown, the representation of STS markers was better when libraries were synthesized with less than 100 ng of DNA (FIG. 17). One hundred percent of the samples amplified from 25 ng or from 5 ng of genomic DNA were within a factor of 2 fold the mean, whereas samples amplified from 100 ng or 10 ng were on average 95%. In this example, the highest median value for the STS markers evaluated was achieved using the 5 ng input template (FIG. 17).

Genomic libraries described herein provide a very efficient resource for highly representative whole genome amplification. Size (200-2,000 bp) and a known priming (known sequence) site make them also very attractive for such applications as DNA archiving, storing, retrieving and re-amplification. Multiple libraries can be immobilized and stored as micro-arrays. Libraries covalently attached by one end to the bottom of tubes, micro-plates or magnetic beads can be used many times by replicating immobilized amplicons, dissociating replicated molecules for immediate use, and returning the original immobilized WGA library for continuing storage.

The structure of WGA amplicons can also be easily modified to introduce a personal identification (ID) DNA tag to every genomic sample to prevent an unauthorized amplification and use of DNA. Only those who know the sequence of the ID tag will be able to amplify and analyze genetic material. The tags can be useful for preventing genomic cross-contaminations when dealing with many clinical DNA samples WGA libraries created from large bacterial clones (BACs, PACs, cosmids, etc) can be amplified and used to produce genomic micro-arrays.

The examples presented below describe processes that can enhance the outlined applications of the WGA libraries.

Example 8

Incorporation of Individual Identification DNA Tags by Whole Genome Amplification Recovery of the Individual WGA Libraries from a Mixture of Several WGA Libraries This example describes two processes of tagging individual WGA library(ies) with the DNA identification sequence (ID) for the purpose of subsequent recovery of this library from the mixture containing other WGA libraries. Such a situation can occur intentionally or unavoidably, such as when manipulating or storing a very large number of WGA DNA samples, or intentionally, such as when there is a need to prevent unauthorized access to genetic information within the stored libraries.

Figure 18:
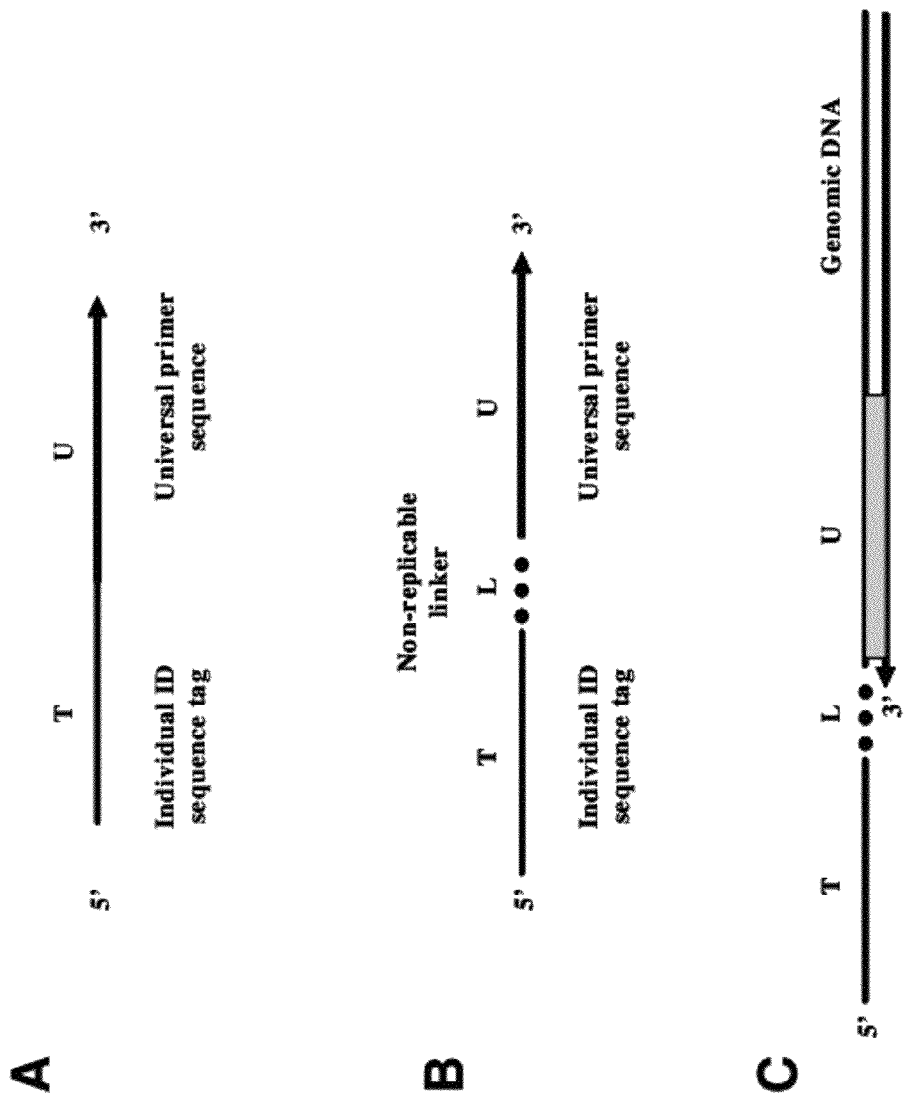
FIGS. 18A through 18C show the structure of the known primer with the ID tags.

Both processes involve known primers with known sequence U at the 3' end and individual ID sequence tag at the 5' end (FIG. 18). In the first case, the known primer is comprised of regular bases (A, T, G and C) and can be replicated (FIG. 18A). In the second case, the known primer has a non-nucleotide linker L (for example, hexa ethylene glycol, HEG) and cannot be replicated (FIGS. 18B and 18C).

Figure 19:
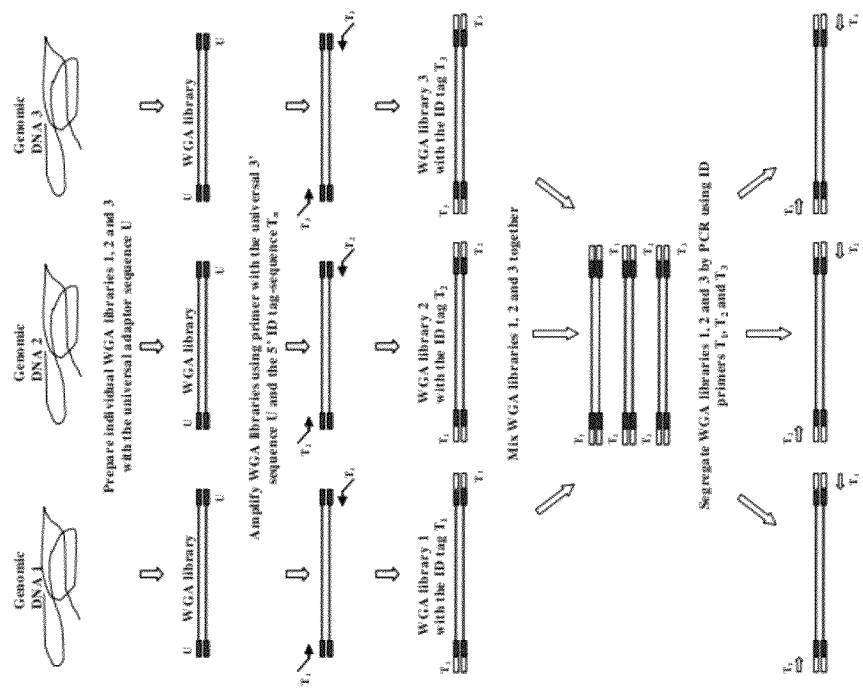
FIG. 19 shows the process of synthesis of WGA libraries with the replicable identification (ID) tag and their usage, for example for security and/or confidentiality purposes, by mixing several libraries and recovering individual library by ID-specific PCR.

The process of tagging, mixing and recovery of 3 different WGA libraries using replicable known primers is shown on FIG. 19. It comprises four steps: 1) Three genomic DNA samples are converted into 3 WGA libraries using the methods described earlier in the patent application; 2) Three WGA libraries are amplified using 3 individual replicable known primers $T_1U$, $T_2U$, and $T_3U$ with the corresponding ID DNA tags $T_1$, $T_2$, and $T_3$ at the 5' end (FIG. 18A); 3) All three libraries are mixed together. Any attempt to amplify and genotype the mix would result in a mixed pattern; and 4) The WGA libraries are segregated by PCR using individual ID primers tags $T_1$, $T_2$, and $T_3$.

Figure 20:
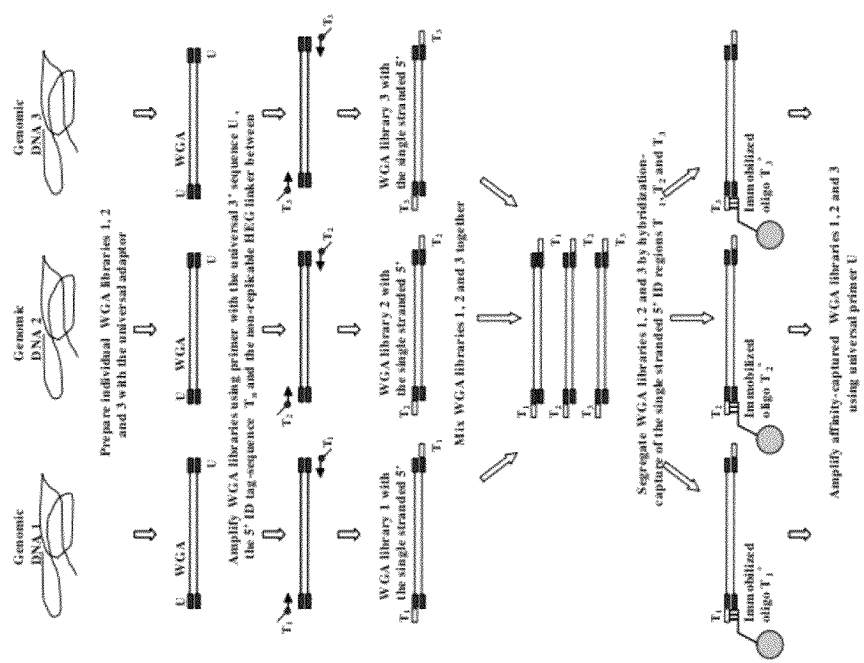
FIG. 20 shows the process of synthesis of WGA libraries with the non-replicable ID tag and their usage, for example for security and/or confidentiality purposes, by mixing several libraries and recovering individual libraries by ID-specific hybridization capture.

The process of tagging, mixing and recovery of 3 different WGA libraries using non-replicable known primers is shown in FIG. 20. It comprises five steps: 1.) Three genomic DNA samples are converted into 3 WGA libraries using the method described earlier in the patent application; 2.) Three WGA libraries are amplified using 3 individual non-replicable known primers $T_1U$, $T_2U$, and $T_3U$ with the corresponding ID DNA tags $T_1$, $T_2$, and $T_3$ at the 5' end (FIGS. 18B and 18C). The resulting products have 5' single stranded tails formed by ID regions of the primers; 3.) All three libraries are mixed together. Any attempt to amplify and genotype the mix would result in a mixed pattern; 4.) The WGA libraries are segregated by hybridization of their 5' tails to the complementary oligonucleotides $T_1^*$, $T_2^*$, and $T_3^*$ immobilized on the solid support; and 5.) The segregated libraries are amplified by PCR using known primer U.

The processes of tagging and recovery described above for genomic libraries can be similarly applied to individual whole transcriptome libraries.

Example 9

Figure 21:
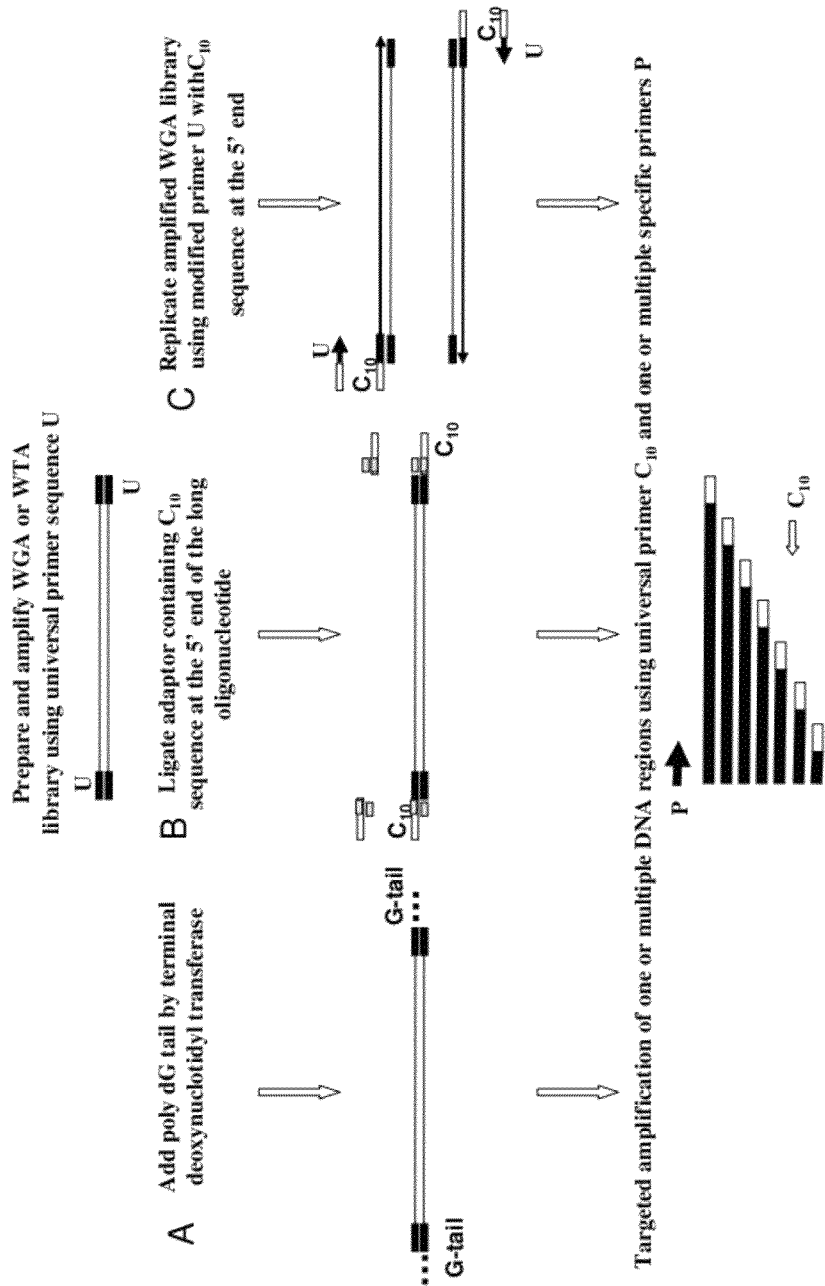
FIG. 21 shows the process of conversion of amplified WGA libraries into libraries with additional $G_n$ or $C_{10}$ sequence tag located at the 3' or 5' end, respectively, of the universal known primer sequence U with subsequent use of these modified WGA libraries for targeted amplification of one or several specific genomic sites using universal primer $C_{10}$ and unique primer P.

Incorporation of Poly-G and Poly-C Functional Tags into WGA/WTA Libraries for Targeted DNA/RNA Amplification WGA (or WTA) libraries prepared by the method of library synthesis described in the invention may be modified or tagged to incorporate specific sequences. The tagging reaction may incorporate a functional tag. For example, the functional 5' tag composed of poly cytosine may serve to suppress library amplification with a terminal C10 sequence as a primer. Terminal complementary homo-polymeric G sequence can be added to the 3' ends of amplified WGA library by terminal deoxynucleotidyl transferase (FIG. 21A), by ligation of adapter containing poly-C sequence (FIG. 21B), or by DNA polymerization with a primer complementary to the universal proximal sequence U with a 5' non-complementary poly-C tail (FIG. 21C). The C-tail may be from 8-30 bases in length. In a preferred embodiment the length of C-tail is from 10 to 12 bases.

As described in U.S. Patent Application 20030143599, hereby incorporated by reference in its entirety, genomic DNA libraries flanked by homo-polymeric tails consisting of G/C base paired double stranded DNA, or poly-G single stranded 3-extensions, are suppressed in their amplification capacity with poly-C primer. This suppression is caused by reduced priming efficiency at poly G region because of formation of alternative G-quartet-like secondary structure within this sequence and it does not depend on the size of DNA amplicons, in contrast to well known "suppression PCR" that results from "pan-like" double-stranded structures formed by self-complementary adaptors and as a result strongly depends on the size of DNA fragments having been more prominent for shortest amplicons (Siebert et al., 1995; US005759822A). This suppression effect is diminished for a targeted site when balanced with a second site-specific primer, whereby amplification of a plurality of fragments containing the unique priming site and the universal terminal sequence are amplified selectively using a specific primer and a poly-C primer, for instance primer $C_{10}$. Those skilled in the art will recognize that genomic complexity may dictate the requirement for sequential or nested amplifications to amplify a single species of DNA to purity from a complex WGA library.

Example 10

WGA Libraries in the Microarray Format

Figure 22:
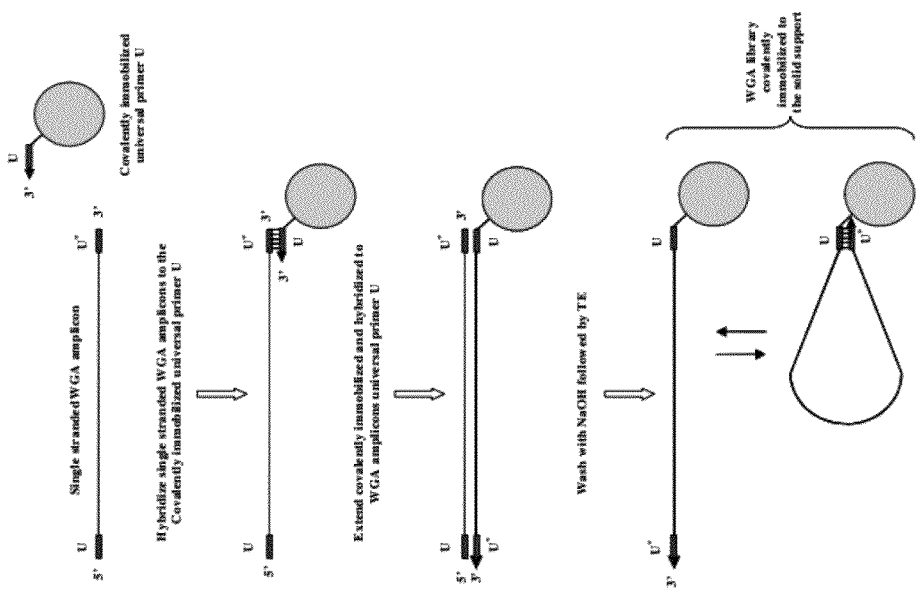
FIG. 22 shows the process for covalent immobilization of WGA library on a solid support.
Figure 23:
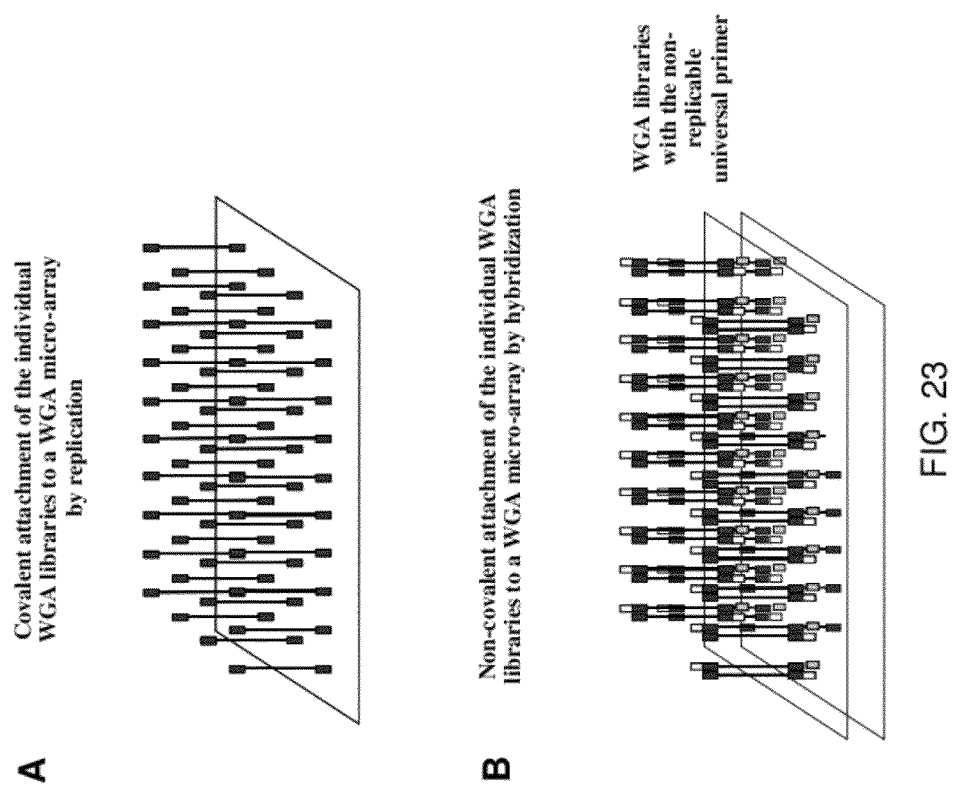
FIGS. 23A through 23B show WGA libraries in the microarray format.

For archiving purposes, for example, individual WGA libraries can be immobilized, such as, for example, on a micro-array. Micro-array format would allow storing tens or even hundreds or thousands of immortalized DNA samples on one small microchip and have fast automated access to them. There are two principal ways that WGA libraries can be immobilized to a micro-array surface: covalently and non-covalently. FIG. 22 shows the process of covalent immobilization. It comprises 3 steps: Step 1. Hybridization of single stranded (denatured) WGA amplicons to the known primer-oligonucleotide U covalently attached to the solid support. Step 2. Extension of the primer U and replication of the hybridized amplicons by DNA polymerase. Step 3. Washing with 100 mM sodium hydroxide solution and TE buffer. Non-covalent immobilization can be achieved by using WGA libraries with affinity tags (like biotin) or DNA sequence tags at the 5' ends of amplicons. Biotin can be located at the 5' end of the known primer U. Single stranded 5' affinity and/or ID tags can be introduced by using non-replicable primers (FIG. 18 and FIG. 20). Biotinylated libraries can be immobilized through streptavidin covalently attached to the surface of the micro-array. WGA libraries with a DNA sequence tag in the form of a 5' overhang can be hybridized to complementary oligonucleotides covalently attached to the surface of the micro-array. Examples of both covalently and non-covalently arrayed libraries are shown in FIG. 23.

Example 11

Repeated Usage of Immobilized WGA Libraries

Covalently immobilized WGA libraries (or libraries immobilized through the biotin-streptavidin interaction) can be used repeatedly to produce replica libraries for whole genome amplification (FIG. 24). In this exemplary, case the process comprises four steps: 1) Retrieval of the immobilized library from the long term storage; 2) Replication of the immobilized library using DNA polymerase and known primer U; 3) Dissociating replica molecules by sodium hydroxide, neutralization and amplification; and 4) Neutralization and return of the solid phase library for a long term storage.

Example 12

Purification of the WGA Products Using a Non-Replicable Primer Affinity Tag and DNA Immobilization by Hybridization For many applications, purity of the amplified DNA is critical. WGA libraries with 5' overhangs can be hybridized to complementary oligonucleotides covalently attached to the surface of magnetic beads, tubes or micro-plates, washed with TE buffer or water to remove excess of dNTPs, buffer and DNA polymerase and then released by heating in a small volume of TE buffer. For this purpose, the single stranded 5'-affinity tag can be introduced by using a non-replicable primer (FIG. 25).

Example 13

Comparison Between Whole Genome Amplification of Libraries Prepared by Klenow Exo− Fragment of DNA Polymerase I with Self-Inert Primers and DOP-PCR Amplification This example describes a side-by-side comparison between the whole genome amplification described in the present invention and a commercially available kit for DOP-PCR amplification.

Human lymphocyte genomic DNA was isolated by standard protocol using phenol-chloroform extraction.

For whole genome amplification with Klenow fragment of DNA polymerase I, samples containing 5 ng or 20 pg in 10 μl of TE-L buffer were randomly fragmented by heating at 95° C. for 4 min. Samples were supplemented with a reaction buffer containing final concentrations of 1× EcoPol buffer (NEB), 200 μM of each dNTP, 1 μM degenerate K(N)$_2$ primer (Table III, primer 14), and 15 ng/μl SSB protein (USB) in a total volume of 14 μl. After a denaturing step of 2 min at 95° C., the samples were cooled to 24° C. and the library synthesis reactions were initiated by adding 5 units GP of Klenow Exo– DNA polymerase (NEB).

After incubation for 60 min at 24° C., reactions were stopped by heating at 75° C. for 5 min. The synthesis reactions were amplified by real-time PCR. The PCR reaction mixture contained: 1× Titanium Taq reaction buffer (Clontech), 200 μM of each dNTP, 100,000× dilutions of fluorescein and SybrGreen I (Molecular Probes) 1 μM universal $K_U$ primer (Table III, primer 16), 5 units of Titanium Taq polymerase (Clontech), and the entire 15 μl library synthesis reactions in a final volume of 75 μl. Reactions were carried out at 94° C. for 15 sec and 65° C. for 2 min on I-Cycler real-time PCR instrument (Bio-Rad).

Amplifications by DOP-PCR were done using DOP PCR Master™ Kit purchased from Roche Molecular Biochemicals (Catalog #1644963). Amplification reactions were carried out under Protocol 2 of the manufacturer's manual. Briefly, samples containing 5 ng or 20 pg of DNA (or control samples without DNA) in a 50 μl standard DOP PCR reaction mixture supplemented with 100,000× dilutions of fluorescein and SybrGreen I (Molecular Probes) were amplified after denaturing for 5 min at 95° C. by cycling for 5 cycles at: 94° C. for 30 sec, 30° C. for 30 sec, ramping at 30° C. to 72° C. for 30 sec (1.4° C./sec), and 72° C. for 1.5 min, followed by 45 cycles at: 94° C. for 30 sec, 62° C. for 30 sec, and 72° C. for 1.5 min, and final extension at 72° C. for 7 min on I-Cycler real-time PCR instrument (Bio-Rad).

FIG. 26A shows the real-time PCR curves of the whole genome amplification by Klenow Exo– and DOP-PCR. As shown, at both input DNA amounts, i.e. 5 ng and 20 pg, the whole genome amplification of libraries prepared with Klenow fragment of DNA polymerase-I and degenerate K(N)$_2$ primer was about 25 PCR cycles more efficient than amplification with DOP-PCR. This result indicates that the methods in the present invention are several orders of magnitude more sensitive than DOP-PCR technology.

Representation analysis was performed using a panel of 16 random human genome STS markers (Table IV, STS markers: 40, 4-44, 46, 47, 49, 52, 54, 55, 58, 60, 62, 63, and 66). The material amplified by PCR with universal $K_U$ primer was purified with Qiaquick filters (Qiagen), and 10 ng aliquots were analyzed in real-time PCR. Reactions were carried out for 45 cycles at 94° C. for 15 sec and 68° C. for 1 min on I-Cycler (Bio-Rad), in a 25 μl volume. Standards corresponding to 10, 1, and 0.2 ng of fragmented genomic DNA were used for each STS. Quantitation was by standard curve fit for each STS.

FIG. 26B shows a logarithmic distribution plot of the STS markers analyzed derived from the real-time PCR standard curve fit. The distribution of all 16 genome markers was tighter and with significantly reduced representation bias in PCR amplified whole genome libraries prepared by Klenow fragment of DNA polymerase I and degenerate K(N)$_2$ primer as compared to DOP-PCR products. Also, the average quantity of STS markers by the proposed method was approximately an order of magnitude higher in the library amplified form 20 pg of genomic DNA (about 3 diploid genome equivalents) as compared to the DNA product prepared from 5 ng DNA (almost 1000 diploid genome equivalents) by DOP-PCR.

Taken together, these results demonstrate the superiority of the methods in the present invention over the DOP-PCR technique (Telenius et al., 1992), both in terms of sensitivity and fidelity of genome sequence representation.

Example 14

Library Generation and Whole Genome Amplification of DNA Isolated from Serum

This example describes the amplification of genomic DNA that has been isolated from serum collected in serum separator tubes (SST). Blood was collected into 8 ml vacutainer SST tubes. The serum tubes were allowed to sit at room temperature for 30'. The tubes were centrifuged for 10' at 1,000×G with minimal acceleration and braking. The serum was subsequently transferred to a clean tube. Isolated serum samples may be used immediately for DNA extraction or stored at –20° C. prior to use.

DNA from 1 ml of serum was purified using the DRI ChargeSwitch Blood Isolation kit according to the manufacturer's protocols. The resulting DNA was precipitated using the pellet paint DNA precipitation kit (Novagen) according to the manufacturer's instructions and the sample was resuspended in TE-Lo to a final volume of 30 ml for serum. The quantity and concentration of DNA present in the sample was quantified by real-time PCR using Yb8 Alu primer pairs; Yb8F 5'-CGAGGCGGGTGGATCATGAGGT-3' (SEQ. ID NO:120), and Yb8R 5'-TCTGTCGCCCAGGCCGGACT-3' (SEQ. ID NO:121). Briefly, 25 ml reactions were amplified for 40 cycles at 94° C. for 15 sec and 74° C. for 1 min. Standards corresponding to 10, 1, 0.1, 0.01, and 0.001 ng of genomic DNA were used and the serum DNA quantities and concentrations were calculated by standard curve fit (I-Cycler software, Bio-Rad).

Figure 27:
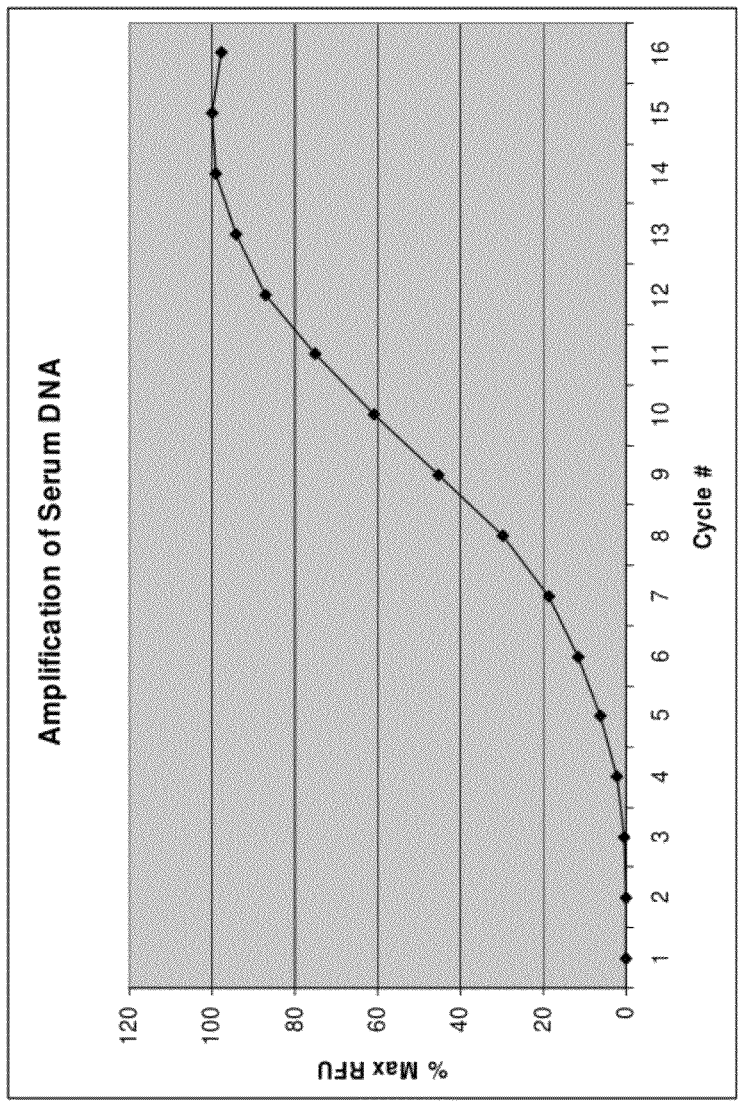

DNA isolated from serum was randomly fragmented in TE-L buffer by heating at 95° C. for 4 min. The reaction mixture contained 10 ng of thermally fragmented DNA in 1× EcoPol buffer (NEB), 200 μM of each dNTP, and 1 uM of degenerate K(N)$_2$ primer (Table III, primer 14) in a final volume of 15 μl. After a denaturing step of 2 min at 95° C., the samples were cooled to 4° C. and the reaction initiated by adding 5 units Klenow Exo– (NEB). WGA library synthesis was carried out by a three-step incubation protocol for 20 min at 16° C., 20 min at 24° C., and 20 min at 37° C. Reactions were stopped by heating for 15 min at 75° C. and subsequently cooling to 4° C. The entire library reaction was further amplified by real-time PCR. The PCR reaction mixture contained: 1× Titanium Taq reaction buffer (Clontech), 200 uM each dNTP, 10,000× dilutions of fluorescein and SybrGold I (Molecular Probes) 1 uM known $K_U$ primer (Table III, primer 15), 0.5× Titanium Taq polymerase (Clontech), and 10 ng input genomic DNA of the library reactions in a final volume of 75 μl. Reactions were carried out for 17 cycles at 94° C. for 15 sec and 65° C. for 2 min on an I-Cycler real-time PCR instrument (Bio-Rad). The amplification curve is illustrated in FIG. 27.

The amplified material was purified by Millipore Multiscreen PCR plates and quantified by optical density. Gel analysis of the amplified products indicated a size distribution (200 bp to 1.6 kb) similar to the original serum DNA (FIG. 28A). Additionally, the amplified DNA was analyzed using real-time, quantitative PCR using a panel of human genomic STS markers. The markers that make up the panel are listed in Table IV. Quantitative Real-Time PCR was performed using an I-Cycler Real-Time Detection System (Bio-Rad), as per the manufacturer's directions. Briefly, 25 µl reactions were amplified for 40 cycles at 94° C. for 15 sec and 65° C. for 1 min. Standards corresponding to 10, 1, and 0.2 ng of fragmented DNA were used for each STS, quantities were calculated by standard curve fit for each STS (I-Cycler software, Bio-Rad) and were plotted as distributions. Quantitative real-time PCR of the WGA products from serum demonstrated that all 8 markers tested were within a factor of 5 of the mean amplification. These results indicate that the representation of the original serum DNA is maintained following WGA. FIG. 28B is a scatterplot of the representation of the human genomic STS markers in the amplified DNA.

Example 15

Whole Genome Amplification of Single Human Cells and Individual Hair Follicles from Libraries Prepared Using Self-Inert Degenerate Primer K and Klenow Exo– Fragment of DNA Polymerase I This example describes the whole genome amplification of total DNA from single human blood cells, single sperm cells, and individual hair follicles.

Three microliters of freshly drawn blood from a healthy female donor were exponentially diluted in PCR tubes containing 27 µl dilution buffer composed of 10 mM Tris-HCl, pH 7.5, 100 mM NaCl, and 0.5 mM EDTA to a level of 1, 0.5, or 0.2 cells per µl, assuming an average blood count of $5\times10^3$ nucleated cells per ml of blood. Similarly, 3 µl of ejaculate from a healthy donor were diluted to the same level assuming a sperm count of 20,000 per µl of ejaculate. A single hair follicle from a healthy female donor was lysed as described below and then exponentially diluted in lysis buffer.

One microliter of the respective cell dilutions was mixed with 9 µl of freshly prepared lysis buffer containing 10 mM Tris-HCl, pH 7.5, 0.5 mM EDTA, 20 mM NaCl, 0.007% (w/v) sodium dodecyl sulfate (SDS), and 0.12 mg/ml proteinase K (USB). In the case of a hair follicle, the follicle was suspended in 10 µl of lysis buffer. The samples were incubated for 1 hr at 50° C. to lyse the cells. The hair follicle sample was further sequentially diluted with lysis buffer from $10^2$ to $10^6$-fold and each dilution was subjected to WGA library preparation.

Samples were heated at 99° C. for 4 min to inactivate the proteinase K, disintegrate the nucleoprotein, and thermally fragment the DNA. The library synthesis step was conducted in a reaction mixture containing 1× EcoPol buffer (NEB), 200 mM of each dNTP, 1 µM degenerate primer K (Table III, sequence ID 15), and 15 ng/µl SSB (USB) in a total volume of 14 µl. After a denaturing step of 2 min at 95° C., the samples were cooled to 24° C. and the reaction initiated by adding 5 units GP of Klenow Exo– DNA polymerase (NEB). After incubation for 60 min at 24° C. reactions were stopped by heating at 75° C. for 5 min. The synthesized libraries were amplified by real-time PCR. The PCR reaction mixture contained: 1× Titanium Taq reaction buffer (Clontech), 200 uM each dNTP, 100,000× dilutions of fluorescein and SybrGreen I (Molecular Probes) 1 uM universal $K_U$ primer (Table III, primer 16), 5 units of Titanium Taq polymerase (Clontech), and the entire 15 µl library synthesis reaction in a final volume of 75 µl. In the case of hair follicle dilutions a blank control without DNA was included. Redundant single cell samples at different dilutions were amplified which served as auto-controls, i.e. one cell or no cells were amplified at the highest dilutions. Reactions were carried out at 94° C. for 15 sec and 65° C. for 2 min on I-Cycler real-time PCR instrument (Bio-Rad).

FIG. 29 shows amplification of single nucleated blood cells. Approximately 8 cycles separate the resulting amplification profiles between single cells and no cells, allowing clear distinction between the presence or absence of a single blood cell.

Representation analysis of 5 single cell samples amplified by PCR was done using a panel of 16 human STS markers (Table IV, STS markers: 40, 4-44, 46, 47, 49, 52, 54, 55, 58, 60, 62, 63, and 66). The material amplified by PCR with universal $K_U$ primer was purified with Qiaquick filters (Qiagen), and 10 ng aliquots were analyzed in real-time PCR. Reactions were carried out for 45 cycles at 94° C. for 15 sec and 68° C. for 1 min on I-Cycler (Bio-Rad), in a 25 µl volume. Standards corresponding to 10, 1, and 0.2 ng of fragmented genomic DNA were used for each STS. Quantitation was by standard curve fit for each STS. To assess the effect of copy number on the amplification bias, ⅙ of the volume of each individual single cell amplification reaction was combined into a pooled sample. The pooled sample was analyzed for STS marker representation as described above. Markers amplified at a level of less than 0.2 ng of standard template were considered dropouts. Table V shows the number of dropout markers for 3 individual single cell amplifications, as compared to the pooled sample.

TABLE V

STS markers amplification from whole genome amplified single blood cells and a pool of six individually amplified single cells

| | # of dropouts | Markers Amplified % of total (n = 16) |
|---|---|---|
| Single cell | 10 | 37.5% |
| Single cell | 8 | 50.0% |
| Single cell | 10 | 37.5% |
| Pooled sample | 4 | 75.0% |

The majority of genomic marker dropouts were random in individual single cell amplification reactions. After pooling of individually amplified single cells, the number of dropouts decreased by approximately half (Table V).

FIG. 30 shows amplification of single sperm cells. The distance between samples with a single cell and samples without cells in this case was only about 2 cycles (not the expected approximately 6 cycles for a haploid genome as compared to blood nucleated cells). In a specific embodiment, this difference is attributed to either inefficient lysis or the presence of inhibitors of the amplification in sperm cells. Nonetheless, even with 2 cycles difference one can still distinguish between a single cell and no cell.

As shown on FIG. 31, exponential dilutions of a lysed hair follicle showed a progressive shift of about 3.5-4 cycles as expected. The highest dilution of 1:1,000,000 amplified about two cycles before the blank control which when compared to purified genomic DNA corresponds to approximately 2 pg of DNA. This demonstrates the potential of the method for forensic applications.

Example 16

Amplification of Single Human Chromosomes with Degenerate K(N)₀ Primer and Klenow Exo– Fragment of DNA Polymerase-I This example describes the amplification of total DNA from single copy human chromosomes.

Single copies of derivative chromosomes from a lymphoblastoid cell line carrying a translocation (11;12)(q21; p13.33) sorted in 5 µl of water in a 96 well microliter plate were obtained from the Wellcome Trust Sanger Institute. Fourteen individual samples of each translocation derivative chromosome were lysed in freshly prepared lysis buffer containing 10 mM Tris-HCl, pH 7.5, 0.5 mM EDTA, 20 mM NaCl, 0.007% (w/v) sodium dodecyl sulfate (SDS), and 0.12 mg/ml proteinase K (USB) in a final volume of 10 µl at 50° C. for 1 hr.

Samples were heated at 99° C. for 4 min to inactivate the proteinase K, disintegrate the nucleoprotein, and thermally fragment the DNA. Library synthesis was conducted in a reaction mixture containing 1× EcoPol buffer (NEB), 200 µM of each dNTP, 1 mM degenerate $K(N)_0$ primer (Table III, sequence ID 15), and 15 ng/µl SSB (USB) in a total volume of 14 µl. After a denaturing step of 2 min at 95° C., the samples were cooled to 24° C. and the reaction initiated by adding 5 units (1 up of Klenow Exo– DNA polymerase (NEB). After incubation for 60 min at 24° C. reactions were stopped by heating at 75° C. for 5 min. The library synthesis reactions were amplified by real-time PCR in a mixture contained: 1× Titanium Taq reaction buffer (Clontech), 200 uM each dNTP, 100,000× dilutions of fluorescein and SybrGreen I (Molecular Probes) 1 uM universal $K_U$ primer (Table III, primer 16), 5 units of Titanium Taq polymerase (Clontech), and the entire 15 µl library synthesis reaction in a final volume of 75 µl. Blank controls without DNA were also included. Reactions were carried out at 94° C. for 15 sec and 65° C. for 2 min on I-Cycler real-time PCR instrument (Bio-Rad).

FIG. 32 shows amplification of single copy human chromosomes. Approximately 4 cycles distance between single chromosomes and no DNA blank controls was observed.

Example 17

Application of Single-Cell WGA for Detection and Analysis of Abnormal Cells

WGA amplified single-cell DNA can be used to analyze tissue cell heterogeneity on the genomic level. In the case of cancer diagnostics it would facilitate the detection and statistical analysis of heterogeneity of cancer cells present in blood and/or biopsies. In the case of prenatal diagnostics it would allow the development of non-invasive approaches based on the identification and genetic analysis of fetal cells isolated from blood and/or cervical smears. Analysis of DNA within individual cells could also facilitate the discovery of new cell markers, features, or properties that are usually hidden by the complexity and heterogeneity of the cell population.

Analysis of the amplified single-cell DNA can be performed in two ways. In the traditional approach shown on FIG. 33, amplified DNA samples are analyzed one by one using hybridization to genomic micro-array, or any other profiling tools such as PCR, sequencing, SNP genotyping, micro-satellite genotyping, etc. The method would include: 1.) Dispersal of the tissue into individual cells; 2.) Preparation and amplification of individual (single-cell) WGA libraries; 3.) Analysis of individual single-cell genomic DNA by conventional methods. This approach can be useful in situations when genome-wide assessment of individual cells is necessary.

In the second approach shown on FIG. 34, amplified DNA samples are spotted on the membrane, glass, or any other solid support, and then hybridized with a nucleic acid probe to detect the copy number of a particular genomic region. The method would include: 1.) Dispersal of the tissue of interest into individual cells; 2.) Preparation and amplification of individual (single-cell) WGA libraries; 3.) Preparation of micro-arrays of individual (single-cell) WGA DNAs; 4.) Hybridization of the single-cell DNA micro-arrays to a locus-specific probe; 5.) and Quantitative analysis of the cell heterogeneity. This approach can be especially valuable in situations when only limited number of genomic regions should be analyzed in a large cell population.

Example 18

Application of Whole Genome Amplification for Detection and Analysis of Gene Copy Number WGA amplified DNA retains both sequence and copy number integrity during library synthesis and amplification. This feature of the libraries facilitates the potential evaluation of cells or tissues suspected of having undergone gene amplification events such as those observed in oncogenic transformation. Early detection of gene amplification events requires the ability to examine the event in a few suspect cells or biopsy material. This application is best illustrated with a set of model samples from patients of known chromosomal aneuploidy in the X-chromosome as described in this example.

DNA from patients with XO, XX, and XXX served as template for WGA library synthesis (kindly provided by Dr. Arul Chinnaiyan, University of Michigan). DNA isolated by standard procedures was randomly fragmented in TE-L buffer by heating at 95° C. for 4 min. The reaction mixtures contained 25 ng of thermally fragmented DNA (or just TE-L buffer as negative control) in 1× EcoPol buffer (NEB), 200 µM of each dNTP, and 1 uM degenerate $K(N)_2$ primer (Table III, primer 14) 15 ng/µl SSB (USB) in a total volume of 14 µl After a denaturing step of 2 min at 95° C., the samples were cooled to 16° C., and the reaction initiated by adding 5 units (1 µl) of Klenow exo– DNA polymerase (USB). WGA library synthesis was done at 16° C. for 20 min 24° C. for 20 min, and 37° C. for 20 min. Reactions were stopped with 1 µl of 83 mM EDTA (pH 8.0), and samples were heated for 5 min at 75° C. Aliquots of the reactions corresponding to 5 ng of input DNA were amplified by real-time PCR. The PCR reaction mixture contained: 1× Titanium Taq reaction buffer (Clontech), 200 µM each dNTP, 100,000× dilutions of fluorescein and SybrGreen I (Molecular Probes) 1 µM known $K_U$ primer (Table III, primer 16), 5 units of Titanium Taq polymerase (Clontech), and 5 ng input genomic DNA of the library synthesis reactions in a final volume of 75 µl. Reactions were carried out for 14 cycles at 94° C. for 15 sec and 65° C. for 2 min on I-Cycler real-time PCR instrument (Bio-Rad).

For analysis, individual 5 ng aliquots of the library were compared to the combined mixture reconstituting the entire 25 ng input template using X chromosome STS primer pairs (152 and 154 Table IV). The material amplified by PCR with universal $K_U$ primer was purified with Qiaquick filters (Qiagen), and 10 ng aliquots were analyzed in real-time PCR. Reactions were carried out for 40 cycles at 94° C. for 15 sec and 68° C. for 1 min on I-Cycler (Bio-Rad), in a 25 µl volume.

FIG. 35 shows the normalized STS real-time PCR curves for each set of primers. Panels A and C display the clustering of the individual 5 ng aliquots amplified from a single 25 ng WGA library for samples with 1×, 2×, and 3× chromosome copies. In each case the variation is approximately +/–0.5 cycles. FIG. 35 panels B and D display how the variation is averaged upon reconstitution of the individual amplifications. In each case the reconstituted mixture is tested in triplicate showing a full cycle shift in the doubling of the template between 1× and 2× and the predicted approximately half cycle shift when a third copy (3×) is added in the case of trisomy for the X chromosome.

The precise copy number measurements shown here for WGA amplified libraries exemplify the potential for clinical applications in gene amplification events. Combined with the ability to generate libraries from low amounts of template the invention can be used in cancer and prenatal diagnostics where DNA sample is frequently very limited.

Example 19

Whole Transcriptome Amplification Using Libraries Prepared from Poly A+ RNA by MMLV Reverse Transcriptase and Self-Inert Degenerate Primers This example describes application of the invention for the creation of an amplifiable library faithfully representing the expression patterns of transcribed RNA within a cell or population of cells herein termed "Whole Transcriptome Amplification" (WTA).

Purified polyA+ RNA from EBV transformed human B lymphocytes, Raji cells (Clontech), served as input template for WTA library preparation. As in the case of WGA protocol, WTA is performed in two steps: library synthesis and library amplification. Library synthesis involves similar self-inert degenerate primers (primers K), but a different DNA polymerase, specifically MMLV reverse transcriptase. It proceeds through the extension/strand displacement reactions similar to WGA, but requires no fragmentation of the RNA template (although fragmentation can be applied to reduce the average amplicon size if desirable). To improve representation of the 3' termini of mRNA molecules primer $K(T)_{20}$ (Table III primer 19) complementary to the polyA tails was also added. To assemble the library synthesis reaction, primers were annealed to polyA+ RNA templates. Annealing was facilitated by briefly heating the mixture of 100 ng or 10 ng polyA+ RNA, primers $K(N)_{2}$ [1 µM] (Table III primer 14) and $K(T)_{20}$ [200 nM] (Table III primer19) either in combination, or $K(N)_{2}$ [1 µM] alone, dNTP mix [1 µM ea.] and RNase free water to 17 µl at 70° C. for 5 minutes followed by immediate removal to ice. The polymerase reaction was initiated by addition of 2 µl of 10×MMLV buffer to a final concentration of 75 mM KCL, 50 mM Tris-HCl, 3 mM MgCl$_2$, 10 mM dithiothreitol, pH 8.3) and 1 µl (200 units) MMLV reverse transcriptase (NEB). Reactions were mixed, and incubated for 1 hour at 42° C. Enzyme activity was halted by heat inactivation for 5 minutes at 95° C.

Aliquots of the WTA library synthesis reactions corresponding to 10 ng of input RNA (or in the case of the 10 ng sample, the entire reaction mixture) were further amplified by real-time PCR. The PCR reaction mixture contained: 1× Titanium Taq reaction buffer (Clontech), 200 nM each dNTP, 100,000× dilutions of fluorescein and SyberGreen I (Molecular Probes) 1 µM $K_U$ primer (Table III primer 16), 5 units of Titanium Taq polymerase (Clontech) and volumes representing 10 ng equivalents of the input polyA+ RNA from the library synthesis reactions in a final volume of 75 µl. Reactions were carried out for 17 cycles (94° C. for 20 sec and 65° C. for 2 min) in real-time PCR I-Cycler™ (Bio-Rad). The effects of input template and subsequent reaction volumes transferred into the PCR amplification are seen in FIG. 36. The entire 10 ng library synthesis product shows delayed real-time PCR kinetics relative to 10 ng taken from the 100 ng library synthesis reaction. The modest effect of the amount of RNA in the library preparation step on the amplification profile (only a single cycle shift) suggests only minor differences in template availability for these RNA amounts.

One specific application of whole transcriptome amplification is to enable micro-array expression analysis from small amounts of RNA. Traditional RNA amplification methods employ priming of polyA tails present within the mRNA pool of transcripts. As a result, the micro-array studies to date have been biased toward the 3' end of mRNAs. To increase compatibility of the present invention with the existing micro-array target bias, the $K(T)_{20}$ primer was employed. To demonstrate the effect of this added priming, the amplifications were tested in the presence and absence of each primer. FIG. 37 shows a two cycle shift in the absence of $K(T)_{20}$ when 10 ng polyA+ RNA serves as template for the library synthesis step, and a six cycle shift in the absence of K(N2). The combined effect of these primers facilitates even priming across the mRNA molecules and exhibits a more uniform representation of the input RNA across the entire message.

Agarose gel electrophoretic analysis of the resulting amplified library products supports the observed real-time improvements with higher input template and polyA tail specific priming. FIG. 38 shows the molecular weight range of products amplified from each of these libraries with the various primer conditions. The combination of priming both at the polyA tail and at random internal sites yields a more robust amplification over a larger product size range. The absence of $K(T)_{20}$ priming has much less of an effect on performance than does the absence of the $K(N)_2$ primer, which essentially eliminates products competent for amplification by failing to generate the second universal priming site on each amplicon. 100 ng input template libraries exhibit a broader size distribution of amplimers suggestive of less frequent priming or simply a greater starting quantity of larger RNA molecules.

Representation of specific mRNA molecules was evaluated by real-time PCR analysis for 11 specific human STS markers residing in known genes represented in the RNA sample at various levels of expression (Table IV, STS markers: 20, 31, 47, 51, 86, 103, 106, 110, 119, 134, 140). The material amplified by PCR with universal $K_U$ primer was purified with Qiaquick filters (Qiagen), and 10 ng aliquots were analyzed in real-time PCR. Reactions were carried out for 45 cycles at 94° C. for 15 sec and 68° C. for 1 min on I-Cycler (Bio-Rad), in a 25 µl volume. Standards corresponding to 10, 1, and 0.2 ng of fragmented genomic DNA were used for each STS. Quantitation was by standard curve fit for each STS. FIG. 39 demonstrates the representation of these STS sites. Each of the chosen STS sites was represented for each condition with noticeable improvement observed when the $K(N)_2$ and $K(T)_{20}$ primers are combined and somewhat improved average performance for the 100 ng input libraries.

Another unique feature of the invention relates to WTA library representation across a particular mRNA locus. One can expect that the combined terminal and semi-random internal priming generates amplicons across the entire RNA molecule population without bias toward the 3' end. To prove this statement three large transcripts were examined using STS primer pairs at varying distances from the 3' end (Table IV STS 42, 42a, 42b, 85, 85a, 85b, 119, 119a, 119b). FIG. 40 illustrates the real-time PCR analysis of WTA amplification for these loci. The results indicate representation at all sites with improvement in 3' representation attributed to the inclusion of the K(T20) primer. Relative differences in specific site amplifications are attributed to variable priming and efficiency of amplification of specific sequences. These results indicate relatively uniform library representation at different distances from the 3' end for three randomly chosen large transcripts. Representation is consistent between libraries made from a broad range of RNA input template (100 ng-10 ng). The lower level of amplification observed at 1795 bp from the 3' end of STS 42a compared to its neighboring more proximal and more distal sequences (42 and 42b, Table IV) suggests that WTA amplification of specific regions may be largely dependent on the nucleotide sequences surrounding the specific site of interest. Reproducibility of amplification of specific markers between libraries suggests the ability to directly compare expression levels of a particular site between two samples (i.e. cancer vs. normal tissue).

Example 20

Whole Transcriptome Amplification

Titration of Input Template and $MgCl_2$ Concentration

WTA amplification of RNA from systematic sampling of tissues such as biopsy tissues and laser capture micro-dissection, or where sample is limiting as in the case of rare collections from unique cohorts, dictates the need for robust amplification from low input template amounts. To evaluate the tolerated range of input template and optimal $MgCl_2$ concentration, total RNA from normal pooled prostate (CPP, Clontech) was examined from 0.25 ng to 10 ng at 3 mM and 10 mM $MgCl_2$. Annealing was facilitated by briefly heating the mixture of 10 ng, 1 ng, 0.5 ng, or 0.25 ng CPP total RNA (Clontech), primers $K(N)_2$ [1 µM] (Table III primer 14) and K(T20) [200 nM] (Table III; primer19), dNTP mix [1 µM ea.] and RNase free water to 17 µl at 70° C. for 5 minutes followed by immediate removal to ice. The library synthesis reaction was initiated by addition of 2 µl of 10×MMLV buffer to a final concentration of 75 mM KCL, 50 mM Tris-HCl, 3 mM or 10 mM $MgCl_2$, 10 mM dithiothreitol, pH 8.3) and 1 µl (200 units) MMLV reverse transcriptase (NEB) or 1 µl (50 units) MMLV reverse transcriptase (Epicentre). Reactions were mixed, and incubated for 1 hour at 42° C. Enzyme activity was halted by heat inactivation for 5 minutes at 95° C.

The library synthesis reactions were amplified by real-time PCR in a reaction mixture that contained: 1× Titanium Taq reaction buffer (Clontech), 200 nM each dNTP, 100,000× dilutions of fluorescein and SyberGreen I (Molecular Probes) 1 µM $K_U$ primer (Table III primer 16), 5 units of Titanium Taq polymerase (Clontech) and 50% of the library synthesis reaction (12.5 µl) representing 5 ng, 0.5 ng, 0.25 ng and 0.125 ng of starting template in a final volume of 75 µl. Reactions were carried out for 17-33 cycles (94° C. for 20 sec and 65° C. for 2 min) in real-time PCR I-Cycler™ (Bio-Rad). FIG. 41 shows the real-time amplification profiles with the expected template dependent titration. Doubling of the template results in the expected two fold increase seen as a one cycle shift, while the 10 fold increase from 0.5 ng to 5 ng gave slightly more than the expected 10 fold (3.4 cycle) shift. A striking difference in performance is observed with the two buffer enzyme combinations.

To evaluate the variation in representation across the input template concentration and buffer conditions, samples from 10 ng and 0.25 ng input template amounts were evaluated by STS analysis. Representation of specific mRNA molecules was evaluated by real-time PCR analysis for 11 specific human STS markers residing in known genes represented in the RNA sample at various levels of expression (Table IV, STS markers: 20, 31, 47, 51, 86, 103, 106, 110, 119, 134, 140). The material amplified by PCR with universal $K_U$ primer was purified with Qiaquick filters (Qiagen), and 10 ng aliquots were analyzed in real-time PCR. Reactions were carried out for 45 cycles at 94° C. for 15 sec and 68° C. for 1 min on I-Cycler (Bio-Rad), in a 25 µl volume. Standards corresponding to 10, 1, and 0.2 ng of fragmented genomic DNA were used for each STS. Quantitation was by standard curve fit for each STS. FIG. 42 shows the relative quantities of each of genes assayed. Reducing the input to 0.25 ng under low (3 mM, NEB) $MgCl_2$ conditions reduces the representation of rare messages below confidence levels. Representation is markedly increased with the increased (10 mM, Epicentre) $MgCl_2$ conditions as predicted by the real-time amplification kinetics.

To further examine the difference between the buffer systems, a titration of $MgCl_2$ concentration was examined. Total RNA from normal pooled prostate (CPP, Clontech) 10 ng was amplified over a 3-12 mM range of $MgCl_2$. Annealing was facilitated by briefly heating the mixture of 10 ng CPP total RNA (Clontech), primers $K(N)_2$ [1 µM] (Table III, primer 14) and $K(T)_{20}$ [200 nM] (Table III, primer19), dNTP mix [1 µM ea.] and RNase free water to 17 µl at 70° C. for 5 minutes followed by immediate removal to ice. The library synthesis reaction was initiated by addition of 2 µl of 10×MMLV buffer to a final concentration of 75 mM KCL, 50 mM Tris-HCl, 3 mM or supplemented in 1 mM increments to 12 mM $MgCl_2$, 10 mM dithiothreitol, pH 8.3) and 1 µl (50 units) MMLV reverse transcriptase (Epicentre). Reactions were mixed, and incubated for 1 hour at 42° C. Enzyme activity was halted by heat inactivation for 5 minutes at 95° C. The library synthesis reactions were further amplified by real-time PCR in a reaction mixture that contained: 1× Titanium Taq reaction buffer (Clontech), 200 nM each dNTP, 100,000× dilutions of fluorescein and SyberGreen I (Molecular Probes) 1 µM $K_U$ primer (Table III, primer 16), 5 units of Titanium Taq polymerase (Clontech) and 50% of each library synthesis reaction (10 µl) representing 5 ng of starting template in a final volume of 75 µl. Reactions were carried out for 19 cycles (94° C. for 20 sec and 65° C. for 2 min) in real-time PCR I-Cycler™ (Bio-Rad). FIG. 43 shows real-time PCR curves detailing the effect of $MgCl_2$ on WTA library generation. Conditions at or above 6 mM to about 12 mM $MgCl_2$ during library preparation step yield optimal kinetics. $MgCl_2$ is known to affect base pairing which can manifest itself at the level of primer binding as well as strand displacement in the WTA application of the invention. A skilled artisan could determine optimal concentrations for specific applications of the invention, including parameters such as template size and complexity, for example.

Example 21

Preferential Amplification of Single Stranded Nucleic Acid Templates Using WTA Methods In applications where residual DNA may be present in a clinical sample, or where total nucleic acids are isolated, the ability to selectively amplify DNA or RNA from the same sample can be beneficial. In this example, the WTA protocol is applied to samples of total RNA or genomic DNA with and without fragmentation and denaturation.

To evaluate WTA library formation from DNA and RNA input templates 10 ng samples of genomic DNA (Coriell CEPH genomic DNA (#7057) or total RNA (Clontech, CPP) were diluted to a final volume of 6.5 µl in water. Fragmentation and denaturation were performed by heating to 95° C. for 4 minutes, snap cooling to ice (4° C.), addition of 1.5 µl of 10×MMLV buffer (Epicentre) to a final concentration of 75 mM KCL, 50 mM Tris-HCl, 10 mM $MgCl_2$, 10 mM dithiothreitol, pH 8.3), primers $K(N)_2$ [1 µM] (Table III primer 14) and $K(T)_{20}$ [200 nM] (Table III, primer19), dNTP mix [1 µM ea.] and RNase free water to 14 µl, followed by a brief 2 minute heating to 95° C. and cooling to ice to anneal primers.

Samples not fragmented or denatured received standard 70° C. treatment for 5 minutes, followed by snap cooling to ice (4° C.) addition of 1.5 µl of 10×MMLV buffer (Epicentre) to a final concentration of 75 mM KCL, 50 mM Tris-HCl, 10 mM $MgCl_2$, 10 mM dithiothreitol, pH 8.3), primers $K(N)_{2}$ [1 µM] (Table III primer 14) and $K(T)_{20}$ [200 nM] (Table III, primer19), dNTP mix [1 µM ea.] and RNase free water to 14 µl. The polymerase reaction was initiated by addition of 1 µl (50 units) MMLV reverse transcriptase (Epicentre). Reactions were mixed, and incubated for 15 minutes at 23° C. followed by 1 hour at 42° C. Enzyme activity was halted by heat inactivation for 5 minutes at 95° C.

The library reactions were amplified by real-time PCR in a reaction mixture that contained: 1× Titanium Taq reaction buffer (Clontech), 200 nM each dNTP, 100,000× dilutions of fluorescein and SyberGreen I (Molecular Probes) 1 µM $K_U$ primer (Table III primer 16), 5 units of Titanium Taq polymerase (Clontech) and 100% of the library reaction (15 µl) representing the entire 10 ng of starting template in a final volume of 75 µl Reactions were carried out for 13-17 cycles (94° C. for 20 sec and 65° C. for 2 min) in real-time PCR I-Cycler™ (Bio-Rad). FIG. 44A shows the real-time amplification profiles from each template. Libraries amplified from DNA after fragmentation and denaturation show profiles similar to WGA embodiments of the invention. As claimed, MMLV polymerase activity can efficiently substitute for other polymerases in WGA library synthesis. In the absence of fragmentation and denaturation, DNA is severely inhibited, showing an approximately 6 cycle delay in amplification, or roughly 1% of template participating in the reaction. RNA templates only display a minor effect of fragmentation and denaturation conditions compared to direct annealing and extension. Differences in the molecular weight of products amplified in each of these reactions and the control reactions without template are shown in FIG. 44B. Each reaction was allowed to proceed to plateau and evaluated by agarose gel electrophoresis. The distribution of library fragments from DNA template is consistent with that observed for WGA products. Thermal treatment of RNA shifts the size distribution of library fragments by 50 to 100 base pairs shorter, demonstrating the ability to tailor amplicon size. No template controls failed to generate amplicons above 200 bp after 28 cycles of amplification.

The ability to distinguish between DNA and RNA templates on the basis of fragmentation and denaturation demonstrate controlled differential access of the template. Residual traces of DNA in RNA preparations will amplify with approximately 1% efficiency with respect to the RNA template under non-denaturing conditions. Although not specifically demonstrated here, as known in the art, Klenow exo– fails to utilize RNA as a template, thereby providing a method to selectively amplify each nucleic acid population from a complex mixture.

Example 22

Total Nucleic Acid Differential Amplification Platform for Synthesis of DNA and RNA Libraries from Limited Archived or Clinical Samples In some genetic profiling studies, both the genomic (DNA) and the expression (RNA) information are required to provide a complete analysis of the tissue or cells evaluated. Only when alterations in gene sequence, copy number, and the effective expression of transcribed sequences are taken together can a complete analysis of the sample be achieved. In many cases, a clinical isolate or archival sample is limited and may only be sufficient for one isolation scheme. Amplification of genomic and expression libraries may be streamlined through a total amplification platform using the present invention.

FIG. 45 illustrates selective amplification of DNA and RNA from a total nucleic acid isolate using self-inert degenerate primers in combination with Klenow Exo– fragment of DNA polymerase I and heat-denatured nucleic acid (WGA) or MMLV reverse transcriptase and non-denatured nucleic acid (WTA). A device is diagrammed for the segregation of DNA and RNA by selective amplification from a total nucleic acid preparation. The invention applied in this format, or applied in a microfluidic platform, for example, uses selective amplification rather than selective degradation or selective isolation of DNA and RNA, eliminating problems such as sample loss associated with preparation of nucleic acids from limited samples.

Example 23

Application of Homopolymeric G/C Tagged WGA Libraries for Targeted DNA Amplification Targeted amplification may be applied to genomes for which limited sequence information is available or where rearrangement or sequence flanking a known region is in question. For example, transgenic constructs are routinely generated by random integration events. To determine the integration site, directed sequencing or primer walking from sequences known to exist in the insert may be applied. The invention described herein can be used in a directed amplification mode using a primer specific to a known region and a universal primer. The universal primer is potentiated in its ability to amplify the entire library, thereby substantially favoring amplification of product between the specific primer and the universal sequence, and substantially inhibiting the amplification of the whole genome library.

Conversion of WGA libraries for targeted applications involves incorporation of homo-polymeric terminal tags. Amplification of libraries with C-tailed universal primers exhibit a dependence on the length of the 5' poly-C extension component of the primer. WGA libraries prepared by the methods described in the invention can be converted for targeted amplification by PCR re-amplification using poly-C extension primers. FIG. 46A shows potentiated amplification with increasing length of poly-C in real-time PCR. The reduced slope of the curves for $C_{15}U$ and $C_{20}U$ show delayed kinetics and suggest reduced template availability or suppression of priming efficiency.

To demonstrate the suppression of library amplification imposed by poly-C tagging, libraries were purified using Qiaquick PCR purification column (Qiagen) and subjected to PCR amplification with poly-C primers corresponding to the length of their respective tag. FIG. 46B shows real-time PCR results that reflect the suppression of whole genome amplification. Only the short $C_{10}$ tagged libraries retain a modest amplification capacity, while $C_{15}$ and $C_{20}$ tags remain completely suppressed after 40 cycles of PCR.

Example 24

Application of Homopolymeric G/C Tagged WGA Libraries for Multiplexed Targeted DNA Amplification Application of G/C tagged libraries for targeted amplification uses a single specific primer to amplify a plurality of library amplimers. The complexity of the target library dictates the relative level of enrichment for each specific primer. In low complexity bacterial genomes a single round of selection is sufficient to amplify an essentially pure product for sequencing or cloning purposes, however in high complexity genomes a secondary, internally "nested", targeting event may be necessary to achieve the highest level of purity.

Using a human WGA library with $C_{10}$ tagged termini incorporated by re-amplification with C-tailed universal U primers, specific sites were targeted and the relative enrichment evaluated in real-time PCR. FIG. 47A shows the chromatograms from real-time PCR amplification for sequential primary 1° and secondary 2° targeting primers in combination with the universal tag specific primer $C_{10}$, or $C_{10}$ alone. The enrichment for this particular targeted amplicon achieved in the primary amplification is approximately 10,000 fold. Secondary amplification with a nested primer enriches to near purity with an additional two orders of magnitude for a total enrichment of 1,000,000 times the starting template. It is understood to those familiar with the art that enrichment levels may vary with primer specificity, while primers of high specificity applied in sequential targeted amplification reactions generally combine to enrich products to near purity.

To apply targeted amplification in a multiplexed format, specific primer concentrations were reduced 5 fold (from 200 nM to 40 nM) without significant loss of enrichment of individual sites (FIG. 47B). This primer concentration reduction allows for the combination of 45 specific primers and universal $C_{10}$ primer to maintain total primer concentrations within reaction tolerances [2 µM].

To evaluate the utility of multiplex-targeted amplification, a set of primers were designed adjacent to STS sites (Table IV) using Oligo Version 6.53 primer analysis software (Molecular Biology Insights, Inc.: Cascade Colo.). Primers were 18-25 bases long, having high internal stability, low 3'-end stability, and melting temperatures of 57-62° C. (at 50 mM salt and 2 mM $MgCl_2$). Primers were designed to meet all standard criteria, such as low primer-dimer and hairpin formation, and are filtered against a human genomic database 6-mer frequency table. Primary multiplexed targeted amplification of G/C tagged WGA libraries was performed using 10-50 ng of tagged WGA library, 10-40 nM each of 45 specific primers (Table VI), 200 nM $C_{10}$ primer, dNTP mix, 1×PCR buffer and 1× Titanium Taq polymerase (Clontech), FCD (1:100,000) and SGI (1:100,000) dyes (Molecular Probes) added for real-time PCR detection using the I-Cycler (Bio-Rad). Amplification is carried out by heating the samples to 95° C. for 3'30", followed by 18-24 cycles of 94° C. 20", 68° C. 2'. The cycle number to reaction plateau is dependent on the absolute template and primer concentrations. The amplified material was purified by Qiaquick spin column (Qiagen), and quantified spectrophotometrically.

The enrichment of each site was evaluated using real-time PCR. Quantitative Real-Time PCR was performed using an I-Cycler Real-Time Detection System (Bio-Rad), as per the manufacturer's directions. Briefly, 25 µl reactions were amplified for 40 cycles at 94° C. for 15 sec and 68° C. for 1 min. Standards corresponding to 10, 1, and 0.2 ng of fragmented DNA were used for each STS, quantities were calculated by standard curve fit for each STS (I-Cycler software, Bio-Rad) and were plotted as distributions. FIG. 48A shows the relative fold amplification for each targeted site. Primary amplification of sites 1 and 29 failed to amplify in multiplex reactions and displayed delayed kinetics in singlet reactions (not shown). A distribution plot of the same data shows an average enrichment of 3000 fold (FIG. 48B). Differences in enrichment level such as highly over-amplified sites are likely to arise from false priming elsewhere on the template. Such variation is compensated with the use of nested amplification of the enriched template.

Secondary targeted amplifications were performed using primary targeting products as template and secondary nested primers (Table VI) in combination with the universal $C_{10}$ primer. Reactant concentrations and amplification parameters were identical to primary amplifications above. Multiplexed secondary amplifications were purified by Qiaquick spin column (Qiagen) and quantified by spectrophotometer. Enrichment of specific sites was evaluated in real-time PCR using an I-Cycler Real-Time Detection System (Bio-Rad), as per the manufacturer's directions. Briefly, 25 µl reactions were amplified for 40 cycles at 94° C. for 15 sec and 68° C. for 1 min. Standards corresponding to 10, 1, and 0.2 ng of fragmented DNA were used for each STS, quantities were calculated by standard curve fit for each STS (I-Cycler software, Bio-Rad) and were plotted as distributions. FIG. 49A shows the relative abundance of each site after nested amplification and FIG. 49B plots the data in terms of frequency.

Targeted amplification applied in this format reduces the primer complexity required for multiplexed PCR. The resulting pool of amplimers can be evaluated on sequencing or genotyping platforms.

Example 25

Non-Redundant Genomic Sequencing of Unculturable or Limited Species Facilitated by Whole Genome and Targeted Amplification Whole genome and targeted amplification provide a unique opportunity for sequencing genomes of microorganisms which are difficult to grow or for species that are already extinct. The diagram illustrating such a hypothetical DNA sequencing project is shown on the FIG. 50. First, limited amounts of DNA for the organism of interest (FIG. 50A) are converted into WGA library using any method described above or as described in U.S. Patent Application 60/453,071, filed Mar. 7, 2003, and the U.S. Nonprovisional patent application claiming priority to same and filed concomitantly herewith, and amplified (FIG. 50B). Second, a fraction of amplified WGA DNA is cloned in a bacterial vector (FIG. 50C) while another fraction of amplified WGA DNA is converted into C-tagged WGA library (FIG. 50D). Third, the cloned DNA is sequenced with minimal redundancy (FIG. 50E) to generate enough sequence information to initiate targeted sequencing and "walking" (FIG. 50F) that should ultimately result in sequencing of all gaps remaining after non-redundant sequencing and finishing the sequencing project (FIG. 50G). The outlined strategy can be used not only for sequencing of limited species but also in any large DNA sequencing projects by replacing the costly and tedious highly redundant "shotgun" method.

Table VI

| Targeted Amplification Primers | | |
|---|---|---|
| Primary | | |
| STS 1P | GCATATCCATATCTCCCGAAT | (SEQ ID NO: 30) |
| STS 2P | CAGAGCACTCCAGACCATACG | (SEQ ID NO: 31) |
| STS 3P | CTTCGTTATGACCCCTGCTCC | (SEQ ID NO: 32) |
| STS 4P | TCCCAAGATGAATGGTAAGACG | (SEQ ID NO: 33) |

Table VI-continued

Targeted Amplification Primers

| | | | |
|---|---|---|---|
| STS 5P | TCCAATCTCATCGGTTTACTG | (SEQ ID NO: 34) |
| STS 8P | TCCAGAGCCCAGTAAACAACA | (SEQ ID NO: 35) |
| STS 10P | TTACTTCAGCCCACATGCTTC | (SEQ ID NO: 36) |
| STS 12P | TTCCGACATAGCGACTTTGTAG | (SEQ ID NO: 37) |
| STS 14P | AAGGATCAGAGATACCCCACGG | (SEQ ID NO: 38) |
| STS 16P | TCCAAGAACCAACTAAGTCCAGA | (SEQ ID NO: 39) |
| STS 22P | CTAAGGGCAAACATAGGGATCAA | (SEQ ID NO: 40) |
| STS 26P | CAACCTTTGAAGCCACTTTGAC | (SEQ ID NO: 41) |
| STS 29P | GCCTCCGTCATTGGTATTTTCT | (SEQ ID NO: 42) |
| STS 30P | TGGCAACACGGTGCTGACCTG | (SEQ ID NO: 43) |
| STS 31P | ATCATGGGTTTGGCAGTAAAGC | (SEQ ID NO: 44) |
| STS 35P | AGAACCAGCAAACCCAGTCCC | (SEQ ID NO: 45) |
| STS 36P | GAAAGGGTGGATGGATTGAAA | (SEQ ID NO: 46) |
| STS 38P | TCAGATTTCCTGGCTCCGCTT | (SEQ ID NO: 47) |
| STS 41P | CCTTCTGCTTCCCTGTGACCT | (SEQ ID NO: 48) |
| STS 42P | TGAACCCCACGAGGTGACAGT | (SEQ ID NO: 49) |
| STS 43P | GACATTACCAGCCCCTCACCTA | (SEQ ID NO: 50) |
| STS 44P | TCCTTGACAGTTCCATTCACCA | (SEQ ID NO: 51) |
| STS 46P | TTTGCAGGTAGCTCTAGGTCA | (SEQ ID NO: 52) |
| STS 47P | GCGGACAGAGAGTAACCTCGGA | (SEQ ID NO: 53) |
| STS 49P | CCCAGAAACCCTGAGACCCTC | (SEQ ID NO: 54) |
| STS 52P | TGTGCCACAAGTTAAGATGCT | (SEQ ID NO: 55) |
| STS 54P | TGCTGTATCGTGCCTGCTCAAT | (SEQ ID NO: 56) |
| STS 60P | TGCCCCACTCCCCAACATTCT | (SEQ ID NO: 57) |
| STS 62P | AACAGAGCCTCAGGGACCAGT | (SEQ ID NO: 58) |
| STS 70P | GGGCTTTGTCTGTGGTTGGTA | (SEQ ID NO: 59) |
| STS 72P | TGGGCTGGCTGAGGTCAAGAT | (SEQ ID NO: 60) |
| STS 74P | TTTTGCTCCGCTGACATTTGG | (SEQ ID NO: 61) |
| STS 77P | TGCTCCTGTCCCTTCCACTTC | (SEQ ID NO: 62) |
| STS 79P | CCTTATTCCCAGCAGCAGTATTC | (SEQ ID NO: 63) |
| STS 82P | TGGGAAGGGAAAGAGGGTACT | (SEQ ID NO: 64) |
| STS 83P | TTGCTGTAGATGGGCTTTCGT | (SEQ ID NO: 65) |
| STS 84P | TCTGCTGGGTTGATGATTTGG | (SEQ ID NO: 66) |
| STS 85P | GGCACAAGCAAAAGGGTGTCT | (SEQ ID NO: 67) |
| STS 86P | CCAGCAATCAGGAAAGCACAA | (SEQ ID NO: 68) |
| STS 89P | CACCTGTCTTGTTGGCATCACC | (SEQ ID NO: 69) |
| STS 92P | TTGTTTTGCCTCACCAGTCATTT | (SEQ ID NO: 70) |
| STS 96P | TCAGCAAACCCAAAGATGTTA | (SEQ ID NO: 71) |
| STS 99P | TTAGTCCTTTGGGCAGCACGA | (SEQ ID NO: 72) |
| STS 103P | TGTCTCTGCTTCTGAAACGGG | (SEQ ID NO: 73) |
| STS 113P | ACTGCCAGGGTCATTGACTT | (SEQ ID NO: 74) |

Secondary

| | | | |
|---|---|---|---|
| STS 1S | TAAGCAGCAAGGTCTGGG | (SEQ ID NO: 75) |
| STS 2S | GTGATTGAACAATTTGGACCCAC | (SEQ ID NO: 76) |
| STS 3S | ATGGCAACATTCCACCTAGTAGC | (SEQ ID NO: 77) |
| STS 4S | CTCCGTCATGATAAGATGCAGT | (SEQ ID NO: 78) |
| STS 5S | ACTGTTTGGGGTGTGAAAGGAC | (SEQ ID NO: 79) |
| STS 8S | ACTAACAACGCCCTTTGCTC | (SEQ ID NO: 80) |
| STS 10S | TCAGCACTCCGTATCTTCATTTG | (SEQ ID NO: 81) |
| STS 12S | TAAACCGCTAAAACGATAGCAGC | (SEQ ID NO: 82) |
| STS 14S | TCATGGTATTAGGGAAGTGGGAG | (SEQ ID NO: 83) |
| STS 16S | GGGAATGAAAAGAAAAGGCATTC | (SEQ ID NO: 84) |
| STS 22S | TCTTTCCCTCTACAACCCTCTAACC | (SEQ ID NO: 85) |
| STS 26S | CAGTACATGGGTCTTATGAGTAC | (SEQ ID NO: 86) |
| STS 29S | AATCGAGAACGCACAGAGCAGA | (SEQ ID NO: 87) |
| STS 30S | GTCTGGGGAGTAAATGCAACATC | (SEQ ID NO: 88) |
| STS 31S | TTCTTGATGACCCTGCACAA | (SEQ ID NO: 89) |
| STS 35S | CAGCAGAAGCACTACCAAAGACA | (SEQ ID NO: 90) |
| STS 36S | TTCACCTAGATGGAATAGCCACC | (SEQ ID NO: 91) |
| STS 38S | GCAAGATTTTGCTTGGCTCTAT | (SEQ ID NO: 92) |
| STS 41S | GAATTTTGGTTTCTTGCTTTGG | (SEQ ID NO: 93) |
| STS 42S | GTCAGAAGACTGAAAACGAAGCC | (SEQ ID NO: 94) |
| STS 43S | CATCTCTTGATCATCCCAGCTCT | (SEQ ID NO: 95) |
| STS 44S | CACCATTGGTTGATAGCAAGGTT | (SEQ ID NO: 96) |
| STS 46S | TAAACATAGCACCAAGGGGC | (SEQ ID NO: 97) |
| STS 47S | TCATGTGTGGGTCACTAAGGATG | (SEQ ID NO: 98) |
| STS 49S | CGTCTCTCCCAGCTAGGATG | (SEQ ID NO: 99) |
| STS 52S | CTTTTTCACAGAACTGGTGTCAGG | (SEQ ID NO: 100) |
| STS 54S | ACCCAGCTTTCAGTGAAGGA | (SEQ ID NO: 101) |
| STS 60S | AATCAAAAGGCCAACAGTGG | (SEQ ID NO: 102) |
| STS 62S | ACTGGCTGAGGGAGCATG | (SEQ ID NO: 103) |
| STS 70S | TAAATGTAACCCCCTTGAGCC | (SEQ ID NO: 104) |
| STS 72S | TATTGACCACATGACCCCCT | (SEQ ID NO: 105) |
| STS 74S | TTGGGTGATGTCTTCACATGG | (SEQ ID NO: 106) |
| STS 77S | GCTCAATAAAAATAGTACGCCC | (SEQ ID NO: 107) |
| STS 79S | TTCTCCCAGCTTTGAGACGT | (SEQ ID NO: 108) |
| STS 82S | TTTGTTACTTGCTACCCTGAG | (SEQ ID NO: 109) |
| STS 83S | GAAGATGAAGTGAACTCCTATCC | (SEQ ID NO: 110) |

Table VI-continued

Targeted Amplification Primers

| STS 84S | GAAGCCTTGATAACGAGAGTGG | (SEQ ID NO: 111) |
|---|---|---|
| STS 85S | ATGTTTCTCTGGCCCCAAG | (SEQ ID NO: 112) |
| STS 86S | TGGCTGCCCTTCAATAC | (SEQ ID NO: 113) |
| STS 89S | TTGGGAAATGTCAGTGACCA | (SEQ ID NO: 114) |
| STS 92S | TGTGGTTAGGATAGCACAAGCATT | (SEQ ID NO: 115) |
| STS 96S | TGCAATTTGAAGGTACGAGTAG | (SEQ ID NO: 116) |
| STS 99S | TGTTAACAATTTGCATAACAAAAGC | (SEQ ID NO: 117) |
| STS 103S | GCATTTTCTGTCCCACAAGATATG | (SEQ ID NO: 118) |
| STS 113S | ATTGCTGTCACAGCACCTTG | (SEQ ID NO: 119) |

*P-denotes primary targeted amplification primer
*S-denotes secondary targeted amplification primer Example 26

Universality of the Novel Nucleic Amplification Method and its Compatibility with Different Sources of DNA and RNA and Different Methods of Analysis of the Amplified Material The diagram presented on FIG. 51 illustrates the diversity of DNA and RNA samples that are compatible with the proposed method of amplification of nucleic acid, universality of the amplification technique, and the diversity of possible applications.

Nucleic acid sources include but not limited to all animals (including humans), plants, fungi, culturable and non-culturable bacteria and viruses, and extinct species found in amber and stones. They can be isolated from any fresh, frozen, or paraffin embedded formalin fixed tissue, body fluids, forensic sample, cell culture, single cell, single chromosome, etc.

The library preparation step can use total nucleic acid as a template (the protocol shown in central part of the diagram, arrow A), and result in the amplification of both DNA and RNA, or use purified DNA, and result in the amplification of the whole genome (the protocol shown in left part of the diagram, arrow B), or use purified RNA, and result in the amplification of the whole transcriptome (the protocol shown in right part of the diagram, arrow C), or use total nucleic acid and a corresponding selection method, and result in the amplification of the whole genome (the protocol shown in left part of the diagram, arrow D), or whole transcriptome (the protocol shown in right part of the diagram, arrow E).

Library prepared and amplified from total nucleic acid, DNA, or RNA can be modified to incorporate polyC regions at the 5' end of the universal constant sequence (arrows F and G). C-tailed libraries can be used for targeted amplification and analysis of specific genomic regions or RNA transcripts.

Library prepared and amplified from total nucleic acid, DNA, or RNA can be modified to incorporate other tags (see FIGS. 19-25) and used for ID identification, immobilization on a solid support or a micro-array, or multiple usage (not shown in FIG. 51).

Applications of the proposed nucleic acid amplification technology include but not limited to genotyping of small DNA/RNA samples, gene expression analysis, sequencing of un-culturable or extinct organisms, molecular diagnostics of different diseases, prenatal diagnostics, viral/bacterial diagnostics, forensics, etc.

Example 27

Amplification of Genomic DNA from Single Cells Using a Mesophilic DNA Polymerase Followed by Universal-Primer PCR with a Thermostable DNA Polymerase, and Analysis of Locus Representation by Real-Time PCR This example describes the synthesis of libraries from single cells with Klenow Exo-followed by amplification with Taq DNA polymerase and analysis of their locus representation by real-time PCR.

Immortalized human prostate epithelial RWPE cells were trypsinized, washed three times with PBS, and single cells were collected by Flow Cytometry in 5 ul of TE buffer (10 mM Tris-HCl pH 8.0, 1 mM EDTA). Control samples containing either 5 cells or just TE buffer were also included in the analysis to assess the locus representation of more than one genome equivalent and the amplification background respectively. Cells were immediately frozen on dry ice after collection and stored at 80° C. prior to use.

Wells containing sorted cells were thawed on ice and DNA was extracted by addition of 5 ul of freshly prepared 2× cell lysis buffer comprising: 0.015% SDS, 40 mM NaCl, 20 mM Tris-HCl pH 7.5, 0.2 mM EDTA, 0.24 mg/mL Proteinase K and incubated for 1 hour at 50° C., followed by 4 min at 99 C. Samples were briefly centrifuged and placed on ice. Four μL of library synthesis buffer comprising 37.5 mM Tris-HCl pH 7.5, 18.75 mM MgCl$_2$, 28.125 mM DTT, 0.75 mM each dNTP, 0.05 mg/mL E. coli SSB, and oligonucleotide 3 (Table VII, SEQ ID NO:128) were added to each well and the samples were heated at 95° C. for 2 min and cooled on ice.

Library synthesis was initiated by addition of 1 μl of Klenow exo at 5 Units/uL. Samples were incubated in a thermal cycler as follows: 16° C. for 20 minutes, 24° C. for 20 minutes, 37° C. for 20 minutes, 75° C. for 5 minutes. Libraries were further amplified to saturation by real-time PCR on BioRad i-Cycler by addition of 60 ul of library amplification buffer comprising: 1.25× Titanium Taq buffer (BD-Clontech), 0.5 mM each dNTP, 7 mM MgCl$_2$, 2.5 uM oligonucleotide 4 (Table VII, SEQ ID NO:129), 0.6× Titanium Taq DNA polymerase (BD-Clontech), and 10000:1 dilutions of fluorescein calibration dye and SybrGreen I (Life Technologies). After initial denaturation at 95° C. for 3 min samples were incubated for 29 cycles at 94° C. for 30 sec and 68° C. for 2 min. Library DNA was purified using MultiScreen HTS PCR kit (Millipore Cat # MSNU03050) following manufacturer's instructions, quantified using absorbance at 260 nm, and 50 ng aliquots were used in locus-specific PCR for representation analysis.

Results show exemplary amplification of 4 individual libraries from sorted single cells, one library of sorted 5 cells, and duplicate "no cells" controls. Locus representation of libraries from sorted cells was analyzed by real-time PCR using a panel of 40 human genomic STS and promoter assays (Table VIII). The PCR reaction mixture comprised: 1× Titanium Taq reaction buffer (Clontech), 200 uM each dNTP, 0.2 uM of each forward and reverse primer, 0.5 ul of Titanium Taq polymerase (Clontech), 50 ng library DNA, and 5000:1 dilutions of fluorescein and SybrGreen I (Life Technologies) in a final volume of 25 ul. In the case of analyzing promoter sequences 4% DMSO and 0.5 M betaine were added to the reaction mixture.

After initial denaturation for 3 min reactions were carried out at 95° C. for 20 sec, 68° C. for 1 min, 75° C. for 30 sec, and 80° C. for 15 sec on i-Cycler real-time PCR instrument (Bio-Rad). Statistical analysis of data was performed using Excel (Microsoft).

Example 28

Amplification of Genomic DNA from Single Cells Using a Thermostable DNA Polymerase and Analysis of Locus Representation by Real-Time PCR This example describes the amplification of genomic DNA from single cells sorted by Flow Cytometry and the analysis of its locus representation by real-time PCR.

Immortalized human prostate epithelial RWPE cells were trypsinized, washed three times with PBS and single cells were collected by Flow Cytometry into 5 ul of cell lysis buffer comprising 5 mM Tris-HCl pH 8.3, and 0.01% Triton X-100 in deionized nuclease-free water. Control samples containing either 5 cells or just lysis buffer (no cells) were also included in the analysis to assess the locus representation of more than one genome equivalent and the amplification background respectively. Cells were immediately frozen on dry ice after collection and stored at −80° C. prior to use.

Wells containing sorted cells were thawed on ice and DNA was extracted by addition of 4 ul of cell lysis buffer containing 0.2 units of proteinase enzyme (prepGEM Saliva 500 Kit, VWR Catalog#95044-052) and incubated for 10 min at 75° C. Five ul of library preparation buffer comprising: 3×KAPA 2G Robust buffer B (KAPA Biosystems, Cat # KB 5003), 0.6 mM each dNTP, 6 mM $MgCl_2$, 12% DMSO, 6 uM oligonucleotide 1 (Table VII, SEQ ID NO:25) [or alternatively 15 uM oligonucleotide 5 (Table VII, SEQ ID NO:130)] were added to each well and the samples were heated at 95° C. for 4 min.

Library synthesis was initiated by addition of 1 ul of KAPA 2G Robust DNA polymerase (KAPA Biosystems, Cat # KE 5004) at a concentration of 1 unit/ul. After initial denaturation for 2 min at 95° C. samples were incubated for 12 cycles at: 95° C. for 15 sec, 15° C. for 50 sec, 25° C. for 40 sec, 35° C. for 30 sec, 65° C. for 40 sec, and 75° C. for 40 sec.

Libraries were further amplified to saturation by real-time PCR on BioRad i-Cycler by addition of 60 ul of library amplification buffer comprising: 1.25×KAPA 2G Robust buffer B (KAPA Biosystems, Cat # KB 5003), 0.5 mM each dNTP, 3.75 mM $MgCl_2$, 6.25% DMSO, 2.5 uM oligonucleotide 2 (Table VII, SEQ ID NO:26), 4.5 units of KAPA 2G Robust DNA polymerase (KAPA Biosystems, Cat # KE 5004), and 5000:1 dilutions of fluorescein calibration dye and SybrGreen I (Life Technologies).

After initial denaturation at 95° C. for 2 min samples were incubated for 13 cycles at 96° C. for 15 sec, 65° C. for 1 min, and 75° C. for 1 min. Library DNA was purified using MultiScreen HTS PCR kit (Millipore Cat # MSNU03050), and 50 ng aliquots were used in locus-specific PCR for representation analysis.

Locus representation of libraries from sorted cells was analyzed by real-time PCR using a panel of 40 human genomic STS and promoter assays (Table VIII). The PCR reaction mixture comprised: 1× Titanium Taq reaction buffer (Clontech), 200 uM each dNTP, 0.2 uM of each forward and reverse primer, 0.5 ul of Titanium Taq polymerase (Clontech), 50 ng library DNA, and 5000:1 dilutions of fluorescein and SybrGreen I (Life Technologies) in a total volume of 25 ul. In the case of analyzing promoter sequences 4% DMSO and 0.5 M betaine were also added to the reaction mixture. After initial denaturation for 3 min reactions were carried out at 95° C. for 20 sec, 68° C. for 1 min, 75° C. for 30 sec, and 80° C. for 15 sec on i-Cycler real-time PCR instrument (BioRad). Statistical analysis of data was performed using Excel (Microsoft).

FIG. 52 shows an exemplary amplification of replicate single-cell and control no-cell whole genome amplification reactions. It demonstrates the ability of the methods and compositions disclosed herein to amplify DNA from a single genome with much higher sensitivity and farther away from the non-specific background characteristic of other methods generally used in the field. This should make it possible to apply the disclosed methods and compositions for analysis of individual chromosomes as well as limited number of bacterial cells and even viral genomes.

An exemplary amplification of 10 individual libraries from sorted single cells, duplicate sorted 5 cells, and quadruplicate "no cells" controls is shown on FIG. 53. It demonstrates that highly consistent and reproducible results are generated by the methods and compositions disclosed in the present invention with small sample-to-sample variation.

FIG. 54 demonstrates the input range and reproducibility of whole genome DNA amplification by the methods and compositions disclosed herein. FIG. 54A shows locus-specific qPCR testing of whole genome amplification from replicate samples corresponding to increasing number of cell equivalent inputs in the range of 1-10,000. FIG. 54B shows that after saturating whole genome amplification form 1, 10, 100, or 1000 cell equivalents the copy number of a single locus as analyzed by qPCR gives practically the same results.

In quantitative genome analysis sample to sample variation represents a significant problem. FIG. 55 shows cell to cell variation for two individual cells in 24 qPCR assays. As seen from the correlation plot highly reproducible representation over multiple loci is achieved by the methods and compositions disclosed in the present invention.

FIG. 56 illustrates the reproducibility of whole genome amplification by the disclosed methods and compositions in representing 25 individual loci assayed by qPCR across 10 replicate cells. This figure demonstrates that there is inherent amplification bias but it is highly reproducible and can be easily corrected for, a feature that can be highly advantageous in quantitative genome analysis.

Example 29

Analyzing Amplification Efficiency

Sample amplification efficiencies can be analyzed by performing the amplification reactions with SYBR® Green I in a real-time thermal cycler. During the amplification reaction, double-stranded amplified molecules are bound by the non-sequence-dependent SYBR® Green I dye, and the accumulation of amplified product is detected as an increase in fluorescence by the real-time instrument.

Data analysis is performed on raw background-subtracted fluorescence, and the instrument/software should be set to the appropriate mode.

Amplification curves will have a similar appearance for successfully amplified single-cell WGA products, with an immediate 8-9 cycle upward sloping phase, followed by a relatively flat "plateau" phase (FIG. 52).

No-cell control amplification curves are delayed (right-shift) by 5-6 PCR cycles compared to single-cell amplification curves. A smaller delay of control curves may indicate DNA contamination introduced with the sample or during the WGA process.

Example 30

Protocol

1. Add 5 uL of PicoPlex Pre-Amp Buffer to 9 uL of single-cell lysate or control no-cell lysate.
2. Incubate samples in a thermal cycler as follows:

| | | |
|---|---|---|
| 1 cycle | Room Temp | Hold |
| 1 cycle | 95 C. | 4 min |

3. Briefly centrifuge samples. 4. Combine the following components and mix well.

| Synthesis Enzyme Mix | Volume Per 5 samples |
|---|---|
| Pre-Amp Enzyme Dilution Buffer | 4 uL |
| PicoPlex Pre-Amp Enzyme | 1 uL |
| Total Volume | 5 uL |

5. Add 1 uL of Pre-Amp Enzyme Mix to sample. 6. Incubate samples according to thermal cycler program below:

| | | |
|---|---|---|
| 1 cycle | 95 C. | 2 min |
| | 95 C. | 15 sec |
| | 15 C. | 50 sec |
| 12 cycles | 25 C. | 40 sec |
| | 35 C. | 30 sec |
| | 65 C. | 40 sec |
| | 75 C. | 40 sec |
| 1 cycle | 4 C. | hold |

7. Briefly centrifuge samples and place synthesis reaction products on ice. 8. Combine the following Amplification Cocktail components and mix well.

| Amplification Cocktail | Volume Per 5 Samples |
|---|---|
| PicoPlex Amplification Buffer | 125 uL |
| PicoPlex Amplification Enzyme | 4 uL |
| Nuclease-Free Water | 171 uL |
| Total Volume | 300 uL |

Note: Sample amplification efficiencies can be analyzed by adding SYBR Green I dye (Invitrogen, 57563) at 0.125× final concentration in the Amplification Cocktail and by performing the amplification in a real-time thermal cycler (see Appendix A). Some instruments may also require additional reference dyes for SYBR signal normalization.

9. Mix 60 uL of the freshly prepared Amplification Cocktail with the 15 uL synthesis reaction product and mix by pipet. 10. Amplify samples according to thermal cycler program below:

| | | |
|---|---|---|
| 1 cycle | 95 C. | 2 min |
| | 95 C. | 15 sec |
| 13 cycles | 65 C. | 1 min |
| | 75 C. | 1 min |

Note: 13 cycles is recommended in certain embodiments based on testing performed with single cultured cells obtained by flow sorting, dilution, and micromanipulation. Some cell types or lysis conditions may require additional cycles (up to 15) to obtain maximal yields.

Example 31

Exemplary Kit Materials and Methods

The methods and compositions disclosed herein amplify DNA directly from many types of cells. Some of the methods used in the isolation and amplification of DNA from cells are as follows:

Single Cell Collection Methods

Flow sorting, dilution, and micromanipulation are collection methods that are compatible with the methods and compositions disclosed herein. Cell staining may negatively affect whole genome amplification performance, especially staining methods that include fixing (e.g. with formaldehyde) steps.

Sample Volume

Single cells may be collected and lysed/extracted in a total of about 9 µL volume.

Cell Lysis and DNA Extraction Methods

Single-cell PCR lysis/extraction methods (e.g. protease/detergent incubation or alkaline treatment followed by neutralization) are compatible with the methods and compositions disclosed herein, as long as, for example, monovalent salt concentrations do not exceed 20 mM in the final 9 µL lysate volume.

Considerable (>5 µL) evaporation may occur, if the incubation is being performed in a PCR plate without a very tight seal. Evaporation during PCR may be minimized by using an appropriate thermal cycler, for example, the combination of iCycler IQ 96-well PCR plates (Bio-Rad, 223-9441) and Axymat silicone sealing mats (Axygen, AM-96-PCR-RD).

Exemplary Kit Components

| Component Name |
|---|
| 1. PicoPlex Pre-Amp Buffer |
| 2. PicoPlex Pre-Amp Enzyme |
| 3. Pre-Amp Enzyme Dilution Buffer |
| 4. PicoPlex Amplification Buffer |
| 5. PicoPlex Amplification Enzyme |
| 6. Nuclease-Free Water |

TABLE VII

OLIGONUCLEOTIDE SEQUENCES USED IN SINGLE GENOME LIBRARIES PREPARATION

| No | Sequence 5'-3'* |
|---|---|
| 1. | TGTGTTGGGTGTGTTTGGKKKKKKKKKKK (SEQ ID NO: 25) |
| 2. | TGTGTTGGGTGTGTTTGG (SEQ ID NO: 26) |
| 3. | TGTTGTGGGTTGTGTTGGKKKKKKKKKKK (SEQ ID NO: 128) |
| 4. | TGTTGTGGGTTGTGTTGG (SEQ ID NO: 129) |
| 5. | TGTGTTGGGTGTGTTTGGNKKNKKNKNKK (SEQ ID NO: 130) |

*Random bases definitions: K = G, T; N = A, G, C, T

TABLE VIII

OLIGONUCLEOTIDE SEQUENCES USED IN LOCUS-SPECIFIC REAL-TIME PCR ASSAYS

| Assay No*** | | Sequence 5'-3'** | |
|---|---|---|---|
| 1 | F | AGAGGCTTCTGGCAGTTTGC | (SEQ ID NO: 131) |
| 1 | R | CCCAGCCTCTGGAAAATCAG | (SEQ ID NO: 132) |
| 2 | F | CCCTAACATGGAGGTAGGAGC | (SEQ ID NO: 133) |
| 2 | R | TCTTCCTGGTGTGAGCCTCT | (SEQ ID NO: 134) |
| 3 | F | GAGAACCGGAGCGTGCTT | (SEQ ID NO: 135) |
| 3 | R | TATTGACCACATGACCCCCT | (SEQ ID NO: 136) |
| 4 | F | GCAAAATCCATACCCTTTCTGC | (SEQ ID NO: 137) |
| 4 | R | TCTTTCCCTCTACAACCCTCTAACC | (SEQ ID NO: 138) |
| 5 | F | GCAAAATGCCTTCTTGTGTTTTC | (SEQ ID NO: 139) |
| 5 | R | GCATTTTCTGTCCCACAAGATATG | (SEQ ID NO: 140) |
| 6 | F | ATGTTTCTCTGGCCCCAAG | (SEQ ID NO: 141) |
| 6 | R | TTCTCCATGAGATTGGACTGG | (SEQ ID NO: 142) |
| 10 | F | TCATCATGATCAACAGGAAAGA | (SEQ ID NO: 143) |
| 10 | R | CAACCCTGGCCTCAGGAT | (SEQ ID NO: 144) |
| 11 | F | GTGAATATAGTGAGTGACAGATGGC | (SEQ ID NO: 145) |
| 11 | R | CTTTATGAAACGGGGCCATA | (SEQ ID NO: 146) |
| 12 | F | CAATGTACAGGTCCTGTTGCC | (SEQ ID NO: 147) |
| 12 | R | AAAACAATGCTTCCAGTGGC | (SEQ ID NO: 148) |
| 13 | F | ACAGTCCCATTCTGGCAAAC | (SEQ ID NO: 149) |
| 13 | R | TCACTCCCTCCAACAATTCC | (SEQ ID NO: 150) |
| 14 | F | TTTGTTACTTGCTACCCTGAG | (SEQ ID NO: 151) |
| 14 | R | CAACCATCATCTTCCACAGTC | (SEQ ID NO: 152) |
| 15 | F | CGGCATGAGGAAGGTGCAGGAG | (SEQ ID NO: 153) |
| 15 | R | CGACACCATGCGAGACACGCTTG | (SEQ ID NO: 154) |
| 16 | F | AATGCCCAGCAGAACCGCC | (SEQ ID NO: 155) |
| 16 | R | ACTCCACAAACTCATCCAGGTCCTC | (SEQ ID NO: 156) |
| 17 | F | GCAAGATTTTGCTTGGCTCTAT | (SEQ ID NO: 157) |
| 17 | R | CTTTGGTATTTGCTTCCACCAAC | (SEQ ID NO: 158) |
| 18 | F | TGAGGCTTCACATTCCAGC | (SEQ ID NO: 159) |
| 18 | R | TATTCCCAGTGCTGGAGAGG | (SEQ ID NO: 160) |
| 19 | F | TCATTGGGGCTGAGCAAT | (SEQ ID NO: 161) |
| 19 | R | TCAGGAGCCTTTTAGTCTGAGG | (SEQ ID NO: 162) |
| 20 | F | TGTTAACAATTTGCATAACAAAAGC | (SEQ ID NO: 163) |
| 20 | R | TGATTAATTTGCGAGACTAACTTTG | (SEQ ID NO: 164) |
| 21 | F | GGTTCCTCCAAAGAACAGCA | (SEQ ID NO: 165) |
| 21 | R | TGAGATTTGGCCTTGCTTCT | (SEQ ID NO: 166) |
| 22 | F | TCCATTGTTTACCCCAAAGC | (SEQ ID NO: 167) |

TABLE VIII-continued

OLIGONUCLEOTIDE SEQUENCES USED IN LOCUS-
SPECIFIC REAL-TIME PCR ASSAYS

| Assay No*** | | Sequence 5'-3'** | |
|---|---|---|---|
| 22 | R | TCTGGGAGTGGGAAGAGTTG | (SEQ ID NO: 168) |
| 23 | F | CCCAGCCCTCTCTCCGCC | (SEQ ID NO: 169) |
| 23 | R | CCTAAACTGGAGACGGATCCTGCCC | (SEQ ID NO: 170) |
| 24 | F | ACAGGCCTCCATTCATGTCCCTTCC | (SEQ ID NO: 171) |
| 24 | R | TCGTGGCCGCCAAGGCAC | (SEQ ID NO: 172) |
| 25 | F | GCATCCTATAAAAGCAGCCATGT | (SEQ ID NO: 173) |
| 25 | R | GGCTGAGTCATCTTCCTCTTGAA | (SEQ ID NO: 174) |
| 26 | F | GACCATCAGGCGACAGATT | (SEQ ID NO: 175) |
| 26 | R | GCTCAGGCATAACCCCTC | (SEQ ID NO: 176) |
| 28 | F | CTACCATGCCTGGCAGAAAT | (SEQ ID NO: 177) |
| 28 | R | TTGCTAACCTAAAAGACAGCAGG | (SEQ ID NO: 178) |
| 29 | F | TGAAAAGGATACCAAAGTGCG | (SEQ ID NO: 179) |
| 29 | R | TTGGGAAATGTCAGTGACCA | (SEQ ID NO: 180) |
| 30 | F | GGCCAACAGGAACAGCAG | (SEQ ID NO: 181) |
| 30 | R | TTCTCTGGATCTTTTCAGCC | (SEQ ID NO: 182) |
| 31 | F | CCGCGAGCTCCCTCTGCC | (SEQ ID NO: 183) |
| 31 | R | CTCTGTAGCCCTAGGACCGGTCTG | (SEQ ID NO: 184) |
| 32 | F | CTGCCGACATTCCACGGGTTTCTTG | (SEQ ID NO: 185) |
| 32 | R | AGCCTTCCGCTGGAAGTCCAACTTT | (SEQ ID NO: 186) |
| 33 | F | TTTCACATTTCCTAAGCAGCC | (SEQ ID NO: 187) |
| 33 | R | TTGCTTTTGCCCCCACTACTG | (SEQ ID NO: 188) |
| 34 | F | TGCCAGAGAAGTTTTAACAATCACA | (SEQ ID NO: 189) |
| 34 | R | GGATGACAACTGCTAAGGTCCAT | (SEQ ID NO: 190) |
| 35 | F | TATTTAAAATGTGGGCAAGATATCA | (SEQ ID NO: 191) |
| 35 | R | TGGTGTAAATAAAGACCTTGCTATC | (SEQ ID NO: 192) |
| 38 | F | CCATTTCGTATCAGTCTAGCCCA | (SEQ ID NO: 193) |
| 38 | R | GTCAGTGCTGCTATGGAGCTTTT | (SEQ ID NO: 194) |
| 41 | F | GCTTACTGATGAAAAACTCATCCA | (SEQ ID NO: 195) |
| 41 | R | TGGTTATAACTAACAAACCTGAACA | (SEQ ID NO: 196) |
| 42 | F | CTCTATGTGGCTCACGCAG | (SEQ ID NO: 197) |
| 42 | R | TTTACAAATGAGGGAACTCCC | (SEQ ID NO: 198) |
| 43 | F | TGGGAAAAGTCAGCTCGTG | (SEQ ID NO: 199) |
| 43 | R | AACTGGGGGCAAGAACAAC | (SEQ ID NO: 200) |
| 44 | F | TCATTAACACCAGTCTGCAACA | (SEQ ID NO: 201) |
| 44 | R | TGCAATTTGAAGGTACGAGTAG | (SEQ ID NO: 202) |
| 45 | F | GCACCTGCTAAGGAGGGAG | (SEQ ID NO: 203) |
| 45 | R | TCATTTTTTGCTGATGGTTCC | (SEQ ID NO: 204) |

TABLE VIII-continued

OLIGONUCLEOTIDE SEQUENCES USED IN LOCUS-SPECIFIC REAL-TIME PCR ASSAYS

| Assay No*** | | Sequence 5'-3'** | |
|---|---|---|---|
| 46 | F | CCGCTGGATTCTTTTTCAAA | (SEQ ID NO: 205) |
| 46 | R | AAGGCTCAAATGCCAAATTG | (SEQ ID NO: 206) |
| 47 | F | AGCGGCCTGGATGAGATGCTG | (SEQ ID NO: 207) |
| 47 | R | CTGGTTCACAGCCCAAAGGCTGA | (SEQ ID NO: 208) |
| 48 | F | CTCCCACAGACCGACCAGCTTCC | (SEQ ID NO: 209) |
| 48 | R | GTGCATCGTGATCTCGGGTGAGAGC | (SEQ ID NO: 210) |

\* F = forward primer, R = reverse primer
\*\* Sequences in bold represent promoter regions
\*\*\* Omitted sequential numbers indicate bad quality or failed assays

TABLE 3

Troubleshooting Guide

| Problem | Potential Cause | Suggested Solutions |
|---|---|---|
| Single-Cell Amplification Curve Looks Like Control No-Cell Amplification Curve | Sample well did not contain a cell | Confirm that single-cell isolation process is properly dispensing a single cell per tube or well |
| | Inefficient sample lysis | Use alternative lysis method or EDTA-free cell collection buffer. |
| | Cell lysate contained WGA inhibitors | Do not exceed 20 mM monovalent salt concentration in cell lysate |
| | Cells have been exposed to fixatives or contain dye molecules | Handle cells without fixation or staining |
| Control No-Cell Amplification Curve Appears Early | DNA contamination of sample | Carefully wash cells in fresh PBS or other serum-free medium |
| | Exogenous DNA contamination in sample or work environment | Clean area thoroughly and use PCR-dedicated plastics and pipettes. |
| | Reagents are contaminated | Use fresh kit |

REFERENCES

All patents and publications mentioned in the specification are indicative of the levels of those skilled in the art to which the invention pertains. All patents and publications are herein incorporated by reference in their entirety to the same extent as if each individual publication was specifically and individually indicated to be incorporated by reference.

PATENTS

U.S. Pat. No. 5,759,822
U.S. Pat. No. 6,107,023
U.S. Pat. No. 6,114,149
U.S. Pat. No. 6,124,120
U.S. Pat. No. 6,280,949
U.S. Pat. No. 6,365,375
US005514545A
US005932451A
US20030186237A1
WO 02/72772
US 2003/0013671
US2003/0017591 A1
US006271002B1
US20030113754A1
Japan Patent No. JP8173164A2
U.S. Pat. No. 4,683,195,
U.S. Pat. No. 4,683,202
U.S. Pat. No. 4,800,159
WO 90/07641
U.S. Pat. No. 5,882,864.
European Patent Application No. 320,308
U.S. Pat. No. 4,883,750
Patent Application No. PCT/US87/00880
PCT Patent Application WO 88/10315
U.S. Pat. No. 5,648,245
British Patent Application No. GB 2,202,328
PCT Patent Application No. PCT/US89/01025
PCT Patent Application WO 89/06700
U.S. Patent Application 20030143599
US005759822A
WO/016545 A1

PUBLICATIONS

Advances in Immunology, Academic Press, New York.
Annual Review of Immunology, Academic Press, New York.
Allsopp, R. C., Chang, E., Kashefi-aazam, M., Rogaev, E. I., Piatyszek, M. A., Shay, J. W. and Harley, C. B. 1995. Telomere shortening is associated with cell division in vitro and in vivo. Exp. Cell Res., 220:194-200.
Allsopp, R. C., Vaziri, H., Patterson, C., Goldstein, S., Younglai, E. V., Futcher, A. B., Greider, C. W. and Harley, C. B. 1992. Telomere length predicts replicative capacity of human fibroblasts. Proc. Natl. Acad. Sci. USA, 89:10114-10118.
Ausubel, F. M., Brent, R., Kingston, R. E., Moore, D. O., Seidman, J. S., Smith, J. A., and Struhl, K. 1987. Current protocols in molecular biology. Wiley, New York, N.Y.
Bodnar, A. G., Ouellette, M., Frolkis, M., Holt, S. E., Chiu, C.-P., Morin, G. B., Harley, C. B., Shay, J. W., Lichtsteiner, S, and Wright W. E. 1998. Extension of life-span by introduction of telomerase into normal human cells. Science, 279:349-352.

Bohlander, S. K., Espinosa, R., LeBeau, M. M., Rowler, J. D., Diaz, M. O. 1992. A method for the rapid sequence-independent amplification of microdissected chromosomal material. Genomics, 13:1322-1324.

Bond, J., Haughton, M., Blaydes, J., Gire, V., Wynfordthomas, D. and Wyllie, F. 1996. Evidence that transcriptional activation by p53 plays a direct role in the induction of cellular senescence. Oncogene, 13:2097-2104.

Buchanan, A. V., Risch, G. M., Robichaux, M., Sherry, S. T., Batzer, m. A., Weiss, K. M. 2000. Long DOP-PCR of rare archival anthropological samples. Hum. Biol., 72:911-925.

Champoux J. J. (2001) DNA topoisomerases: structure, function, and mechanism Annu Rev Biochem, 70:369-413.

Chang, K. S., Vyas, R. C., Deaven, L. L., Trujillo, J. M., Stass, S. A., Hittelman W. N. 1992. PCR amplification of chromosome-specific DNA isolated from flow cytometry-sorted chromosomes. Genomics, 12:307-312.

Cheng, J., Waters, L. C., Fortina, P., Hvichia, G., Jacobson, S. C., Ramsey, J. M., Kricka, L. J., Wilding, P. 1998. Degenerate oligonucleotide-primed polymerase chain reaction and capillary electrophoretic analysis of human DNA on a microchip-based devices. Anal. Biochem., 257:101-106.

Cheung, V. G., Nelson, S. F. 1996. Whole genome amplification using a degenerate oligonucleotide primer allows hundreds of genotypes to be performed on less than one nanogram of genomic DNA. Proc. Natl. Acad. Sci. USA, 93:14676-14679.

Coligan, J. E., Kruisbeek A. M., Margulies, D. H., Shevach, E. M., Strober, W. 1991. Current protocols in immunology. John Wiley and Sons, Hoboken, N.J.

Counter, C. M., Avilion, A. A., LeFeuvre, C. E., Stewart, N. G., Greider, C. W., Harley, C. B. and Bacchetti, S. 1992. Telomere shortening associated with chromosome instability is arrested in immortal cells which express telomerase activity. EMBO J., 11:1921-1929.

Dean, F., hosono, S., Fang, L., Wu, X., Faruqi, A. F., Bray-Ward, P., Sun, Z., Zong, Q., Du, Y., Du, J., Driscoll, M., Song, W., Kingsmore, S., Egholm, M., Lasken, R. S. 2002. Comprehensive human genome amplification using multiple displacement amplification. Proc. Natl. Acad. Sci. USA, 99:5261-5266.

Dean, F., Nelson, J., Giesler, T., Lasken, R. 2001. Rapid amplification of plasmid and phage DNA using φ29 DNA polymerase and multiply-primed rolling circle amplification. Genome Res., 11:1095-1099.

DeRisi Laboratory, Dept. of Biochemistry & Biophysics, Univ. of California at San Francisco (2001) Random DNA Amplification. Directions for amplifying products for printing on arrays. World Wide Web website available.

Di Leonardo, A., Linke, S. P., Clarkin, K. and Wahl, G. M. 1994. DNA damage triggers a prolonged p53-dependent G1 arrest and long-term induction of Cip1 in normal human fibroblasts. Genes Dev., 8:2540-2551.

Dietmaier, W., Hartmann, A., Wallinger, S., Heinmöller, E., Kerner, T., Endl, E., Jauch, K. W., Hofstädter, F., Rüschoff, J. 1999. Multiple mutation analyses in single tumor cells with improved whole genome amplification. Am. J. Path., 154:83-95.

Freshney, R. I. 1987. Culture of animal cells: a manual of basic technique, 2d ed., Wiley-Liss, London.

Frohman, M. A. 1990. Race: Rapid amplification of cDNA ends. In Innis, M. A., Gelfand, D. H., Sninsky, J. J., and White, T. J. eds., PCR protocols. Academic press, New York. Pp 28-38.

Gait, M. 1984. Oligonucleotide Synthesis. Practical Approach Series. IRL Press, Oxford, U.K.

Grothues, D., Cantor, C. R., Smith, C. L. 1993. PCR amplification of megabase DNA with tagged random primers (T-PCR). Nucleic Acids Res., 21:1321-1322.

Guan X Y, Trent J M, Meltzer P S. 1993 Generation of band-specific painting probes from a single microdissected chromosome. Hum Mol Genet, 2(8):1117-1121

Hadano, S., Watanabe, M., Yokoi, H., Kogi, M., Kondo, I., Tsuchiya, H., Kanazawa, I., Wakasa, K., Ikeda, J. E. 1991. Laser microdissection and single unique primer PCR allow generation of regional chromosome DNA clones from a single human chromosome. Genomics, 11:364-373.

Hara, E., Smith, R., Parry, D., Tahara, H. and Peters, G. 1996. Regulation of p16 (CdkN2) expression and its implications for cell immortalization and senescence. Mol. Cell. Biol., 16: 859-867.

Hayflick, L. and Moorhead, P. S. 1961. The serial cultivation of human diploid cell strains. Exp. Cell Res., 25:585-621.

Hayflick, L. 1965. The limited in vitro lifetime of human diploid cell strains. Exp. Cell Res., 37:614-636.

Hiyama, E., Tatsumoto, N., Kodama, T., Hiyama, K., Shay, J. W. and Yokoyama, T. 1996. Telomerase activity in human intestine. Int. J. Oncol., 9:453-458.

Jiang, X. R., Jimenez, G., Chang, E., Frolkis, M., Kusler, B., Sage, M., Beeche, M., Bodnar, A. G., Wahl, G. M., Tlsty, T. D. and Chiu, C. P. 1999. Telomerase expression in human somatic cells does not induce changes associated with a transformed phenotype. Nature Genet., 21:111-114

Johnson, D. H. 1990. Molecular cloning of DNA from specific chromosomal regions by microdissection and sequence-independent amplification of DNA. Genomics, 6:243-251.

Kao, F. T., Yu, J. W. 1991. Chromosome microdissection and cloning in human genome and genetic disease analysis. Proc. Natl. Acad. Sci. USA, 88:1844-1848.

Kinzer, K. W., Vogelstein, B. 1989. Whole genome PCR: application to the identification of sequences bound by gene regulatory proteins. Nucleic Acid Res., 17:3645-3653.

Kittler, R., Stoneking, M., Kayser, M. 2002. A whole genome amplification method to generate long fragments from low quantities of genomic DNA. Anal. Biochem., 300:237-244.

Klein, C. A., Schmidt-Kittler, O., Schardt, J. A., Pantel, K., Speicher, M. R., Riethmüller, G. 1999. Comparative genomic hybridization, loss of heterozygosity, and DNA sequence analysis of single cells. Proc. Natl. Acad. Sci. USA, 96:4494-4499.

Kleyn, P. W., Wang, C. H., Lien, L. L., Vitale, E., Pan, J., Ross, B. M., Grunn, A., Palmer, D. A., Warburton, D., Brzustowicz, L. M. 1993. Construction of yeast artificial chromosome contig spanning the spinal muscular atrophy disease gene region. Proc. Natl. Acad. Sci., 90:6801-6805.

Ko, M. S. H., Ko, S. B. H., Takahashi, N., Nishiguchi, K., Abe, K. 1990. Unbiased amplification of highly complex mixture of DNA fragments by 'lone linker'-tagged PCR. Nucleic Acids Res., 18:4293-4294.

Korenburg, J. R., Rykowski, M. C. 1988. Human genome organization: Alu, LINES, and the molecular structure of metaphase chromosome bands. Cell, 53:391-400.

Kwoh, D. Y., Davis, G. R., Whitfield, K. M., Chappelle, H. L., DiMichele, L. J., and Gingeras, T. R. 1989. Transcription-based amplification system and detection of amplified human immunodeficiency virus type 1 with a bead-based sandwich hybridization format.

Lüdecke, H. J., Senger, G., Claussen, U., Horsthemke, B. 1989. Cloning defined regions of human genome by microdissection of banded chromosomes and enzymatic amplification. Nature, 338:348-350.

Makrigiorgos, M. G., Chakrabarti, s., Zhang, Y., Kauer. M., and Price, B. D. 2002. A PCR-based amplification method retaining the quantitative difference between two complex genomes. Nature Biotechnology, 20:936-939.

Martin, G. M., Sprague, C. A. and Epstein, C. J. 1970. Replicative lifespan of cultivated human cells: effect of donor's age, tissue and genotype. Lab. Invest., 23:86-92.

Methods in Enzymology. Academic Press, New York.

Milan, D., Yerle, M., Schmitz, A., Chaput, B., Vaiman, M., Frelatm, G., Gellin, J. 1993. A PCR-base method to amplify DNA with random primers: Determining the chromosomal content of porcine flow-karyotype peaks by chromosome painting. Cytogenet. Cell Genet., 62:139-141.

Miller, J. M., and Calos, M. P. 1987. Gene Transfer Vectors for Mammalian Cells. Cold Spring Harbor Laboratory, Cold Spring Harbor.

Miyashita, K., Vooijs, M. A., Tucker, J. D., Lee, D. A., Gray, J. W., Pallavicini, M. G. 1994. A mouse chromosome 11 library generated from sorted chromosomes using linker-adapter polymerase chain reaction. Cytogenet. Cell Genet., 66:54-57.

Morales, C. P., Holt, S. E., Ouellette, M., Kaur, K. J., Yan, Y., Wilson, K. S., White, M. A., Wright, W. E. and Shay, J. W. 1999. Lack of cancer-associated changes in human fibroblasts immortalized with telomerase. Nature Genet., 21:115-118.

Naylor, J., Brinke, A., Hassock, S., Green, P. M., Giannelli, F. 1993. Characteristic mRNA abnormality found in half the patients with sever hemophilia A is due to large DNA inversions. Hum. Mol. Genet., 2:1773-1778.

Nelson, D. G., Ledbetter, S. A., Corbo, L., Victoria, M. F., Ramirez-Solis, R., Webster, T. D., Ledbetter, D. H., Caskey, C. T. 1989. Alu polymerase chain reaction: A method for rapid isolation of human-specific sequences from complex DNA sources. Proc. Natl. Acad. Sci. USA, 86:6686-6690.

Ohara O., Dorit, R. L., and Gilbert, W. 1989. One-sided polymerase chain reaction: the amplification of cDNA. Proc. Natl. Acad. Sci. USA, 86:5673-5677.

Olovnikov, A. M. 1973. A theory of marginotomy. The incomplete copying of template margin in enzymic synthesis of polynucleotides and biological significance of the phenomenon. J. Theor. Biol., 41:181-190.

Paunio, T., Reima I., Syvanen, A. C. 1996. Preimplantation diagnosis by whole-genome amplification, PCR amplification, and solid-phase minisequencing of blastomere DNA. Mol. Path. Genet., 42:1382-1390.

Phillips J., Eberwine J. H., 1996. Antisense RNA amplification: a linear amplification method for analyzing the mRNA population from single living cells. Methods 10:283-8

Ramirez, R. D., Wright, W. E., Shay, J. W. and Taylor, R. S. 1997. Telomerase activity concentrates in the mitotically active segments of human hair follicles. J. Invest. Dermatol., 108:113-117.

Riley, J., Butler, R., Ogilvie, D., Finniear, R., Jenner, D., Powell, S., Smith, J. C., Markham, A. F. 1990. A novel, rapid method for the isolation of terminal sequences from yeast artificial chromosome (YAC) clones. Nucleic Acids Res., 18:2887-2890.

Robles, S. J. and Adami, G. R. 1998. Agents that cause DNA double strand breaks lead to p16-ink4a enrichment and to premature senescence of normal fibroblasts. Oncogene, 6:1113-1123.

Saiki, R. K., Scharf, S., Faloona, F. A., Mullis, K. B., Horn, G. T., Erlich, H. A., Arnheim, N. 1985. Enzymatic amplification of fl-globin sequences and restriction site amplification for diagnosis of sickle cell anemia. Science, 230:1350-1354.

Sambrook, J., Fritsch, E. F. and Maniatis, T. (1989) Molecular Cloning: A Laboratory Manual, second edition, Cold Spring Harbor Laboratory, Cold Spring Harbor.

Sanchez-Cespedes, M., Cairns, P., Jen, J., Sidransky, D. 1998. Degenerate oligonucleotide-primed PCR (DOP-PCR): Evaluation of its reliability for screening of genetic alteration in neoplasia. Biotechniques, 25:1036-1038.

Saunders, R. D. C., Glover, D. M., Ashburner, M., Siden-Kiamos, I., Louis, C., Monastirioti, M., Savakis, C., Kafatos, F. 1989. PCR amplification of DNA microdissected from a single polytene chromosome band: A comparison with conventional microcloning. Nucleic Acids Res., 17:9027-9037.

Schmidt, W. M. and Meuller, M. W. 1999. CapSelect: a highly sensitive method for 5' CAP-dependent enrichment of full-length cDNA in PCR-mediated analysis of mRNAs. Nucleic Acids Res., 27:e31

Shay, J. W., Pereira-Smith, O. M. and Wright, W. E. 1991. A role for both RB and p53 in the regulation of human cellular senescence. Exp. Cell Res., 196:33-39.

Shay, J. W., Van Der Haegen, B. A., Ying, Y. and Wright, W. E. 1993. The frequency of immortalization of human fibroblasts and mammary epithelial cells transfected with SV40 large T-antigen. Exp. Cell Res., 209:45-52.

Siebert, P. D., Chenchik, A., Kellogg, D. E., Lukyanov, K. A., Lukyanov, S. A. 1995. An improved PCR method for walking in uncloned genomic DNA. Nucleic Acids Res., 23:1087-1088.

Smith, L., Underhill, P., Pritchard, C., Tymowska-Lalanee, Zuzanna., Abdul-Hussein, S., Hilton, H., Winchester, L., Williams, D., Freeman, T., Webb, S., and Greenfield, A. 2003. Nucleic Acids Res. 31: No. 3 e9.

Studier F. W. (1979) Relationships among different strains of T7 and among T7-related bacteriophages. Virology, 95(1): 70-84.

Telenius, H., Carter, N. P., Bebb, C. E., Nordenskjold, M., Ponder, B. A. J., Tunnacliffe, A. 1992. Degenerate oligonucleotide-primed PCR: General amplification of target DNA by a single degenerate primer. Genomics, 13:718-725.

Ulaner, G. A. and Giudice, L. C. 1997. Developmental regulation of telomerase activity in human fetal tissues during gestation. Mol. Hum. Reprod., 3:769-773.

Valdes, J. M., Tagle, D. A., Collins, F. S. 1994. Island rescue sequences from yeast artificial chromosomes and cosmids. Proc. Natl. Acad. Sci. USA, 91:5377-5381.

VanDevanter, D. R., Choongkittaworn, N. M., Dyer, K. A., Aten, J., Otto, P., Behler, C., Bryant, E. M., Rabinovitch, P. S. 1994. Pure chromosome-specific PCR libraries from single sorted chromosome. Proc. Natl. Acad. Sci. USA, 91-5858-5862.

Vaziri, H. and Benchimol, S. 1996. From telomere loss to p53 induction and activation of a DNA-damage pathway at senescence: the telomere loss/DNA damage model of cell aging. Exp. Gerontol., 31:295-301.

Vaziri, H. and Benchimol, S. 1998. Reconstitution of telomerase activity in normal human cells leads to elongation of telomeres and extended replicative life span. Curr. Biol., 8:279-282.

Vooijs, M., Yu, L. C., Tkachuk, D., Pinkel, D., Johnson, D., Gray, J. W. 1993. Libraries for each human chromosome, constructed from sorter-enriched chromosomes by using linker-adaptor PCR. Am. J. Hum. Genet., 52:586-597.

Walker, G. T., Frasier, M. S., Schram, J. L., Little, M. C., Nadeau, J. G., and Malinowski, D. P. 1992. Strand displacement amplification—an isothermal, in vitro DNA amplification technique. Nucleic Acids Res., 20:1691-1696.

Watson, J. D. 1972. Origin of concatemeric T4 DNA. Nature, 239:197-201.

Weir, D. M. 1978. Handbook of Experimental Immunology. Blackwell Scientific Publications, Oxford, U.K.

Wells, D., Sherlock, J. K., handyside, A. H., Delhanty, J. D. A. 1999. Detailed chromosomal and molecular genetic analysis of single cells by whole genome amplification and comparative genomic hybridisation. Nucleic Acids Res., 27:1214-1218.

Wesley, C. S., Ben M., Kreitman, M., Haga, N., Easnes, W. F. 1990. Cloning regions of the *Drosophila* genome by microdissection of polytene chromosome DNA and PCR with nonspecific primer. Nucleic Acids Res., 18:599-603.

Wold, M S (1997) Replication protein A: A heterotrimeric, single-stranded DNA-binding protein required for eukaryotic DNA metabolism. Ann. Rev. Biochem. 66:61-92.

Wong, K. K., Stillwell, L. C., Dockery, C. A., Saffer, J. D. 1996. Use of tagged random hexamer amplification (TRHA) to clone and sequence minute quantities of DNA-applications to a 180 kb plasmid from *Sphingomonas* F199. Nucleic Acids Res., 24:3778-3783.

Wright, W. E., Piatyszek, M. A., Rainey, W. E., Byrd, W. and Shay, J. W. 1996. Telomerase activity in human germline and embryonic tissues and cells. Dev. Genet., 18:173-179.

Wright, W. E. and Shay, J. W. 1992. The two-stage mechanism controlling cellular senescence and immortalization. Exp. Gerontol., 27:383-389.

Wu, D. Y., and Wallace R. B. 1989. The ligation amplification reaction (LAR)-amplification of specific DNA sequences using sequential rounds of template-dependent ligation. Genomics, 4:560-569

Yui, J., Chiu, C. P. and Lansdorp, P. M. 1998. Telomerase activity in candidate stem cells from fetal liver and adult bone marrow. Blood, 91:3255-3262.

Zhang, L., Cui, X., Schmitt, K., Hubert, R., Navidi, W., Arnheim, N. 1992. Whole genome amplification from a single cell: Implications for genetic analysis. Proc. Natl. Acad. Sci. USA, 89:5847-5851.

Zheleznaya L A, Kossykh V G, Svad'bina I V, Oshman T S, Matvienko N I. 1999. PCR Fragmentation of DNA. Biochemistry (Mosc), 64(4):373-378.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, manufacture, composition of matter, means, methods and steps described in the specification. As one of ordinary skill in the art will readily appreciate from the disclosure of the present invention, processes, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A method of preparing a plurality of nucleic acid molecules having known constant region at each end, comprising:
    a) obtaining a sample comprising nucleic acid molecules;
    b) subjecting said nucleic acid molecules to a population of primers to form a nucleic acid molecule/primer mixture, wherein the primers of the population are non-self-complementary and non-complementary to other primers in the population, and comprise in a 5' to 3' orientation a constant region and a variable region, wherein the constant region sequence has a known sequence that is constant among a plurality of primers of the population and the variable region sequence is degenerate among said plurality of primers of the population, and further wherein the sequence of the constant and variable regions consists essentially of only two types of non-complementary nucleotides selected from the group consisting of adenines and guanines; adenines and cytosines; guanines and thymidines; and cytosines and thymidines, such that the primers of the population will not cross-hybridize or self-hybridize under the conditions employed in step c); and
    c) subjecting said nucleic acid molecule/primer mixture to a polymerase under conditions to generate the plurality of molecules including the known constant region at each end.

2. The method of claim 1, wherein the method further comprises a step d) of amplifying the plurality of the molecules to produce amplified molecules.

3. The method of claim 2, wherein said amplifying step is carried out using a polymerase chain reaction.

4. The method of claim 2, wherein said method further comprises the steps of:
    modifying the amplified molecules to incorporate modified nucleotide bases, thereby producing labeled molecules, said amplified molecules further defined as single stranded DNA, double stranded DNA, or a mixture thereof;
    generating single stranded molecules from the labeled molecules, said single stranded molecules capable of hybridizing to complementary sequences arrayed in known locations on a substrate; and
    analyzing at least one hybridization signal.

5. The method of claim 2, wherein a tag is incorporated on the ends of the amplified molecules and wherein said constant region is penultimate to the tags on each end of the amplified molecules.

6. The method of claim 5, wherein the tag is a homopolymeric sequence that comprises poly cytosine (poly C) or poly guanine (poly G).

7. The method of claim 6, wherein the incorporation of the homopolymeric poly C or poly G is carried out through the use of terminal deoxynucleotidyl transferase.

8. The method of claim 6, wherein the incorporation of the homopolymeric poly G or poly C comprises ligation of an adaptor comprising the homopolymeric poly G or poly C to the ends of the amplified molecules.

9. The method of claim 6, wherein the incorporation of the homopolymeric poly C or poly G comprises replicating the amplified molecules with DNA polymerase, said replicating utilizing a primer comprising in a 5' to 3' orientation:
    the homopolymeric poly C or poly G; and
    the constant region.

10. The method of claim 6, wherein the amplified molecules comprising the homopolymeric poly C or poly G are further amplified using a first primer complementary to a desired sequence in the nucleic acid molecule and a second primer complementary to the poly C or poly G.

11. The method of claim 6, wherein the amplified molecules comprising the homopolymeric sequence poly C or poly G are further amplified using a mixture of primers complementary to different desired sequences in the nucleic acid molecule and a separate poly C or poly G primer.

12. The method of claim 1, wherein said constant region is 6 to 100 nucleotides in length.

13. The method of claim 1, wherein said variable region is 4 nucleotides to 20 nucleotides in length.

14. The method of claim 1, wherein the primers of the population further comprise 0 to 3 random bases at its distal 3' end.

15. The method of claim 1, wherein the constant region and the variable region are each comprised of guanines and thymidines and wherein the primers of the population further comprise 0, 1, 2, or 3 random bases at their 3' ends.

16. The method of claim 1, wherein the polymerase is a thermostable polymerase.

17. The method of claim 1, wherein the nucleic acid molecule/primer mixture is subjected to polymerase chain reaction having polymerization steps comprising two or more DNA denaturation steps.

18. The method of claim 1, wherein step c) is further defined as comprising:
    (1) a first series of polymerase chain reaction steps comprising subjecting the nucleic acid molecule/primer mixture to a thermostable polymerase in the presence of the primers under conditions having two or more cycling DNA denaturation steps; and
    (2) a second series of polymerase chain reaction steps using primers that comprise the constant region sequence.

* * * * *

SEQUENCE LISTING

```
<160> NUMBER OF SEQ ID NOS: 210

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
gagtagaatt ctaatatcta                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
gagatattag aattctactc                                                    20

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
```
agtgggattc cgcatgctag t    21

<210> SEQ ID NO 4
<211> LENGTH: 12
<212> TYPE: DNA
<213> ORGANISM: Artificial Sequence
<220> FEATURE:
<223> OTHER INFORMATION: Synthetic primer

<400> SEQUENCE: 4
taactagcat gc    12

<210> SEQ ID NO 5
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)..(17)
<223> OTHER INFORMATION: n is a, c, g, or t

<400> SEQUENCE: 5
ttgcggccgc attnnnnttc    20

<210> SEQ ID NO 6
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (11)..(16)
<223> OTHER INFORMATION: n is a, c, g, or t

<400> SEQUENCE: 6
ccgactcgac nnnnnnatgt gg    22

<210> SEQ ID NO 7
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(21)
<223> OTHER INFORMATION: n is a, c, g, or t

<400> SEQUENCE: 7
tggtagctct tgatcannnn n    21

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
agagttggta gctcttgatc    20

<210> SEQ ID NO 9
<211> LENGTH: 28
<212> TYPE: DNA
<213> ORGANISM: Artificial Sequence
<220> FEATURE:

```
<223> OTHER INFORMATION: Synthetic primer
<220> FEATURE:
<221> NAME/KEY: misc_feature
<222> LOCATION: (23)..(28)
<223> OTHER INFORMATION: n is a, c, g, or t

<400> SEQUENCE: 9
gtaatacgac tcactatagg gcnnnnnn                                               28

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
gtaatacgac tcactatagg gc                                                    22

<210> SEQ ID NO 11
<211> LENGTH: 28
<212> TYPE: DNA
<213> ORGANISM: Artificial Sequence
<220> FEATURE:
<223> OTHER INFORMATION: Synthetic primer

<400> SEQUENCE: 11
cctttctctc cctctctyy yyyyyyyy                                               28

<210> SEQ ID NO 12
<211> LENGTH: 29
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (29)..(29)
<223> OTHER INFORMATION: n is a, c, g, or t

<400> SEQUENCE: 12
cctttctctc cctctctyy yyyyyyyyn                                              29

<210> SEQ ID NO 13
<211> LENGTH: 30
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (29)..(30)
<223> OTHER INFORMATION: n is a, c, g, or t

<400> SEQUENCE: 13
cctttctctc cctctctyy yyyyyyyynn                                             30

<210> SEQ ID NO 14
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (29)..(31)
<223> OTHER INFORMATION: n is a, c, g, or t

<400> SEQUENCE: 14
```

```
cctttctctc ccttctctyy yyyyyyyynn n                                           31
```

<210> SEQ ID NO 15
<211> LENGTH: 32
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (29)..(32)
<223> OTHER INFORMATION: n is a, c, g, or t

<400> SEQUENCE: 15

```
cctttctctc ccttctctyy yyyyyyyynn nn                                          32
```

<210> SEQ ID NO 16
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (29)..(33)
<223> OTHER INFORMATION: n is a, c, g, or t

<400> SEQUENCE: 16

```
cctttctctc ccttctctyy yyyyyyyynn nnn                                         33
```

<210> SEQ ID NO 17
<211> LENGTH: 34
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (29)..(34)
<223> OTHER INFORMATION: n is a, c, g, or t

<400> SEQUENCE: 17

```
cctttctctc ccttctctyy yyyyyyyynn nnnn                                        34
```

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18

```
cctttctctc ccttctct                                                          18
```

<210> SEQ ID NO 19
<211> LENGTH: 30
<212> TYPE: DNA
<213> ORGANISM: Artificial Sequence
<220> FEATURE:
<223> OTHER INFORMATION: Synthetic primer

<400> SEQUENCE: 19

```
gtaatacgac tcactatagg rrrrrrrrrr                                             30
```

<210> SEQ ID NO 20
<211> LENGTH: 30
<212> TYPE: DNA
<213> ORGANISM: Artificial Sequence
<220> FEATURE:

```
<223> OTHER INFORMATION: Synthetic primer
<220> FEATURE:
<221> NAME/KEY: misc_feature
<222> LOCATION: (29)..(30)
<223> OTHER INFORMATION: n is a, c, g, or t

<400> SEQUENCE: 20
agagaaggga gagaaaggrr rrrrrrrrnn                                    30

<210> SEQ ID NO 21
<211> LENGTH: 18
<212> TYPE: DNA
<213> ORGANISM: Artificial Sequence
<220> FEATURE:
<223> OTHER INFORMATION: Synthetic primer

<400> SEQUENCE: 21
agagaaggga gagaaagg                                                 18

<210> SEQ ID NO 22
<211> LENGTH: 30
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (29)..(30)
<223> OTHER INFORMATION: n is a, c, g, or t

<400> SEQUENCE: 22
ccaaacacac ccaacacamm mmmmmmmmnn                                    30

<210> SEQ ID NO 23
<211> LENGTH: 18
<212> TYPE: DNA
<213> ORGANISM: Artificial Sequence
<220> FEATURE:
<223> OTHER INFORMATION: Synthetic primer

<400> SEQUENCE: 23
ccaaacacac ccaacaca                                                 18

<210> SEQ ID NO 24
<211> LENGTH: 30
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (19)..(28)
<223> OTHER INFORMATION: K = G or T
<220> FEATURE:
<221> NAME/KEY: misc_feature
<222> LOCATION: (29)..(30)
<223> OTHER INFORMATION: n is a, c, g, or t

<400> SEQUENCE: 24
tgtgttgggt gtgtttggkk kkkkkkkknn                                    30

<210> SEQ ID NO 25
<211> LENGTH: 18
<212> TYPE: DNA
<213> ORGANISM: Artificial Sequence
<220> FEATURE:
<223> OTHER INFORMATION: Synthetic primer

<400> SEQUENCE: 25
```
tgtgttgggt gtgtttgg                                                          18

<210> SEQ ID NO 26
<211> LENGTH: 26
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (21)..(26)
<223> OTHER INFORMATION: n is a, c, g, or t

<400> SEQUENCE: 26
gtaatacgac tcactatagg nnnnnn                                                 26

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
gtaatacgac tcactatagg                                                        20

<210> SEQ ID NO 28
<211> LENGTH: 38
<212> TYPE: DNA
<213> ORGANISM: Artificial Sequence
<220> FEATURE:
<223> OTHER INFORMATION: Synthetic primer

<400> SEQUENCE: 28
tgtgttgggt gtgtttggtt tttttttttt ttttttt                                     38

<210> SEQ ID NO 29
<211> LENGTH: 38
<212> TYPE: DNA
<213> ORGANISM: Artificial Sequence
<220> FEATURE:
<223> OTHER INFORMATION: Synthetic primer

<400> SEQUENCE: 29
tgtgttgggt gtgtttggtt tttttttttt ttttttt                                     38

<210> SEQ ID NO 30
<211> LENGTH: 21
<212> TYPE: DNA
<213> ORGANISM: Artificial Sequence
<220> FEATURE:
<223> OTHER INFORMATION: Synthetic primer

<400> SEQUENCE: 30
gcatatccat atctcccgaa t                                                      21

<210> SEQ ID NO 31
<211> LENGTH: 21
<212> TYPE: DNA
<213> ORGANISM: Artificial Sequence
<220> FEATURE:
<223> OTHER INFORMATION: Synthetic primer

<400> SEQUENCE: 31
cagagcactc cagaccatac g                                                      21

<210> SEQ ID NO 32

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 32
cttcgttatg acccctgctc c                                              21

<210> SEQ ID NO 33
<211> LENGTH: 22
<212> TYPE: DNA
<213> ORGANISM: Artificial Sequence
<220> FEATURE:
<223> OTHER INFORMATION: Synthetic primer

<400> SEQUENCE: 33
tcccaagatg aatggtaaga cg                                             22

<210> SEQ ID NO 34
<211> LENGTH: 21
<212> TYPE: DNA
<213> ORGANISM: Artificial Sequence
<220> FEATURE:
<223> OTHER INFORMATION: Synthetic primer

<400> SEQUENCE: 34
tccaatctca tcggtttact g                                              21

<210> SEQ ID NO 35
<211> LENGTH: 21
<212> TYPE: DNA
<213> ORGANISM: Artificial Sequence
<220> FEATURE:
<223> OTHER INFORMATION: Synthetic primer

<400> SEQUENCE: 35
tccagagccc agtaaacaac a                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetic primer

<400> SEQUENCE: 36
ttacttcagc ccacatgctt c                                              21

<210> SEQ ID NO 37
<211> LENGTH: 22
<212> TYPE: DNA
<213> ORGANISM: Artificial Sequence
<220> FEATURE:
<223> OTHER INFORMATION: Synthetic primer

<400> SEQUENCE: 37
ttccgacata gcgactttgt ag                                             22

<210> SEQ ID NO 38
<211> LENGTH: 22
<212> TYPE: DNA
<213> ORGANISM: Artificial Sequence
<220> FEATURE:
<223> OTHER INFORMATION: Synthetic primer

<400> SEQUENCE: 38
```
aaggatcaga gatacccccac gg 22

<210> SEQ ID NO 39
<211> LENGTH: 23
<212> TYPE: DNA
<213> ORGANISM: Artificial Sequence
<220> FEATURE:
<223> OTHER INFORMATION: Synthetic primer

<400> SEQUENCE: 39
tccaagaacc aactaagtcc aga 23

<210> SEQ ID NO 40
<211> LENGTH: 23
<212> TYPE: DNA
<213> ORGANISM: Artificial Sequence
<220> FEATURE:
<223> OTHER INFORMATION: Synthetic primer

<400> SEQUENCE: 40
ctaagggcaa acatagggat caa 23

<210> SEQ ID NO 41
<211> LENGTH: 22
<212> TYPE: DNA
<213> ORGANISM: Artificial Sequence
<220> FEATURE:
<223> OTHER INFORMATION: Synthetic primer

<400> SEQUENCE: 41
caacctttga agccactttg ac 22

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
gcctccgtca ttggtatttt ct 22

<210> SEQ ID NO 43
<211> LENGTH: 21
<212> TYPE: DNA
<213> ORGANISM: Artificial Sequence
<220> FEATURE:
<223> OTHER INFORMATION: Synthetic primer

<400> SEQUENCE: 43
tggcaacacg gtgctgacct g 21

<210> SEQ ID NO 44
<211> LENGTH: 22
<212> TYPE: DNA
<213> ORGANISM: Artificial Sequence
<220> FEATURE:
<223> OTHER INFORMATION: Synthetic primer

<400> SEQUENCE: 44
atcatgggtt tggcagtaaa gc 22

<210> SEQ ID NO 45
<211> LENGTH: 21
<212> TYPE: DNA
<213> ORGANISM: Artificial Sequence
<220> FEATURE:

-continued

<223> OTHER INFORMATION: Synthetic primer

<400> SEQUENCE: 45
agaaccagca aacccagtcc c                                             21

<210> SEQ ID NO 46
<211> LENGTH: 21
<212> TYPE: DNA
<213> ORGANISM: Artificial Sequence
<220> FEATURE:
<223> OTHER INFORMATION: Synthetic primer

<400> SEQUENCE: 46
gaaagggtgg atggattgaa a                                             21

<210> SEQ ID NO 47
<211> LENGTH: 21
<212> TYPE: DNA
<213> ORGANISM: Artificial Sequence
<220> FEATURE:
<223> OTHER INFORMATION: Synthetic primer

<400> SEQUENCE: 47
tcagatttcc tggctccgct t                                             21

<210> SEQ ID NO 48
<211> LENGTH: 21
<212> TYPE: DNA
<213> ORGANISM: Artificial Sequence
<220> FEATURE:
<223> OTHER INFORMATION: Synthetic primer

<400> SEQUENCE: 48
ccttctgctt ccctgtgacc t                                             21

<210> SEQ ID NO 49
<211> LENGTH: 21
<212> TYPE: DNA
<213> ORGANISM: Artificial Sequence
<220> FEATURE:
<223> OTHER INFORMATION: Synthetic primer

<400> SEQUENCE: 49
tgaaccccac gaggtgacag t                                             21

<210> SEQ ID NO 50
<211> LENGTH: 22
<212> TYPE: DNA
<213> ORGANISM: Artificial Sequence
<220> FEATURE:
<223> OTHER INFORMATION: Synthetic primer

<400> SEQUENCE: 50
gacattacca gcccctcacc ta                                            22

<210> SEQ ID NO 51
<211> LENGTH: 22
<212> TYPE: DNA
<213> ORGANISM: Artificial Sequence
<220> FEATURE:
<223> OTHER INFORMATION: Synthetic primer

<400> SEQUENCE: 51
tccttgacag ttccattcac ca                                            22

<210> SEQ ID NO 52

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 52
tttgcaggta gctctaggtc a                                              21

<210> SEQ ID NO 53
<211> LENGTH: 22
<212> TYPE: DNA
<213> ORGANISM: Artificial Sequence
<220> FEATURE:
<223> OTHER INFORMATION: Synthetic primer

<400> SEQUENCE: 53
gcggacagag agtaacctcg ga                                             22

<210> SEQ ID NO 54
<211> LENGTH: 21
<212> TYPE: DNA
<213> ORGANISM: Artificial Sequence
<220> FEATURE:
<223> OTHER INFORMATION: Synthetic primer

<400> SEQUENCE: 54
cccagaaacc ctgagaccct c                                              21

<210> SEQ ID NO 55
<211> LENGTH: 21
<212> TYPE: DNA
<213> ORGANISM: Artificial Sequence
<220> FEATURE:
<223> OTHER INFORMATION: Synthetic primer

<400> SEQUENCE: 55
tgtgccacaa gttaagatgc t                                              21

<210> SEQ ID NO 56
<211> LENGTH: 22
<212> TYPE: DNA
<213> ORGANISM: Artificial Sequence
<220> FEATURE:
<223> OTHER INFORMATION: Synthetic primer

<400> SEQUENCE: 56
tgctgtatcg tgcctgctca at                                             22

<210> SEQ ID NO 57
<211> LENGTH: 21
<212> TYPE: DNA
<213> ORGANISM: Artificial Sequence
<220> FEATURE:
<223> OTHER INFORMATION: Synthetic primer

<400> SEQUENCE: 57
tgccccactc cccaacattc t                                              21

<210> SEQ ID NO 58
<211> LENGTH: 21
<212> TYPE: DNA
<213> ORGANISM: Artificial Sequence
<220> FEATURE:
<223> OTHER INFORMATION: Synthetic primer

<400> SEQUENCE: 58
```

```
aacagagcct cagggaccag t                                           21
```

<210> SEQ ID NO 59
<211> LENGTH: 21
<212> TYPE: DNA
<213> ORGANISM: Artificial Sequence
<220> FEATURE:
<223> OTHER INFORMATION: Synthetic primer

<400> SEQUENCE: 59

```
gggctttgtc tgtggttggt a                                           21
```

<210> SEQ ID NO 60
<211> LENGTH: 21
<212> TYPE: DNA
<213> ORGANISM: Artificial Sequence
<220> FEATURE:
<223> OTHER INFORMATION: Synthetic primer

<400> SEQUENCE: 60

```
tgggctggct gaggtcaaga t                                           21
```

<210> SEQ ID NO 61
<211> LENGTH: 21
<212> TYPE: DNA
<213> ORGANISM: Artificial Sequence
<220> FEATURE:
<223> OTHER INFORMATION: Synthetic primer

<400> SEQUENCE: 61

```
ttttgctccg ctgacatttg g                                           21
```

<210> SEQ ID NO 62
<211> LENGTH: 21
<212> TYPE: DNA
<213> ORGANISM: Artificial Sequence
<220> FEATURE:
<223> OTHER INFORMATION: Synthetic primer

<400> SEQUENCE: 62

```
tgctcctgtc ccttccactt c                                           21
```

<210> SEQ ID NO 63
<211> LENGTH: 23
<212> TYPE: DNA
<213> ORGANISM: Artificial Sequence
<220> FEATURE:
<223> OTHER INFORMATION: Synthetic primer

<400> SEQUENCE: 63

```
ccttattccc agcagcagta ttc                                         23
```

<210> SEQ ID NO 64
<211> LENGTH: 21
<212> TYPE: DNA
<213> ORGANISM: Artificial Sequence
<220> FEATURE:
<223> OTHER INFORMATION: Synthetic primer

<400> SEQUENCE: 64

```
tgggaaggga aagagggtac t                                           21
```

<210> SEQ ID NO 65
<211> LENGTH: 21
<212> TYPE: DNA
<213> ORGANISM: Artificial Sequence
<220> FEATURE:

<223> OTHER INFORMATION: Synthetic primer

<400> SEQUENCE: 65
ttgctgtaga tgggctttcg t                                    21

<210> SEQ ID NO 66
<211> LENGTH: 21
<212> TYPE: DNA
<213> ORGANISM: Artificial Sequence
<220> FEATURE:
<223> OTHER INFORMATION: Synthetic primer

<400> SEQUENCE: 66
tctgctgggt tgatgatttg g                                    21

<210> SEQ ID NO 67
<211> LENGTH: 21
<212> TYPE: DNA
<213> ORGANISM: Artificial Sequence
<220> FEATURE:
<223> OTHER INFORMATION: Synthetic primer

<400> SEQUENCE: 67
ggcacaagca aaagggtgtc t                                    21

<210> SEQ ID NO 68
<211> LENGTH: 21
<212> TYPE: DNA
<213> ORGANISM: Artificial Sequence
<220> FEATURE:
<223> OTHER INFORMATION: Synthetic primer

<400> SEQUENCE: 68
ccagcaatca ggaaagcaca a                                    21

<210> SEQ ID NO 69
<211> LENGTH: 22
<212> TYPE: DNA
<213> ORGANISM: Artificial Sequence
<220> FEATURE:
<223> OTHER INFORMATION: Synthetic primer

<400> SEQUENCE: 69
cacctgtctt gttggcatca cc                                   22

<210> SEQ ID NO 70
<211> LENGTH: 23
<212> TYPE: DNA
<213> ORGANISM: Artificial Sequence
<220> FEATURE:
<223> OTHER INFORMATION: Synthetic primer

<400> SEQUENCE: 70
ttgttttgcc tcaccagtca ttt                                  23

<210> SEQ ID NO 71
<211> LENGTH: 21
<212> TYPE: DNA
<213> ORGANISM: Artificial Sequence
<220> FEATURE:
<223> OTHER INFORMATION: Synthetic primer

<400> SEQUENCE: 71
tcagcaaacc caaagatgtt a                                    21

<210> SEQ ID NO 72

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 72
ttagtccttt gggcagcacg a                                              21

<210> SEQ ID NO 73
<211> LENGTH: 21
<212> TYPE: DNA
<213> ORGANISM: Artificial Sequence
<220> FEATURE:
<223> OTHER INFORMATION: Synthetic primer

<400> SEQUENCE: 73
tgtctctgct tctgaaacgg g                                              21

<210> SEQ ID NO 74
<211> LENGTH: 20
<212> TYPE: DNA
<213> ORGANISM: Artificial Sequence
<220> FEATURE:
<223> OTHER INFORMATION: Synthetic primer

<400> SEQUENCE: 74
actgccaggg tcattgactt                                                20

<210> SEQ ID NO 75
<211> LENGTH: 18
<212> TYPE: DNA
<213> ORGANISM: Artificial Sequence
<220> FEATURE:
<223> OTHER INFORMATION: Synthetic primer

<400> SEQUENCE: 75
taagcagcaa ggtctggg                                                  18

<210> SEQ ID NO 76
<211> LENGTH: 23
<212> TYPE: DNA
<213> ORGANISM: Artificial Sequence
<220> FEATURE:
<223> OTHER INFORMATION: Synthetic primer

<400> SEQUENCE: 76
gtgattgaac aatttggacc cac                                            23

<210> SEQ ID NO 77
<211> LENGTH: 23
<212> TYPE: DNA
<213> ORGANISM: Artificial Sequence
<220> FEATURE:
<223> OTHER INFORMATION: Synthetic primer

<400> SEQUENCE: 77
atggcaacat tccacctagt agc                                            23

<210> SEQ ID NO 78
<211> LENGTH: 22
<212> TYPE: DNA
<213> ORGANISM: Artificial Sequence
<220> FEATURE:
<223> OTHER INFORMATION: Synthetic primer

<400> SEQUENCE: 78
```
ctccgtcatg ataagatgca gt                                            22

<210> SEQ ID NO 79
<211> LENGTH: 22
<212> TYPE: DNA
<213> ORGANISM: Artificial Sequence
<220> FEATURE:
<223> OTHER INFORMATION: Synthetic primer

<400> SEQUENCE: 79
actgtttggg gtgtgaaagg ac                                            22

<210> SEQ ID NO 80
<211> LENGTH: 20
<212> TYPE: DNA
<213> ORGANISM: Artificial Sequence
<220> FEATURE:
<223> OTHER INFORMATION: Synthetic primer

<400> SEQUENCE: 80
actaacaacg ccctttgctc                                               20

<210> SEQ ID NO 81
<211> LENGTH: 23
<212> TYPE: DNA
<213> ORGANISM: Artificial Sequence
<220> FEATURE:
<223> OTHER INFORMATION: Synthetic primer

<400> SEQUENCE: 81
tcagcactcc gtatcttcat ttg                                           23

<210> SEQ ID NO 82
<211> LENGTH: 23
<212> TYPE: DNA
<213> ORGANISM: Artificial Sequence
<220> FEATURE:
<223> OTHER INFORMATION: Synthetic primer

<400> SEQUENCE: 82
taaaccgcta aaacgatagc agc                                           23

<210> SEQ ID NO 83
<211> LENGTH: 23
<212> TYPE: DNA
<213> ORGANISM: Artificial Sequence
<220> FEATURE:
<223> OTHER INFORMATION: Synthetic primer

<400> SEQUENCE: 83
tcatggtatt agggaagtgg gag                                           23

<210> SEQ ID NO 84
<211> LENGTH: 23
<212> TYPE: DNA
<213> ORGANISM: Artificial Sequence
<220> FEATURE:
<223> OTHER INFORMATION: Synthetic primer

<400> SEQUENCE: 84
gggaatgaaa agaaaaggca ttc                                           23

<210> SEQ ID NO 85
<211> LENGTH: 25
<212> TYPE: DNA
<213> ORGANISM: Artificial Sequence
<220> FEATURE:

<223> OTHER INFORMATION: Synthetic primer

<400> SEQUENCE: 85
tctttccctc tacaaccctc taacc    25

<210> SEQ ID NO 86
<211> LENGTH: 23
<212> TYPE: DNA
<213> ORGANISM: Artificial Sequence
<220> FEATURE:
<223> OTHER INFORMATION: Synthetic primer

<400> SEQUENCE: 86
cagtacatgg gtcttatgag tac    23

<210> SEQ ID NO 87
<211> LENGTH: 22
<212> TYPE: DNA
<213> ORGANISM: Artificial Sequence
<220> FEATURE:
<223> OTHER INFORMATION: Synthetic primer

<400> SEQUENCE: 87
aatcgagaac gcacagagca ga    22

<210> SEQ ID NO 88
<211> LENGTH: 23
<212> TYPE: DNA
<213> ORGANISM: Artificial Sequence
<220> FEATURE:
<223> OTHER INFORMATION: Synthetic primer

<400> SEQUENCE: 88
gtctggggag taaatgcaac atc    23

<210> SEQ ID NO 89
<211> LENGTH: 20
<212> TYPE: DNA
<213> ORGANISM: Artificial Sequence
<220> FEATURE:
<223> OTHER INFORMATION: Synthetic primer

<400> SEQUENCE: 89
ttcttgatga ccctgcacaa    20

<210> SEQ ID NO 90
<211> LENGTH: 23
<212> TYPE: DNA
<213> ORGANISM: Artificial Sequence
<220> FEATURE:
<223> OTHER INFORMATION: Synthetic primer

<400> SEQUENCE: 90
cagcagaagc actaccaaag aca    23

<210> SEQ ID NO 91
<211> LENGTH: 23
<212> TYPE: DNA
<213> ORGANISM: Artificial Sequence
<220> FEATURE:
<223> OTHER INFORMATION: Synthetic primer

<400> SEQUENCE: 91
ttcacctaga tggaatagcc acc    23

<210> SEQ ID NO 92

```
<211> LENGTH: 23
<212> TYPE: DNA
<213> ORGANISM: Artificial Sequence
<220> FEATURE:
<223> OTHER INFORMATION: Synthetic primer

<400> SEQUENCE: 92
gcaagatttt tgcttggctc tat                                              23

<210> SEQ ID NO 93
<211> LENGTH: 22
<212> TYPE: DNA
<213> ORGANISM: Artificial Sequence
<220> FEATURE:
<223> OTHER INFORMATION: Synthetic primer

<400> SEQUENCE: 93
gaattttggt ttcttgcttt gg                                               22

<210> SEQ ID NO 94
<211> LENGTH: 23
<212> TYPE: DNA
<213> ORGANISM: Artificial Sequence
<220> FEATURE:
<223> OTHER INFORMATION: Synthetic primer

<400> SEQUENCE: 94
gtcagaagac tgaaaacgaa gcc                                              23

<210> SEQ ID NO 95
<211> LENGTH: 23
<212> TYPE: DNA
<213> ORGANISM: Artificial Sequence
<220> FEATURE:
<223> OTHER INFORMATION: Synthetic primer

<400> SEQUENCE: 95
catctcttga tcatcccagc tct                                              23

<210> SEQ ID NO 96
<211> LENGTH: 23
<212> TYPE: DNA
<213> ORGANISM: Artificial Sequence
<220> FEATURE:
<223> OTHER INFORMATION: Synthetic primer

<400> SEQUENCE: 96
caccattggt tgatagcaag gtt                                              23

<210> SEQ ID NO 97
<211> LENGTH: 20
<212> TYPE: DNA
<213> ORGANISM: Artificial Sequence
<220> FEATURE:
<223> OTHER INFORMATION: Synthetic primer

<400> SEQUENCE: 97
taaacatagc accaaggggc                                                  20

<210> SEQ ID NO 98
<211> LENGTH: 23
<212> TYPE: DNA
<213> ORGANISM: Artificial Sequence
<220> FEATURE:
<223> OTHER INFORMATION: Synthetic primer

<400> SEQUENCE: 98
```
tcatgtgtgg gtcactaagg atg                                    23

<210> SEQ ID NO 99
<211> LENGTH: 20
<212> TYPE: DNA
<213> ORGANISM: Artificial Sequence
<220> FEATURE:
<223> OTHER INFORMATION: Synthetic primer

<400> SEQUENCE: 99
cgtctctccc agctaggatg                                        20

<210> SEQ ID NO 100
<211> LENGTH: 24
<212> TYPE: DNA
<213> ORGANISM: Artificial Sequence
<220> FEATURE:
<223> OTHER INFORMATION: Synthetic primer

<400> SEQUENCE: 100 cttttcaca gaactggtgt cagg                                    24

<210> SEQ ID NO 101
<211> LENGTH: 20
<212> TYPE: DNA
<213> ORGANISM: Artificial Sequence
<220> FEATURE:
<223> OTHER INFORMATION: Synthetic primer

<400> SEQUENCE: 101
acccagcttt cagtgaagga                                        20

<210> SEQ ID NO 102
<211> LENGTH: 20
<212> TYPE: DNA
<213> ORGANISM: Artificial Sequence
<220> FEATURE:
<223> OTHER INFORMATION: Synthetic primer

<400> SEQUENCE: 102
aatcaaaagg ccaacagtgg                                        20

<210> SEQ ID NO 103
<211> LENGTH: 18
<212> TYPE: DNA
<213> ORGANISM: Artificial Sequence
<220> FEATURE:
<223> OTHER INFORMATION: Synthetic primer

<400> SEQUENCE: 103
actggctgag ggagcatg                                          18

<210> SEQ ID NO 104
<211> LENGTH: 21
<212> TYPE: DNA
<213> ORGANISM: Artificial Sequence
<220> FEATURE:
<223> OTHER INFORMATION: Synthetic primer

<400> SEQUENCE: 104
taaatgtaac ccccttgagc c                                      21

<210> SEQ ID NO 105
<211> LENGTH: 20
<212> TYPE: DNA
<213> ORGANISM: Artificial Sequence
<220> FEATURE:

<223> OTHER INFORMATION: Synthetic primer

<400> SEQUENCE: 105
tattgaccac atgaccccct                                      20

<210> SEQ ID NO 106
<211> LENGTH: 21
<212> TYPE: DNA
<213> ORGANISM: Artificial Sequence
<220> FEATURE:
<223> OTHER INFORMATION: Synthetic primer

<400> SEQUENCE: 106
ttgggtgatg tcttcacatg g                                    21

<210> SEQ ID NO 107
<211> LENGTH: 22
<212> TYPE: DNA
<213> ORGANISM: Artificial Sequence
<220> FEATURE:
<223> OTHER INFORMATION: Synthetic primer

<400> SEQUENCE: 107
gctcaataaa aatagtacgc cc                                   22

<210> SEQ ID NO 108
<211> LENGTH: 20
<212> TYPE: DNA
<213> ORGANISM: Artificial Sequence
<220> FEATURE:
<223> OTHER INFORMATION: Synthetic primer

<400> SEQUENCE: 108
ttctcccagc tttgagacgt                                      20

<210> SEQ ID NO 109
<211> LENGTH: 21
<212> TYPE: DNA
<213> ORGANISM: Artificial Sequence
<220> FEATURE:
<223> OTHER INFORMATION: Synthetic primer

<400> SEQUENCE: 109
tttgttactt gctaccctga g                                    21

<210> SEQ ID NO 110
<211> LENGTH: 23
<212> TYPE: DNA
<213> ORGANISM: Artificial Sequence
<220> FEATURE:
<223> OTHER INFORMATION: Synthetic primer

<400> SEQUENCE: 110
gaagatgaag tgaactccta tcc                                  23

<210> SEQ ID NO 111
<211> LENGTH: 22
<212> TYPE: DNA
<213> ORGANISM: Artificial Sequence
<220> FEATURE:
<223> OTHER INFORMATION: Synthetic primer

<400> SEQUENCE: 111
gaagccttga taacgagagt gg                                   22

<210> SEQ ID NO 112

```
<211> LENGTH: 19
<212> TYPE: DNA
<213> ORGANISM: Artificial Sequence
<220> FEATURE:
<223> OTHER INFORMATION: Synthetic primer

<400> SEQUENCE: 112
atgtttctct ggccccaag                                           19

<210> SEQ ID NO 113
<211> LENGTH: 17
<212> TYPE: DNA
<213> ORGANISM: Artificial Sequence
<220> FEATURE:
<223> OTHER INFORMATION: Synthetic primer

<400> SEQUENCE: 113
tggctgccct tcaatac                                             17

<210> SEQ ID NO 114
<211> LENGTH: 20
<212> TYPE: DNA
<213> ORGANISM: Artificial Sequence
<220> FEATURE:
<223> OTHER INFORMATION: Synthetic primer

<400> SEQUENCE: 114
ttgggaaatg tcagtgacca                                          20

<210> SEQ ID NO 115
<211> LENGTH: 24
<212> TYPE: DNA
<213> ORGANISM: Artificial Sequence
<220> FEATURE:
<223> OTHER INFORMATION: Synthetic primer

<400> SEQUENCE: 115
tgtggttagg atagcacaag catt                                     24

<210> SEQ ID NO 116
<211> LENGTH: 22
<212> TYPE: DNA
<213> ORGANISM: Artificial Sequence
<220> FEATURE:
<223> OTHER INFORMATION: Synthetic primer

<400> SEQUENCE: 116
tgcaatttga aggtacgagt ag                                       22

<210> SEQ ID NO 117
<211> LENGTH: 25
<212> TYPE: DNA
<213> ORGANISM: Artificial Sequence
<220> FEATURE:
<223> OTHER INFORMATION: Synthetic primer

<400> SEQUENCE: 117
tgttaacaat ttgcataaca aaagc                                    25

<210> SEQ ID NO 118
<211> LENGTH: 24
<212> TYPE: DNA
<213> ORGANISM: Artificial Sequence
<220> FEATURE:
<223> OTHER INFORMATION: Synthetic primer

<400> SEQUENCE: 118
```
gcattttctg tcccacaaga tatg                                              24

<210> SEQ ID NO 119
<211> LENGTH: 20
<212> TYPE: DNA
<213> ORGANISM: Artificial Sequence
<220> FEATURE:
<223> OTHER INFORMATION: Synthetic primer

<400> SEQUENCE: 119
attgctgtca cagcaccttg                                                   20

<210> SEQ ID NO 120
<211> LENGTH: 22
<212> TYPE: DNA
<213> ORGANISM: Artificial Sequence
<220> FEATURE:
<223> OTHER INFORMATION: Synthetic primer

<400> SEQUENCE: 120
cgaggcgggt ggatcatgag gt                                                22

<210> SEQ ID NO 121
<211> LENGTH: 20
<212> TYPE: DNA
<213> ORGANISM: Artificial Sequence
<220> FEATURE:
<223> OTHER INFORMATION: Synthetic primer

<400> SEQUENCE: 121
tctgtcgccc aggccggact                                                   20

<210> SEQ ID NO 122
<211> LENGTH: 28
<212> TYPE: DNA
<213> ORGANISM: Artificial Sequence
<220> FEATURE:
<223> OTHER INFORMATION: Synthetic primer

<400> SEQUENCE: 122
cccccccccc gtaatacgac tcactata                                          28

<210> SEQ ID NO 123
<211> LENGTH: 33
<212> TYPE: DNA
<213> ORGANISM: Artificial Sequence
<220> FEATURE:
<223> OTHER INFORMATION: Synthetic primer

<400> SEQUENCE: 123
cccccccccc cccccgtaat acgactcact ata                                    33

<210> SEQ ID NO 124
<211> LENGTH: 38
<212> TYPE: DNA
<213> ORGANISM: Artificial Sequence
<220> FEATURE:
<223> OTHER INFORMATION: Synthetic primer

<400> SEQUENCE: 124
cccccccccc cccccccccc gtaatacgac tcactata                               38

<210> SEQ ID NO 125
<211> LENGTH: 10
<212> TYPE: DNA
<213> ORGANISM: Artificial Sequence
<220> FEATURE:

<223> OTHER INFORMATION: Synthetic primer

<400> SEQUENCE: 125
cccccccccc                                                                 10

<210> SEQ ID NO 126
<211> LENGTH: 15
<212> TYPE: DNA
<213> ORGANISM: Artificial Sequence
<220> FEATURE:
<223> OTHER INFORMATION: Synthetic primer

<400> SEQUENCE: 126
cccccccccc ccccc                                                           15

<210> SEQ ID NO 127
<211> LENGTH: 20
<212> TYPE: DNA
<213> ORGANISM: Artificial Sequence
<220> FEATURE:
<223> OTHER INFORMATION: Synthetic primer

<400> SEQUENCE: 127
cccccccccc cccccccccc                                                      20

<210> SEQ ID NO 128
<211> LENGTH: 28
<212> TYPE: DNA
<213> ORGANISM: Artificial Sequence
<220> FEATURE:
<223> OTHER INFORMATION: Synthetic primer

<400> SEQUENCE: 128
tgttgtgggt tgtgttggkk kkkkkkkk                                             28

<210> SEQ ID NO 129
<211> LENGTH: 18
<212> TYPE: DNA
<213> ORGANISM: Artificial Sequence
<220> FEATURE:
<223> OTHER INFORMATION: Synthetic primer

<400> SEQUENCE: 129
tgttgtgggt tgtgttgg                                                        18

<210> SEQ ID NO 130
<211> LENGTH: 27
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 130
tgtgttgggt gtgtttggnk knkknkk                                              27

<210> SEQ ID NO 131

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 131
agaggcttct ggcagtttgc                                              20

<210> SEQ ID NO 132
<211> LENGTH: 20
<212> TYPE: DNA
<213> ORGANISM: Artificial Sequence
<220> FEATURE:
<223> OTHER INFORMATION: Synthetic primer

<400> SEQUENCE: 132
cccagcctct ggaaaatcag                                              20

<210> SEQ ID NO 133
<211> LENGTH: 21
<212> TYPE: DNA
<213> ORGANISM: Artificial Sequence
<220> FEATURE:
<223> OTHER INFORMATION: Synthetic primer

<400> SEQUENCE: 133
ccctaacatg gaggtaggag c                                            21

<210> SEQ ID NO 134
<211> LENGTH: 20
<212> TYPE: DNA
<213> ORGANISM: Artificial Sequence
<220> FEATURE:
<223> OTHER INFORMATION: Synthetic primer

<400> SEQUENCE: 134
tcttcctggt gtgagcctct                                              20

<210> SEQ ID NO 135
<211> LENGTH: 18
<212> TYPE: DNA
<213> ORGANISM: Artificial Sequence
<220> FEATURE:
<223> OTHER INFORMATION: Synthetic primer

<400> SEQUENCE: 135
gagaaccgga gcgtgctt                                                18

<210> SEQ ID NO 136
<211> LENGTH: 20
<212> TYPE: DNA
<213> ORGANISM: Artificial Sequence
<220> FEATURE:
<223> OTHER INFORMATION: Synthetic primer

<400> SEQUENCE: 136
tattgaccac atgacccect                                              20

<210> SEQ ID NO 137
<211> LENGTH: 22
<212> TYPE: DNA
<213> ORGANISM: Artificial Sequence
<220> FEATURE:
<223> OTHER INFORMATION: Synthetic primer

<400> SEQUENCE: 137
```

```
gcaaaatcca taccctttct gc                                              22

<210> SEQ ID NO 138
<211> LENGTH: 25
<212> TYPE: DNA
<213> ORGANISM: Artificial Sequence
<220> FEATURE:
<223> OTHER INFORMATION: Synthetic primer

<400> SEQUENCE: 138
tctttccctc tacaaccctc taacc                                           25

<210> SEQ ID NO 139
<211> LENGTH: 24
<212> TYPE: DNA
<213> ORGANISM: Artificial Sequence
<220> FEATURE:
<223> OTHER INFORMATION: Synthetic primer

<400> SEQUENCE: 139
gcaaaatgcc ttcttgtgtt tttc                                            24

<210> SEQ ID NO 140
<211> LENGTH: 24
<212> TYPE: DNA
<213> ORGANISM: Artificial Sequence
<220> FEATURE:
<223> OTHER INFORMATION: Synthetic primer

<400> SEQUENCE: 140
gcattttctg tcccacaaga tatg                                            24

<210> SEQ ID NO 141
<211> LENGTH: 19
<212> TYPE: DNA
<213> ORGANISM: Artificial Sequence
<220> FEATURE:
<223> OTHER INFORMATION: Synthetic primer

<400> SEQUENCE: 141
atgtttctct ggccccaag                                                  19

<210> SEQ ID NO 142
<211> LENGTH: 21
<212> TYPE: DNA
<213> ORGANISM: Artificial Sequence
<220> FEATURE:
<223> OTHER INFORMATION: Synthetic primer

<400> SEQUENCE: 142
ttctccatga gattggactg g                                               21

<210> SEQ ID NO 143
<211> LENGTH: 22
<212> TYPE: DNA
<213> ORGANISM: Artificial Sequence
<220> FEATURE:
<223> OTHER INFORMATION: Synthetic primer

<400> SEQUENCE: 143
tcatcatgat caacaggaaa ga                                              22

<210> SEQ ID NO 144
<211> LENGTH: 18
<212> TYPE: DNA
<213> ORGANISM: Artificial Sequence
<220> FEATURE:
```

<223> OTHER INFORMATION: Synthetic primer

<400> SEQUENCE: 144
caaccctggc ctcaggat                                              18

<210> SEQ ID NO 145
<211> LENGTH: 25
<212> TYPE: DNA
<213> ORGANISM: Artificial Sequence
<220> FEATURE:
<223> OTHER INFORMATION: Synthetic primer

<400> SEQUENCE: 145
gtgaatatag tgagtgacag atggc                                      25

<210> SEQ ID NO 146
<211> LENGTH: 20
<212> TYPE: DNA
<213> ORGANISM: Artificial Sequence
<220> FEATURE:
<223> OTHER INFORMATION: Synthetic primer

<400> SEQUENCE: 146
ctttatgaaa cggggccata                                            20

<210> SEQ ID NO 147
<211> LENGTH: 21
<212> TYPE: DNA
<213> ORGANISM: Artificial Sequence
<220> FEATURE:
<223> OTHER INFORMATION: Synthetic primer

<400> SEQUENCE: 147
caatgtacag gtcctgttgc c                                          21

<210> SEQ ID NO 148
<211> LENGTH: 20
<212> TYPE: DNA
<213> ORGANISM: Artificial Sequence
<220> FEATURE:
<223> OTHER INFORMATION: Synthetic primer

<400> SEQUENCE: 148
aaaacaatgc ttccagtggc                                            20

<210> SEQ ID NO 149
<211> LENGTH: 20
<212> TYPE: DNA
<213> ORGANISM: Artificial Sequence
<220> FEATURE:
<223> OTHER INFORMATION: Synthetic primer

<400> SEQUENCE: 149
acagtcccat tctggcaaac                                            20

<210> SEQ ID NO 150
<211> LENGTH: 20
<212> TYPE: DNA
<213> ORGANISM: Artificial Sequence
<220> FEATURE:
<223> OTHER INFORMATION: Synthetic primer

<400> SEQUENCE: 150
tcactccctc caacaattcc                                            20

<210> SEQ ID NO 151

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 151
tttgttactt gctaccctga g                                              21

<210> SEQ ID NO 152
<211> LENGTH: 21
<212> TYPE: DNA
<213> ORGANISM: Artificial Sequence
<220> FEATURE:
<223> OTHER INFORMATION: Synthetic primer

<400> SEQUENCE: 152
caaccatcat cttccacagt c                                              21

<210> SEQ ID NO 153
<211> LENGTH: 22
<212> TYPE: DNA
<213> ORGANISM: Artificial Sequence
<220> FEATURE:
<223> OTHER INFORMATION: Synthetic primer

<400> SEQUENCE: 153
cggcatgagg aaggtgcagg ag                                             22

<210> SEQ ID NO 154
<211> LENGTH: 23
<212> TYPE: DNA
<213> ORGANISM: Artificial Sequence
<220> FEATURE:
<223> OTHER INFORMATION: Synthetic primer

<400> SEQUENCE: 154
cgacaccatg cgagacacgc ttg                                            23

<210> SEQ ID NO 155
<211> LENGTH: 19
<212> TYPE: DNA
<213> ORGANISM: Artificial Sequence
<220> FEATURE:
<223> OTHER INFORMATION: Synthetic primer

<400> SEQUENCE: 155
aatgcccagc agaaccgcc                                                 19

<210> SEQ ID NO 156
<211> LENGTH: 25
<212> TYPE: DNA
<213> ORGANISM: Artificial Sequence
<220> FEATURE:
<223> OTHER INFORMATION: Synthetic primer

<400> SEQUENCE: 156
actccacaaa ctcatccagg tcctc                                          25

<210> SEQ ID NO 157
<211> LENGTH: 23
<212> TYPE: DNA
<213> ORGANISM: Artificial Sequence
<220> FEATURE:
<223> OTHER INFORMATION: Synthetic primer

<400> SEQUENCE: 157
```

```
gcaagatttt tgcttggctc tat                                              23
```

```
<210> SEQ ID NO 158
<211> LENGTH: 23
<212> TYPE: DNA
<213> ORGANISM: Artificial Sequence
<220> FEATURE:
<223> OTHER INFORMATION: Synthetic primer

<400> SEQUENCE: 158
ctttggtatt tgcttccacc aac                                              23
```

```
<210> SEQ ID NO 159
<211> LENGTH: 19
<212> TYPE: DNA
<213> ORGANISM: Artificial Sequence
<220> FEATURE:
<223> OTHER INFORMATION: Synthetic primer

<400> SEQUENCE: 159
tgaggcttca cattccagc                                                   19
```

```
<210> SEQ ID NO 160
<211> LENGTH: 20
<212> TYPE: DNA
<213> ORGANISM: Artificial Sequence
<220> FEATURE:
<223> OTHER INFORMATION: Synthetic primer

<400> SEQUENCE: 160
tattcccagt gctggagagg                                                  20
```

```
<210> SEQ ID NO 161
<211> LENGTH: 18
<212> TYPE: DNA
<213> ORGANISM: Artificial Sequence
<220> FEATURE:
<223> OTHER INFORMATION: Synthetic primer

<400> SEQUENCE: 161
tcattggggc tgagcaat                                                    18
```

```
<210> SEQ ID NO 162
<211> LENGTH: 22
<212> TYPE: DNA
<213> ORGANISM: Artificial Sequence
<220> FEATURE:
<223> OTHER INFORMATION: Synthetic primer

<400> SEQUENCE: 162
tcaggagcct tttagtctga gg                                               22
```

```
<210> SEQ ID NO 163
<211> LENGTH: 25
<212> TYPE: DNA
<213> ORGANISM: Artificial Sequence
<220> FEATURE:
<223> OTHER INFORMATION: Synthetic primer

<400> SEQUENCE: 163
tgttaacaat ttgcataaca aaagc                                            25
```

```
<210> SEQ ID NO 164
<211> LENGTH: 25
<212> TYPE: DNA
<213> ORGANISM: Artificial Sequence
<220> FEATURE:
```

<223> OTHER INFORMATION: Synthetic primer

<400> SEQUENCE: 164
tgattaattt gcgagactaa ctttg    25

<210> SEQ ID NO 165
<211> LENGTH: 20
<212> TYPE: DNA
<213> ORGANISM: Artificial Sequence
<220> FEATURE:
<223> OTHER INFORMATION: Synthetic primer

<400> SEQUENCE: 165
ggttcctcca aagaacagca    20

<210> SEQ ID NO 166
<211> LENGTH: 20
<212> TYPE: DNA
<213> ORGANISM: Artificial Sequence
<220> FEATURE:
<223> OTHER INFORMATION: Synthetic primer

<400> SEQUENCE: 166
tgagatttgg ccttgcttct    20

<210> SEQ ID NO 167
<211> LENGTH: 20
<212> TYPE: DNA
<213> ORGANISM: Artificial Sequence
<220> FEATURE:
<223> OTHER INFORMATION: Synthetic primer

<400> SEQUENCE: 167
tccattgttt accccaaagc    20

<210> SEQ ID NO 168
<211> LENGTH: 20
<212> TYPE: DNA
<213> ORGANISM: Artificial Sequence
<220> FEATURE:
<223> OTHER INFORMATION: Synthetic primer

<400> SEQUENCE: 168
tctgggagtg ggaagagttg    20

<210> SEQ ID NO 169
<211> LENGTH: 18
<212> TYPE: DNA
<213> ORGANISM: Artificial Sequence
<220> FEATURE:
<223> OTHER INFORMATION: Synthetic primer

<400> SEQUENCE: 169
cccagccctc tctccgcc    18

<210> SEQ ID NO 170
<211> LENGTH: 25
<212> TYPE: DNA
<213> ORGANISM: Artificial Sequence
<220> FEATURE:
<223> OTHER INFORMATION: Synthetic primer

<400> SEQUENCE: 170
cctaaactgg agacggatcc tgccc    25

<210> SEQ ID NO 171

```
<211> LENGTH: 25
<212> TYPE: DNA
<213> ORGANISM: Artificial Sequence
<220> FEATURE:
<223> OTHER INFORMATION: Synthetic primer

<400> SEQUENCE: 171
acaggcctcc attcatgtcc cttcc                                               25

<210> SEQ ID NO 172
<211> LENGTH: 18
<212> TYPE: DNA
<213> ORGANISM: Artificial Sequence
<220> FEATURE:
<223> OTHER INFORMATION: Synthetic primer

<400> SEQUENCE: 172
tcgtggccgc caaggcac                                                       18

<210> SEQ ID NO 173
<211> LENGTH: 23
<212> TYPE: DNA
<213> ORGANISM: Artificial Sequence
<220> FEATURE:
<223> OTHER INFORMATION: Synthetic primer

<400> SEQUENCE: 173
gcatcctata aaagcagcca tgt                                                 23

<210> SEQ ID NO 174
<211> LENGTH: 23
<212> TYPE: DNA
<213> ORGANISM: Artificial Sequence
<220> FEATURE:
<223> OTHER INFORMATION: Synthetic primer

<400> SEQUENCE: 174
ggctgagtca tcttcctctt gaa                                                 23

<210> SEQ ID NO 175
<211> LENGTH: 19
<212> TYPE: DNA
<213> ORGANISM: Artificial Sequence
<220> FEATURE:
<223> OTHER INFORMATION: Synthetic primer

<400> SEQUENCE: 175
gaccatcagg cgacagatt                                                      19

<210> SEQ ID NO 176
<211> LENGTH: 18
<212> TYPE: DNA
<213> ORGANISM: Artificial Sequence
<220> FEATURE:
<223> OTHER INFORMATION: Synthetic primer

<400> SEQUENCE: 176
gctcaggcat aacccctc                                                       18

<210> SEQ ID NO 177
<211> LENGTH: 20
<212> TYPE: DNA
<213> ORGANISM: Artificial Sequence
<220> FEATURE:
<223> OTHER INFORMATION: Synthetic primer

<400> SEQUENCE: 177
```

-continued ctaccatgcc tggcagaaat                    20

<210> SEQ ID NO 178
<211> LENGTH: 23
<212> TYPE: DNA
<213> ORGANISM: Artificial Sequence
<220> FEATURE:
<223> OTHER INFORMATION: Synthetic primer

<400> SEQUENCE: 178
ttgctaacct aaaagacagc agg                23

<210> SEQ ID NO 179
<211> LENGTH: 21
<212> TYPE: DNA
<213> ORGANISM: Artificial Sequence
<220> FEATURE:
<223> OTHER INFORMATION: Synthetic primer

<400> SEQUENCE: 179
tgaaaaggat accaaagtgc g                  21

<210> SEQ ID NO 180
<211> LENGTH: 20
<212> TYPE: DNA
<213> ORGANISM: Artificial Sequence
<220> FEATURE:
<223> OTHER INFORMATION: Synthetic primer

<400> SEQUENCE: 180
ttgggaaatg tcagtgacca                    20

<210> SEQ ID NO 181
<211> LENGTH: 18
<212> TYPE: DNA
<213> ORGANISM: Artificial Sequence
<220> FEATURE:
<223> OTHER INFORMATION: Synthetic primer

<400> SEQUENCE: 181
ggccaacagg aacagcag                      18

<210> SEQ ID NO 182
<211> LENGTH: 20
<212> TYPE: DNA
<213> ORGANISM: Artificial Sequence
<220> FEATURE:
<223> OTHER INFORMATION: Synthetic primer

<400> SEQUENCE: 182
ttctctggat cttttcagcc                    20

<210> SEQ ID NO 183
<211> LENGTH: 18
<212> TYPE: DNA
<213> ORGANISM: Artificial Sequence
<220> FEATURE:
<223> OTHER INFORMATION: Synthetic primer

<400> SEQUENCE: 183
ccgcgagctc cctctgcc                      18

<210> SEQ ID NO 184
<211> LENGTH: 24
<212> TYPE: DNA
<213> ORGANISM: Artificial Sequence
<220> FEATURE:

-continued

<223> OTHER INFORMATION: Synthetic primer

<400> SEQUENCE: 184
ctctgtagcc ctaggaccgg tctg                                              24

<210> SEQ ID NO 185
<211> LENGTH: 25
<212> TYPE: DNA
<213> ORGANISM: Artificial Sequence
<220> FEATURE:
<223> OTHER INFORMATION: Synthetic primer

<400> SEQUENCE: 185
ctgccgacat tccacgggtt tcttg                                             25

<210> SEQ ID NO 186
<211> LENGTH: 25
<212> TYPE: DNA
<213> ORGANISM: Artificial Sequence
<220> FEATURE:
<223> OTHER INFORMATION: Synthetic primer

<400> SEQUENCE: 186
agccttccgc tggaagtcca acttt                                             25

<210> SEQ ID NO 187
<211> LENGTH: 21
<212> TYPE: DNA
<213> ORGANISM: Artificial Sequence
<220> FEATURE:
<223> OTHER INFORMATION: Synthetic primer

<400> SEQUENCE: 187
tttcacattt cctaagcagc c                                                 21

<210> SEQ ID NO 188
<211> LENGTH: 21
<212> TYPE: DNA
<213> ORGANISM: Artificial Sequence
<220> FEATURE:
<223> OTHER INFORMATION: Synthetic primer

<400> SEQUENCE: 188
ttgcttttgc ccccactact g                                                 21

<210> SEQ ID NO 189
<211> LENGTH: 25
<212> TYPE: DNA
<213> ORGANISM: Artificial Sequence
<220> FEATURE:
<223> OTHER INFORMATION: Synthetic primer

<400> SEQUENCE: 189
tgccagagaa gttttaacaa tcaca                                             25

<210> SEQ ID NO 190
<211> LENGTH: 23
<212> TYPE: DNA
<213> ORGANISM: Artificial Sequence
<220> FEATURE:
<223> OTHER INFORMATION: Synthetic primer

<400> SEQUENCE: 190
ggatgacaac tgctaaggtc cat                                               23

<210> SEQ ID NO 191

```
<211> LENGTH: 25
<212> TYPE: DNA
<213> ORGANISM: Artificial Sequence
<220> FEATURE:
<223> OTHER INFORMATION: Synthetic primer

<400> SEQUENCE: 191
tatttaaaat gtgggcaaga tatca                                    25

<210> SEQ ID NO 192
<211> LENGTH: 25
<212> TYPE: DNA
<213> ORGANISM: Artificial Sequence
<220> FEATURE:
<223> OTHER INFORMATION: Synthetic primer

<400> SEQUENCE: 192
tggtgtaaat aaagaccttg ctatc                                    25

<210> SEQ ID NO 193
<211> LENGTH: 23
<212> TYPE: DNA
<213> ORGANISM: Artificial Sequence
<220> FEATURE:
<223> OTHER INFORMATION: Synthetic primer

<400> SEQUENCE: 193
ccatttcgta tcagtctagc cca                                      23

<210> SEQ ID NO 194
<211> LENGTH: 23
<212> TYPE: DNA
<213> ORGANISM: Artificial Sequence
<220> FEATURE:
<223> OTHER INFORMATION: Synthetic primer

<400> SEQUENCE: 194
gtcagtgctg ctatggagct ttt                                      23

<210> SEQ ID NO 195
<211> LENGTH: 24
<212> TYPE: DNA
<213> ORGANISM: Artificial Sequence
<220> FEATURE:
<223> OTHER INFORMATION: Synthetic primer

<400> SEQUENCE: 195
gcttactgat gaaaaactca tcca                                     24

<210> SEQ ID NO 196
<211> LENGTH: 25
<212> TYPE: DNA
<213> ORGANISM: Artificial Sequence
<220> FEATURE:
<223> OTHER INFORMATION: Synthetic primer

<400> SEQUENCE: 196
tggttataac taacaaacct gaaca                                    25

<210> SEQ ID NO 197
<211> LENGTH: 19
<212> TYPE: DNA
<213> ORGANISM: Artificial Sequence
<220> FEATURE:
<223> OTHER INFORMATION: Synthetic primer

<400> SEQUENCE: 197
```

| | |
|---|---|
| ctctatgtgg ctcacgcag | 19 |

<210> SEQ ID NO 198
<211> LENGTH: 21
<212> TYPE: DNA
<213> ORGANISM: Artificial Sequence
<220> FEATURE:
<223> OTHER INFORMATION: Synthetic primer

<400> SEQUENCE: 198

| | |
|---|---|
| tttacaaatg agggaactcc c | 21 |

<210> SEQ ID NO 199
<211> LENGTH: 19
<212> TYPE: DNA
<213> ORGANISM: Artificial Sequence
<220> FEATURE:
<223> OTHER INFORMATION: Synthetic primer

<400> SEQUENCE: 199

| | |
|---|---|
| tgggaaaagt cagctcgtg | 19 |

<210> SEQ ID NO 200
<211> LENGTH: 19
<212> TYPE: DNA
<213> ORGANISM: Artificial Sequence
<220> FEATURE:
<223> OTHER INFORMATION: Synthetic primer

<400> SEQUENCE: 200

| | |
|---|---|
| aactgggggc aagaacaac | 19 |

<210> SEQ ID NO 201
<211> LENGTH: 22
<212> TYPE: DNA
<213> ORGANISM: Artificial Sequence
<220> FEATURE:
<223> OTHER INFORMATION: Synthetic primer

<400> SEQUENCE: 201

| | |
|---|---|
| tcattaacac cagtctgcaa ca | 22 |

<210> SEQ ID NO 202
<211> LENGTH: 22
<212> TYPE: DNA
<213> ORGANISM: Artificial Sequence
<220> FEATURE:
<223> OTHER INFORMATION: Synthetic primer

<400> SEQUENCE: 202

| | |
|---|---|
| tgcaatttga aggtacgagt ag | 22 |

<210> SEQ ID NO 203
<211> LENGTH: 19
<212> TYPE: DNA
<213> ORGANISM: Artificial Sequence
<220> FEATURE:
<223> OTHER INFORMATION: Synthetic primer

<400> SEQUENCE: 203

| | |
|---|---|
| gcacctgcta aggagggag | 19 |

<210> SEQ ID NO 204
<211> LENGTH: 21
<212> TYPE: DNA
<213> ORGANISM: Artificial Sequence
<220> FEATURE:

<223> OTHER INFORMATION: Synthetic primer

<400> SEQUENCE: 204
tcattttttg ctgatggttc c                                    21

<210> SEQ ID NO 205
<211> LENGTH: 20
<212> TYPE: DNA
<213> ORGANISM: Artificial Sequence
<220> FEATURE:
<223> OTHER INFORMATION: Synthetic primer

<400> SEQUENCE: 205
ccgctggatt cttttcaaa                                       20

<210> SEQ ID NO 206
<211> LENGTH: 20
<212> TYPE: DNA
<213> ORGANISM: Artificial Sequence
<220> FEATURE:
<223> OTHER INFORMATION: Synthetic primer

<400> SEQUENCE: 206
aaggctcaaa tgccaaattg                                      20

<210> SEQ ID NO 207
<211> LENGTH: 21
<212> TYPE: DNA
<213> ORGANISM: Artificial Sequence
<220> FEATURE:
<223> OTHER INFORMATION: Synthetic primer

<400> SEQUENCE: 207
agcggcctgg atgagatgct g                                    21

<210> SEQ ID NO 208
<211> LENGTH: 23
<212> TYPE: DNA
<213> ORGANISM: Artificial Sequence
<220> FEATURE:
<223> OTHER INFORMATION: Synthetic primer

<400> SEQUENCE: 208
ctggttcaca gcccaaaggc tga                                  23

<210> SEQ ID NO 209
<211> LENGTH: 23
<212> TYPE: DNA
<213> ORGANISM: Artificial Sequence
<220> FEATURE:
<223> OTHER INFORMATION: Synthetic primer

<400> SEQUENCE: 209
ctcccacaga ccgaccagct tcc                                  23

<210> SEQ ID NO 210
<211> LENGTH: 25
<212> TYPE: DNA
<213> ORGANISM: Artificial Sequence
<220> FEATURE:
<223> OTHER INFORMATION: Synthetic primer

<400> SEQUENCE: 210
gtgcatcgtg atctcgggtg agagc                                25